United States Patent
Minshull et al.

(10) Patent No.: US 9,574,209 B2
(45) Date of Patent: *Feb. 21, 2017

(54) ENHANCED NUCLEIC ACID CONSTRUCTS FOR EUKARYOTIC GENE EXPRESSION

(71) Applicant: DNA2.0, INC., Newark, CA (US)

(72) Inventors: Jeremy Minshull, Los Altos, CA (US); Mark Welch, Fremont, CA (US); Sridhar Govindrajan, Los Altos, CA (US); Kate Caves, San Jose, CA (US)

(73) Assignee: DNA2.0, INC., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/195,905

(22) Filed: Aug. 2, 2016

(65) Prior Publication Data

US 2016/0340691 A1  Nov. 24, 2016

Related U.S. Application Data

(63) Continuation of application No. 14/683,121, filed on Apr. 9, 2015, now Pat. No. 9,428,767.

(60) Provisional application No. 61/977,474, filed on Apr. 9, 2014, provisional application No. 62/003,397, filed on May 27, 2014, provisional application No. 62/046,875, filed on Sep. 5, 2014, provisional application No. 62/046,705, filed on Sep. 5, 2014, provisional application No. 62/069,656, filed on Oct. 28, 2014, provisional application No. 62/120,522, filed on Feb. 25, 2015.

(51) Int. Cl.
| | | |
|---|---|---|
| *C12N 15/85* | (2006.01) | |
| *C07K 16/00* | (2006.01) | |
| *C12N 9/12* | (2006.01) | |
| *C07K 16/32* | (2006.01) | |
| *C12N 15/90* | (2006.01) | |

(52) U.S. Cl.
CPC .............. *C12N 15/85* (2013.01); *C07K 16/32* (2013.01); *C12N 9/1241* (2013.01); *C12N 15/907* (2013.01); *C12Y 207/07* (2013.01); *C07K 2317/24* (2013.01); *C12N 2800/90* (2013.01); *C12N 2830/40* (2013.01)

(58) Field of Classification Search
CPC .... A61K 31/00; A61K 31/7105; A61K 38/00; C07K 14/43586; C07K 14/463; C07K 16/00; C07K 2317/10; C07K 2317/56; C07K 2319/80; C12N 15/85; C12N 2800/90; C12N 2830/40; C12N 2830/60; C12N 9/1241
USPC .................................................. 435/320.1
See application file for complete search history.

(56) References Cited

U.S. PATENT DOCUMENTS

| | | |
|---|---|---|
| 6,312,912 B1 | 11/2001 | Hope et al. |
| 8,399,643 B2 | 3/2013 | Ostertag et al. |
| 9,428,767 B2 * | 8/2016 | Minshull ............ A61K 31/00 |
| 2003/0150007 A1 | 8/2003 | Savakis et al. |
| 2005/0060762 A1 | 3/2005 | Bleck |
| 2009/0197244 A1 | 8/2009 | Stuyver et al. |
| 2010/0154070 A1 | 6/2010 | Xu et al. |
| 2010/0223683 A1 | 9/2010 | Wu et al. |
| 2011/0099649 A1 | 4/2011 | Meir et al. |
| 2011/0130444 A1 | 6/2011 | Moisyadi et al. |
| 2013/0160152 A1 | 6/2013 | Ostertag et al. |
| 2015/0158927 A1 | 6/2015 | Hantash |
| 2015/0291975 A1 | 10/2015 | Minshull et al. |
| 2015/0291977 A1 | 10/2015 | Minshull et al. |

FOREIGN PATENT DOCUMENTS

WO   WO 2015/157579 A2   10/2015

OTHER PUBLICATIONS

Abe et al. "Novel non-autonomous transposable elements on W chromosome of the silkworm, *Bombyx mori*," Journal of Genetics, 89(3):375-387, (2010).
Bauser et. al., "Proteins from nuclear extracts of two lepidopteran cell lines recognize the ends of TTAA-specific transposons piggyBac and tagalong," Insect Mol. Biol., 8(2):223-230, (1999).
Daimon et. al., "Recent transposition of yabusame, a novel piggyBac-like transposable element in the genome of the silkworm, *Bombyx mori*," Genome, 53:585-593, (2010).
GenBank: AB162707.1, "Bombyx mori gene for putative transposase yabusame-.1, complete cds," Sep. 2015. [Retrieved from the Internet Sep. 17, 2015: <URL: http://www.ncbi.nlm.nih.gov/nuccore/AB162707.>].
GenBank: AB480234.1, "Bombyx mori DNA, contig W-5A2G-0O3, contains SINE:Bml," Sep. 2015. [Retrieved from the Internet Sep. 17, 2015: <URL: http://www.ncbi.nlm.nih.gov/nuccore/AB480234>].
Hikosaka et. al., "Evolution of the Xenopus piggyBac Transposon Family TxpB: Domesticated and Untamed Strategies of Transposon Subfamilies," Mol. Biol. Evol., 24(12):2648-2656, (2007). [Retrieved from the Internet Apr. 14, 2014: <URL: http://mbe.oxfordj.
Keith et al., "Analysis of the piggyBac transposase reveals a functional nuclear targeting signal in the 94 c-terminal residues," BMC Molecular Biology, 9:72, doi:10.1 186/1471-2199-9-72, pp. 1-13, (2008).

(Continued)

*Primary Examiner* — Janet Epps-Smith
(74) *Attorney, Agent, or Firm* — Alston & Bird LLP

(57) ABSTRACT

The present invention provides polynucleotide vectors for high expression of heterologous genes, and methods for constructing such vectors. Some vectors further comprise novel transposons and transposases that further improve expression. Further disclosed are vectors that can be used in a gene transfer system for stably introducing nucleic acids into the DNA of a cell. The gene transfer systems can be used in methods, for example, but not limited to, gene expression, gene therapy, insertional mutagenesis, or gene discovery.

20 Claims, 5 Drawing Sheets

(56) References Cited

OTHER PUBLICATIONS

Figure 1:
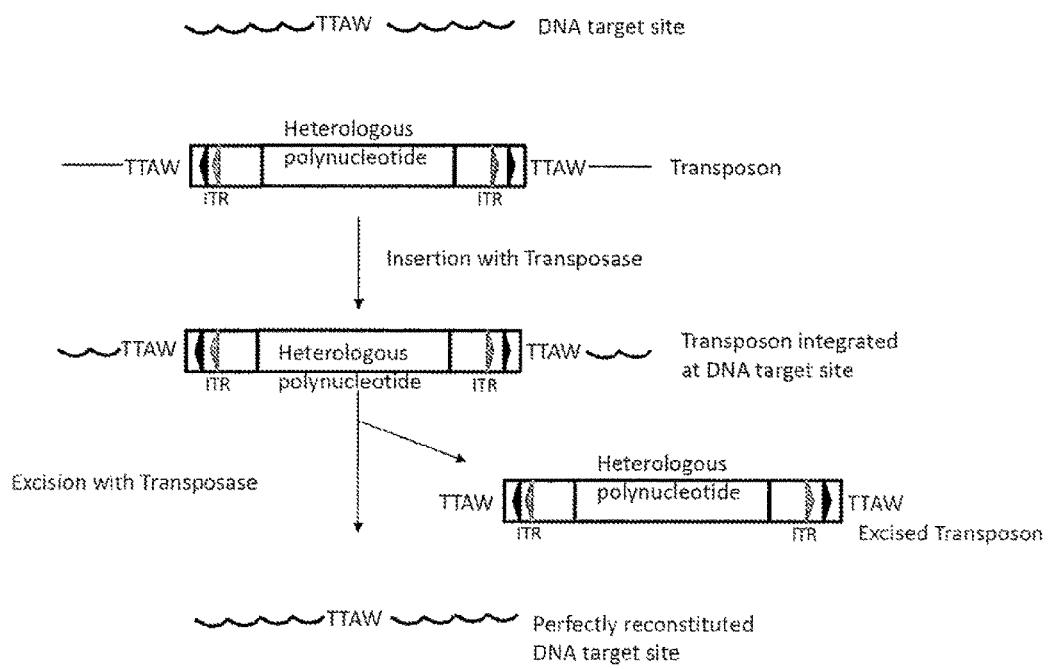

Li et al. "A resurrected mammalian hAT transposable element and a closely related insect element are highly active in human cell culture," PNAS, 110(6):E478-E487, (2013). Published online Oct. 22, 2012.

Li et al., "The piggyBac Transposon Displays Local and Distant Reintegration Preferences and Can Cause Mutations at Noncanonical Integration Sites," Mol Cell Biol, 33(7):1317-1330, (2013).

Maragathavally et al., "Chimeric Mos1 and piggyBac transposases result in site-directed integration," FASEB J., 20:E1188-1195, (2006).

Mitra et al., "piggyBac can bypass DNA synthesis during cut and paste transposition," The EMBO Journal, 27:1097-1109, (2008).

Sarkar et. al., "Molecular evolutionary analysis of widespread piggyBac transposon family and related 'domesticated' sequences," Mol Gen Genomics, 270:173-180, (2003).

Szuts et al., "LexA chimeras reveal the function of *Drosophila* Fos as a context-dependent transcriptional activator," PNAS, 97(10):5351-5356, (2000).

U.S. Appl. No. 14/683,097, Requirement for Restriction/Election mailed Apr. 12, 2016.

U.S. Appl. No. 14/683,097, Requirement for Restriction/Election mailed Jul. 20, 2016.

U.S. Appl. No. 14/683,121, Final Office Action mailed Jan. 12, 2016.

U.S. Appl. No. 14/683,121, Non-Final Office Action mailed Aug. 26, 2015.

U.S. Appl. No. 14/683,121, Notice of Allowance mailed Apr. 25, 2016.

U.S. Appl. No. 14/683,126, Final Office Action mailed Mar. 1, 2016.

U.S. Appl. No. 14/683,126, Notice of Allowance mailed Jul. 20, 2016.

U.S. Appl. No. 14/683,126, Requirement for Restriction/Election mailed Aug. 6, 2015.

U.S. Appl. No. 15/222,830, Non-Final Office Action mailed Sep. 9, 2016.

WIPO Application No. PCT/US2015/025209, PCT International Search Report and Written Opinion of the International Searching Authority mailed Oct. 26, 2015.

WIPO Application No. PCT/US2015/025209, PCT Invitation to Pay Additional Fees mailed Jul. 30, 2015.

Wu et.al., "Cloning and characterization of piggyBac-like elements in lepidopteran insects," Genetica, 139:149-154, (2011).

Yusa et. al., "A hyperactive piggyBac transposase for mammalian applications," PNAS, 108(4):1531-1536, (2011).

Yusufzai et. al., "The 5-HS4 chicken β-globin insulator is a CTCF-dependent nuclear matrix-associated element," PNAS, 101(23):8620-8624, (2004).

Zheng et al., "Cell-Type-Specific Regulation of Degradation of Hypoxia-Inducible Factor 1α:Role of Subcelluar Compartmentalization," Mol. Cell. Biol., 26(12):4628-4641, (2006).

U.S. Appl. No. 14/683,097, Non-Final Office Action and List of References Cited by Examiner mailed Oct. 14, 2016.

U.S. Appl. No. 15/222,830, Notice of Allowance mailed Oct. 7, 2016.

* cited by examiner

SEQUENCE LISTING

```
<160> NUMBER OF SEQ ID NOS: 130

<210> SEQ ID NO 1
<211> LENGTH: 375
<212> TYPE: DNA
<213> ORGANISM: Bombyx mori

<400> SEQUENCE: 1
ttatcccggc gagcatgagg cagggtatct catacccctgg taaaatttta aagttgtgta    60
ttttataaaa ttttcgtctg acaacactag cgcgctcagt agctggaggc aggagcgtgc   120
gggaggggat agtggcgtga tcgcagtgtg gcacgggaca ccggcgagat attcgtgtgc   180
aaacctgttt cgggtatgtt ataccctgcc tcattgttga cgtatttttt ttatgtaatt   240
tttccgatta ttaatttcaa ctgttttatt ggtattttta tgttatccat tgttctttt    300 ttatgattta ctgtatcggt tgtctttcgt tcctttagtt gagttttttt ttattattt    360 cagttttttga tcaaa                                                    375

<210> SEQ ID NO 2
<211> LENGTH: 368
<212> TYPE: DNA
<213> ORGANISM: Bombyx mori

<400> SEQUENCE: 2
tcatattttt agtttaaaaa aataattata tgttttataa tgaaaagaat ctcattatct    60
ttcagtatta ggttgattta tattccaaag aataatattt ttgttaaatt gttgattttt   120
gtaaacctct aaatgtttgt tgctaaaatt actgtgttta agaaaaagat taataaataa   180
taataatttc ataattaaaa acttctttca ttgaatgcca ttaaataaac cattatttta   240
caaaataaga tcaacataat tgagtaaata ataataagaa caatattata gtacaacaaa   300
atatgggtat gtcatacct gccacattct tgatgtaact tttttttcacc tcatgctcgc   360 cgggttat                                                             368

<210> SEQ ID NO 3
<211> LENGTH: 214
<212> TYPE: DNA
```

<213> ORGANISM: Bombyx mori

<400> SEQUENCE: 3

```
ttatcccggc gagcatgagg cagggtatct catacccctgg taaaattta aagttgtgta      60 ttttataaaa ttttcgtctg acaacactag cgcgctcagt agctggaggc aggagcgtgc     120
gggaggggat agtggcgtga tcgcagtgtg gcacgggaca ccggcgagat attcgtgtgc    180
aaacctgttt cgggtatgtt ataccctgcc tcat                                 214
```

<210> SEQ ID NO 4
<211> LENGTH: 195
<212> TYPE: DNA
<213> ORGANISM: Bombyx mori

<400> SEQUENCE: 4

```
taaataataa taatttcata attaaaaact tctttcattg aatgccatta aataaaccat      60
tattttacaa aataagatca acataattga gtaaataata ataagaacaa tattatagta    120
caacaaaata tgggtatgtc ataccctgcc acattcttga tgtaactttt tttcacctca    180
tgctcgccgg gttat                                                      195
```

<210> SEQ ID NO 5
<211> LENGTH: 185
<212> TYPE: DNA
<213> ORGANISM: Xenopus tropicalis

<400> SEQUENCE: 5

```
ttaaccttt tactgccaat gacgcatggg atacgtcgtg gcagtaaaag ggcttaaatg       60
ccaacgacgc gtcccatacg ttgttggcat tttaagtctt ctctctgcag cggcagcatg    120
tgccgccgct gcagagagtt tctagcgatg acagcccctc tgggcaacga gccgggggg    180 ctgtc                                                                 185
```

<210> SEQ ID NO 6
<211> LENGTH: 237
<212> TYPE: DNA
<213> ORGANISM: Xenopus tropicalis

<400> SEQUENCE: 6

```
tttgcatttt tagacattta gaagcctata tcttgttaca gaattggaat tacacaaaaa      60
ttctaccata ttttgaaagc ttaggttgtt ctgaaaaaaa caatatattg ttttcctggg    120
taaactaaaa gtcccctcga ggaaaggccc ctaaagtgaa acagtgcaaa acgttcaaaa    180
actgtctggc aatacaagtt ccactttgac caaaacggct ggcagtaaaa gggttaa      237
```

<210> SEQ ID NO 7
<211> LENGTH: 185
<212> TYPE: DNA
<213> ORGANISM: Xenopus tropicalis

<400> SEQUENCE: 7

```
ttaacccttt gcctgccaat cacgcatggg atacgtcgtg gcagtaaaag ggcttaaatg      60
ccaacgacgc gtcccatacg ttgttggcat tttaagtctt ctctctgcag cggcagcatg    120
tgccgccgct gcagagagtt tctagcgatg acagcccctc tgggcaacga gccgggggg    180 ctgtc                                                                 185
```

<210> SEQ ID NO 8
<211> LENGTH: 238

<212> TYPE: DNA
<213> ORGANISM: Xenopus tropicalis

<400> SEQUENCE: 8

```
tttgcatttt tagacattta gaagcctata tcttgttaca gaattggaat tacacaaaaa      60
ttctaccata ttttgaaagc ttaggttgtt ctgaaaaaaa caatatattg ttttcctggg     120
taaactaaaa gtcccctcga ggaaaggccc ctaaagtgaa acagtgcaaa acgttcaaaa     180
actgtctggc aatacaagtt ccactttggg acaaatcggc tggcagtgaa agggttaa      238
```

<210> SEQ ID NO 9
<211> LENGTH: 185
<212> TYPE: DNA
<213> ORGANISM: Xenopus tropicalis

<400> SEQUENCE: 9

```
ttaaccttt tactgccaat gacgcatggg atacgtcgtg gcagtaaaag ggcttaaatg       60
ccaacgacgc gtcccatacg ttgttggcat tttaattctt ctctctgcag cggcagcatg     120
tgccgccgct gcagagagtt tctagcgatg acagcccctc tgggcaacga gccgggggg      180
ctgtc                                                                  185
```

<210> SEQ ID NO 10
<211> LENGTH: 347
<212> TYPE: DNA
<213> ORGANISM: Helicoverpa armigera

<400> SEQUENCE: 10

```
ttaaccctag aagcccaatc tacgtaaatt tgacgtatac cgcggcgaaa tatctctgtc      60
tctttcatgt ttaccgtcgg atcgccgcta acttctgaac caactcagta gccattggga     120
cctcgcagga cacagttgcg tcatctcggt aagtgccgcc attttgttgt actctctatt     180
acaacacacg tcacgtcacg tcgttgcacg tcattttgac gtataattgg gctttgtgta     240
acttttgaat ttgttttcaaa ttttttatgt ttgtgattta tttgagttaa tcgtattgtt     300
tcgttacatt tttcatataa taataatatt ttcaggttga gtacaaa                    347
```

<210> SEQ ID NO 11
<211> LENGTH: 367
<212> TYPE: DNA
<213> ORGANISM: Helicoverpa armigera

<400> SEQUENCE: 11

```
agactgtttt tttctaagag acttctaaaa tattattacg agttgattta attttatgaa      60
aacatttaaa actagttgat ttttttttata attacataat tttaagaaaa agtgttagag    120
gcttgatttt tttgttgatt ttttctaaga tttgattaaa gtgccataat agtattaata     180
aagagtattt tttaacttaa aatgtatttt atttattaat taaaacttca attatgataa     240
ctcatgcaaa aatatagttc attaacagaa aaaatagga aaactttgaa gttttgtttt      300
tacacgtcat ttttacgtat gattgggctt tatagctagt taaatatgat tgggcttcta    360
gggttaa                                                                367
```

<210> SEQ ID NO 12
<211> LENGTH: 406
<212> TYPE: DNA
<213> ORGANISM: Pectinophora gossypiella

<400> SEQUENCE: 12

```
ttaaccctag ataactaaac attcgtccgc tcgacgacgc gctatgccgc gaaattgaag    60
tttacctatt attccgcgtc ccccgccccc gccgcttttt ctagcttcct gatttgcaaa   120
atagtgcatc gcgtgacacg ctcgaggtca cacgacaatt aggtcgaaag ttacaggaat   180
ttcgtcgtcc gctcgacgaa agtttagtaa ttacgtaagt ttggcaaagg taagtgaatg   240
aagtattttt ttataattat tttttaattc tttatagtga taacgtaagg tttatttaaa   300
tttattactt ttatagttat ttagccaatt gttataaatt ccttgttatt gctgaaaaat   360
ttgcctgttt tagtcaaaat ttattaactt ttcgatcgtt ttttag                  406
```

<210> SEQ ID NO 13
<211> LENGTH: 179
<212> TYPE: DNA
<213> ORGANISM: Pectinophora gossypiella

<400> SEQUENCE: 13

```
tttcactaag taattttgtt cctatttagt agataagtaa cacataatta ttgtgatatt    60
caaaacttaa gaggtttaat aaataataat aaaaaaaaaa tggtttttat ttcgtagtct   120
gctcgacgaa tgtttagtta ttacgtaacc gtgaatatag tttagtagtc tagggttaa    179
```

<210> SEQ ID NO 14
<211> LENGTH: 326
<212> TYPE: DNA
<213> ORGANISM: Ctenoplusia agnata

<400> SEQUENCE: 14

```
ttaaccctag aagcccaatc tacgtcattc tgacgtgtat gtcgccgaaa atactctgtc    60
tctttctcct gcacgatcgg attgccgcga acgctcgatt caacccagtt ggcgccgaga   120
tctattggag gactgcggcg ttgattcggt aagtcccgcc atttttgtcat agtaacagta   180 ttgcacgtca gcttgacgta tatttgggct ttgtgttatt tttgtaaatt ttcaacgtta   240
gtttattatt gcatcttttt gttacattac tggtttattt gcatgtatta ctcaaatatt   300
attttatttt tagcgtagaa aataca                                         326
```

<210> SEQ ID NO 15
<211> LENGTH: 370
<212> TYPE: DNA
<213> ORGANISM: Ctenoplusia agnata

<400> SEQUENCE: 15

```
agactgtttt ttttgtattt gcattatata ttatattcta aagttgattt aattctaaga    60
aaaacattaa aataagtttc tttttgtaaa atttaattaa ttataagaaa aagtttaagt   120
tgatctcatt ttttataaaa atttgcaatg tttccaaagt tattattgta aaagaataaa   180
taaaagtaaa ctgagtttta attgatgttt tattatatca ttatactata tattacttaa   240
ataaaacaat aactgaatgt atttctaaaa ggaatcacta gaaaatatag tgatcaaaaa   300
tttacacgtc atttttgcgt atgattgggc tttataggtt ctaaaaatat gattgggcct   360
ctagggttaa                                                           370
```

<210> SEQ ID NO 16
<211> LENGTH: 323
<212> TYPE: DNA
<213> ORGANISM: Agrotis ipsilon

<400> SEQUENCE: 16

```
ttaaccctag aagcccaatc tacgtaaatt tgacgtatac cgcggcgaaa tatatctgtc    60
```

```
tctttcacgt ttaccgtcgg attcccgcta acttcggaac caactcagta gccattgaga    120
actcccagga cacagttgcg tcatctcggt aagtgccgcc attttgttgt aatagacagg    180
ttgcacgtca ttttgacgta taattgggct tgtgtaact tttgaaatta tttataattt     240
ttattgatgt gatttatttg agttaatcgt attgtttcgt tacattttc atatgatatt     300 aatattttca gattgaatat aaa                                            323

<210> SEQ ID NO 17
<211> LENGTH: 367
<212> TYPE: DNA
<213> ORGANISM: Agrotis ipsilon

<400> SEQUENCE: 17
agactgtttt ttttaaaagg cttataaagt attactattg cgtgatttaa ttttataaaa    60
atatttaaaa ccagttgatt tttttaataa ttacctaatt ttaagaaaaa atgttagaag   120
cttgatattt ttgttgattt ttttctaaga tttgattaaa aggccataat tgtattaata   180
aagagtattt ttaacttcaa atttatttta tttattaatt aaaacttcaa ttatgataat   240
acatgcaaaa atatagttca tcaacagaaa aatataggaa aactctaata gttttatttt   300
tacacgtcat ttttacgtat gattgggctt tatagctagt caaatatgat tgggcttcta   360
gggttaa                                                              367

<210> SEQ ID NO 18
<211> LENGTH: 242
<212> TYPE: DNA
<213> ORGANISM: Messor bouvieri

<400> SEQUENCE: 18
agtcagaaat gacacctcga tcgacgacta atcgacgtct aatcgacgtc gattttatgt    60
caacatgtta ccaggtgtgt cggtaattcc tttccggttt ttccggcaga tgtcactagc   120
cataagtatg aaatgttatg atttgataca tatgtcattt tattctactg acattaacct   180
taaaactaca caagttacgt tccgccaaaa taacagcgtt atagatttat aatttttga   240 aa                                                                  242

<210> SEQ ID NO 19
<211> LENGTH: 146
<212> TYPE: DNA
<213> ORGANISM: Messor bouvieri

<400> SEQUENCE: 19
ataaatttga actatccatt ctaagtaacg tgttttcttt aacgaaaaaa ccggaaaaga    60
attaccgaca ctcctggtat gtcaacatgt tattttcgac attgaatcgc gtcgattcga   120
agtcgatcga ggtgtcattt ctgact                                         146

<210> SEQ ID NO 20
<211> LENGTH: 246
<212> TYPE: DNA
<213> ORGANISM: Megachile rotundata

<400> SEQUENCE: 20
ttaaataatg cccactctag atgaacttaa cactttaccg accggccgtc gattattcga    60
cgtttgctcc ccagcgctta ccgaccggcc atcgattatt cgacgtttgc ttcccagcgc   120
ttaccgaccg gtcatcgact tttgatcttt ccgttagatt tggttaggtc agattgacaa   180
```

```
gtagcaagca tttcgcattc tttattcaaa taatcggtgc ttttttctaa gctttagccc    240
ttagaa                                                                246

<210> SEQ ID NO 21
<211> LENGTH: 244
<212> TYPE: DNA
<213> ORGANISM: Megachile rotundata

<400> SEQUENCE: 21
acaacttctt ttttcaacaa atattgttat atggattatt tatttattta tttatttatg     60
gtatatttta tgtttattta tttatggtta ttatggtata ttttatgtaa ataataaact    120
gaaaacgatt gtaatagatg aaataaatat tgttttaaca ctaatataat taaagtaaaa    180
gattttaata aatttcgtta ccctacaata cacgaagcg tacaatttta ccagagttta    240
ttaa                                                                 244

<210> SEQ ID NO 22
<211> LENGTH: 278
<212> TYPE: DNA
<213> ORGANISM: Bombus impatiens

<400> SEQUENCE: 22
ttaatttttt aacattttac cgaccgatag ccgattaatc gggttttttgc cgctgacgct    60 taccgaccga taacctatta atcggctttt tgtcgtcgaa gcttaccaac ctatagccta   120
cctatagtta atcggttgcc atggcgataa acaatctttc tcattatatg agcagtaatt   180
tgttatttag tactaaggta ccttgctcag ttgcgtcagt tgcgttgctt tgtaagctcc    240
cacagtttta taccaattcg aaaaacttac cgttcgcg                            278

<210> SEQ ID NO 23
<211> LENGTH: 384
<212> TYPE: DNA
<213> ORGANISM: Bombus impatiens

<400> SEQUENCE: 23
actatttcac atttgaacta aaaaccgttg taatagataa aataaatata atttagtatt    60
aatattatgg aaacaaaaga ttttattcaa tttaattatc ctatagtaac aaaaagcggc   120
caattttatc tgagcatacg aaaagcacag atactcccgc ccgacagtct aaaccgaaac    180
agagccggcg ccagggagaa tctgcgcctg agcagccggt cggacgtgcg tttgctgttg   240
aaccgctagt ggtcagtaaa ccagaaccag tcagtaagcc agtaactgat cagttaacta   300
gattgtatag ttcaaattga acttaatcta gttttttaagc gtttgaatgt tgtctaactt    360
cgttatatat tatattctttt ttaa                                          384

<210> SEQ ID NO 24
<211> LENGTH: 174
<212> TYPE: DNA
<213> ORGANISM: Mamestra brassicae

<400> SEQUENCE: 24
ttattgggtt gcccaaaaag taattgcgga ttttcatat acctgtcttt taaacgtaca    60
tagggatcga actcagtaaa actttgacct tgtgaaataa caaacttgac tgtccaacca   120
ccatagtttg gcgcgaattg agcgtcataa ttgttttgac ttttttgcagt caac         174

<210> SEQ ID NO 25
<211> LENGTH: 79
```

```
<212> TYPE: DNA
<213> ORGANISM: Mamestra brassicae

<400> SEQUENCE: 25 atgattttt  cttttaaac   caattttaat  tagttaattg  atataaaat   ccgcaattac     60 tttttgggca  acccaataa                                                     79

<210> SEQ ID NO 26
<211> LENGTH: 267
<212> TYPE: DNA
<213> ORGANISM: Mayetiola destructor

<400> SEQUENCE: 26
taagacttcc  aaaatttcca  cccgaacttt  accttccccg  cgcattatgt  ctctcttttc     60
accctctgat  ccctggtatt  gttgtcgagc  acgatttata  ttgggtgtac  aacttaaaaa    120
ccggaattgg  acgctagatg  tccacactaa  cgaatagtgt  aaaagcacaa  atttcatata    180
tacgtcattt  tgaaggtaca  tttgacagct  atcaaaatca  gtcaataaaa  ctattctatc    240
tgtgtgcatc  atatttttt   attaact                                          267

<210> SEQ ID NO 27
<211> LENGTH: 188
<212> TYPE: DNA
<213> ORGANISM: Mayetiola destructor

<400> SEQUENCE: 27
tgcattcatt  cattttgtta  tcgaaataaa  gcattaattt  tcactaaaaa  attccggttt     60
ttaagttgta  cacccaatat  catccttagt  gacaattttc  aaatggcttt  cccattgagc    120
tgaaaccgtg  gctctagtaa  gaaaaacgcc  caacccgtca  tcatatgcct  ttttttctc    180 aacatccg                                                                 188

<210> SEQ ID NO 28
<211> LENGTH: 184
<212> TYPE: DNA
<213> ORGANISM: Apis mellifera

<400> SEQUENCE: 28
ttgggttggc  aactaagtaa  ttgcggattt  cactcataga  tggcttcagt  tgaatttta     60 ggtttgctgg  cgtagtccaa  atgtaaaaca  cattttgtta  tttgatagtt  ggcaattcag    120
ctgtcaatca  gtaaaaaaag  tttttttgatc  ggttgcgtag  ttttcgtttg  gcgttcgttg   180
aaaa                                                                     184

<210> SEQ ID NO 29
<211> LENGTH: 74
<212> TYPE: DNA
<213> ORGANISM: Apis mellifera

<400> SEQUENCE: 29
agttatttag  ttccatgaaa  aaattgtctt  tgattttcta  aaaaaaatcc  gcaattactt     60
agttgccaat  ccaa                                                          74

<210> SEQ ID NO 30
<211> LENGTH: 313
<212> TYPE: DNA
<213> ORGANISM: Trichoplusia ni

<400> SEQUENCE: 30
```

```
ttaaccctag aaagatagtc tgcgtaaaat tgacgcatgc attcttgaaa tattgctctc    60
tctttctaaa tagcgcgaat ccgtcgctgt gcatttagga catctcagtc gccgcttgga   120
gctcccgtga ggcgtgcttg tcaatgcggt aagtgtcact gattttgaac tataacgacc   180
gcgtgagtca aaatgacgca tgattatctt ttacgtgact tttaagattt aactcatacg   240
ataattatat tgttatttca tgttctactt acgtgataac ttattatata tatattttct   300
tgttatagat atc                                                      313

<210> SEQ ID NO 31
<211> LENGTH: 235
<212> TYPE: DNA
<213> ORGANISM: Trichoplusia ni

<400> SEQUENCE: 31
tttgttactt tatagaagaa attttgagtt tttgttttttt tttaataaat aaataaacat    60
aaataaattg tttgttgaat ttattattag tatgtaagtg taaatataat aaaacttaat   120
atctattcaa attaataaat aaacctcgat atacagaccg ataaaacaca tgcgtcaatt   180
ttacgcatga ttatctttaa cgtacgtcac aatatgatta tctttctagg gttaa        235

<210> SEQ ID NO 32
<211> LENGTH: 16
<212> TYPE: DNA
<213> ORGANISM: Bombyx mori

<400> SEQUENCE: 32
cccggcgagc atgagg                                                    16

<210> SEQ ID NO 33
<211> LENGTH: 20
<212> TYPE: DNA
<213> ORGANISM: Bombyx mori

<400> SEQUENCE: 33
ttatcccggc gagcatgagg                                                20

<210> SEQ ID NO 34
<211> LENGTH: 20
<212> TYPE: DNA
<213> ORGANISM: Bombyx mori

<400> SEQUENCE: 34
cctcatgctc gccgggttat                                                20

<210> SEQ ID NO 35
<211> LENGTH: 20
<212> TYPE: DNA
<213> ORGANISM: Bombyx mori

<400> SEQUENCE: 35
ttaacccggc gagcatgagg                                                20

<210> SEQ ID NO 36
<211> LENGTH: 20
<212> TYPE: DNA
<213> ORGANISM: Bombyx mori

<400> SEQUENCE: 36
cctcatgctc gccgggttaa                                                20
```

```
<210> SEQ ID NO 37
<211> LENGTH: 18
<212> TYPE: DNA
<213> ORGANISM: Xenopus tropicalis

<400> SEQUENCE: 37 ttaaccttt tactgcca                                                      18

<210> SEQ ID NO 38
<211> LENGTH: 18
<212> TYPE: DNA
<213> ORGANISM: Xenopus tropicalis

<400> SEQUENCE: 38
ttaacccttt gcctgcca                                                     18

<210> SEQ ID NO 39
<211> LENGTH: 18
<212> TYPE: DNA
<213> ORGANISM: Xenopus tropicalis

<400> SEQUENCE: 39
ttaaccyttt tactgcca                                                     18

<210> SEQ ID NO 40
<211> LENGTH: 18
<212> TYPE: DNA
<213> ORGANISM: Xenopus tropicalis

<400> SEQUENCE: 40
tggcagtaaa agggttaa                                                     18

<210> SEQ ID NO 41
<211> LENGTH: 18
<212> TYPE: DNA
<213> ORGANISM: Xenopus tropicalis

<400> SEQUENCE: 41
tggcagtgaa agggttaa                                                     18

<210> SEQ ID NO 42
<211> LENGTH: 18
<212> TYPE: DNA
<213> ORGANISM: Xenopus tropicalis

<400> SEQUENCE: 42
ttaaccyttt kmctgcca                                                     18

<210> SEQ ID NO 43
<211> LENGTH: 610
<212> TYPE: PRT
<213> ORGANISM: Bombyx mori

<400> SEQUENCE: 43
```

Met Asp Ile Glu Arg Gln Glu Glu Arg Ile Arg Ala Met Leu Glu Glu
1               5                  10                  15

Glu Leu Ser Asp Tyr Ser Asp Glu Ser Ser Ser Glu Asp Glu Thr Asp
                20                  25                  30

His Cys Ser Glu His Glu Val Asn Tyr Asp Thr Glu Glu Glu Arg Ile
            35                  40                  45

Asp Ser Val Asp Val Pro Ser Asn Ser Arg Gln Glu Glu Ala Asn Ala
        50                  55                  60

-continued

```
Ile Ile Ala Asn Glu Ser Asp Ser Asp Pro Asp Asp Leu Pro Leu
 65                  70                  75                  80

Ser Leu Val Arg Gln Arg Ala Ser Ala Ser Arg Gln Val Ser Gly Pro
                 85                  90                  95

Phe Tyr Thr Ser Lys Asp Gly Thr Lys Trp Tyr Lys Asn Cys Gln Arg
                100                 105                 110

Pro Asn Val Arg Leu Arg Ser Glu Asn Ile Val Thr Glu Gln Ala Gln
                115                 120                 125

Val Lys Asn Ile Ala Arg Asp Ala Ser Thr Glu Tyr Glu Cys Trp Asn
    130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
                180                 185                 190

Ala Leu Ile Ala Leu Leu Tyr Leu Ala Gly Leu Ile Lys Ser Asn Arg
                195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240

Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
                260                 265                 270

Gln Asn Ala Tyr Ser Pro Ser Glu Phe Leu Thr Ile Asp Glu Met Leu
    275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Asp Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
                340                 345                 350

Gln Pro Val Ala Arg Ser His Arg Asn Val Thr Phe Asp Asn Trp Phe
                355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
                420                 425                 430

Val Met Ser Thr Met His His Asp Asn Ser Ile Asp Glu Ser Thr Gly
                435                 440                 445

Glu Lys Gln Lys Pro Glu Met Ile Thr Phe Tyr Asn Ser Thr Lys Ala
    450                 455                 460

Gly Val Asp Val Val Asp Glu Leu Ser Ala Asn Tyr Asn Val Ser Arg
465                 470                 475                 480

Asn Ser Lys Arg Trp Pro Met Thr Leu Phe Tyr Gly Val Leu Asn Met
```

```
                485                 490                 495
Ala Ala Ile Asn Ala Cys Ile Ile Tyr Arg Ala Asn Lys Asn Val Thr
            500                 505                 510
Ile Lys Arg Thr Glu Phe Ile Arg Ser Leu Gly Leu Ser Met Ile Tyr
            515                 520                 525
Glu His Leu His Ser Arg Asn Lys Lys Asn Ile Pro Thr Tyr Leu
            530                 535                 540
Arg Gln Arg Ile Glu Lys Gln Leu Gly Glu Pro Ser Pro Arg His Val
545                 550                 555                 560
Asn Val Pro Gly Arg Tyr Val Arg Cys Gln Asp Cys Pro Tyr Lys Lys
                565                 570                 575
Asp Arg Lys Thr Lys His Ser Cys Asn Ala Cys Ala Lys Pro Ile Cys
            580                 585                 590
Met Glu His Ala Lys Phe Leu Cys Glu Asn Cys Ala Glu Leu Asp Ser
            595                 600                 605
Ser Leu
    610

<210> SEQ ID NO 44
<211> LENGTH: 610
<212> TYPE: PRT
<213> ORGANISM: Bombyx mori

<400> SEQUENCE: 44

Met Asp Ile Glu Arg Gln Glu Arg Ile Arg Ala Met Leu Glu Glu
1               5                   10                  15

Glu Leu Ser Asp Tyr Ser Asp Glu Ser Ser Glu Asp Glu Thr Asp
            20                  25                  30

His Cys Ser Glu His Glu Val Asn Tyr Asp Thr Glu Glu Arg Ile
            35                  40                  45

Asp Ser Val Asp Val Pro Ser Asn Ser Arg Gln Glu Glu Ala Asn Ala
    50                  55                  60

Ile Ile Ala Asn Glu Ser Asp Ser Asp Pro Asp Asp Asp Leu Pro Leu
65                  70                  75                  80

Ser Leu Val Arg Gln Arg Ala Ser Ala Ser Arg Gln Val Ser Gly Pro
                85                  90                  95

Phe Tyr Thr Ser Lys Asp Gly Thr Lys Trp Tyr Lys Asn Cys Gln Arg
            100                 105                 110

Pro Asn Val Arg Leu Arg Ser Glu Asn Ile Val Thr Glu Gln Ala Gln
            115                 120                 125

Val Lys Asn Ile Ala Arg Asp Ala Ser Thr Glu Tyr Glu Cys Trp Asn
130                 135                 140

Ile Phe Val Thr Ser Asp Met Leu Gln Glu Ile Leu Thr His Thr Asn
145                 150                 155                 160

Ser Ser Ile Arg His Arg Gln Thr Lys Thr Ala Ala Glu Asn Ser Ser
                165                 170                 175

Ala Glu Thr Ser Phe Tyr Met Gln Glu Thr Thr Leu Cys Glu Leu Lys
            180                 185                 190

Ala Leu Ile Ala Leu Leu Tyr Leu Ala Gly Leu Ile Lys Ser Asn Arg
            195                 200                 205

Gln Ser Leu Lys Asp Leu Trp Arg Thr Asp Gly Thr Gly Val Asp Ile
    210                 215                 220

Phe Arg Thr Thr Met Ser Leu Gln Arg Phe Gln Phe Leu Gln Asn Asn
225                 230                 235                 240
```

```
Ile Arg Phe Asp Asp Lys Ser Thr Arg Asp Glu Arg Lys Gln Thr Asp
                245                 250                 255

Asn Met Ala Ala Phe Arg Ser Ile Phe Asp Gln Phe Val Gln Cys Cys
            260                 265                 270

Gln Asn Ala Tyr Ser Pro Ser Glu Phe Leu Thr Ile Asp Glu Met Leu
        275                 280                 285

Leu Ser Phe Arg Gly Arg Cys Leu Phe Arg Val Tyr Ile Pro Asn Lys
    290                 295                 300

Pro Ala Lys Tyr Gly Ile Lys Ile Leu Ala Leu Val Asp Ala Lys Asn
305                 310                 315                 320

Phe Tyr Val Val Asn Leu Glu Val Tyr Ala Gly Lys Gln Pro Ser Gly
                325                 330                 335

Pro Tyr Ala Val Ser Asn Arg Pro Phe Glu Val Val Glu Arg Leu Ile
            340                 345                 350

Gln Pro Val Ala Arg Ser His Arg Asn Val Thr Phe Asp Asn Trp Phe
        355                 360                 365

Thr Gly Tyr Glu Leu Met Leu His Leu Leu Asn Glu Tyr Arg Leu Thr
    370                 375                 380

Ser Val Gly Thr Val Arg Lys Asn Lys Arg Gln Ile Pro Glu Ser Phe
385                 390                 395                 400

Ile Arg Thr Asp Arg Gln Pro Asn Ser Ser Val Phe Gly Phe Gln Lys
                405                 410                 415

Asp Ile Thr Leu Val Ser Tyr Ala Pro Lys Lys Asn Lys Val Val Val
            420                 425                 430

Val Met Ser Thr Met His His Asp Asn Ser Ile Asp Glu Ser Thr Gly
        435                 440                 445

Glu Lys Gln Lys Pro Glu Met Ile Thr Phe Tyr Asn Ser Thr Lys Ala
    450                 455                 460

Gly Val Asp Val Val Asp Glu Leu Cys Ala Asn Tyr Asn Val Ser Arg
465                 470                 475                 480

Asn Ser Lys Arg Trp Pro Met Thr Leu Phe Tyr Gly Val Leu Asn Met
                485                 490                 495

Ala Ala Ile Asn Ala Cys Ile Ile Tyr Arg Thr Asn Lys Asn Val Thr
            500                 505                 510

Ile Lys Arg Thr Glu Phe Ile Arg Ser Leu Gly Leu Ser Met Ile Tyr
        515                 520                 525

Glu His Leu His Ser Arg Asn Lys Lys Asn Ile Pro Thr Tyr Leu
    530                 535                 540

Arg Gln Arg Ile Glu Lys Gln Leu Gly Glu Pro Ser Pro Arg His Val
545                 550                 555                 560

Asn Val Pro Gly Arg Tyr Val Arg Cys Gln Asp Cys Pro Tyr Lys Lys
                565                 570                 575

Asp Arg Lys Thr Lys Arg Ser Cys Asn Ala Cys Ala Lys Pro Ile Cys
            580                 585                 590

Met Glu His Ala Lys Phe Leu Cys Glu Asn Cys Ala Glu Leu Asp Ser
        595                 600                 605

Ser Leu
    610

<210> SEQ ID NO 45
<211> LENGTH: 589
<212> TYPE: PRT
<213> ORGANISM: Xenopus tropicalis

<400> SEQUENCE: 45
```

Met Ala Lys Arg Phe Tyr Ser Ala Glu Ala Ala His Cys Met
1               5                   10                  15

Ala Ser Ser Ser Glu Phe Ser Gly Ser Asp Ser Glu Tyr Val Pro
            20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
            115                 120                 125

Asp Met Val Leu Tyr Thr Asn Val Tyr Ala Glu Gln Tyr Leu Thr Gln
130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asp Thr Thr Val Leu
                180                 185                 190

Ser Ile Pro Val Phe Ser Ala Thr Met Ser Arg Asn Arg Tyr Gln Leu
            195                 200                 205

Leu Leu Arg Phe Leu His Phe Asn Asn Asn Ala Thr Ala Val Pro Pro
210                 215                 220

Asp Gln Pro Gly His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
            245                 250                 255

Cys Ile Asp Glu Ser Leu Leu Leu Phe Lys Gly Arg Leu Gln Phe Arg
            260                 265                 270

Gln Tyr Ile Pro Ser Lys Arg Ala Arg Tyr Gly Ile Lys Phe Tyr Lys
        275                 280                 285

Leu Cys Glu Ser Ser Ser Gly Tyr Thr Ser Tyr Phe Leu Ile Tyr Glu
        290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
            355                 360                 365

Asn Arg Lys Gly Leu Pro Arg Ala Leu Leu Asp Lys Lys Leu Asn Arg
370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
            405                 410                 415

```
Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
            435                 440                 445

Gln Leu Gln His Tyr Tyr Asn Ala Thr Arg Lys Thr Arg Ala Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                    485                 490                 495

Tyr Gln Leu Gln Ile Leu Pro Ala Leu Leu Phe Gly Gly Val Glu Glu
            500                 505                 510

Gln Thr Val Pro Glu Met Pro Pro Ser Asp Asn Val Ala Arg Leu Ile
            515                 520                 525

Gly Lys His Phe Ile Asp Thr Leu Pro Pro Thr Pro Gly Lys Gln Arg
            530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                    565                 570                 575

Lys Pro Cys Phe Glu Ile Tyr His Thr Gln Leu His Tyr
            580                 585

<210> SEQ ID NO 46
<211> LENGTH: 589
<212> TYPE: PRT
<213> ORGANISM: Xenopus tropicalis

<400> SEQUENCE: 46

Met Ala Lys Arg Phe Tyr Ser Ala Glu Glu Ala Ala His Cys Met
1               5                   10                  15

Ala Pro Ser Ser Glu Glu Phe Ser Gly Ser Asp Ser Glu Tyr Val Pro
                20                  25                  30

Pro Ala Ser Glu Ser Asp Ser Ser Thr Glu Glu Ser Trp Cys Ser Ser
            35                  40                  45

Ser Thr Val Ser Ala Leu Glu Glu Pro Met Glu Val Asp Glu Asp Val
        50                  55                  60

Asp Asp Leu Glu Asp Gln Glu Ala Gly Asp Arg Ala Asp Ala Ala Ala
65                  70                  75                  80

Gly Gly Glu Pro Ala Trp Gly Pro Pro Cys Asn Phe Pro Pro Glu Ile
                85                  90                  95

Pro Pro Phe Thr Thr Val Pro Gly Val Lys Val Asp Thr Ser Asn Phe
            100                 105                 110

Glu Pro Ile Asn Phe Phe Gln Leu Phe Met Thr Glu Ala Ile Leu Gln
        115                 120                 125

Asp Met Val Leu Tyr Thr Asn Val Tyr Ala Glu Gln Tyr Leu Thr Gln
130                 135                 140

Asn Pro Leu Pro Arg Tyr Ala Arg Ala His Ala Trp His Pro Thr Asp
145                 150                 155                 160

Ile Ala Glu Met Lys Arg Phe Val Gly Leu Thr Leu Ala Met Gly Leu
                165                 170                 175

Ile Lys Ala Asn Ser Leu Glu Ser Tyr Trp Asn Thr Thr Thr Val Leu
            180                 185                 190

Ser Ile Pro Val Phe Ser Ala Thr Met Ser Arg Asn Arg Tyr Gln Leu
        195                 200                 205
```

Leu Leu Arg Phe Leu His Phe Asn Asn Asn Ala Thr Ala Val Pro Pro
            210                 215                 220

Asp Gln Pro Asp His Asp Arg Leu His Lys Leu Arg Pro Leu Ile Asp
225                 230                 235                 240

Ser Leu Ser Glu Arg Phe Ala Ala Val Tyr Thr Pro Cys Gln Asn Ile
                245                 250                 255

Cys Ile Asp Glu Ser Leu Leu Leu Phe Lys Gly Arg Leu Arg Phe Arg
            260                 265                 270

Gln Tyr Ile Pro Ser Lys Arg Ala Arg Tyr Gly Ile Lys Phe Tyr Lys
                275                 280                 285

Leu Cys Glu Ser Ser Ser Gly Tyr Thr Ser Tyr Phe Leu Ile Tyr Glu
            290                 295                 300

Gly Lys Asp Ser Lys Leu Asp Pro Pro Gly Cys Pro Pro Asp Leu Thr
305                 310                 315                 320

Val Ser Gly Lys Ile Val Trp Glu Leu Ile Ser Pro Leu Leu Gly Gln
                325                 330                 335

Gly Phe His Leu Tyr Val Asp Asn Phe Tyr Ser Ser Ile Pro Leu Phe
            340                 345                 350

Thr Ala Leu Tyr Cys Leu Asp Thr Pro Ala Cys Gly Thr Ile Asn Arg
                355                 360                 365

Thr Arg Lys Gly Leu Pro Arg Ala Leu Leu Asp Lys Lys Leu Asn Arg
            370                 375                 380

Gly Glu Thr Tyr Ala Leu Arg Lys Asn Glu Leu Leu Ala Ile Lys Phe
385                 390                 395                 400

Phe Asp Lys Lys Asn Val Phe Met Leu Thr Ser Ile His Asp Glu Ser
                405                 410                 415

Val Ile Arg Glu Gln Arg Val Gly Arg Pro Pro Lys Asn Lys Pro Leu
            420                 425                 430

Cys Ser Lys Glu Tyr Ser Lys Tyr Met Gly Gly Val Asp Arg Thr Asp
            435                 440                 445

Gln Leu Gln His Tyr Tyr Asn Ala Thr Arg Lys Thr Ser Ala Trp Tyr
            450                 455                 460

Lys Lys Val Gly Ile Tyr Leu Ile Gln Met Ala Leu Arg Asn Ser Tyr
465                 470                 475                 480

Ile Val Tyr Lys Ala Ala Val Pro Gly Pro Lys Leu Ser Tyr Tyr Lys
                485                 490                 495

Tyr Gln Leu Gln Ile Leu Pro Ala Leu Leu Phe Gly Gly Val Glu Glu
            500                 505                 510

Gln Thr Val Pro Glu Met Leu Pro Ser Asp Asn Val Ala Arg Leu Ile
            515                 520                 525

Gly Lys His Phe Ile Asp Thr Leu Pro Pro Thr Pro Gly Lys Gln Arg
            530                 535                 540

Pro Gln Lys Gly Cys Lys Val Cys Arg Lys Arg Gly Ile Arg Arg Asp
545                 550                 555                 560

Thr Arg Tyr Tyr Cys Pro Lys Cys Pro Arg Asn Pro Gly Leu Cys Phe
                565                 570                 575

Lys Pro Cys Phe Glu Ile Tyr His Thr Gln Leu His Tyr
            580                 585

<210> SEQ ID NO 47
<211> LENGTH: 597
<212> TYPE: PRT
<213> ORGANISM: Helicoverpa armigera

<400> SEQUENCE: 47

```
Met Ala Ser Arg Gln Arg Leu Asn His Asp Glu Ile Ala Thr Ile Leu
1               5                   10                  15

Glu Asn Asp Asp Asp Tyr Ser Pro Leu Asp Ser Glu Ser Glu Lys Glu
            20                  25                  30

Asp Cys Val Val Glu Asp Val Trp Ser Asp Asn Glu Asp Ala Ile
        35                  40                  45

Val Asp Phe Val Glu Asp Thr Ser Ala Gln Glu Asp Pro Asp Asn Asn
    50                  55                  60

Ile Ala Ser Arg Glu Ser Pro Asn Leu Glu Val Thr Ser Leu Thr Ser
65                  70                  75                  80

His Arg Ile Ile Thr Leu Pro Gln Arg Ser Ile Arg Gly Lys Asn Asn
                85                  90                  95

His Val Trp Ser Thr Thr Lys Gly Arg Thr Thr Gly Arg Thr Ser Ala
            100                 105                 110

Ile Asn Ile Ile Arg Thr Asn Arg Gly Pro Thr Arg Met Cys Arg Asn
        115                 120                 125

Ile Val Asp Pro Leu Leu Cys Phe Gln Leu Phe Ile Thr Asp Glu Ile
    130                 135                 140

Ile His Glu Ile Val Lys Trp Thr Asn Val Glu Ile Ile Val Lys Arg
145                 150                 155                 160

Gln Asn Leu Lys Asp Ile Ser Ala Ser Tyr Arg Asp Thr Asn Thr Met
                165                 170                 175

Glu Ile Trp Ala Leu Val Gly Ile Leu Thr Leu Thr Ala Val Met Lys
            180                 185                 190

Asp Asn His Leu Ser Thr Asp Glu Leu Phe Asp Ala Thr Phe Ser Gly
        195                 200                 205

Thr Arg Tyr Val Ser Val Met Ser Arg Glu Arg Phe Glu Phe Leu Ile
    210                 215                 220

Arg Cys Ile Arg Met Asp Asp Lys Thr Leu Arg Pro Thr Leu Arg Ser
225                 230                 235                 240

Asp Asp Ala Phe Leu Pro Val Arg Lys Ile Trp Glu Ile Phe Ile Asn
                245                 250                 255

Gln Cys Arg Gln Asn His Val Pro Gly Ser Asn Leu Thr Val Asp Glu
            260                 265                 270

Gln Leu Leu Gly Phe Arg Gly Arg Cys Pro Phe Arg Met Tyr Ile Pro
        275                 280                 285

Asn Lys Pro Asp Lys Tyr Gly Ile Lys Phe Pro Met Met Cys Ala Ala
    290                 295                 300

Ala Thr Lys Tyr Met Ile Asp Ala Ile Pro Tyr Leu Gly Lys Ser Thr
305                 310                 315                 320

Lys Thr Asn Gly Leu Pro Leu Gly Glu Phe Tyr Val Lys Asp Leu Thr
                325                 330                 335

Lys Thr Val His Gly Thr Asn Arg Asn Ile Thr Cys Asp Asn Trp Phe
            340                 345                 350

Thr Ser Ile Pro Leu Ala Lys Asn Met Leu Gln Ala Pro Tyr Asn Leu
        355                 360                 365

Thr Ile Val Gly Thr Ile Arg Ser Asn Lys Arg Glu Met Pro Glu Glu
    370                 375                 380

Ile Lys Asn Ser Arg Ser Arg Pro Val Gly Ser Ser Met Phe Cys Phe
385                 390                 395                 400

Asp Gly Pro Leu Thr Leu Val Ser Tyr Lys Pro Lys Pro Ser Lys Met
                405                 410                 415
```

```
Val Phe Leu Leu Ser Ser Cys Asp Glu Asn Ala Val Ile Asn Glu Ser
            420                 425                 430

Asn Gly Lys Pro Asp Met Ile Leu Phe Tyr Asn Gln Thr Lys Gly Gly
            435                 440                 445

Val Asp Ser Phe Asp Gln Met Cys Lys Ser Met Ser Ala Asn Arg Lys
450                 455                 460

Thr Asn Arg Trp Pro Met Ala Val Phe Tyr Gly Met Leu Asn Met Ala
465                 470                 475                 480

Phe Val Asn Ser Tyr Ile Ile Tyr Cys His Asn Lys Ile Asn Lys Gln
                485                 490                 495

Glu Lys Pro Ile Ser Arg Lys Glu Phe Met Lys Lys Leu Ser Ile Gln
            500                 505                 510

Leu Thr Thr Pro Trp Met Gln Glu Arg Leu Gln Ala Pro Thr Leu Lys
            515                 520                 525

Arg Thr Leu Arg Asp Asn Ile Thr Asn Val Leu Lys Asn Val Val Pro
530                 535                 540

Ala Ser Ser Glu Asn Ile Ser Asn Glu Pro Glu Pro Lys Lys Arg Arg
545                 550                 555                 560

Tyr Cys Gly Val Cys Ser Tyr Lys Lys Arg Arg Met Thr Lys Ala Gln
                565                 570                 575

Cys Cys Lys Cys Lys Lys Ala Ile Cys Gly Glu His Asn Ile Asp Val
            580                 585                 590

Cys Gln Asp Cys Ile
            595

<210> SEQ ID NO 48
<211> LENGTH: 628
<212> TYPE: PRT
<213> ORGANISM: Pectinophora gossypiella

<400> SEQUENCE: 48

Met Asp Leu Arg Lys Gln Asp Glu Lys Ile Arg Gln Trp Leu Glu Gln
1               5                   10                  15

Asp Ile Glu Glu Asp Ser Lys Gly Glu Ser Asp Asn Ser Ser Ser Glu
            20                  25                  30

Thr Glu Asp Ile Val Glu Met Glu Val His Lys Asn Thr Ser Ser Glu
        35                  40                  45

Ser Glu Val Ser Ser Glu Ser Asp Tyr Glu Pro Val Cys Pro Ser Lys
    50                  55                  60

Arg Gln Arg Thr Gln Ile Ile Glu Ser Glu Ser Asp Asn Ser Glu
65                  70                  75                  80

Ser Ile Arg Pro Ser Arg Arg Gln Thr Ser Arg Val Ile Asp Ser Asp
                85                  90                  95

Glu Thr Asp Glu Asp Val Met Ser Ser Thr Pro Gln Asn Ile Pro Arg
            100                 105                 110

Asn Pro Asn Val Ile Gln Pro Ser Ser Arg Phe Leu Tyr Gly Lys Asn
        115                 120                 125

Lys His Lys Trp Ser Ser Ala Ala Lys Pro Ser Ser Val Arg Thr Ser
    130                 135                 140

Arg Arg Asn Ile Ile His Phe Ile Pro Gly Pro Lys Glu Arg Ala Arg
145                 150                 155                 160

Glu Val Ser Glu Pro Ile Asp Ile Phe Ser Leu Phe Ile Ser Glu Asp
                165                 170                 175

Met Leu Gln Gln Val Val Thr Phe Thr Asn Ala Glu Met Leu Ile Arg
```

```
                    180                 185                 190
Lys Asn Lys Tyr Lys Thr Glu Thr Phe Thr Val Ser Pro Thr Asn Leu
            195                 200                 205

Glu Glu Ile Arg Ala Leu Leu Gly Leu Leu Phe Asn Ala Ala Ala Met
        210                 215                 220

Lys Ser Asn His Leu Pro Thr Arg Met Leu Phe Asn Thr His Arg Ser
225                 230                 235                 240

Gly Thr Ile Phe Lys Ala Cys Met Ser Ala Glu Arg Leu Asn Phe Leu
                245                 250                 255

Ile Lys Cys Leu Arg Phe Asp Asp Lys Leu Thr Arg Asn Val Arg Gln
            260                 265                 270

Arg Asp Asp Arg Phe Ala Pro Ile Arg Asp Leu Trp Gln Ala Leu Ile
        275                 280                 285

Ser Asn Phe Gln Lys Trp Tyr Thr Pro Gly Ser Tyr Ile Thr Val Asp
    290                 295                 300

Glu Gln Leu Val Gly Phe Arg Gly Arg Cys Ser Phe Arg Met Tyr Ile
305                 310                 315                 320

Pro Asn Lys Pro Asn Lys Tyr Gly Ile Lys Leu Val Met Ala Ala Asp
                325                 330                 335

Val Asn Ser Lys Tyr Ile Val Asn Ala Ile Pro Tyr Leu Gly Lys Gly
            340                 345                 350

Thr Asp Pro Gln Asn Gln Pro Leu Ala Thr Phe Phe Ile Lys Glu Ile
        355                 360                 365

Thr Ser Thr Leu His Gly Thr Asn Arg Asn Ile Thr Met Asp Asn Trp
    370                 375                 380

Phe Thr Ser Val Pro Leu Ala Asn Glu Leu Leu Met Ala Pro Tyr Asn
385                 390                 395                 400

Leu Thr Leu Val Gly Thr Leu Arg Ser Asn Lys Arg Glu Ile Pro Glu
                405                 410                 415

Lys Leu Lys Asn Ser Lys Ser Arg Ala Ile Gly Thr Ser Met Phe Cys
            420                 425                 430

Tyr Asp Gly Asp Lys Thr Leu Val Ser Tyr Lys Ala Lys Ser Asn Lys
        435                 440                 445

Val Val Phe Ile Leu Ser Thr Ile His Asp Gln Pro Asp Ile Asn Gln
    450                 455                 460

Glu Thr Gly Lys Pro Glu Met Ile His Phe Tyr Asn Ser Thr Lys Gly
465                 470                 475                 480

Ala Val Asp Thr Val Asp Gln Met Cys Ser Ser Ile Ser Thr Asn Arg
                485                 490                 495

Lys Thr Gln Arg Trp Pro Leu Cys Val Phe Tyr Asn Met Leu Asn Leu
            500                 505                 510

Ser Ile Ile Asn Ala Tyr Val Val Tyr Val Tyr Asn Asn Val Arg Asn
        515                 520                 525

Asn Lys Lys Pro Met Ser Arg Arg Asp Phe Val Ile Lys Leu Gly Asp
    530                 535                 540

Gln Leu Met Glu Pro Trp Leu Arg Gln Arg Leu Gln Thr Val Thr Leu
545                 550                 555                 560

Arg Arg Asp Ile Lys Val Met Ile Gln Asp Ile Leu Gly Glu Ser Ser
                565                 570                 575

Asp Leu Glu Ala Pro Val Pro Ser Val Ser Asn Val Arg Lys Ile Tyr
            580                 585                 590

Tyr Leu Cys Pro Ser Lys Ala Arg Arg Met Thr Lys His Arg Cys Ile
        595                 600                 605
```

```
Lys Cys Lys Gln Ala Ile Cys Gly Pro His Asn Ile Asp Ile Cys Ser
            610                 615                 620

Arg Cys Ile Glu
625

<210> SEQ ID NO 49
<211> LENGTH: 599
<212> TYPE: PRT
<213> ORGANISM: Ctenoplusia agnata

<400> SEQUENCE: 49

Met Ala Ser Arg Gln His Leu Tyr Gln Asp Glu Ile Ala Ala Ile Leu
1               5                   10                  15

Glu Asn Glu Asp Asp Tyr Ser Pro His Asp Thr Asp Ser Glu Met Glu
            20                  25                  30

Asp Cys Val Thr Gln Asp Val Arg Ser Asp Val Glu Asp Glu Met
        35                  40                  45

Val Asp Asn Ile Gly Asn Gly Thr Ser Pro Ala Ser Arg His Glu Asp
50                  55                  60

Pro Glu Thr Pro Asp Pro Ser Ser Glu Ala Ser Asn Leu Glu Val Thr
65                  70                  75                  80

Leu Ser Ser His Arg Ile Ile Leu Pro Gln Arg Ser Ile Arg Glu
                85                  90                  95

Lys Asn Asn His Ile Trp Ser Thr Thr Lys Gly Gln Ser Ser Gly Arg
            100                 105                 110

Thr Ala Ala Ile Asn Ile Val Arg Thr Asn Arg Gly Pro Thr Arg Met
        115                 120                 125

Cys Arg Asn Ile Val Asp Pro Leu Leu Cys Phe Gln Leu Phe Ile Lys
130                 135                 140

Glu Glu Ile Val Glu Glu Ile Val Lys Trp Thr Asn Val Glu Met Val
145                 150                 155                 160

Gln Lys Arg Val Asn Leu Lys Asp Ile Ser Ala Ser Tyr Arg Asp Thr
                165                 170                 175

Asn Glu Met Glu Ile Trp Ala Ile Ile Ser Met Leu Thr Leu Ser Ala
            180                 185                 190

Val Met Lys Asp Asn His Leu Ser Thr Asp Glu Leu Phe Asn Val Ser
        195                 200                 205

Tyr Gly Thr Arg Tyr Val Ser Val Met Ser Arg Glu Arg Phe Glu Phe
210                 215                 220

Leu Leu Arg Leu Leu Arg Met Gly Asp Lys Leu Leu Arg Pro Asn Leu
225                 230                 235                 240

Arg Gln Glu Asp Ala Phe Thr Pro Val Arg Lys Ile Trp Glu Ile Phe
                245                 250                 255

Ile Asn Gln Cys Arg Leu Asn Tyr Val Pro Gly Thr Asn Leu Thr Val
            260                 265                 270

Asp Glu Gln Leu Leu Gly Phe Arg Gly Arg Cys Pro Phe Arg Met Tyr
        275                 280                 285

Ile Pro Asn Lys Pro Asp Lys Tyr Gly Ile Lys Phe Pro Met Val Cys
290                 295                 300

Asp Ala Ala Thr Lys Tyr Met Val Asp Ala Ile Pro Tyr Leu Gly Lys
305                 310                 315                 320

Ser Thr Lys Thr Gln Gly Leu Pro Leu Gly Glu Phe Tyr Val Lys Glu
                325                 330                 335

Leu Thr Gln Thr Val His Gly Thr Asn Arg Asn Val Thr Cys Asp Asn
```

```
                    340                 345                 350
Trp Phe Thr Ser Val Pro Leu Ala Lys Ser Leu Leu Asn Ser Pro Tyr
            355                 360                 365

Asn Leu Thr Leu Val Gly Thr Ile Arg Ser Asn Lys Arg Glu Ile Pro
        370                 375                 380

Glu Glu Val Lys Asn Ser Arg Ser Arg Gln Val Gly Ser Ser Met Phe
385                 390                 395                 400

Cys Phe Asp Gly Pro Leu Thr Leu Val Ser Tyr Lys Pro Lys Pro Ser
                405                 410                 415

Lys Met Val Phe Leu Leu Ser Ser Cys Asn Glu Asp Ala Val Val Asn
            420                 425                 430

Gln Ser Asn Gly Lys Pro Asp Met Ile Leu Phe Tyr Asn Gln Thr Lys
        435                 440                 445

Gly Gly Val Asp Ser Phe Asp Gln Met Cys Ser Met Ser Thr Asn
            450                 455                 460

Arg Lys Thr Asn Arg Trp Pro Met Ala Val Phe Tyr Gly Met Leu Asn
465                 470                 475                 480

Met Ala Phe Val Asn Ser Tyr Ile Ile Tyr Cys His Asn Met Leu Ala
                485                 490                 495

Lys Lys Glu Lys Pro Leu Ser Arg Lys Asp Phe Met Lys Lys Leu Ser
            500                 505                 510

Thr Asp Leu Thr Thr Pro Ser Met Gln Lys Arg Leu Glu Ala Pro Thr
        515                 520                 525

Leu Lys Arg Ser Leu Arg Asp Asn Ile Thr Asn Val Leu Lys Ile Val
530                 535                 540

Pro Gln Ala Ala Ile Asp Thr Ser Phe Asp Glu Pro Glu Pro Lys Lys
545                 550                 555                 560

Arg Arg Tyr Cys Gly Phe Cys Ser Tyr Lys Lys Arg Met Thr Lys
                565                 570                 575

Thr Gln Cys Phe Lys Cys Lys Lys Pro Val Cys Gly Glu His Asn Ile
        580                 585                 590

Asp Val Cys Gln Asp Cys Ile
        595

<210> SEQ ID NO 50
<211> LENGTH: 597
<212> TYPE: PRT
<213> ORGANISM: Agrotis ipsilon

<400> SEQUENCE: 50

Met Glu Ser Arg Gln Arg Leu Asn Gln Asp Glu Ile Ala Thr Ile Leu
1               5                   10                  15

Glu Asn Asp Asp Asp Tyr Ser Pro Leu Asp Ser Asp Ser Glu Ala Glu
            20                  25                  30

Asp Arg Val Val Glu Asp Val Trp Ser Asp Asn Glu Asp Ala Met
        35                  40                  45

Ile Asp Tyr Val Glu Asp Thr Ser Arg Gln Glu Asp Pro Asp Asn Asn
    50                  55                  60

Ile Ala Ser Gln Glu Ser Ala Asn Leu Glu Val Thr Ser Leu Thr Ser
65                  70                  75                  80

His Arg Ile Ile Ser Leu Pro Gln Arg Ser Ile Cys Gly Lys Asn Asn
                85                  90                  95

His Val Trp Ser Thr Thr Lys Gly Arg Thr Thr Gly Arg Thr Ser Ala
            100                 105                 110
```

```
Ile Asn Ile Ile Arg Thr Asn Arg Gly Pro Thr Arg Met Cys Arg Asn
            115                 120                 125

Ile Val Asp Pro Leu Leu Cys Phe Gln Leu Phe Ile Thr Asp Glu Ile
        130                 135                 140

Ile His Glu Ile Val Lys Trp Thr Asn Val Glu Met Ile Val Lys Arg
145                 150                 155                 160

Gln Asn Leu Ile Asp Ile Ser Ala Ser Tyr Arg Asp Thr Asn Thr Met
                165                 170                 175

Glu Met Trp Ala Leu Val Gly Ile Leu Thr Leu Thr Ala Val Met Lys
            180                 185                 190

Asp Asn His Leu Ser Thr Asp Glu Leu Phe Asp Ala Thr Phe Ser Gly
        195                 200                 205

Thr Arg Tyr Val Ser Val Met Ser Arg Glu Arg Phe Glu Phe Leu Ile
    210                 215                 220

Arg Cys Met Arg Met Asp Asp Lys Thr Leu Arg Pro Thr Leu Arg Ser
225                 230                 235                 240

Asp Asp Ala Phe Ile Pro Val Arg Lys Leu Trp Glu Ile Phe Ile Asn
                245                 250                 255

Gln Cys Arg Leu Asn Tyr Val Pro Gly Gly Asn Leu Thr Val Asp Glu
            260                 265                 270

Gln Leu Leu Gly Phe Arg Gly Arg Cys Pro Phe Arg Met Tyr Ile Pro
        275                 280                 285

Asn Lys Pro Asp Lys Tyr Gly Ile Arg Phe Pro Met Met Cys Asp Ala
    290                 295                 300

Ala Thr Lys Tyr Met Ile Asp Ala Ile Pro Tyr Leu Gly Lys Ser Thr
305                 310                 315                 320

Lys Thr Asn Gly Leu Pro Leu Gly Glu Phe Tyr Val Lys Glu Leu Thr
                325                 330                 335

Lys Thr Val His Gly Thr Asn Arg Asn Val Thr Cys Asp Asn Trp Phe
            340                 345                 350

Thr Ser Ile Pro Leu Ala Lys Asn Met Leu Gln Ala Pro Tyr Asn Leu
        355                 360                 365

Thr Ile Val Gly Thr Ile Arg Ser Asn Lys Arg Glu Ile Pro Glu Glu
    370                 375                 380

Ile Lys Asn Ser Arg Ser Arg Pro Val Gly Ser Ser Met Phe Cys Phe
385                 390                 395                 400

Asp Gly Pro Leu Thr Leu Val Ser Tyr Lys Pro Lys Pro Ser Arg Met
                405                 410                 415

Val Phe Leu Leu Ser Ser Cys Asp Glu Asn Ala Val Ile Asn Glu Ser
            420                 425                 430

Asn Gly Lys Pro Asp Met Ile Leu Phe Tyr Asn Gln Thr Lys Gly Gly
        435                 440                 445

Val Asp Ser Phe Asp Gln Met Cys Lys Ser Met Ser Ala Asn Arg Lys
    450                 455                 460

Thr Asn Arg Trp Pro Met Ala Val Phe Tyr Gly Met Leu Asn Met Ala
465                 470                 475                 480

Phe Val Asn Ser Tyr Ile Ile Tyr Cys His Asn Lys Ile Asn Lys Gln
                485                 490                 495

Lys Lys Pro Ile Asn Arg Lys Glu Phe Met Lys Asn Leu Ser Thr Asp
            500                 505                 510

Leu Thr Thr Pro Trp Met Gln Glu Arg Leu Lys Ala Pro Thr Leu Lys
        515                 520                 525

Arg Thr Leu Arg Asp Asn Ile Thr Asn Val Leu Lys Asn Val Val Pro
```

```
                  530               535               540
Pro Ser Pro Ala Asn Asn Ser Glu Glu Pro Gly Pro Lys Lys Arg Ser
545                 550               555               560

Tyr Cys Gly Phe Cys Ser Tyr Lys Lys Arg Arg Met Thr Lys Thr Gln
                565               570               575

Phe Tyr Lys Cys Lys Lys Ala Ile Cys Gly Glu His Asn Ile Asp Val
                580               585               590

Cys Gln Asp Cys Val
        595

<210> SEQ ID NO 51
<211> LENGTH: 520
<212> TYPE: PRT
<213> ORGANISM: Megachile rotundata

<400> SEQUENCE: 51

Met Asn Gly Lys Asp Ser Leu Gly Glu Phe Tyr Leu Asp Asp Leu Ser
1               5                   10                  15

Asp Cys Leu Asp Cys Arg Ser Ala Ser Ser Thr Asp Glu Ser Asp
                20                  25                  30

Ser Ser Asn Ile Ala Ile Arg Lys Arg Cys Pro Ile Pro Leu Ile Tyr
            35                  40                  45

Ser Asp Ser Glu Asp Glu Asp Met Asn Asn Asn Val Glu Asp Asn Asn
50                  55                  60

His Phe Val Lys Glu Ser Asn Arg Tyr His Tyr Gln Ile Val Glu Lys
65                  70                  75                  80

Tyr Lys Ile Thr Ser Lys Thr Lys Lys Trp Lys Asp Val Thr Val Thr
                85                  90                  95

Glu Met Lys Lys Phe Leu Gly Leu Ile Ile Leu Met Gly Gln Val Lys
                100                 105                 110

Lys Asp Val Leu Tyr Asp Tyr Trp Ser Thr Asp Pro Ser Ile Glu Thr
            115                 120                 125

Pro Phe Phe Ser Lys Val Met Ser Arg Asn Arg Phe Leu Gln Ile Met
130                 135                 140

Gln Ser Trp His Phe Tyr Asn Asn Asn Asp Ile Ser Pro Asn Ser His
145                 150                 155                 160

Arg Leu Val Lys Ile Gln Pro Val Ile Asp Tyr Phe Lys Glu Lys Phe
                165                 170                 175

Asn Asn Val Tyr Lys Ser Asp Gln Gln Leu Ser Leu Asp Glu Cys Leu
            180                 185                 190

Ile Pro Trp Arg Gly Arg Leu Ser Ile Lys Thr Tyr Asn Pro Ala Lys
            195                 200                 205

Ile Thr Lys Tyr Gly Ile Leu Val Arg Val Leu Ser Glu Ala Arg Thr
210                 215                 220

Gly Tyr Val Ser Asn Phe Cys Val Tyr Ala Ala Asp Gly Lys Lys Ile
225                 230                 235                 240

Glu Glu Thr Val Leu Ser Val Ile Gly Pro Tyr Lys Asn Met Trp His
                245                 250                 255

His Val Tyr Gln Asp Asn Tyr Tyr Asn Ser Val Asn Ile Ala Lys Ile
            260                 265                 270

Phe Leu Lys Asn Lys Leu Arg Val Cys Gly Thr Ile Arg Lys Asn Arg
            275                 280                 285

Ser Leu Pro Gln Ile Leu Gln Thr Val Lys Leu Ser Arg Gly Gln His
        290                 295                 300
```

-continued

```
Gln Phe Leu Arg Asn Gly His Thr Leu Leu Glu Val Trp Asn Asn Gly
305                 310                 315                 320

Lys Arg Asn Val Asn Met Ile Ser Thr Ile His Ser Ala Gln Met Ala
            325                 330                 335

Glu Ser Arg Asn Arg Ser Arg Thr Ser Asp Cys Pro Ile Gln Lys Pro
        340                 345                 350

Ile Ser Ile Ile Asp Tyr Asn Lys Tyr Met Lys Gly Val Asp Arg Ala
            355                 360                 365

Asp Gln Tyr Leu Ser Tyr Tyr Ser Ile Phe Arg Lys Thr Lys Lys Trp
        370                 375                 380

Thr Lys Arg Val Val Met Phe Phe Ile Asn Cys Ala Leu Phe Asn Ser
385                 390                 395                 400

Phe Lys Val Tyr Thr Thr Leu Asn Gly Gln Lys Ile Thr Tyr Lys Asn
            405                 410                 415

Phe Leu His Lys Ala Ala Leu Ser Leu Ile Glu Asp Cys Gly Thr Glu
            420                 425                 430

Glu Gln Gly Thr Asp Leu Pro Asn Ser Glu Pro Thr Thr Thr Arg Thr
        435                 440                 445

Thr Ser Arg Val Asp His Pro Gly Arg Leu Glu Asn Phe Gly Lys His
450                 455                 460

Lys Leu Val Asn Ile Val Thr Ser Gly Gln Cys Lys Lys Pro Leu Arg
465                 470                 475                 480

Gln Cys Arg Val Cys Ala Ser Lys Lys Lys Leu Ser Arg Thr Gly Phe
            485                 490                 495

Ala Cys Lys Tyr Cys Asn Val Pro Leu His Lys Gly Asp Cys Phe Glu
        500                 505                 510

Arg Tyr His Ser Leu Lys Lys Tyr
        515                 520

<210> SEQ ID NO 52
<211> LENGTH: 570
<212> TYPE: PRT
<213> ORGANISM: Bombus impatiens

<400> SEQUENCE: 52

Met Asn Glu Lys Asn Gly Ile Gly Glu Phe Tyr Leu Asp Asp Leu Ser
1               5                   10                  15

Asp Cys Pro Asp Ser Tyr Ser Arg Ser Asn Ser Gly Asp Glu Ser Asp
            20                  25                  30

Gly Ser Asp Thr Ile Ile Arg Lys Arg Gly Ser Val Leu Pro Pro Arg
        35                  40                  45

Tyr Ser Asp Ser Glu Asp Glu Ile Asn Asn Val Glu Asp Asn Ala
50                  55                  60

Asn Asn Val Glu Asn Asn Asp Asp Ile Trp Ser Thr Asn Asp Glu Ala
65                  70                  75                  80

Ile Ile Leu Glu Pro Phe Glu Gly Ser Pro Gly Leu Lys Ile Met Pro
            85                  90                  95

Ser Ser Ala Glu Ser Val Thr Asp Asn Val Asn Leu Phe Phe Gly Asp
            100                 105                 110

Asp Phe Phe Glu His Leu Val Arg Glu Ser Asn Arg Tyr His Tyr Gln
        115                 120                 125

Val Met Glu Lys Tyr Lys Ile Pro Ser Lys Ala Lys Lys Trp Thr Asp
    130                 135                 140

Ile Thr Val Pro Glu Met Lys Lys Phe Leu Gly Leu Ile Val Leu Met
145                 150                 155                 160
```

```
Gly Gln Ile Lys Lys Asp Val Leu Tyr Asp Tyr Trp Ser Thr Asp Pro
            165                 170                 175

Ser Ile Glu Thr Pro Phe Phe Ser Gln Val Met Ser Arg Asn Arg Phe
            180                 185                 190

Val Gln Ile Met Gln Ser Trp His Phe Cys Asn Asn Asp Asn Ile Pro
            195                 200                 205

His Asp Ser His Arg Leu Ala Lys Ile Gln Pro Val Ile Asp Tyr Phe
            210                 215                 220

Arg Arg Lys Phe Asn Asp Val Tyr Lys Pro Cys Gln Gln Leu Ser Leu
225                 230                 235                 240

Asp Glu Ser Ile Ile Pro Trp Arg Gly Arg Leu Ser Ile Lys Thr Tyr
            245                 250                 255

Asn Pro Ala Lys Ile Thr Lys Tyr Gly Ile Leu Val Arg Val Leu Ser
            260                 265                 270

Glu Ala Val Thr Gly Tyr Val Cys Asn Phe Asp Val Tyr Ala Ala Asp
            275                 280                 285

Gly Lys Lys Leu Glu Asp Thr Ala Val Ile Glu Pro Tyr Lys Asn Ile
            290                 295                 300

Trp His Gln Ile Tyr Gln Asp Asn Tyr Asn Ser Val Lys Met Ala
305                 310                 315                 320

Arg Ile Leu Leu Lys Asn Lys Val Arg Val Cys Gly Thr Ile Arg Lys
            325                 330                 335

Asn Arg Gly Leu Pro Arg Ser Leu Lys Thr Ile Gln Leu Ser Arg Gly
            340                 345                 350

Gln Tyr Glu Phe Arg Arg Asn His Gln Ile Leu Leu Glu Val Trp Asn
            355                 360                 365

Asn Gly Arg Arg Asn Val Asn Met Ile Ser Thr Ile His Ser Ala Gln
            370                 375                 380

Leu Met Glu Ser Arg Ser Lys Ser Lys Arg Ser Asp Val Pro Ile Gln
385                 390                 395                 400

Lys Pro Asn Ser Ile Ile Asp Tyr Asn Lys Tyr Met Lys Gly Val Asp
            405                 410                 415

Arg Ala Asp Gln Tyr Leu Ala Tyr Ser Ile Phe Arg Lys Thr Lys
            420                 425                 430

Lys Trp Thr Lys Arg Val Val Met Phe Phe Ile Asn Cys Ala Leu Phe
            435                 440                 445

Asn Ser Phe Arg Val Tyr Thr Ile Leu Asn Gly Lys Asn Ile Thr Tyr
450                 455                 460

Lys Asn Phe Leu His Lys Val Ala Val Ser Trp Ile Glu Asp Gly Glu
465                 470                 475                 480

Thr Asn Cys Thr Glu Gln Asp Asn Leu Pro Asn Ser Glu Pro Thr
            485                 490                 495

Arg Arg Ala Pro Arg Leu Asp His Pro Gly Arg Leu Ser Asn Tyr Gly
            500                 505                 510

Lys His Lys Leu Ile Asn Ile Val Thr Ser Gly Arg Ser Leu Lys Pro
            515                 520                 525

Gln Arg Gln Cys Arg Val Cys Ala Val Gln Lys Lys Arg Ser Arg Thr
            530                 535                 540

Cys Phe Val Cys Lys Phe Cys Asn Val Pro Leu His Lys Gly Asp Cys
545                 550                 555                 560

Phe Glu Arg Tyr His Thr Leu Lys Lys Tyr
            565                 570
```

<210> SEQ ID NO 53
<211> LENGTH: 345
<212> TYPE: PRT
<213> ORGANISM: Mamestra brassicae

<400> SEQUENCE: 53

Met Phe Ser Phe Val Pro Asn Lys Glu Gln Thr Arg Thr Val Leu Ile
1               5                   10                  15

Phe Cys Phe His Leu Lys Thr Thr Ala Ala Glu Ser His Arg Pro Leu
            20                  25                  30

Val Glu Ala Phe Gly Glu Gln Val Pro Thr Val Lys Thr Cys Glu Arg
        35                  40                  45

Trp Phe Gln Arg Phe Lys Ser Gly Asp Phe Asp Val Asp Asp Lys Glu
    50                  55                  60

His Gly Lys Pro Pro Lys Arg Tyr Glu Asp Ala Glu Leu Gln Ala Leu
65                  70                  75                  80

Leu Asp Glu Asp Ala Gln Thr Gln Lys Gln Leu Ala Glu Gln Leu
                85                  90                  95

Glu Val Ser Gln Gln Ala Val Ser Asn Arg Leu Arg Glu Gly Gly Lys
            100                 105                 110

Ile Gln Lys Val Gly Arg Trp Val Pro His Glu Leu Asn Glu Arg Gln
        115                 120                 125

Arg Glu Arg Arg Lys Asn Thr Cys Glu Ile Leu Leu Ser Arg Tyr Lys
130                 135                 140

Arg Lys Ser Phe Leu His Arg Ile Val Thr Gly Glu Glu Lys Trp Ile
145                 150                 155                 160

Phe Phe Val Asn Pro Lys Arg Lys Ser Tyr Val Asp Pro Gly Gln
            165                 170                 175

Pro Ala Thr Ser Thr Ala Arg Pro Asn Arg Phe Gly Lys Lys Thr Arg
        180                 185                 190

Leu Cys Val Trp Trp Asp Gln Ser Gly Val Ile Tyr Tyr Glu Leu Leu
    195                 200                 205

Lys Pro Gly Glu Thr Val Asn Thr Ala Arg Tyr Gln Gln Gln Leu Ile
210                 215                 220

Asn Leu Asn Arg Ala Leu Gln Arg Lys Arg Pro Glu Tyr Gln Lys Arg
225                 230                 235                 240

Gln His Arg Val Ile Phe Leu His Asp Asn Ala Pro Ser His Thr Ala
            245                 250                 255

Arg Ala Val Arg Asp Thr Leu Glu Thr Leu Asn Trp Glu Val Leu Pro
        260                 265                 270

His Ala Ala Tyr Ser Pro Asp Leu Ala Pro Ser Asp Tyr His Leu Phe
    275                 280                 285

Ala Ser Met Gly His Ala Leu Ala Glu Gln Arg Phe Asp Ser Tyr Glu
    290                 295                 300

Ser Val Glu Glu Trp Leu Asp Glu Trp Phe Ala Ala Lys Asp Asp Glu
305                 310                 315                 320

Phe Tyr Trp Arg Gly Ile His Lys Leu Pro Glu Arg Trp Asp Asn Cys
            325                 330                 335

Val Ala Ser Asp Gly Lys Tyr Phe Glu
            340                 345

<210> SEQ ID NO 54
<211> LENGTH: 347
<212> TYPE: PRT
<213> ORGANISM: Mayetiola destructor

<400> SEQUENCE: 54

```
Met Glu Asn Phe Glu Asn Trp Arg Lys Arg His Leu Arg Glu Val
1               5                   10                  15

Leu Leu Gly His Phe Ala Lys Lys Thr Ala Ala Glu Ser His Arg
            20                  25                  30

Leu Leu Val Glu Val Tyr Gly Glu His Ala Leu Ala Lys Thr Gln Cys
            35                  40                  45

Phe Glu Trp Phe Gln Arg Phe Lys Ser Gly Asp Phe Asp Thr Glu Asp
50                  55                  60

Lys Glu Arg Pro Gly Gln Pro Lys Lys Phe Glu Asp Glu Leu Glu
65                  70                  75                  80

Ala Leu Leu Asp Glu Asp Cys Cys Gln Thr Gln Glu Glu Leu Ala Lys
                85                  90                  95

Ser Leu Gly Val Thr Gln Gln Ala Ile Ser Lys Arg Leu Lys Ala Ala
                100                 105                 110

Gly Tyr Ile Gln Lys Gln Gly Asn Trp Val Pro His Glu Leu Lys Pro
            115                 120                 125

Arg Asp Val Glu Arg Arg Phe Cys Met Ser Glu Met Leu Leu Gln Arg
130                 135                 140

His Lys Lys Lys Ser Phe Leu Ser Arg Ile Ile Thr Gly Asp Glu Lys
145                 150                 155                 160

Trp Ile His Tyr Asp Asn Ser Lys Arg Lys Ser Tyr Val Lys Arg
                165                 170                 175

Gly Gly Arg Ala Lys Ser Thr Pro Lys Ser Asn Leu His Gly Ala Lys
            180                 185                 190

Val Met Leu Cys Ile Trp Trp Asp Gln Arg Gly Val Leu Tyr Tyr Glu
            195                 200                 205

Leu Leu Glu Pro Gly Gln Thr Ile Thr Gly Asp Leu Tyr Arg Thr Gln
210                 215                 220

Leu Ile Arg Leu Lys Gln Ala Leu Ala Glu Lys Arg Pro Glu Tyr Ala
225                 230                 235                 240

Lys Arg His Gly Ala Val Ile Phe His His Asp Asn Ala Arg Pro His
                245                 250                 255

Val Ala Leu Pro Val Lys Asn Tyr Leu Glu Asn Ser Gly Trp Glu Val
            260                 265                 270

Leu Pro His Pro Pro Tyr Ser Pro Asp Leu Ala Pro Ser Asp Tyr His
            275                 280                 285

Leu Phe Arg Ser Met Gln Asn Asp Leu Ala Gly Lys Arg Phe Thr Ser
290                 295                 300

Glu Gln Gly Ile Arg Lys Trp Leu Asp Ser Phe Leu Ala Ala Lys Pro
305                 310                 315                 320

Ala Lys Phe Phe Glu Lys Gly Ile His Glu Leu Ser Glu Arg Trp Glu
                325                 330                 335

Lys Val Ile Ala Ser Asp Gly Gln Tyr Phe Glu
                340                 345
```

<210> SEQ ID NO 55
<211> LENGTH: 342
<212> TYPE: PRT
<213> ORGANISM: Apis mellifera

<400> SEQUENCE: 55

```
Met Glu Asn Gln Lys Glu His Tyr Arg His Ile Leu Leu Phe Tyr Phe
1               5                   10                  15
```

Arg Lys Gly Lys Asn Ala Ser Gln Ala His Lys Lys Leu Cys Ala Val
            20                  25                  30

Tyr Gly Asp Glu Ala Leu Lys Glu Arg Gln Cys Gln Asn Trp Phe Asp
        35                  40                  45

Lys Phe Arg Ser Gly Asp Phe Ser Leu Lys Asp Glu Lys Arg Ser Gly
 50                  55                  60

Arg Pro Val Glu Val Asp Asp Leu Ile Lys Ala Ile Ile Asp Ser
65                  70                  75                  80

Asp Arg His Ser Thr Thr Arg Glu Ile Ala Glu Lys Leu His Val Ser
                85                  90                  95

His Thr Cys Ile Glu Asn His Leu Lys Gln Leu Gly Tyr Val Gln Lys
            100                 105                 110

Leu Asp Thr Trp Val Pro His Glu Leu Lys Lys His Leu Thr Gln
        115                 120                 125

Arg Ile Asn Ser Cys Asp Leu Leu Lys Lys Arg Asn Glu Asn Asp Pro
130                 135                 140

Phe Leu Lys Arg Leu Ile Thr Gly Asp Glu Lys Trp Val Val Tyr Asn
145                 150                 155                 160

Asn Ile Lys Arg Lys Arg Ser Trp Ser Arg Pro Arg Glu Pro Ala Gln
                165                 170                 175

Thr Thr Ser Lys Ala Gly Ile His Arg Lys Lys Val Leu Leu Ser Val
            180                 185                 190

Trp Trp Asp Tyr Lys Gly Ile Val Tyr Phe Glu Leu Leu Pro Pro Asn
        195                 200                 205

Arg Thr Ile Asn Ser Val Val Tyr Ile Glu Gln Leu Thr Lys Leu Asn
        210                 215                 220

Asn Ala Val Glu Glu Lys Arg Pro Glu Leu Thr Asn Arg Lys Gly Val
225                 230                 235                 240

Val Phe His His Asp Asn Ala Arg Pro His Thr Ser Leu Val Thr Arg
                245                 250                 255

Gln Lys Leu Leu Glu Leu Gly Trp Asp Val Leu Pro His Pro Pro Tyr
            260                 265                 270

Ser Pro Asp Leu Ala Pro Ser Asp Tyr Phe Leu Phe Arg Ser Leu Gln
        275                 280                 285

Asn Ser Leu Asn Gly Lys Asn Phe Asn Asn Asp Asp Ile Lys Ser
290                 295                 300

Tyr Leu Ile Gln Phe Phe Ala Asn Lys Asn Gln Lys Phe Tyr Glu Arg
305                 310                 315                 320

Gly Ile Met Met Leu Pro Glu Arg Trp Gln Lys Val Ile Asp Gln Asn
                325                 330                 335

Gly Gln His Ile Thr Glu
            340

<210> SEQ ID NO 56
<211> LENGTH: 345
<212> TYPE: PRT
<213> ORGANISM: Messor bouvieri

<400> SEQUENCE: 56

Met Ser Ser Phe Val Pro Glu Asn Val His Leu Arg His Ala Leu Leu
1               5                   10                  15

Phe Leu Phe His Gln Lys Lys Arg Ala Ala Glu Ser His Arg Leu Leu
            20                  25                  30

Val Glu Thr Tyr Gly Glu His Ala Pro Thr Ile Arg Thr Cys Glu Thr

```
                35                  40                  45
Trp Phe Arg Gln Phe Lys Cys Gly Asp Phe Asn Val Gln Asp Lys Glu
 50                  55                  60

Arg Pro Gly Arg Pro Lys Thr Phe Glu Asp Ala Glu Leu Gln Glu Leu
 65                  70                  75                  80

Leu Asp Glu Asp Ser Thr Gln Thr Gln Lys Gln Leu Ala Glu Lys Leu
                 85                  90                  95

Asn Val Ser Arg Val Ala Ile Cys Glu Arg Leu Gln Ala Met Gly Lys
            100                 105                 110

Ile Gln Lys Met Gly Arg Trp Val Pro His Glu Leu Asn Asp Arg Gln
        115                 120                 125

Met Glu Asn Arg Lys Ile Val Ser Glu Met Leu Leu Gln Arg Tyr Glu
130                 135                 140

Arg Lys Ser Phe Leu His Arg Ile Val Thr Gly Asp Glu Lys Trp Ile
145                 150                 155                 160

Tyr Phe Glu Asn Pro Lys Arg Lys Lys Ser Trp Leu Ser Pro Gly Glu
                165                 170                 175

Ala Gly Pro Ser Thr Ala Arg Pro Asn Arg Phe Gly Arg Lys Thr Met
            180                 185                 190

Leu Cys Val Trp Trp Asp Gln Ile Gly Val Val Tyr Tyr Glu Leu Leu
        195                 200                 205

Lys Pro Gly Glu Thr Val Asn Thr Asp Arg Tyr Arg Gln Gln Met Ile
210                 215                 220

Asn Leu Asn Cys Ala Leu Ile Glu Lys Arg Pro Gln Tyr Ala Gln Arg
225                 230                 235                 240

His Asp Lys Val Ile Leu Gln His Asp Asn Ala Pro Ser His Thr Ala
                245                 250                 255

Lys Pro Val Lys Glu Met Leu Lys Ser Leu Gly Trp Glu Val Leu Ser
            260                 265                 270

His Pro Pro Tyr Ser Pro Asp Leu Ala Pro Ser Asp Tyr His Leu Phe
        275                 280                 285

Ala Ser Met Gly His Ala Leu Ala Glu Gln His Phe Ala Asp Phe Glu
290                 295                 300

Glu Val Lys Lys Trp Leu Asp Glu Trp Phe Ser Ser Lys Glu Lys Leu
305                 310                 315                 320

Phe Phe Trp Asn Gly Ile His Lys Leu Ser Glu Arg Trp Thr Lys Cys
                325                 330                 335

Ile Glu Ser Asn Gly Gln Tyr Phe Glu
            340                 345

<210> SEQ ID NO 57
<211> LENGTH: 594
<212> TYPE: PRT
<213> ORGANISM: Trichoplusia ni

<400> SEQUENCE: 57

Met Gly Ser Ser Leu Asp Asp Glu His Ile Leu Ser Ala Leu Leu Gln
 1               5                  10                  15

Ser Asp Asp Glu Leu Val Gly Glu Asp Ser Asp Ser Glu Val Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
 50                  55                  60
```

```
Asp Glu Gln Asn Val Ile Glu Gln Pro Gly Ser Ser Leu Ala Ser Asn
 65                  70                  75                  80

Arg Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
                100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
```

```
                485                 490                 495
Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
                515                 520                 525

Arg Asp Asn Ile Ser Asn Ile Leu Pro Lys Glu Val Pro Gly Thr Ser
        530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 58
<211> LENGTH: 574
<212> TYPE: DNA
<213> ORGANISM: Encephalomyocarditis virus

<400> SEQUENCE: 58
taaaaaattc cgcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat cctagggtt ctttcccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaacgtc taggcccccc gaaccacggg     540
gacgtggttt tcctttgaaa aacacgatga taat                                 574

<210> SEQ ID NO 59
<211> LENGTH: 589
<212> TYPE: DNA
<213> ORGANISM: Encephalomyocarditis virus

<400> SEQUENCE: 59
taaaaaattc cgcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat cctagggtt ctttcccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaacgtc taggcccccc gaaccacggg     540
gacgtggttt tcctttgaaa aacacgatga taatatggcc acaacctag                 589
```

<210> SEQ ID NO 60
<211> LENGTH: 837
<212> TYPE: DNA
<213> ORGANISM: Cardio virus

<400> SEQUENCE: 60
cagcattttc cggcccaggc taagagaaac atataagtta gaaacgattc taatcccttg 60
acgaaatcag aacgagatgt tctccctccc ttgccgcttg ttcacaccca cttgattgat 120
tcggcctttt gtgacaagcc ccttggtgaa aggacctctc tctttctggc gtggttggaa 180
ttaacatcct ttccgacgaa agtgctatca tgcctccccg attatgtgat gttttctgcc 240
ctgctgggcg gagcattctc gggttgagaa atctcaaacc ttttcttttg gaactttggt 300
tcccccggtc taagccgctc ggaatatgac agggttattt tcttaatctt atttctactt 360
ttatgggttc tatccataaa aagggtatgt gctgcccctt ccttctttgg agaattcaca 420
cggcggtctt tccgtctctc aacaagtgtg aatgcagcat gccggaaacg gtgaagaaaa 480
cagttttctg cggaagtcta gagtgcacat cgaaacagct gtagcgaccc cacagtagca 540
gcggactccc ctcttggtga caagagcctc tgcggccaaa agccccgtgg attagatcca 600
ctgctgtgag cggtgcaacc ccagcaccct gattcgatgg tcattctcta cggaatcaga 660
gaatggtttt cctaagccct ccggtagaga agccaagaat gtcctgaagg taccccgcgt 720
gcgggatctg atcagaagac caattgacag tgctttacac tgccactttg gtttaaaaat 780
tgtcacagct tctccaaacc aagtggtctt ggttttccaa ctttattgaa tggcaat 837

<210> SEQ ID NO 61
<211> LENGTH: 1064
<212> TYPE: DNA
<213> ORGANISM: Theiler's murine encephalomyocarditis virus

<400> SEQUENCE: 61
ttgaaagggg gcccggggga tctaccccgc ggtaactggt gacagttgtc gcggacggag 60
atcatccccc ggttaccccc tttcgacgcg ggtactgcga tagtgccacc ccagtctttc 120
ctactcccga ctcccgaccc taacccaggt tcctcggaac aggaacacca atttactcat 180
cccctggatg ctgactaatc agaggaacgt cagcattttc cggcccaggc taagagaagt 240
agataagtta gaatccaaat tgatttatca tccccttgac gaattcgcgt tggaaaaaca 300
cctctcactt gcccctcttc acacccatta atttaattcg gcctctgtgt tgagcccctt 360
gttgaagtgt ttccctccat cgcgacgtgg ttggagatct aagtcaaccg actccgacga 420
aactaccatc atgcctcccc gattatgtga tgctttctgc cctgctgggt ggagcaccct 480
cgggttgaga aaccttcttc ccttttttcct tggactccgg tcccccggtc taagccgctc 540
ggaatatgac agggttattt tcacctcttc ttttctactc cacagtgttc tatactgtgg 600
aagggtatgt gttgcccctt ccttcttgga gaacgtgcgc ggcggtcttt ccgtctctcg 660
acaagcgcgc gtgcaacata cagagtaacg cgaagaaagc agttctcggt ctagctctag 720
tgcccacaag aaaacagctg tagcgaccac acaaaggcag cggaaccccc ctcctggtaa 780
caggagcctc tgcggccaaa agccacgtgg ataagatcca cctttgtgtg cggtgcaacc 840
ccagcaccct ggtttcttgg tgacactcta gtgaacccct gaatggcaat ctcaagcgcc 900
tctgtaggga agccaagaat gtccaggagg taccccttcc tctcggaagg gatctgacct 960
ggagacacat cacacgtgct ttacacctgt gcttgtgttt aaaaattgtt acagcttccc 1020
cgaaccaagt ggtcttggtt ttcacttttt atcacactgt caat 1064

<210> SEQ ID NO 62
<211> LENGTH: 410
<212> TYPE: DNA
<213> ORGANISM: Picornavirus

<400> SEQUENCE: 62

```
gaaacccgta tacaccggac cttttctccc ctccctctcc acttaccttt ttcccctctt      60
cggcatgaaa caaggattat tcaagtggaa acgcgattta atatgcggct ggccaccgcg     120
gaataacggc aattgtgtat ctgctggaag ccaagcctgc ctagccgata gcccttgacc     180
gggtgtgtag gatagcccag gaaccagcaa tacgcgacag gttatggtag agtagatacc     240
tagccagggg caatgggact gcattgcata tccctaatga accattgaga tttctctggt     300
cattacccgg tgatggttac tagaggggggg cctctagtac tagatctata ctgcctgata     360
gggtcgcggc tggccgacca tgacctgtat agtcagttga tttgagcaat              410
```

<210> SEQ ID NO 63
<211> LENGTH: 1052
<212> TYPE: DNA
<213> ORGANISM: Sikhote-Alin virus

<400> SEQUENCE: 63
ggggatctcc cccgcggcag ctggttacag ctgtcgcgga cggagatcat cccccggcca 60
ccccctttcg acgcgggtac tgcgatagtg ccaccccagt ctttcctact cccgactccc 120
gactctaacc caggttcctt ggaacaggaa caccaatata ctcatcccct ggatgctgac 180
taatcagagg aacgtcagca ttttccggcc caggctaaga gaagtagata agttagattc 240
caaattgatt tatcatcccc ttgacgaatt cgcgttggaa atgcacctct cacttgccgc 300
tctccacacc cattaacttg attcggcctc tgtgttgagc cccttgttga agtgcttccc 360
tccatcgtga cgtggttgga gatctaagtc aaccgactcc gacgaaacta ccatcatgcc 420
tccccgatta tgtgatgctt tctgccctgc tgggtggagc atcctcgggt tgagaaaacc 480
ttcttccttt ttccttggac cccggtcccc cggtctaagc cgcttggaat aagacagggt 540
tatcttcacc tcttccttct tctacttcat agtgttctat actatgaaag ggtatgtgtc 600
gccccttcct tctttggaga acacgcgcgg cggtctttcc gtctctcgaa aagcgcgtgt 660
gcgacatgca gagaaccgtg aagaaagcag tttgcggact agctttagtg cccacaagaa 720
aacagctgta gcgaccacac aaaggcagcg gaccccccct cctggcaaca ggagcctctg 780
cggccaaaag ccacgtggat aagatccacc tttgtgtgcg gcacaacccc agtgccctgg 840
tttcttggtg acacttcagt gaaaacgcaa atggcgatct gaagcgcctc tgtaggaaag 900
ccaagaatgt ccaggaggta ccccttccct cgggaaggga tctgacctgg agacacatca 960
catgtgcttt acacctgtgc ttgtgtttaa aaattgtcac agctttccca aaccaagtgg 1020
tcttggtttt cactctttaa actgatttca ct 1052

<210> SEQ ID NO 64
<211> LENGTH: 1049
<212> TYPE: DNA
<213> ORGANISM: Theilovirus

<400> SEQUENCE: 64
ttcaaagggg ggccccgggg tcttcgccgc ggacacgcgt tagtgtgttc gcggtgaaga 60
tcaccccggg aaaccccctt tggacgcggg acctgcgaca gtgccatccc ccgtctctcc 120
tattccaact acccgaccct aacccagggt ccaggacact ggatcaatac aagtcatccc 180

```
ctgaatgctg gctaatcaga ggaaagtcag catttccgg cccaggctaa gagaaacaca    240
ataagttaga atctaaatta atcaccttga cgaattcgca aagataagtc ctccctccct    300
tgccgctcga tcacacccag aactaacaat tcggcctctc gtgacgagcc ccttggtgaa    360
aggacctctt tcaacgcgac gtggttggag attaaaaccg actccgacga aagtgctatc    420
atgcctcccc gattatgtga tgttttctgc cctgctgggc ggagcattct cgggttgata    480
taccttgaat ccttcatcct tggacctccc ggtcccccgg tctaagccac ttggaatatg    540
acagggttat tttccaaaat tcttatttcc actttcatga gttcttttca tgaaagggt     600 atgtgctgcc ccttccttct tggagaatcc gcgtggcggt ctttccgtct ctcgaaaaac    660
gtggatgcag catgctggaa acggtgaaga aagtagttct ctgtggaaac ttagaacaga    720
catcgaaaca gctgtagcga cctcacagta gcagcggaac cccctcctgg cgacaggagc    780
ctctgcggcc aaaagccccg tggataagat ccactgctgt gagcggtgca accccagcac    840
cctggttcga tggttgttct ctgtggaatc agagaatggc tttcctaagc cctccagtag    900
agaagccaag aatgtcctga aggtaccccg cgtgcgggat ctgatcagaa gaccaattgc    960
cagtgctata cactggtact ttggtttaaa aattgtcaca gcttctccaa accaagtggt   1020
cttggttttc tatctttaat aattggttc                                     1049
```

<210> SEQ ID NO 65
<211> LENGTH: 959
<212> TYPE: DNA
<213> ORGANISM: Theiler's murine encephalomyocarditis virus

<400> SEQUENCE: 65

```
ctctacctgc gacagtgcca acccacatct cttcccacta ttattattcc ggttcccgcc     60
ttaggtccat tgaaaagacc aaacatgtca tcccttggat gctggctaat cagaggaaag    120
tcagcatttt ccggcccagg ctaagagaaa catataagtt agaaatgatt ctaatccctt    180
gacgaattcg gaacgagaag ttctccctcc cttgccgctt gttcacaccc atcatttaat    240
tcggcccttt gtgacaagcc cctcggtgaa aggacctctc tctttccgac gtggttggaa    300
ttaacatctt ttccgacgaa agtgctatta tgcctccccg attgtgtgat gctttctgcc    360
ctgctgggcg gagcgtcctc gggttgagaa accttgaatc ttttcctttg gagccttggc    420 tccccggtc taagccgctt ggaatatgac agggttattt ccaaactct ttatttctac     480 tttcatgggt tctatccatg aaagggtat gtgttgcccc ttccttcttt ggagaatctg    540
cgcggcggtc tttccgtctc tcaacaggcg tggatgcaac atgccggaaa cggtgaagaa    600
aacagttttc tgtggaaatt tagagtggac atcgaaacag ctgtagcgac ctcacagtag    660
cagcggattc ccctcttggc gacaagagcc tctgcggcca aaagcccgt ggataagatc     720 cactgctgtg agcggtgcaa ccccagcacc ctggttcgat ggccattctc tatggaacca    780
gaaaatggtt ttctcaagcc ctccggtaga gaagccaaga atgtcctgaa ggtaccccgc    840
gcgcgggatc tgatcagaag accaattggc agtgctttac gctgccactt tggtttaaaa    900
actgtcacag cttctccaaa ccaagtggtc ttggttttcc aattttgttg actgacaat     959
```

<210> SEQ ID NO 66
<211> LENGTH: 1040
<212> TYPE: DNA
<213> ORGANISM: Saffold virus

<400> SEQUENCE: 66

-continued

```
tttcaaaggg ggccctgggg tctttgtcgc ggagatgcgc tagcatcttc gcggtaaaga     60
acaccccagg ggtaacccct ttgaacgcgg gactgcgata gtgccacccc acgtctttcc    120
cactcctaac ccgactccca cctcgggtcc aatgaaagga ccaaataatt catcccttga    180
atgttggcta atcagaggaa agtcagcatt ttccggccca ggctaagaga aacatataag    240
ttagatttga ttcaaatccc ttgacgaatt cgaaacgaga tgttctccct cccttgccgc    300
ttgttcacac ccatacattt aattcggcct cctgtgacaa gcccctcggt gaaagaacct    360
ctctcttttc gacgtggttg gaattaacat catttccgac gaaagtgcta tcatgcctcc    420
ccgattatgt gatgttttct gccctgctgg gcggagcatt ctcgggttga gaaaccttga    480
atcttttcct ttggaacctt ggttccccccg gtctaagccg cttggaatat gacagggtta    540
ttttctttat cttatttcta ctttcacggg ttctatccgt gaaaagggta cgtgttgccc    600
cttccttctt cggagaattc acacggcggt ctttccgtct ctcgacaagt gtgaatgcaa    660
catgccggaa acggtgaaga aaacagtttt ctgcggaagt ctagagtgcg catcgaaaca    720
gctgtagcga cctcacagta gcagcggact cccctcttgg cgacaagagc ctctgcggcc    780
aaaagccccg tggataagat ccactgctgt gagcggtgca accccagcac cctgattcga    840
tgaacgttct ttacggaacc agaggatggt tttcctaagc cctccggtag agaagccaag    900
aatgtcctga aggtaccccg cgtgcgggat ctgatcaggg gaccaattga ctgtgcttta    960
caccgtcact ttggtttaaa aactgtcaca gcttctccaa accaagtggt cttggttttc   1020
caattttatt aactggcaat                                                1040
```

```
<210> SEQ ID NO 67
<211> LENGTH: 741
<212> TYPE: DNA
<213> ORGANISM: Echovirus

<400> SEQUENCE: 67
ttaaaacagc ctgtgggttg tacccaccca cagggcccac tgggcgctag cactctggta     60
ctacggtacc tttgtgtgcc tgttttatac ccctccccct actgaaactt agaagcaatt    120
cataccgatc aatagtgggc gtggcacacc agccgtgtct agatcaagca ctcctgtttc    180
cccggaccga gtatcaatag actgctcacg cggttgaagg agaaaacgtt cgttatccgg    240
ctaactactt cgaaaaacct agtaacacca tgaaagttgc ggagtgtttc actcagcact    300
tccccagtgt agatcaggtc gatgagtcac cgcattcctc acgggcgacc gtggcggtgg    360
ctgcgctggc ggcctgccta tggggtgacc cataggacgc tctaatacag acatggtgcg    420
aagagtctat tgagctagtt agtagtcctc cggcccctga atgcggataa tcctaactgt    480
ggagcagata cccacgaacc agtgggcagt ctgtcgtaac gggcaactcc gcagcggaac    540
cgactacttt gggtgtccgt gtttcctttt attccaaatc tggctgctta tggtgacaat    600
tgagagattg ttgccatata gctattggat tggccatccg gtgaataata gagcgataat    660
atatttgttt gttggattcg tgccacttag tctgaaagtt ttgagaacac tcaactacgt    720
tttattgctg aatagtgcaa g                                              741
```

```
<210> SEQ ID NO 68
<211> LENGTH: 419
<212> TYPE: DNA
<213> ORGANISM: Picornavirus

<400> SEQUENCE: 68
gggttttacg aaacccgtat acaccagacc ttttctcccc tccccctcca cctacctttt     60
```

```
ccccctcttt ggaccgaaac aaggacacgt aagtggaaac gcgattttat atgtggttgg    120
ccaccacgga ataacggcaa ttgtctacat gtgggaagtg caacctccct agccgataac    180
ccctgaccgg gtgtgtagga taggaaaggt gcccactgtg ggcgacaggt tatggtagag    240
tggataccta gccaggggca atgggactgc tttgcatatc cctaatgaag tattgagatt    300
tctctgctca ttacccggtg atggttgtgt ggggggggcc ccatacacta gatccatact    360
gcctgatagg gtcgcggctg gccgaccata acctgtatag tcagttgaat tcagccaag     419
```

<210> SEQ ID NO 69
<211> LENGTH: 244
<212> TYPE: DNA
<213> ORGANISM: Picornavirus

<400> SEQUENCE: 69

```
ctctggtgtc cgggtgtgtg ggatagaccc agatgtgcag tggatgcgag catttgagtc     60
agagtaggag caagcccagg ggcaaaggga ccacattgtg tatcccgaat gaaggatcga    120
gatttctctc ctcattaccc ggtgtcttgt cactgttggg ggggcccaac agtcttagtc    180
ctatactgcc tgatagggtc gcggctggcc ggactcaagt gctatagtca gttgattttc    240
actc                                                                 244
```

<210> SEQ ID NO 70
<211> LENGTH: 331
<212> TYPE: DNA
<213> ORGANISM: Picornavirus

<400> SEQUENCE: 70

```
gcaagtggaa acgcgatttt atatgtggct ggccaccacg gaataacggc aattgtttac     60
atgtgggaag tgcaacctcc ctagccgata gcccttgacc gggtgtgtag gataggaaag    120
gtgcccactg tgagcgacag gttatggtag agtggatacc tagccagggg caatgggact    180
gctttgcata tccctaatga agcatcgaga gttctctgct cattacccgg tgacggttgt    240
gtgggggggg ccccacacac tagatccata ctgcctgata gggtcgcggc tggccgacca    300
taacctgtat agtcagttga ttttaaccaa g                                   331
```

<210> SEQ ID NO 71
<211> LENGTH: 305
<212> TYPE: DNA
<213> ORGANISM: Sikhote-Alin virus

<400> SEQUENCE: 71

```
gtggctggcc accacggaat aacggcaatt gtttgtatgt gggaggtcaa gcctgcctag     60
ccgataacct ttgaccgggt gtgtaggata gaacaggaac ccactacagg cgacaggtta    120
tggtagagtg gatacctagc caggggcaat gggactgcgt tgcatatccc taatgagcca    180
tcgagatttc tctggccatt acccggtgat ggttgtgtgg ggggggcccc acacactaga    240
tccatactgc ctgatagggt cgcggctggc cgaccataac ctgtatagtc agttgacttt    300
gaatc                                                                305
```

<210> SEQ ID NO 72
<211> LENGTH: 579
<212> TYPE: DNA
<213> ORGANISM: Rhopalosiphum padi virus

<400> SEQUENCE: 72

| | |
|---|---|
| gataaaagaa cctataatcc cttcgcacac cgcgtcacac cgcgctatat gctgctcatt | 60 |
| aggaattacg gctccttttt tgtggataca atctcttgta tacgatatac ttattgttaa | 120 |
| tttcattgac ctttacgcaa tcctgcgtaa atgctggtat agggtgtact tcggatttcc | 180 |
| gagcctatat tggttttgaa aggaccttta agtccctact atactacatt gtactagcgt | 240 |
| aggccacgta ggcccgtaag atattataac tattttatta tattttattc acccccacaa | 300 |
| ttaatcccag ttaaagcttt ataactataa gtaagccgtg ccgaaacgtt aatcggtcgc | 360 |
| tagttgcgta acaactgtta gtttaatttt ccaaaattta tttttcacaa ttttagtta | 420 |
| agattttagc ttgccttaag cagtctttat atcttctgta tattatttta aagtttatag | 480 |
| gagcaaagtt cgctttactc gcaatagcta ttttatttat tttaggaata ttatcacctc | 540 |
| gtaattattt aattataaca ttagctttat ctatttata | 579 |

<210> SEQ ID NO 73
<211> LENGTH: 742
<212> TYPE: DNA
<213> ORGANISM: Coxsackievirus

<400> SEQUENCE: 73
ttaaaacagc ctgtgggttg atcccaccca cagggcccat tgggcgctag cactctggta 60
tcacggtacc tttgtgcgcc tgttttatac cccctccccc aactgtaact tagaagtaac 120
acacaccgat caacagtcag cgtggcacac cagccacgtt ttgatcaagc acttctgtta 180
ccccggactg agtatcaata gactgctcac gcggttgaag gagaaagcgt tcgttatccg 240
gccaactact tcgaaaaacc tagtaacacc gtggaagttg cagagtgttt cgctcagcac 300
taccccagtg tagatcaggt cgatgagtca ccgcattccc cacgggcgac cgtggcggtg 360
gctgcgttgg cggcctgccc atggggaaac ccatgggacg ctctaataca gacatggtgc 420
gaagagtcta ttgagctagt tggtagtcct ccggcccctg aatgcggcta atcctaactg 480
cggagcacac accctcaagc cagagggcag tgtgtcgtaa cgggcaactc tgcagcggaa 540
ccgactactt tgggtgtccg tgtttcattt tattcctata ctggctgctt atggtgacaa 600
ttgagagatt gttaccatat agctattgga ttggccatcc ggtgaccaat agagctatta 660
tatatctctt tgttgggttt ataccactta gcttgaaaga ggttaaaaca ttacaattca 720
ttgttaagtt gaatacagca aa 742

<210> SEQ ID NO 74
<211> LENGTH: 641
<212> TYPE: DNA
<213> ORGANISM: Echovirus

<400> SEQUENCE: 74
actgaaactt agaagcaatt cataccgatc aatagtgggc gtggcacacc agccgtgtct 60
agatcaagca ctcctgtttc cccggaccga gtatcaatag actgctcacg cggttgaagg 120
agaaaacgtt cgttatccgg ctaactactt cgaaaaacct agtaacacca tgaaagttgc 180
ggagtgtttc actcagcact tccccagtgt agatcaggtc gatgagtcac cgcattcctc 240
acgggcgacc gtggcggtgg ctgcgctggc ggcctgccta tggggtgacc cataggacgc 300
tctaatacag acatggtgcg aagagtctat tgagctagtt agtagtcctc cggcccctga 360
atgcggataa tcctaactgt ggagcagata cccacgaacc agtgggcagt ctgtcgtaac 420
gggcaactcc gcagcggaac cgactacttt gggtgtccgt gtttcctttt attccaaatc 480
tggctgctta tggtgacaat tgagagattg ttgccatata gctattggat tggccatccg 540

```
gtgaataata gagcgataat atatttgttt gttggattcg tgccacttag tctgaaagtt    600
ttgagaacac tcaactacgt tttattgctg aatagtgcaa g                        641

<210> SEQ ID NO 75
<211> LENGTH: 652
<212> TYPE: DNA
<213> ORGANISM: Sikhote-Alin virus

<400> SEQUENCE: 75
gacgaaacta ccatcatgcc tccccgatta tgtgatgctt tctgccctgc tgggtggagc     60
atcctcgggt tgagaaaacc ttcttccttt tccttggac cccggtcccc cggtctaagc    120
cgcttggaat aagacagggt tatcttcacc tcttccttct tctacttcat agtgttctat   180
actatgaaag ggtatgtgtc gccccttcct tctttggaga acacgcgcgg cggtctttcc   240
gtctctcgaa aagcgcgtgt gcgacatgca gagaaccgtg aagaaagcag tttgcggact   300
agctttagtg cccacaagaa aacagctgta gcgaccacac aaaggcagcg acccccccct   360
cctggcaaca ggagcctctg cggccaaaag ccacgtggat aagatccacc tttgtgtgcg   420
gcacaacccc agtgccctgg tttcttggtg acacttcagt gaaaacgcaa atggcgatct   480
gaagcgcctc tgtaggaaag ccaagaatgt ccaggaggta ccccttccct cgggaaggga   540
tctgacctgg agacacatca catgtgcttt acacctgtgc ttgtgtttaa aaattgtcac   600
agctttccca aaccaagtgg tcttggtttt cactctttaa actgatttca ct           652

<210> SEQ ID NO 76
<211> LENGTH: 552
<212> TYPE: DNA
<213> ORGANISM: Sikhote-Alin virus

<400> SEQUENCE: 76
cccggtcccc cggtctaagc cgcttggaat aagacagggt tatcttcacc tcttccttct    60
tctacttcat agtgttctat actatgaaag ggtatgtgtc gccccttcct tctttggaga   120
acacgcgcgg cggtctttcc gtctctcgaa aagcgcgtgt gcgacatgca gagaaccgtg   180
aagaaagcag tttgcggact agctttagtg cccacaagaa aacagctgta gcgaccacac   240
aaaggcagcg acccccccct cctggcaaca ggagcctctg cggccaaaag ccacgtggat   300
aagatccacc tttgtgtgcg gcacaacccc agtgccctgg tttcttggtg acacttcagt   360
gaaaacgcaa atggcgatct gaagcgcctc tgtaggaaag ccaagaatgt ccaggaggta   420
ccccttccct cgggaaggga tctgacctgg agacacatca catgtgcttt acacctgtgc   480
ttgtgtttaa aaattgtcac agctttccca aaccaagtgg tcttggtttt cactctttaa   540
actgatttca ct                                                       552

<210> SEQ ID NO 77
<211> LENGTH: 1473
<212> TYPE: DNA
<213> ORGANISM: Artificial sequence
<220> FEATURE:
<223> OTHER INFORMATION: Viral

<400> SEQUENCE: 77
ttaaaacagc ctgtgggttg tacccaccca cagggcccac tgggcgctag cactctggta     60
ctacggtacc tttgtgtgcc tgttttatac ccctcccccct actgaaactt agaagcaatt   120
cataccgatc aatagtgggc gtggcacacc agccgtgtct agatcaagca ctcctgtttc   180
```

```
cccggaccga gtatcaatag actgctcacg cggttgaagg agaaaacgtt cgttatccgg      240
ctaactactt cgaaaaacct agtaacacca tgaaagttgc ggagtgtttc actcagcact      300
tccccagtgt agatcaggtc gatgagtcac cgcattcctc acgggcgacc gtggcggtgg      360
ctgcgctggc ggcctgccta tggggtgacc cataggacgc tctaatacag acatggtgcg      420
aagagtctat tgagctagtt agtagtcctc cggcccctga atgcggataa tcctaactgt      480
ggagcagata cccacgaacc agtgggcagt ctgtcgtaac gggcaactcc gcagcggaac      540
cgactacttt gggtgtccgt gtttcctttt attccaaatc tggctgctta tggtgacaat      600
tgagagattg ttgccatata gctattggat tggccatccg gtgaataata gagcgataat      660
atatttgttt gttggattcg tgccacttag tctgaaagtt ttgagaacac tcaactacgt      720
tttattgctg aatagtgcaa gtctttaaga aggagataaa aaatgactgc cctgaccgaa      780
ggtgctaagc tgtttgagaa ggagattccg tacatcaccg agctggaagg ggacgtcgaa      840
ggaatgaagt tcatcatcaa gggagaagga accggggacg ctacgactgg aaccattaag      900
gccaagtata tctgtaccac tggagatctg ccagtgcctt gggccaccct tgtgtcaacc      960
ctctcgtatg gagtgcagtg ttttgctaag taccctagcc acattaagga cttcttcaaa     1020
tccgccatgc cggaaggtta tacccaagag cgcaccattt cttttgaggg agatggagtg     1080
tacaagaccc gcgcgatggt cacctatgag aggggatcta tctacaaccg ggtgactctg     1140
actggagaaa actttaagaa ggacgggcat attcttcgga agaatgtcgc cttccagtgc     1200
cctcccagca tcctttacat tctccccgac actgtgaaca acggaatccg cgtggagttc     1260
aatcaagcct acgacatcga gggggtgacg gagaagctgg tgaccaagtg tagccagatg     1320
aatcggccac tggccggttc agcggctgtc cacattccgc gctaccatca tatcacttat     1380
cacactaagc tctccaaaga ccgcgatgag aggagagatc acatgtgcct ggtggaagtg     1440
gtcaaggccg tcgatctcga tacctatcag taa                                  1473

<210> SEQ ID NO 78
<211> LENGTH: 709
<212> TYPE: DNA
<213> ORGANISM: Echovirus

<400> SEQUENCE: 78
ttaaaacagc ctgtgggttg tacccaccca cagggcccac tgggcgctag cactctggta       60
ctacggtacc tttgtgtgcc tgttttatac ccctcccccl actgaaactt agaagcaatt      120
cataccgatc aatagtgggc gtggcacacc agccgtgtct agatcaagca ctcctgtttc      180
cccggaccga gtatcaatag actgctcacg cggttgaagg agaaaacgtt cgttatccgg      240
ctaactactt cgaaaaacct agtaacacca tgaaagttgc ggagtgtttc actcagcact      300
tccccagtgt agatcaggtc gatgagtcac cgcattcctc acgggcgacc gtggcggtgg      360
ctgcgctggc ggcctgccta tggggtgacc cataggacgc tctaatacag acatggtgcg      420
aagagtctat tgagctagtt agtagtcctc cggcccctga atgcggataa tcctaactgt      480
ggagcagata cccacgaacc agtgggcagt ctgtcgtaac gggcaactcc gcagcggaac      540
cgactacttt gggtgtccgt gtttcctttt attccaaatc tggctgctta tggtgacaat      600
tgagagattg ttgccatata gctattggat tggccatccg gtgaataata gagcgataat      660
atatttgttt gttggattcg tgccacttag tctgaaagtt ttgagaaca                  709

<210> SEQ ID NO 79
<211> LENGTH: 686
```

```
<212> TYPE: DNA
<213> ORGANISM: Echovirus

<400> SEQUENCE: 79
ttaaaacagc ctgtgggttg tacccaccca cagggcccac tgggcgctag cactctggta      60
ctacggtacc tttgtgtgcc tgttttatac ccctcccccct actgaaactt agaagcaatt    120
cataccgatc aatagtgggc gtggcacacc agccgtgtct agatcaagca ctcctgtttc    180
cccggaccga gtatcaatag actgctcacg cggttgaagg agaaaacgtt cgttatccgg    240
ctaactactt cgaaaaacct agtaacacca tgaaagttgc ggagtgtttc actcagcact    300
tccccagtgt agatcaggtc gatgagtcac cgcattcctc acgggcgacc gtggcggtgg    360
ctgcgctggc ggcctgccta tggggtgacc cataggacgc tctaatacag acatggtgcg    420
aagagtctat tgagctagtt agtagtcctc cggcccctga atgcggataa tcctaactgt    480
ggagcagata cccacgaacc agtgggcagt ctgtcgtaac gggcaactcc gcagcggaac    540
cgactacttt gggtgtccgt gtttcctttt attccaaatc tggctgctta tggtgacaat    600
tgagagattg ttgccatata gctattggat tggccatccg gtgaataata gagcgataat    660
atatttgttt gttggattcg tgccac                                          686

<210> SEQ ID NO 80
<211> LENGTH: 656
<212> TYPE: DNA
<213> ORGANISM: Echovirus

<400> SEQUENCE: 80
ttaaaacagc ctgtgggttg tacccaccca cagggcccac tgggcgctag cactctggta      60
ctacggtacc tttgtgtgcc tgttttatac ccctcccccct actgaaactt agaagcaatt    120
cataccgatc aatagtgggc gtggcacacc agccgtgtct agatcaagca ctcctgtttc    180
cccggaccga gtatcaatag actgctcacg cggttgaagg agaaaacgtt cgttatccgg    240
ctaactactt cgaaaaacct agtaacacca tgaaagttgc ggagtgtttc actcagcact    300
tccccagtgt agatcaggtc gatgagtcac cgcattcctc acgggcgacc gtggcggtgg    360
ctgcgctggc ggcctgccta tggggtgacc cataggacgc tctaatacag acatggtgcg    420
aagagtctat tgagctagtt agtagtcctc cggcccctga atgcggataa tcctaactgt    480
ggagcagata cccacgaacc agtgggcagt ctgtcgtaac gggcaactcc gcagcggaac    540
cgactacttt gggtgtccgt gtttcctttt attccaaatc tggctgctta tggtgacaat    600
tgagagattg ttgccatata gctattggat tggccatccg gtgaataata gagcga        656

<210> SEQ ID NO 81
<211> LENGTH: 741
<212> TYPE: DNA
<213> ORGANISM: Artificial sequence
<220> FEATURE:
<223> OTHER INFORMATION: Viral

<400> SEQUENCE: 81
ttaaaacagc ctgtgggttg tacccaccca cagggcccac tgggcgctag cactctggta      60
ctacggtacc tttgtgtgcc tgttttatac ccctcccccct actgaaactt agaagcaatt    120
cataccgatc aatagtgggc gtggcacacc agccgtgtct agatcaagca ctcctgtttc    180
cccggaccga gtatcaatag actgctcacg cggttgaagg agaaaacgtt cgttatccgg    240
ctaactactt cgaaaaacct agtaacacca tgaaagttgc ggagtgtttc actcagcact    300
```

| | |
|---|---|
| tccccagtgt agatcaggtc gatgagtcac cgcattcctc acgggcgacc gtggcggtgg | 360 |
| ctgcgctggc ggcctgccta tggggtgacc cataggacgc tctaatacag acatggtgcg | 420 |
| aagagtctat tgagctagtt agtagtcctc cggcccctga atgcggataa tcctaactgt | 480 |
| ggagcagata cccacgaacc agtgggcagt ctgtcgtaac gggcaactcc gcagcggaac | 540 |
| cgactacttt gggtgtccgt gtttcctttt attccaaatc tggctgctta tggtgacaat | 600 |
| tgagagattg ttgccatata gctattggat tggccatccg gtgaataata gagcgataat | 660 |
| atatttgttt gttggattcg tgccacttag tctgaaagtt ttgagaacat tacaattcat | 720 |
| tgttaagttg aatacagcaa a | 741 |

<210> SEQ ID NO 82
<211> LENGTH: 741
<212> TYPE: DNA
<213> ORGANISM: Artificial sequence
<220> FEATURE:
<223> OTHER INFORMATION: Viral

<400> SEQUENCE: 82

| | |
|---|---|
| ttaaaacagc ctgtgggttg tacccaccca cagggcccac tgggcgctag cactctggta | 60 |
| ctacggtacc tttgtgtgcc tgttttatac ccctccccct actgaaactt agaagcaatt | 120 |
| cataccgatc aatagtgggc gtggcacacc agccgtgtct agatcaagca ctcctgtttc | 180 |
| cccggaccga gtatcaatag actgctcacg cggttgaagg agaaaacgtt cgttatccgg | 240 |
| ctaactactt cgaaaaacct agtaacacca tgaaagttgc ggagtgtttc actcagcact | 300 |
| tccccagtgt agatcaggtc gatgagtcac cgcattcctc acgggcgacc gtggcggtgg | 360 |
| ctgcgctggc ggcctgccta tggggtgacc cataggacgc tctaatacag acatggtgcg | 420 |
| aagagtctat tgagctagtt agtagtcctc cggcccctga atgcggataa tcctaactgt | 480 |
| ggagcagata cccacgaacc agtgggcagt ctgtcgtaac gggcaactcc gcagcggaac | 540 |
| cgactacttt gggtgtccgt gtttcctttt attccaaatc tggctgctta tggtgacaat | 600 |
| tgagagattg ttgccatata gctattggat tggccatccg gtgaataata gagcgataat | 660 |
| atatttgttt gttggattcg tgccacttag tctgaaagag gttaaaacat tacaattcat | 720 |
| tgttaagttg aatacagcaa a | 741 |

<210> SEQ ID NO 83
<211> LENGTH: 741
<212> TYPE: DNA
<213> ORGANISM: Artificial sequence
<220> FEATURE:
<223> OTHER INFORMATION: Viral

<400> SEQUENCE: 83

| | |
|---|---|
| ttaaaacagc ctgtgggttg tacccaccca cagggcccac tgggcgctag cactctggta | 60 |
| ctacggtacc tttgtgtgcc tgttttatac ccctccccct actgaaactt agaagcaatt | 120 |
| cataccgatc aatagtgggc gtggcacacc agccgtgtct agatcaagca ctcctgtttc | 180 |
| cccggaccga gtatcaatag actgctcacg cggttgaagg agaaaacgtt cgttatccgg | 240 |
| ctaactactt cgaaaaacct agtaacacca tgaaagttgc ggagtgtttc actcagcact | 300 |
| tccccagtgt agatcaggtc gatgagtcac cgcattcctc acgggcgacc gtggcggtgg | 360 |
| ctgcgctggc ggcctgccta tggggtgacc cataggacgc tctaatacag acatggtgcg | 420 |
| aagagtctat tgagctagtt agtagtcctc cggcccctga atgcggataa tcctaactgt | 480 |
| ggagcagata cccacgaacc agtgggcagt ctgtcgtaac gggcaactcc gcagcggaac | 540 |

```
cgactacttt gggtgtccgt gtttcctttt attccaaatc tggctgctta tggtgacaat    600
tgagagattg ttgccatata gctattggat tggccatccg gtgaataata gagcgataat    660
atatttgttt gttgggttta taccacttag cttgaaagag gttaaaacat tacaattcat    720
tgttaagttg aatacagcaa a                                              741
```

```
<210> SEQ ID NO 84
<211> LENGTH: 649
<212> TYPE: DNA
<213> ORGANISM: Theiler's murine encephalomyocarditis virus

<400> SEQUENCE: 84
```

```
gacgaaacta ccatcatgcc tccccgatta tgtgatgctt tctgccctgc tgggtggagc     60
accctcgggt tgagaaaacc ttcttccttt tccttggac tccggtcccc cggtctaagc    120
cgctcggaat atgacagggt tattttcacc tcttcttttc tactccacag tgttctatac    180
tgtggaaggg tatgtgttgc cccttccttc ttggagaacg tgcgcggcgg tctttccgtc    240
tctcgacaag cgcgcgtgca acatacagag taacgcgaag aaagcagttc tcggtctagc    300
tctagtgccc acaagaaaac agctgtagcg accacacaaa ggcagcggaa ccccctcct    360 ggtaacagga gcctctgcgg ccaaaagcca cgtggataag atccacccttt gtgtgcggtg    420 caacccagc accctggttt cttggtgaca ctcagtgaa cccctgaatg gcaatctcaa    480
gcgcctctgt agggaagcca agaatgtcca ggaggtaccc cttcctctcg aagggatct    540 gacctggaga cacatcacac gtgctttaca cctgtgcttg tgtttaaaaa ttgttacagc    600
ttccccgaac caagtggtct tggttttcac tttttatcac actgtcaat                649
```

```
<210> SEQ ID NO 85
<211> LENGTH: 1064
<212> TYPE: DNA
<213> ORGANISM: Artificial sequence
<220> FEATURE:
<223> OTHER INFORMATION: Viral

<400> SEQUENCE: 85
```

```
ttgaaagggg gcccggggga tctcccccgc ggtaactggt gacagttgtc gcggacggag     60
atcatccccc ggttaccccc tttcgacgcg ggtactgcga tagtgccacc ccagtctttc    120
ctactcccga ctcccgaccc taacccaggt tcctcggaac aggaacacca atttactcat    180
cccctggatg ctgactaatc agaggaacgt cagcattttc cggcccaggc taagagaagt    240
agataagtta gaatccaaat tgatttatca tccccttgac gaattcgcgt tggaaaaaca    300
cctctcactt gccgctcgtt acacccatta atttaattcg gcctctgtgt tgagcccctt    360
gttgaagtgt ttccctccat cgcgacgtgg ttggagatct aagtcaaccg actccgacga    420
aactaccatc atgcctcccc gattatgtga tgctttctgc cctgctgggt ggagcaccct    480
cgggttgaga aaaccttctt cctttttcct tggactccgg tccccggtc taagccgctc    540 ggaatatgac agggttattt tcacctcttc ttttctactc cacagtgttc tatactgtgg    600
aagggtatgt gttgcccctt ccttcttgga gaacgtgcgc ggcggtcttt ccgtctctcg    660
acaagcgcgc gtgcaacata cagagtaacg cgaagaaagc agttctcggt ctagctctag    720
tgcccacaag aaaacagctg tagcgaccac acaaaggcag cggaaccccc tcctggtaa    780 caggagcctc tgcggccaaa agccacgtgg ataagatcca cctttgtgtg cggtgcaacc    840
ccagcaccct ggtttcttgg tgacactcta gtgaaccccct gaatggcaat ctcaagcgcc    900
```

| | | |
|---|---|---|
| tctgtaggga agccaagaat gtccaggagg tacccccttcc tctcggaagg gatctgacct | | 960 |
| ggagacacat cacacgtgct ttacacctgt gcttgtgttt aaaaattgtt acagcttccc | | 1020 |
| cgaaccaagt ggtcttggtt ttcactttttt atcacactgt caat | | 1064 |

<210> SEQ ID NO 86
<211> LENGTH: 1051
<212> TYPE: DNA
<213> ORGANISM: Artificial sequence
<220> FEATURE:
<223> OTHER INFORMATION: Viral

<400> SEQUENCE: 86

| | | |
|---|---|---|
| ttcaaagggg ggccccgggg tcttcgccgc ggacacgcgt tagtgtgttc gcggtgaaga | | 60 |
| tcacccccggg aaaccccctt tggacgcggg acctgcgaca gtgccatccc ccgtctctcc | | 120 |
| tattccaact acccgaccct aacccagggt ccaggacact ggatcaatac aagtcatccc | | 180 |
| ctgaatgctg gctaatcaga ggaaagtcag catttttccgg cccaggctaa gagaaacaca | | 240 |
| ataagttaga atctaaatta atcaccttga cgaattcgca aagataagtc ctccctccct | | 300 |
| tgccgctcga tcacacccag aactaacaat tcggcctctc gtgacgagcc ccttggtgaa | | 360 |
| aggacctctt tcaacgcgac gtggttggag attaaaaccg actccgacga aagtgctatc | | 420 |
| atgcctcccc gattatgtga tgttttctgc cctgctgggc ggagcattct cgggttgata | | 480 |
| taccttgaat ccttcatcct tggacctccc ggtcccccgg tctaagccac ttggaatatg | | 540 |
| acagggttat tttccaaaat tcttatttcc actttcatga gttcttttca tgaaaagggt | | 600 |
| atgtgctgcc ccttccttct tggagaatcc gcgtggcggt cttttccgtct ctcgaaaaac | | 660 |
| gtggatgcag catgctggaa acggtgaaga aagtagttct ctgtggaaac ttagaacaga | | 720 |
| catcgaaaca gctgtagcga cctcacagta gcagcggaac ccctcctgg cgacaggagc | | 780 |
| ctctgcggcc aaaagccccg tggataagat ccactgctgt gagcggtgca accccagcac | | 840 |
| cctggttcga tggttgttct ctgtggaatc agagaatggc tttcctaagc cctccagtag | | 900 |
| agaagccaag aatgtcctga aggtaccccg cgtgcgggat ctgatcagga gacacatcac | | 960 |
| acgtgcttta cacctgtgct tgtgtttaaa aattgttaca gcttccccga accaagtggt | | 1020 |
| cttggttttc acttttttatc acactgtcaa t | | 1051 |

<210> SEQ ID NO 87
<211> LENGTH: 646
<212> TYPE: DNA
<213> ORGANISM: Artificial sequence
<220> FEATURE:
<223> OTHER INFORMATION: Viral

<400> SEQUENCE: 87

| | | |
|---|---|---|
| gacgaaagtg ctatcatgcc tccccgatta tgtgatgttt tctgccctgc tgggcggagc | | 60 |
| attctcgggt tgatataccct tgaatccttc atccttggac ctcccggtcc cccggtctaa | | 120 |
| gccacttgga atatgacagg gttatttttcc aaaattctta tttccactttt catgagttct | | 180 |
| tttcatgaaa agggtatgtg ctgcccctttc ccttcttggag aatccgcgtg gcggtctttc | | 240 |
| cgtctctcga aaaacgtgga tgcagcatgc tggaaacggt gaagaaagta gttctctgtg | | 300 |
| gaaacttaga acagacatcg aaacagctgt agcgacctca cagtagcagc ggaaccccct | | 360 |
| cctggcgaca ggagcctctg cggccaaaag ccccgtggat aagatccact gctgtgagcg | | 420 |
| gtgcaacccc agcaccctgg ttcgatggtt gttctctgtg gaatcagaga atggctttcc | | 480 |
| taagccctcc agtagagaag ccaagaatgt cctgaaggta ccccgcgtgc gggatctgat | | 540 |

-continued

```
caggagacac atcacacgtg ctttacacct gtgcttgtgt ttaaaaattg ttacagcttc    600
cccgaaccaa gtggtcttgg ttttcacttt ttatcacact gtcaat                   646

<210> SEQ ID NO 88
<211> LENGTH: 741
<212> TYPE: DNA
<213> ORGANISM: Artificial sequence
<220> FEATURE:
<223> OTHER INFORMATION: Viral

<400> SEQUENCE: 88
ttaaaacagc ctgtgggttg tacccaccca cagggcccac tgggcgctag cactctggta    60
ctacggtacc tttgtgtgcc tgttttatac ccctcccccct actgaaactt agaagcaatt   120
cataccgatc aatagtgggc gtggcacacc agccgtgtct agatcaagca ctcctgtttc   180
cccggaccga gtatcaatag actgctcacg cggttgaagg agaaaacgtt cgttatccgg   240
ctaactactt cgaaaaacct agtaacacca tgaaagttgc ggagtgtttc actcagcact   300
tccccagtgt agatcaggtc gatgagtcac cgcattcctc acgggcgacc gtggcggtgg   360
ctgcgctggc ggcctgccta tggggtgacc cataggacgc tctaatacag acatggtgcg   420
aagagtctat tgagctagtt agtagtcctc cggcccctga atgcggataa tcctaactgt   480
ggagcagata cccacgaacc agtgggcagt ctgtcgtaac gggcaactcc gcagcggaac   540
cgactacttt gggtgtccgt gtttccttt attccaaatc tggctgctta tggtgacaat   600
tgagagattg ttgccatata gctattggat tggccatccg gtgagcaata gagcgattat   660
ttactctttt gttggatttg tgccattgga tcacaccaca atcatcacac taaagtatat   720
tttactatta aatacagcaa a                                              741

<210> SEQ ID NO 89
<211> LENGTH: 742
<212> TYPE: DNA
<213> ORGANISM: Coxsackievirus

<400> SEQUENCE: 89
ttaaaacagc ctgtgggttg atcccaccca cagggcccat tgggcgctag cactctggta    60
tcacggtacc tttgtgcgcc tgttttatac ccctccccc aactgtaact tagaagtaac   120
acacaccgat caacagtcag cgtggcacac cagccacgtt ttgatcaagc acttctgtta   180
ccccggactg agtatcaata gactgctcac gcggttgaag gagaaagcgt tcgttatccg   240
gccaactact tcgaaaaacc tagtaacacc gtggaagttg cagagtgttt cgctcagcac   300
taccccagtg tagatcaggt cgatgagtca ccgcattccc cacgggcgac cgtggcggtg   360
gctgcgttgg cggcctgccc atggggaaac ccatgggacg ctctaataca gacatggtgc   420
gaagagtcta ttgagctagt tggtagtcct ccggcccctg aatgcggcta atcctaactg   480
cggagcacac accctcaagc cagagggcag tgtgtcgtaa cgggcaactc tgcagcggaa   540
ccgactactt tgggtgtccg tgtttcattt tattcctata ctggctgctt atggtgacaa   600
ttgagagatt gttaccatat agctattgga ttggccatcc ggtgagcaat agagcgatta   660
tttactcttt tgttggattt gtgccattgg atcacaccac aatcatcaca ctaaagtata   720
ttttactatt aaatacagca aa                                             742

<210> SEQ ID NO 90
<211> LENGTH: 710
<212> TYPE: DNA
```

<213> ORGANISM: Coxsackievirus

<400> SEQUENCE: 90

| | | | | | |
|---|---|---|---|---|---|
| ttaa

```
cctctcactt gccoctcttc acacccatta atttaattcg gcctctgtgt tgagcccctt    360
gttgaagtgt ttccctccat cgcgacgtgg ttggagatct aagtcaaccg actccgacga    420
aactaccatc atgcctcccc gattatgtga tgctttctgc cctgctgggt ggagcaccct    480
cgggttgaga aaaccttctt ccttttcct tggactccgg tcccccggtc taagccgctc    540
ggaatatgac agggttattt tcacctcttc ttttctactc cacagtgttc tatactgtgg    600
aagggtatgt gttgcccctt ccttcttgga aacgtgcgc ggcggtcttt ccgtctctcg    660
acaagcgcgc gtgcaacata cagagtaacg cgaagaaagc agttctcggt ctagctctag    720
tgcccacaag aaaacagctg tagcgaccac acaaaggcag cggaaccccc ctcctggtaa    780
caggagcctc tgcggccaaa agccacgtgg ataagatcca cctttgtgtg cggtgcaacc    840
ccagcaccct ggtttcttgg tgacactcta gtgaaccct gaatggcaat ctcaagcgcc    900
tctgtaggga agccaagaat gtccaggagg taccccttcc tctcggaagg gatctgacct    960
ggagacacat cacacgtgct ttacacctgt gcttgtgttt aaaaattgtt acagcttccc   1020
cgaaccaagt ggtcttggtt ttcactttt atcacactgt caat                     1064
```

<210> SEQ ID NO 93
<211> LENGTH: 652
<212> TYPE: DNA
<213> ORGANISM: Saffold virus

<400> SEQUENCE: 93

```
gacgaaacta ccatcatgcc tccccgatta tgtgatgctt tctgccctgc tgggtggagc     60
atcctcgggt tgagaaaacc ttcttccttt ttccttggac cccggtcccc cggtctaagc    120
cgcttggaat aagacagggt tatcttcacc tcttccttct tctacttcat agtgttctat    180
actatgaaag ggtatgtgtc gccccttcct tctttggaga cacgcgcgg cggtctttcc    240
gtctctcgaa aagcgcgtgt gcgacatgca gagaaccgtg aagaaagcag tttgcggact    300
agctttagtg cccacaagaa aacagctgta gcgaccacac aaaggcagcg accccccct    360
cctggcaaca ggagcctctg cggccaaaag ccacgtggat aagatccacc tttgtgtgcg    420
gcacaaccc agtgccctgg tttcttggtg acacttcagt gaaaacgcaa atggcgatct    480
gaagcgcctc tgtaggaaag ccaagaatgt ccaggaggta ccccttccct cgggaaggga    540
tctgacctgg agacacatca catgtgcttt acacctgtgc ttgtgtttaa aaattgtcac    600
agctttccca aaccaagtgg tcttggtttt cactctttaa actgatttca ct           652
```

<210> SEQ ID NO 94
<211> LENGTH: 741
<212> TYPE: DNA
<213> ORGANISM: Echovirus

<400> SEQUENCE: 94

```
ttaaaacagc ctgtgggttg tacccaccca cagggcccac tgggcgctag cactctggta     60
ctacggtacc tttgtgtgcc tgttttatac ccctccccct actgaaactt agaagcaatt    120
cataccgatc aatagtgggc gtggcacacc agccgtgtct agatcaagca ctcctgtttc    180
cccggaccga gtatcaatag actgctcacg cggttgaagg agaaaacgtt cgttatccgg    240
ctaactactt cgaaaaacct agtaacacca tgaaagttgc ggagtgtttc actcagcact    300
tccccagtgt agatcaggtc gatgagtcac cgcattcctc acgggcgacc gtggcggtgg    360
ctgcgctggc ggcctgccta tggggtgacc cataggacgc tctaatacag acatggtgcg    420
```

| | |
|---|---|
| aagagtctat tgagctagtt agtagtcctc cggcccctga atgcggataa tcctaactgt | 480 |
| ggagcagata cccacgaacc agtgggcagt ctgtcgtaac gggcaactcc gcagcggaac | 540 |
| cgactacttt gggtgtccgt gtttcctttt attccaaatc tggctgctta tggtgacaat | 600 |
| tgagagattg ttgccatata gctattggat tggccatccg gtgaataata gagcgataat | 660 |
| atatttgttt gttggattcg tgccacttag tctgaaagtt ttgagaacac tcaactacgt | 720 |
| tttattgctg aagccgccac c | 741 |

<210> SEQ ID NO 95
<211> LENGTH: 742
<212> TYPE: DNA
<213> ORGANISM: Artificial sequence
<220> FEATURE:
<223> OTHER INFORMATION: Viral

<400> SEQUENCE: 95

| | |
|---|---|
| ttaaaacagc ctgtgggttg tacccaccca cagggcccac tgggcgctag cactctggta | 60 |
| ctacggtacc tttgtgtgcc tgttttatac ccctccccct actgaaactt agaagcaatt | 120 |
| cataccgatc aatagtgggc gtggcacacc agccgtgtct agatcaagca cttctgtttc | 180 |
| cccgggaccg agtatcaata gactgctcac gcggttgaag gagaaagcgt tcgttacccg | 240 |
| gccatctact tcgagaagcc tagtaacacc atgaaagttg cagagcgttt cgctcagcac | 300 |
| ttcccccgtg tagatcaggc cgatgagtca ctgcaaccct cacgggcgac cgtggcagtg | 360 |
| gctgcgttgg cggcctgccc atgggattac ccatgggacg ctctaataca gacatggtgt | 420 |
| gaagaaccta ttgagctagt tggtagtcct ccggcccctg aatgcggcta atcctaactg | 480 |
| cggagcatac accctcaatc caggggggcag tgtgtcgtaa cgggcaactc tgcagcggaa | 540 |
| ccgactactt gggtgtccg tgtttccttt tattcttatt atggctgctt atggtgacaa | 600 |
| ttgagagatt gttgccatat agctattgga ttggccatcc ggtgagcaat agagcgatta | 660 |
| tttactcttt tgttggattt gtgccattgg atcacaccac aatcatcaca ctaaagtata | 720 |
| ttttactatt aaatacagca aa | 742 |

<210> SEQ ID NO 96
<211> LENGTH: 668
<212> TYPE: DNA
<213> ORGANISM: Artificial sequence
<220> FEATURE:
<223> OTHER INFORMATION: Viral

<400> SEQUENCE: 96

| | |
|---|---|
| gttttacacc cccttaccct aatagcaact tagaaggctc aatgcatcta cgaccaatag | 60 |
| caggcgcgac ggcaccaagt cgtgtctcgg tcaagcactc ctgtttcccc ggaccgagta | 120 |
| tcaatagact gctcacgcgg ttgaaggaga aaacgttcgt tatccggcta actacttcga | 180 |
| aaaacctagt aacaccatga agttgcggga gtgtttcact cagcacttcc ccagtgtaga | 240 |
| tcaggtcgat gagtcaccgc attcctcacg ggcgaccgtg gcggtggctg cgctggcggc | 300 |
| ctgcctatgg ggtgacccat aggacgctct aatacagaca tggtgcgaag agtctattga | 360 |
| gctagttagt agtcctccgg cccctgaatg cggataatcc taactgtgga gcagataccc | 420 |
| acgaaccagt gggcagtctg tcgtaacggg caactccgca gcggaaccga ctactttggg | 480 |
| tgtccgtgtt tccttttatt ccaaatctgg ctgcttatgg tgacaattga gagattgttg | 540 |
| ccatatagct attggattgg ccatccggtg aataatagag cgataatata tttgtttgtt | 600 |
| ggattcgtgc cacttagtct gaaagttttg agaacactca actacgtttt attgctgaat | 660 |

```
agtgcaag                                                             668

<210> SEQ ID NO 97
<211> LENGTH: 669
<212> TYPE: DNA
<213> ORGANISM: Artificial sequence
<220> FEATURE:
<223> OTHER INFORMATION: Viral

<400> SEQUENCE: 97
gttttacacc cccttaccct aatagcaact tagaaggctc aatgcatcta cgaccaatag    60
caggcgcgac ggcaccaagt cgtgtctcgg tcaagcactt ctgtttcccc gggaccgagt   120
atcaatagac tgctcacgcg gttgaaggag aaagcgttcg ttacccggcc atctacttcg   180
agaagcctag taacaccatg aaagttgcag agcgtttcgc tcagcacttc ccccgtgtag   240
atcaggccga tgagtcactg caaccctcac gggcgaccgt ggcagtggct gcgttggcgg   300
cctgcccatg ggattaccca tgggacgctc taatacagac atggtgtgaa gaacctattg   360
agctagttgg tagtcctccg gccctgaat gcggctaatc ctaactgcgg agcatacacc    420
ctcaatccag ggggcagtgt gtcgtaacgg gcaactctgc agcggaaccg actactttgg   480
gtgtccgtgt ttcctttat tcttattatg gctgcttatg gtgacaattg agagattgtt    540
gccatatagc tattggattg gccatccggt gaataataga gcgataatat atttgtttgt   600
tggattcgtg ccacttagtc tgaaagtttt gagaacactc aactacgttt tattgctgaa   660
tagtgcaag                                                            669

<210> SEQ ID NO 98
<211> LENGTH: 1055
<212> TYPE: DNA
<213> ORGANISM: Theilovirus

<400> SEQUENCE: 98
ttcaaagggg ggccccgggg tcttcgccgc ggacacgcgt tagtgtgttc gcggtgaaga    60
tcaccccggg aaacccctt tggacgcggg acctgcgaca gtgccatccc ccgtctctcc    120
tattccaact acccgaccct aacccagggt ccaggacact ggatcaatac aagtcatccc   180
ctgaatgctg gctaatcaga ggaaagtcag cattttccgg cccaggctaa gagaaacaca   240
ataagttaga atctaaatta atcaccttga cgaattcgca aagataagtc ctccctccct   300
tgccgctcga tcacacccag aactaacaat tcggcctctc gtgacgagcc ccttggtgaa   360
aggacctctt tcaacgcgac gtggttggag attaaaaccg actccgacga aagtgctatc   420
atgcctcccc gattatgtga tgttttctgc cctgctgggc ggagcattct cgggttgata   480
taccttgaat ccttcatcct tggacctccc ggtcccccgg tctaagccac ttggaatatg   540
acagggttat tttccaaaat tcttatttcc actttcatga gttcttttca tgaaaagggt   600
atgtgctgcc ccttccttct tggagaatcc gcgtggcgt ctttccgtct ctcgaaaaac    660
gtggatgcag catgctggaa acggtgaaga aagtagttct ctgtggaaac ttagaacaga   720
catcgaaaca gctgtagcga cctcacagta gcagcggaac cccctcctgg cgacaggagc   780
ctctgcggcc aaaagccccg tggataagat ccactgctgt gagcggtgca accccagcac   840
cctggttcga tggttgttct ctgtggaatc agagaatggc tttcctaagc cctccagtag   900
agaagccaag aatgtcctga aggtaccccg cgtgcgggat ctgatcagaa gaccaattgc   960
cagtgctata cactggtact ttggtttaaa aattgtcaca gcttctccaa accaagtggt  1020
```
cttggttttc tatctttaat aattggttca tgatg 1055

<210> SEQ ID NO 99
<211> LENGTH: 742
<212> TYPE: DNA
<213> ORGANISM: Poliovirus

<400> SEQUENCE: 99
ttaaaacagc tctggggttg tacccacccc agaggcccac gtggcggcta gtactccggt 60
attgcggtac ccttgtacgc ctgttttata ctcccttccc gtaacttaga cgcacaaaac 120
caagttcaat agaagggggt acaaaccagt accaccacga acaagcactt ctgtttcccc 180
ggtgatgtcg tatagactgc ttgcgtggtt gaaagcgacg gatccgttat ccgcttatgt 240
acttcgagaa gcccagtacc acctcggaat cttcgatgcg ttgcgctcag cactcaaccc 300
cagagtgtag cttaggctga tgagtctgga catccctcac cggtgacggt ggtccaggct 360
gcgttggcgg cctacctatg gctaacgcca tgggacgcta gttgtgaaca aggtgtgaat 420
agcctattga gctacataag aatcctccgg cccctgaatg cggctaatcc caacctcgga 480
gcaggtggtc acaaaccagt gattggcctg tcgtaacgcg caagtccgtg gcggaaccga 540
ctactttggg tgtccgtgtt tccttttatt ttattgtggc tgcttatggt gacaatcaca 600
gattgttatc ataaagcgaa ttggattggc catccggtga aagtgagact cattatctat 660
ctgtttgctg gatccgctcc attgagtgtg tttactctaa gtacaatttc aacagttatt 720
tcaatcagac aattgtatca ta 742

<210> SEQ ID NO 100
<211> LENGTH: 669
<212> TYPE: DNA
<213> ORGANISM: Coxsackievirus

<400> SEQUENCE: 100
gttttacacc ccttaccct aatagcaact tagaaggctc aatgcatcta cgaccaatag 60
caggcgcgac ggcaccaagt cgtgtctcgg tcaagcactt ctgtttcccc gggaccgagt 120
atcaatagac tgctcacgcg gttgaaggag aaagcgttcg ttacccggcc atctacttcg 180
agaagcctag taacaccatg aaagttgcag agcgtttcgc tcagcacttc ccccgtgtag 240
atcaggccga tgagtcactg caaccctcac gggcgaccgt ggcagtggct gcgttggcgg 300
cctgcccatg ggattaccca tgggacgctc taatacagac atggtgtgaa gaacctattg 360
agctagttgg tagtcctccg gcccctgaat gcggctaatc ctaactgcgg agcatacacc 420
ctcaatccag gggcagtgt gtcgtaacgg gcaactctgc agcggaaccg actactttgg 480
gtgtccgtgt ttccttttat tcttattatg gctgcttatg gtgacaattg agagattgtt 540
gccatatagc tattggattg gccatccggt gagcaataga gcgattattt actcttttgt 600
tggatttgtg ccattggatc acaccacaat catcacacta aagtatattt tactattaaa 660
tacagcaaa 669

<210> SEQ ID NO 101
<211> LENGTH: 20
<212> TYPE: PRT
<213> ORGANISM: Teschovirus

<400> SEQUENCE: 101

Arg Ala Glu Gly Arg Gly Ser Leu Leu Thr Cys Gly Asp Val Glu Glu
1 5 10 15

Asn Pro Gly Pro
            20

<210> SEQ ID NO 102
<211> LENGTH: 236
<212> TYPE: PRT
<213> ORGANISM: Artificial sequence
<220> FEATURE:
<223> OTHER INFORMATION: Mammalian

<400> SEQUENCE: 102

Met Thr Ala Leu Thr Glu Gly Ala Lys Leu Phe Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
            35                  40                  45

Tyr Ile Cys Thr Thr Gly Asp Leu Pro Val Pro Trp Ala Thr Leu Val
        50                  55                  60

Ser Thr Leu Ser Tyr Gly Val Gln Cys Phe Ala Lys Tyr Pro Ser His
65                  70                  75                  80

Ile Lys Asp Phe Phe Lys Ser Ala Met Pro Glu Gly Tyr Thr Gln Glu
                85                  90                  95

Arg Thr Ile Ser Phe Glu Gly Asp Gly Val Tyr Lys Thr Arg Ala Met
            100                 105                 110

Val Thr Tyr Glu Arg Gly Ser Ile Tyr Asn Arg Val Thr Leu Thr Gly
        115                 120                 125

Glu Asn Phe Lys Lys Asp Gly His Ile Leu Arg Lys Asn Val Ala Phe
130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175

Glu Lys Leu Val Thr Lys Cys Ser Gln Met Asn Arg Pro Leu Ala Gly
            180                 185                 190

Ser Ala Ala Val His Ile Pro Arg Tyr His His Ile Thr Tyr His Thr
        195                 200                 205

Lys Leu Ser Lys Asp Arg Asp Glu Arg Arg Asp His Met Cys Leu Val
    210                 215                 220

Glu Val Val Lys Ala Val Asp Leu Asp Thr Tyr Gln
225                 230                 235

<210> SEQ ID NO 103
<211> LENGTH: 237
<212> TYPE: PRT
<213> ORGANISM: Artificial sequence
<220> FEATURE:
<223> OTHER INFORMATION: Mammalian

<400> SEQUENCE: 103

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Arg Thr Phe Ile Lys Tyr Pro Lys Gly Ile
65                  70                  75                  80

Pro Asp Phe Phe Lys Gln Ser Phe Pro Glu Gly Phe Thr Trp Glu Arg
            85                  90                  95

Val Thr Thr Tyr Glu Asp Gly Gly Val Val Thr Val Met Gln Asp Thr
            100                 105                 110

Ser Leu Glu Asp Gly Cys Leu Val Tyr Asn Val Lys Ile Arg Gly Val
        115                 120                 125

Asn Phe Pro Ser Asn Gly Pro Val Met Gln Lys Lys Thr Leu Gly Trp
130                 135                 140

Glu Ala Asn Thr Glu Met Leu Tyr Pro Ala Asp Gly Gly Leu Glu Gly
145                 150                 155                 160

Arg Ser Asp Met Ala Leu Lys Leu Val Gly Gly Gly His Leu Ser Cys
                165                 170                 175

Ser Phe Val Thr Thr Tyr Arg Ser Lys Lys Pro Ala Lys Asn Leu Lys
            180                 185                 190

Met Pro Gly Ile His Ala Val Asp His Arg Leu Glu Arg Leu Glu Glu
        195                 200                 205

Ser Asp Asn Glu Met Phe Val Val Gln Arg Glu His Ala Val Ala Arg
210                 215                 220

Tyr Cys Asp Leu Pro Ser Lys Leu Gly His Lys Leu Asn
225                 230                 235

<210> SEQ ID NO 104
<211> LENGTH: 721
<212> TYPE: DNA
<213> ORGANISM: Hepatitis B virus

<400> SEQUENCE: 104
aacaggccta ttgattggaa agtttgtcaa cgaattgtgg gtcttttggg gtttgctgcc      60
ccttttacgc aatgtggata tcctgcttta atgcctttat atgcatgtat acaagcaaaa     120
caggctttta ctttctcgcc aacttacaag gcctttctca gtaaacagta tatgaccctt     180
taccccgttg ctcggcaacg gcctggtctg tgccaagtgt ttgctgacgc aaccccact     240 ggttggggct tggccatagg ccatcagcgc atgcgtggaa cctttgtgtc tcctctgccg     300
atccatactg cggaactcct agccgcttgt tttgctcgca gcaggtctgg agcaaacctc     360
atcgggaccg acaattctgt cgtactctcc cgcaagtata catcgtttcc atggctgcta     420
ggctgtgctg ccaactggat cctgcgcggg acgtcctttg tttacgtccc gtcggcgctg     480
aatcccgcgg acgaccccctc ccggggccgc ttggggctct accgcccgct tctccgtctg     540
ccgtaccgtc cgaccacggg gcgcacctct ctttacgcgg actccccgtc tgtgccttct     600
catctgccgg accgtgtgca cttcgcttca cctctgcacg tcgcatggag gccaccgtga     660
acgcccaccg gaacctgccc aaggtcttgc ataagaggac tcttggactt tcagcaatgt     720
c                                                                   721

<210> SEQ ID NO 105
<211> LENGTH: 726
<212> TYPE: DNA
<213> ORGANISM: Hepatitis B virus

<400> SEQUENCE: 105
ataacaggcc tattgattgg aaagtttgtc aacgaattgt gggtcttttg gggtttgctg      60
ccccttttac gcaatgtgga tatcctgctt taatgccttt atatgcatgt atacaagcaa     120

```
aacaggcttt tactttctcg ccaacttaca aggcctttct cagtaaacag tatatgaccc    180 tttacccgt  tgctcggcaa cggcctggtc tgtgccaagt gtttgctgac gcaaccccca    240
ctggttgggg cttggccata ggccatcagc gcatgcgtgg aacctttgtg tctcctctgc    300
cgatccatac tgcggaactc ctagccgctt gttttgctcg cagctggact ggagcaaacc    360
tcatcgggac cgacaattct gtcgtactct cccgcaagta tacatcgttt ccatggctgc    420
taggctgtgc tgccaactgg atcctgcgcg ggacgtcctt tgtttacgtc ccgtcggcgc    480
tgaatcccgc ggacgacccc tcccggggcc gcttggggct ctaccgcccg cttctccgtc    540
tgccgtaccg tccgaccacg gggcgcacct ctctttacgc ggactccccg tctgtgcctt    600
ctcatctgcc ggaccgtgtg cacttcgctt cacctctgca cgtcgcatgg aggccaccgt    660
gaacgcccac cggaacttgc ccaaggtctt gcataagagg actcttggac tttcagcaat    720
gtcatc                                                              726

<210> SEQ ID NO 106
<211> LENGTH: 578
<212> TYPE: DNA
<213> ORGANISM: Spermophilus parryii

<400> SEQUENCE: 106
aacctttaga ttataaaatc tgtgaaaggt taacaggcat tctgaattat gttggtcctt     60
ttactaaatg tggttatgct gctctccttc ctttgtatca agctacttcg cgtacggcat    120
ttgtgttttc ttctctctac cacagctggt tgctgtccct ttatgctgag ttgtggcctg    180
ttgccaggca acgaggcgtg gtgtgctctg tgtctgacgc aaccccctct ggttggggca    240
tttgcaccac ctatcaactc atttccccga cgggcgcttt tgccctgccg atcgccaccg    300
cggacgtcat cgccgcatgc cttgcgcgct gctggacagg cgctcggctg ttaggcactg    360
acaactcggt ggttctttcg ggcaaactga cttcctatcc atggctgctc gcctctgttg    420
ccaactggat tcttcgcggg acgtcgttct gctacgtgcc ttcggcagcg aatccggcgg    480
accttccttc tcgaggcctt ctgccggctc tgcatcccgt gccgactctc cgcttccgtc    540
cgcagctgag tcgcatctcc ctttggcccg cctccccg                            578

<210> SEQ ID NO 107
<211> LENGTH: 657
<212> TYPE: DNA
<213> ORGANISM: Spermophilus parryii

<400> SEQUENCE: 107
gctcggcaac ggcctggtct gtgccaagtg tttgctgacg caaccccac  tggttggggc     60 ttggccatag gccatcagcg catgcgtgga acctttgtgt ctcctctgcc gatccatact    120
gcggaactcc tagccgcttg ttttgctcgc agcaggtctg agcaaacct  catcgggacc    180 gacaattctg tcgtactctc ccgcaagtat acatcgtttc catggctgct aggctgtgct    240
gccaactgga tcctgcgcgg ggccaggcaa cgaggcgtgg tgtgctctgt gtctgacgca    300 accccactg  gttggggcat ttgcaccacc tatcaactca tttccccgac gggcgctttt    360
gccctgccga tcgccaccgc ggacgtcatc gccgcatgcc ttgcgcgctg ctggacaggc    420
gctcggctgt taggcactga caactcggtg gttctttcgg gcaaactgac ttcctatcca    480
tggctgctcg cctctgttgc caactggatt cttcgcggga cgtcgttctg ctacgtccgt    540
tcggcagcga atccggcgga cccgccttct cgaggccttc tgccggctct gcatcccgtg    600
```

-continued

| ccgactctcc gcttccgtcc gcagctgagt cgcatctccc ttcgggccgc ctccccg | 657 |

<210> SEQ ID NO 108
<211> LENGTH: 810
<212> TYPE: DNA
<213> ORGANISM: Homo sapiens

<400> SEQUENCE: 108

| ctgttctcat cacatcatat caaggttata taccatcaat attgccacag atgttactta | 60 |
| gccttttaat atttctctaa tttagtgtat atgcaatgat agttctctga tttctgagat | 120 |
| tgagtttctc atgtgtaatg attatttaga gtttctcttt catctgttca aattttttgtc | 180 |
| tagttttatt ttttactgat ttgtaagact tcttttttata atctgcatat tacaattctc | 240 |
| tttactgggg tgttgcaaat attttctgtc attctatggc ctgacttttc ttaatggttt | 300 |
| tttaattttta aaaataagtc ttaatattca tgcaatctaa ttaacaatct tttctttgtg | 360 |
| gttaggactt tgagtcataa gaattttttc tctacactga agtcatgatg gcatgcttct | 420 |
| atattatttt ctaaaagatt taaagttttg ccttctccat ttagacttat aattcactgg | 480 |
| aatttttttg tgtgtatggt atgacatatg ggttcccttt tattttttac atataaatat | 540 |
| atttccctgt ttttctaaaa aagaaaaaga tcatcatttt cccattgtaa aatgccatat | 600 |
| ttttttcata ggtcacttac atatatcaat gggtctgttt ctgagctcta ctctatttta | 660 |
| tcagcctcac tgtctatccc cacacatctc atgcttgct ctaaatcttg atatttagtg | 720 |
| gaacattctt tcccattttg ttctacaaga atattttttgt tattgtctttt gggctttcta | 780 |
| tatacatttt gaaatgaggt tgacaagtta | 810 |

<210> SEQ ID NO 109
<211> LENGTH: 2168
<212> TYPE: DNA
<213> ORGANISM: Rattus rattus

<400> SEQUENCE: 109

| aagctttaga ctctgggtag aatgttctgt ttcctgtaat ataaaatcat aaagtgatga | 60 |
| tattatcaag tgaaaaggaa atgtggtacc ttaatctttc cacatcaagc caatatcatg | 120 |
| ctgaaggcca gagaatcttt tttgctaaaa aacacaatac agatataatt aatagttatc | 180 |
| atttatgttt gatattaatc atatgaatat aattaatatg ttttattgta tcgattattg | 240 |
| ttgatattaa tgtaattact actaatacat aacaaatata actaatggtt atggctcagt | 300 |
| aactaaggta agatataagc tacactggta aagaaagatc aatattgctt cagagtacac | 360 |
| tgaagtaaat gaataactta accggtctag gttgtcactt atatttatac aacattttaa | 420 |
| gaactaagaa cctctcttct atgcttagta gatgaacaaa atcatgtaat agatgaatga | 480 |
| ggccaggaag tacaaaggtt tacaaaattg ccaagccact ctggggtgat tttatgagta | 540 |
| atgcggcatt tggtagcttg ccttaaagaa tattattgga cattatcaag tgtgtgtgtg | 600 |
| tgtgtgtgtg tgtgtgtgtg tgtgtgtaac tgaactctct tgtagtttca tttttgtttg | 660 |
| aaaaagacat gtatctcatg tagcccaggc tggaatcaaa ctctatcctt ctgtctccac | 720 |
| ctctcaggtt ctgggttcc tggcatgcag cacccaagcc cagctacctc tgtgaaaact | 780 |
| ataacttagt aatcagatcc tggaccattt aaagaatata tatatgta tgtgtgtgtg | 840 |
| tgtgtatata tataatatat acatatgtat gtatatatac atatatatgt atgtgtatat | 900 |
| atgtatgtat agagaggctg actatatata tatatatata tatgaggctg aatatatata | 960 |
| tatatatgaa tacacataca catagtgcca tggcacattc ctttaatctg agctctcagg | 1020 |

```
caaaggcaga ccaatctctg agttgttcaa ggccagtgtg atccatagtc tcagaaatta    1080
tatactgaga cactcctgag gatgttatca catttctagt ttccttatct tactttagga    1140
catgattcca aaaaaagggg ggggggaca cacagtcaat ggtagagtta caagactatg    1200
ccgatgtggt gactcaagaa gagagggctg agggagctga acaggcatg ttcccatgaa     1260 ttccgggcaa gcctaggcta tagagtgaga ccaccatgat ttaaaaaaaa aaaaaaagtg    1320
gcacgcgaga aagtcaacaa tgctttgcat aagtgtttta cctcaaaatc gctgaatagt    1380
tgactagaac aaattaaaac cttgtccaaa gtcaaggcca gtgggatcag ggactccctc    1440
cagtcctgaa gcttctagat ttcccgtccc tcaacagccc gattccggat gagtctggac    1500
tcctccaacg cctcggcggc ttcagctccg cgccactctc cggccggccg catagcggcc    1560
ggcacaccat tccggcccag agaggaaagg aggggcctgg agactcacgc ggcctgggct    1620
gctggccagc cctcgaggcc tccctgcagt cagcttctac ctaataggcc gccgcgcgtg    1680
cacaggggga ccgaccttcc gggacgcgga cgcatcttag agctctcagg agcccgtgcc    1740
tccggcccgc gaccggcgcg cgccccgct agccccgccc cgcgagcat gcgcaccaag      1800 cccacctgcg agtgcgcgcc gccgacgccg acgccgcacg cgccgacgcc tggaggcctg    1860
gcgaggcgcg gccgaggcaa gacccagcgc cctgcggcgc gcggccgccg aagtccgtcc    1920
tcccggtggg gcgacaagcg gcgcagggga ggggacagcc agacaagcag gaagctgcgg    1980
cttaaaaggg cagctcgcgc ccagcccttc ctcccgcagt ccaggcctgc aagctctgat    2040
cttctgtgct cccgccgctc tcgcctcagc ccgccgccat gtaccgccgt ctgggcgaag    2100
tgctgctact gtcccgcgcc gggcccgctg ccctgggctc tgcggctgca gactcagccg    2160
cactgctg                                                             2168

<210> SEQ ID NO 110
<211> LENGTH: 300
<212> TYPE: DNA
<213> ORGANISM: Homo sapiens

<400> SEQUENCE: 110
ggttcccttt tattttttac atataaatat atttccctgt ttttctaaaa aagaaaaaga    60
tcatcatttt cccattgtaa aatgccatat ttttttcata ggtcacttac atatatcaat    120
gggtctgttt ctgagctcta ctctatttta tcagcctcac tgtctatccc cacacatctc    180
atgctttgct ctaaatcttg atatttagtg gaacattctt tcccattttg ttctacaaga    240 atattttgt tattgtcttt gggctttcta tatacatttt gaaatgaggt tgacaagtta     300

<210> SEQ ID NO 111
<211> LENGTH: 155
<212> TYPE: DNA
<213> ORGANISM: Homo sapiens

<400> SEQUENCE: 111
ggcatgcttc tatattattt tctaaaagat ttaaagtttt gccttctcca tttagactta    60
taattcactg gaattttttt gtgtgtatgg tatgacatat gggttccctt ttatttttta    120
catataaata tatttccctg tttttctaaa aaaga                               155

<210> SEQ ID NO 112
<211> LENGTH: 1213
<212> TYPE: DNA
<213> ORGANISM: Homo sapiens
```

<400> SEQUENCE: 112

```
gcgagctcac gggacagcc cccccccaaa gccccagggg atgtaattac gtccctcccc    60
cgctaggggg cagcagcgag ccgcccgggg ctccgctccg gtccggcgct ccccccgcat   120
ccccgagccg gcagcgtgcg gggacagccc gggcacgggg aaggtggcac gggatcgctt   180
tcctctgaac gcttctcgct gctctttgag cctgcagaca cctgggggga tacgggaaa    240
aagctttagg ctgaaagaga gatttagaat gacagaatca tagaacggcc tgggttgcaa   300
aggagcacag tgctcatcca gatccaaccc cctgctatgt gcagggtcat caaccagcag   360
cccaggctgc ccagagccac atccagcctg gccttgaatg cctgcaggga tggggcatcc   420
acagcctcct tgggcaacct gttcagtgcg tcaccaccct ctgggggaaa aactgcctcc   480
tcatatccaa cccaaacctc ccctgtctca gtgtaaagcc attccccctt gtcctatcaa   540
gggggagttt gctgtgacat tgttggtctg gggtgacaca tgtttgccaa ttcagtgcat   600
cacggagagg cagatcttgg ggataaggaa gtgcaggaca gcatggacgt gggacatgct   660
ggtgttgagg gctctgggac actctccaag tcacagcgtt cagaacagcc ttaaggataa   720
gaagatagga tagaaggaca aagagcaagt taaaacccag catggagagg agcacaaaaa   780
ggccacagac actgctggtc cctgtgtctg agcctgcatg tttgatggtg tctggatgca   840
agcagaaggg gtggaagtgc ttgcctggag agatacagct gggtcagtag gactgggaca   900
ggcagctgga gaattgccat gtagatgttc atacaatcgt caaatcatga aggctggaaa   960
agccctccaa gatccccaag accaaccccca acccacccac cgtgcccact ggccatgtcc  1020
ctcagtgcca catccccaca gttcttcatc acctccaggg acggtgaccc cccaccctcc  1080
gtgggcagct gtgccactgc agcaccgctc tttggagaag gtaaatcttg ctaaatccag  1140
cccgaccctc ccctggcaca acgtaaggcc attatctctc atccaactcc aggacggagt  1200
cagtgagaat att                                                      1213
```

<210> SEQ ID NO 113
<211> LENGTH: 246
<212> TYPE: DNA
<213> ORGANISM: Homo sapiens

<400> SEQUENCE: 113

```
gcgagctcac gggacagcc cccccccaaa gccccagggg atgtaattac gtccctcccc    60
cgctaggggg cagcagcgag ccgcccgggg ctccgctccg gtccggcgct ccccccgcat   120
ccccgagccg gcagcgtgcg gggacagccc gggcacgggg aaggtggcac gggatcgctt   180
tcctctgaac gcttctcgct gctctttgag cctgcagaca cctgggggga tacgggaaa    240
aagctt                                                              246
```

<210> SEQ ID NO 114
<211> LENGTH: 19
<212> TYPE: PRT
<213> ORGANISM: Homo sapiens

<400> SEQUENCE: 114

```
Met Glu Leu Gly Leu Cys Trp Val Phe Leu Val Ala Ile Leu Glu Gly
  1               5                  10                  15

Val Gln Cys
```

<210> SEQ ID NO 115
<211> LENGTH: 19
<212> TYPE: PRT

<213> ORGANISM: Homo sapiens

<400> SEQUENCE: 115

```
Met Ala Val Leu Gly Leu Leu Phe Cys Leu Val Thr Phe Pro Ser Cys
1               5                   10                  15
Val Leu Ser
```

<210> SEQ ID NO 116
<211> LENGTH: 258
<212> TYPE: DNA
<213> ORGANISM: Homo sapiens

<400> SEQUENCE: 116

```
caacctttgg agctaagcca gcaatggtag agggaagatt ctgcacgtcc cttccaggcg    60
gcctccccgt caccaccccc cccaacccgc cccgaccgga gctgagagta attcatacaa   120
aaggactcgc ccctgccttg gggaatccca gggaccgtcg ttaaactccc actaacgtag   180
aacccagaga tcgctgcgtt cccgcccccct caccgcccg ctctcgtcat cactgaggtg   240
gagaatagca tgcgtgag                                                 258
```

<210> SEQ ID NO 117
<211> LENGTH: 144
<212> TYPE: DNA
<213> ORGANISM: Simian virus 40

<400> SEQUENCE: 117

```
ggtgtggaaa gtccccaggc tccccagcag gcagaagtat gcaaagcatg catctcaatt    60
agtcagcaac caggtgtgga agtccccag gctccccagc aggcagaagt atgcaaagca   120
tgcatctcaa ttagtcagca acca                                         144
```

<210> SEQ ID NO 118
<211> LENGTH: 102
<212> TYPE: DNA
<213> ORGANISM: adeno-associated virus 2

<400> SEQUENCE: 118

```
ccagctgttg gggtgagtac tccctctcaa aagcgggcat tacttctgcg ctaagattgt    60
cagtttccaa aaacgaggag gatttgatat tcacctggcc cg                     102
```

<210> SEQ ID NO 119
<211> LENGTH: 188
<212> TYPE: DNA
<213> ORGANISM: adeno-associated virus 2

<400> SEQUENCE: 119

```
gtgtggcagg cttgagatcc agctgttggg gtgagtactc cctctcaaaa gcgggcatta    60
cttctgcgct aagattgtca gtttccaaaa acgaggagga tttgatattc acctggcccg   120
atctggccat acacttgagt gacaatgaca tccactttgc ctttctctcc acaggtgtcc   180
actcccag                                                           188
```

<210> SEQ ID NO 120
<211> LENGTH: 318
<212> TYPE: DNA
<213> ORGANISM: Homo sapiens

<400> SEQUENCE: 120

```
ctcactctct tccgcatcgc tgtctgcgag ggccagctgt tgggctcgcg gttgaggaca    60
```

```
aactcttcgc ggtctttcca gtactcttgg atcggaaacc cgtcggcctc cgaacggtac    120
tccgccaccg agggacctga gcgagtccgc atcgaccgga tcggaaaacc tctcgagaaa    180
ggcgtctaac cagtcacagt cgcaaggtag gctgagcacc gtggcgggcg cagcgggtg     240 gcggtcgggt tgtttctgg cggaggtgct gctgatgatg taattaaagt aggcggtctt     300
gagacggcgg atggtcga                                                  318

<210> SEQ ID NO 121
<211> LENGTH: 375
<212> TYPE: DNA
<213> ORGANISM: Bombyx mori

<400> SEQUENCE: 121
ttaacccggc gagcatgagg cagggtatct catacccctgg taaaattttta aagttgtgta    60 ttttataaaa ttttcgtctg acaacactag cgcgctcagt agctggaggc aggagcgtgc    120
gggaggggat agtggcgtga tcgcagtgtg gcacgggaca ccggcgagat attcgtgtgc    180
aaacctgttt cgggtatgtt ataccctgcc tcattgttga cgtatttttt ttatgtaatt    240
tttccgatta ttaatttcaa ctgttttatt ggtatttta tgttatccat tgttcttttt     300
ttatgattta ctgtatcggt tgtctttcgt tcctttagtt gagtttttt ttattatttt     360 cagttttga tcaaa                                                     375

<210> SEQ ID NO 122
<211> LENGTH: 797
<212> TYPE: DNA
<213> ORGANISM: Bombyx mori

<400> SEQUENCE: 122
tcatattttt agtttaaaaa aataattata tgttttataa tgaaaagaat ctcattatct     60
ttcagtatta ggttgattta tattccaaag aataatattt ttgttaaatt gttgattttt    120
gtaaacctct aaatgtttgt tgctaaaatt actgtgtttta agaaaagat taataaataa    180 taataattc ataattaaaa acttctttca ttgaatgcca ttaaataatt cattattta     240 caaaataaga tcaacataat tgagtaaata ataataagaa caatattata gtacaacaaa    300
atatgggtat gtcataccct ttttttttt ttttttttt tttttttcggg tagagggccg    360 aacctcctac gaggtccccg cgcaaaaggg gcgcgcgggg tatgtgagac tcaacgatct    420
gcatggtgtt gtgagcagac cgcgggccca aggattttag agcccaccca ctaaacgact    480
cctctgcact cttacacccg acgtccgatc ccctccgagg tcagaacccg gatgaggtag    540
gggggctacc gcggtcaaca ctacaaccag acggcgcggc tcaccccaag gacgcccagc    600
cgacggagcc ttcgaggcga atcgaaggct ctgaaacgtc ggccgtctcg gtacggcagc    660
ccgtcgggcc gcccagacgg tgccgctggt gtcccggaat accccgctgg accagaacca    720
gcctgccggg tcgggacgcg atacaccgtc gaccggtcgc tctaatcact ccacggcagc    780
gcgctagagt gctggta                                                   797

<210> SEQ ID NO 123
<211> LENGTH: 1014
<212> TYPE: DNA
<213> ORGANISM: Homo sapiens

<400> SEQUENCE: 123
gtcgctgcgc gctgccttcg ccccgtgccc cgctccgccg ccgcctcgcg ccgcccgccc     60
cggctctgac tgaccgcgtt actcccacag gtgagcgggc gggacggccc ttctcctccg    120
```

```
ggctgtaatt agcgcttggt ttaatgacgg cttgtttctt ttctgtggct gcgtgaaagc    180
cttgaggggc tccgggaggg cccttttgtgc ggggggagcg gctcgggggg tgcgtgcgtg    240
tgtgtgtgcg tgggagcgc cgcgtgcggc tccgcgctgc ccggcggctg tgagcgctgc    300
gggcgcggcg cggggctttg tgcgctccgc agtgtgcgcg aggggagcgc ggccgggggc    360
ggtgccccgc ggtgcggggg gggctgcgag gggaacaaag gctgcgtgcg gggtgtgtgc    420
gtgggggggt gagcaggggg tgtgggcgcg tcggtcgggc tgcaaccccc cctgcacccc    480
cctccccgag ttgctgagca cggcccggct tcgggtgcgg ggctccgtac ggggcgtggc    540
gcggggctcg ccgtgccggg cgggggggtgg cggcaggtgg gggtgccggg cggggcgggg    600
ccgcctcggg ccggggaggg ctcggggggag gggcgcggcg gcccccggag cgccggcggc    660
tgtcgaggcg cggcgagccg cagccattgc ctttttatggt aatcgtgcga gagggcgcag    720
ggacttcctt tgtcccaaat ctgtgcggag ccgaaatctg ggaggcgccg ccgcaccccc    780
tctagcgggc gcggggcgaa gcggtgcggc gccggcagga aggaaatggg cggggagggc    840
cttcgtgcgt cgccgcgccg ccgtccccctt ctccctctcc agcctcgggg ctgtccgcgg    900
ggggacggct gccttcgggg gggacggggc agggcggggt tcggcttctg gcgtgtgacc    960
ggcggctcta gagcctctgc taaccatgtt catgccttct tctttttcct acag         1014

<210> SEQ ID NO 124
<211> LENGTH: 14
<212> TYPE: DNA
<213> ORGANISM: Xenopus tropicalis

<400> SEQUENCE: 124
ccytttkmct gcca                                                        14

<210> SEQ ID NO 125
<211> LENGTH: 16
<212> TYPE: DNA
<213> ORGANISM: Argyrogramma agnata

<400> SEQUENCE: 125
ccctagaagc ccaatc                                                      16

<210> SEQ ID NO 126
<211> LENGTH: 17
<212> TYPE: DNA
<213> ORGANISM: Aphis gossypii

<400> SEQUENCE: 126
ccttccagcg ggcgcgc                                                     17

<210> SEQ ID NO 127
<211> LENGTH: 13
<212> TYPE: DNA
<213> ORGANISM: Chilo suppressalis

<400> SEQUENCE: 127
cccagattag cct                                                         13

<210> SEQ ID NO 128
<211> LENGTH: 16
<212> TYPE: DNA
<213> ORGANISM: Heliothis virescens

<400> SEQUENCE: 128
```

```
ccacttaatta ctcgcg                                              16

<210> SEQ ID NO 129
<211> LENGTH: 16
<212> TYPE: DNA
<213> ORGANISM: Pectinophora gossypiella

<400> SEQUENCE: 129
ccctagataa ctaaac                                               16

<210> SEQ ID NO 130
<211> LENGTH: 13
<212> TYPE: DNA
<213> ORGANISM: Anopheles stephensi

<400> SEQUENCE: 130
ccctagaaag ata                                                  13
```

ENHANCED NUCLEIC ACID CONSTRUCTS FOR EUKARYOTIC GENE EXPRESSION

CROSS REFERENCE TO RELATED APPLICATIONS

The present application is a continuation of U.S. application Ser. No. 14/683,121 filed Apr. 9, 2015, which claims the benefit of U.S. Provisional Application No. 61/977,474 filed Apr. 9, 2014; 62/003,397 filed May 27, 2014; 62/046,875 filed Sep. 5, 2014; 62/046,705 filed Sep. 5, 2014; 62/069,656 filed Oct. 28, 2014; and 62/120,522 filed Feb. 25, 2015, each incorporated by reference in its entirety for all purposes.

REFERENCE TO A SEQUENCE LISTING

This application includes sequence listing in a txt file named "479917_SEQLST.txt", created on Jun. 28, 2016 and containing 153,266 bytes, which is hereby incorporated by reference in its entirety for all purposes.

1. FIELD OF THE INVENTION

The field of the present invention relates to configurations of DNA vectors for heterologous gene expression, methods for identifying preferred configurations including those that are able to achieve stable modifications of the genomes of target cells, and the use of transposons and transposases.

2. BACKGROUND OF THE INVENTION

DNA constructs are typically propagated as plasmids. Plasmids are frequently constructed by cloning a first polynucleotide sequence into a vector. The vector generally comprises sequences required for propagation in at least one host cell, but it often also comprises sequences that contribute to the functioning of the first polynucleotide sequence. For example a vector may comprise elements that affect the expression of a polypeptide encoded by the first polynucleotide sequence such as promoters, enhancers, introns, terminators, translational initiation signals, polyadenylation signals, replication elements, RNA processing and export elements, and elements that affect chromatin structure that become operably linked to the first polynucleotide. The process of optimizing a polynucleotide for a specific function often comprises creating a plurality of polynucleotides, cloning them into the same vector to create a first plurality of cloned polynucleotides and measuring a property of some of the cloned polynucleotides.

Because the process of cloning polynucleotides into a single vector is relatively simple, while the process of constructing a vector is more complex and costly, optimization almost always focuses on creating variation in the cloned polynucleotide and very rarely on variations in the vector. Even if the vector sequence is varied, this will typically be done by selecting from a small number of pre-existing vectors rather than by deliberately constructing a new set of vectors. However vectors frequently contain many or even most of the elements that determine the function of the cloned polynucleotide, for example the expression of the polynucleotide in an expression-host. The functional performance of many of these elements may depend on the precise host cell being used, for example some elements that perform well in human cells may perform poorly in rodent cells, the same vector is often used in both.

Furthermore, many available vectors have been constructed by standard restriction site cloning methods and derived from other vectors wherein the functional elements have not been well defined. Consequently many vectors contain "fossil" sequences that are unnecessary for their function but have just been included because of imprecise cloning methods or a lack of understanding of function (for example the fl phage origin of replication, originally incorporated for generation of phagemids which can be found in many vectors that are never used to make phagemids), or they contain sequences that actually compromise function (for example the use of the beta lactamase gene as a selectable marker which exacerbates instability in vectors such as lentiviruses).

Because of the immense size of sequence space, there is no effective way to test all possible permutations of a polymeric biological molecule such as a nucleic acid or protein for a desired property. To test each possible nucleotide base at each position in a vector, rapidly leads to such a large number of molecules to be tested such that no available methods of synthesis or testing are feasible, even for a polymer of modest length. Furthermore, most molecules generated in such a way would lack any measurable level of the desired property. Total sequence space is very large and the functional solutions in this space are sparsely distributed.

There is thus a need in the art for methods to efficiently identify vector components that contribute to performance, and to assess this performance.

Typical methods for introducing DNA into a cell include DNA condensing reagents such as calcium phosphate, polyethylene glycol, lipid-containing reagents such as liposomes, multi-lamellar vesicles as well as virus-mediated strategies. However, such methods can have certain limitations. For example, there are size constraints associated with DNA condensing reagents and virus-mediated strategies. Further, the amount of nucleic acid that can be transfected into a cell is limited in viral strategies. In addition, not all methods facilitate insertion of the delivered nucleic acid into cellular nucleic acid, and while DNA condensing methods and lipid-containing reagents are relatively easy to prepare, the insertion of nucleic acid into viral vectors can be labor intensive. Virus-mediated strategies can be cell-type specific or tissue-type specific, and the use of virus-mediated strategies can create immunologic problems when used in vivo.

Integration of heterologous DNA into a target genome, and the expression levels of genes encoded by the integrated heterologous DNA can be increased by the configuration of DNA elements. The efficiency of integration, the size of the heterologous DNA sequence that can be integrated, and the number of copies of the heterologous DNA sequence that are integrated into each genome can often be further improved by using transposons. Transposons or transposable elements include a short nucleic acid sequence with terminal repeat sequences upstream and downstream. Active transposons can encode enzymes that facilitate the excision and insertion of the nucleic acid into target DNA sequences. A number of transposable elements have been described in the art that facilitate insertion of nucleic acids into the genome of vertebrates. For example, transposable elements discovered from various sources, for example, an engineered transposon from the genome of salmonid fish called sleeping beauty; piggyBac transposon from lepidopteran cells; piggyBac transposon from the bat *Myosis lucifugus*; mariner transposon first discovered in *Drosophila* and; an engineered transposon and transposon inverted repeats from the frog species, *Rana pipiens* called frog prince.

Different transposable elements show different preferences for the genomic sites at which they integrate. For example the piggyBac and piggyBat transposons have a preference for transcriptionally inactive regions. Although this may be an advantage for the "wild" transposon which does not wish to disrupt gene expression in its host and risk killing it, it is a disadvantage for transposons that are being used to maximize gene expression. Thus although a number of transposable elements capable of facilitating insertion of nucleic acids into the eukaryotic genome have been identified in the art, there exists a need for alternative transposable elements and enhanced constructs that facilitate higher expression levels from inserted DNA, either because of higher insertion efficiency or because the genomic insertions are made at more favorable positions within the genome, compared with transposable elements currently described in the art.

3. SUMMARY OF THE INVENTION

We describe novel ways to assess the performance of individual vector elements by analyzing the function of small numbers of vectors. The results of this analysis can then be used to create high performing combinations of the sequence elements. Such maps are used to direct perturbations or modifications of the nucleic acid construct sequences to perturb or modify the activity of the nucleic acid construct in a controlled fashion.

Specific combinations of vector elements are described that contribute to vector performance in mammalian cells, in particular to yielding high levels of expression of polypeptides in either transiently or stably transfected cells. Vector elements include promoters, enhancers, introns, terminators, translational initiation signals, polyadenylation signals, virally derived replication elements, RNA processing and export elements, transposons, transposases and elements that affect chromatin structure.

In some embodiments, heterologous gene expression can be improved when the construct further comprises sequence elements that enhance expression by effects on chromatin structure, or by affecting RNA processing or RNA export including scaffold and matrix attachment regions, introns and post transcriptional responsive elements such as WPRE, HPRE and AGS. In some embodiments, heterologous expression is improved when the construct further comprises sequences that reduce the spread of heterochromatin or the interference between one expression control region and another such as HS4 insulators or their core sequence.

Heterologous gene expression from constructs that stably integrate into the target cell genome can be further improved by incorporating transposon ends: sequence elements that are recognized and transposed by transposases. DNA sequences inserted between a pair of Transposon ends can be excised by a transposase from one DNA molecule and (unless the transposase is integration-deficient) inserted into a second DNA molecule. Two novel transposon-transposase systems are disclosed, one derived from the silkworm *Bombyx mori* and the other from the frog *Xenopus tropicalis*. Each of these comprises sequences that function as transposon ends and that can be used in conjunction with a transposase that recognizes and acts upon those transposon ends, as gene transfer systems for stably introducing nucleic acids into the DNA of a cell. The gene transfer systems of the present invention can be used in methods, for example, but not limited to, heterologous gene expression, gene therapy, insertional mutagenesis, or gene discovery.

In one aspect the invention features a transposon comprising a segment of heterologous DNA flanked by a pair of transposon end sequences or variants, derivatives and fragments of the transposon end sequences such that the transposon retains transposon activity. In one embodiment, the sequence of the transposon ends is derived from the species *Bombyx mori*. In one embodiment, the sequence of the transposon ends is derived from the species *Xenopus tropicalis*.

In some embodiments the invention further comprises a transposase that recognizes the transposon and effects the integration of the heterologous DNA between the transposon ends into the genomic DNA of a target cell. In one embodiment, the transposase has a higher activity for transposon excision compared to activity for transposon integration. In some preferred embodiments, the transposase further comprises a heterologous nuclear localization signal (NLS). In some embodiments, the transposase may further comprise a DNA binding domain. In some embodiments the transposase is encoded in a polynucleotide.

In one embodiment, a polynucleotide encodes a transposase operably linked to a heterologous promoter, wherein the transposase inserts a transposon at the sequence 5'-TTAT-3' within a target polynucleotide. In one embodiment, a polynucleotide encodes a transposase operably linked to a heterologous promoter, wherein the transposase excises a transposon by recognizing the sequence 5'-TTAT-3' adjacent to the transposon inverted terminal repeats. The polynucleotide encoding the transposase is at least 85%, at least 90%, at least 95% or at least 98% identical to SEQ ID NO: 44. In one embodiment the polynucleotide encoding the transposase further encodes a heterologous nuclear localization signal (NLS) expressible fused to the transposase. In one embodiment the polynucleotide encoding the transposase further encodes a DNA binding domain (DBD) expressible as a fusion protein with the transposase. In some embodiments, the transposase is a hyperactive variant of SEQ ID NO: 44. In some embodiments, the transposase is an integration defective variant of SEQ ID NO: 44.

In one embodiment, a polynucleotide encodes a transposase fused to a heterologous NLS and operably linked to a heterologous promoter, wherein the transposase is at least 85%, at least 90%, at least 95% or at least 98% identical to SEQ ID NO: 45. In one embodiment, the polynucleotide encoding the transposase further encodes a DNA binding domain (DBD) expressible as a fusion protein with the transposase. In some embodiments, the transposase is a hyperactive variant of SEQ ID NO:45. In other embodiments, the transposase is an integration defective variant of SEQ ID NO: 45.

In some embodiments, a first polynucleotide comprises a transposon comprising inverted repeats of a piggyBac-like transposon from the species *Xenopus tropicalis* flanking a heterologous polynucleotide, the inverted repeats being flanked by copies of the target sequence 5'-TTAA-3' at each end, such that the transposon can be excised leaving a single copy of the 5'-TTAA-3' target sequence in place of the transposon in the polynucleotide. Some embodiments further comprise a second polynucleotide encoding a transposase such that the transposon, but not the transposase, is excisable from their respective polynucleotides, and integratable into a recipient DNA molecule at a 5'-TTAA-3' target sequence by action of the transposase. In some embodiments the first and second polynucleotides are part of the same molecule, in some embodiments they are different molecules, in some embodiments they are different molecules provided together as part of a kit.

In some embodiments, a first polynucleotide comprises a transposon comprising inverted repeats of a piggyBac-like transposon flanking a heterologous polynucleotide, the inverted repeats being flanked by copies of the target sequence 5'-TTAT-3' at each end, such that the transposon can be excised leaving a single copy of the 5'-TTAT-3' target sequence in place of the transposon in the polynucleotide. Some embodiments further comprise a second polynucleotide encoding a transposase such that the transposon, but not the transposase, is excisable from their respective polynucleotides, and integratable into a recipient DNA molecule at a 5'-TTAT-3' target sequence by action of the transposase. In some embodiments the first and second polynucleotides are part of the same molecule, in some embodiments they are different molecules, in some embodiments they are different molecules provided together as part of a kit. In some embodiments the piggyBac-like transposon is derived from the species Bombyx mori.

In some embodiments a transposon or transposase is modified to increase its integration activity or its excision activity, or to modify its target sequence specificity. This modification may be effected by transfecting into a cell (a) a first polynucleotide comprising a gene encoding a marker whose expression is interrupted by a transposon, and (b) a second polynucleotide encoding a transposase expressible from the polynucleotide, wherein if the transposase has activity for the transposon it transposes the transposon out of the first polynucleotide thereby causing expression of the marker to generate a signal indicating the transposase is active on the transposon. The transposon may have ends comprising SEQ ID NOS. 1 and 2 or a variant of either or both of these having at least 90% sequence identity to SEQ ID NO: 1 or 2, and the transposase has the sequence of SEQ ID NO:44 or a variant showing at least 90% sequence identity thereto. The transposon may have ends comprising SEQ ID NOS. 5 and 6 or a variant of either or both of these having at least 90% sequence identity to SEQ ID NO: 5 or 6, and the transposase has the sequence of SEQ ID NO:45 or a variant showing at least 90% sequence identity thereto.

In one embodiment, a transposon comprises a heterologous polynucleotide inserted between a pair of inverted repeats, where the transposon is capable of transposition by a transposase that is at least 85%, at least 90%, at least 95%, at least 98% identical to SEQ ID NOS: 44. In some preferred embodiments, the transposon is capable of insertion by the transposase at the sequence 5'-TTAT-3' within a target nucleic acid.

In some embodiments, the transposon end comprises at least 16 contiguous nucleotides from SEQ ID NO: 1 and the other transposon end comprises at least 16 contiguous nucleotides from SEQ ID NO: 2. In some embodiments, the transposon end comprises at least 17, at least 18, at least 19, at least 20, at least 22, at least 25, at least 30 contiguous nucleotides from SEQ ID NO: 1 and the other transposon end comprises at least 17, at least 18, at least 19, at least 20, at least 22, at least 25, at least 30 contiguous nucleotides from SEQ ID NO: 2. In some embodiments, each inverted terminal repeat (ITR) is at least 90% identical to SEQ ID NO: 32, in some embodiments, each inverted terminal repeat (ITR) comprises SEQ ID NO: 32. In some embodiments, one transposon end is at least 85%, at least 90%, at least 95%, at least 98% identical to SEQ ID NO: 1 and the other transposon end is at least 85%, at least 90%, at least 95%, at least 98% identical to SEQ ID NO: 2.

In one embodiment, a polynucleotide comprises a transposon comprising inverted terminal repeats of a piggyBac-like transposon flanking a heterologous nucleic acid, the inverted repeats being flanked by copies of a target sequence, where the transposon is capable of transposition by a transposase identical to SEQ NO: 45 fused to a heterologous nuclear localization signal (NLS). In some embodiments, the transposon end comprises at least 14 contiguous nucleotides from SEQ ID NO: 5 or 7 or 9 and the other transposon end comprises at least 14 contiguous nucleotides from SEQ ID NO: 6 or 8.

In some embodiments, the transposon end comprises at least 15, at least 16, at least 17, at least 18, at least 19, at least 20, at least 22, at least 25, at least 30 contiguous nucleotides from SEQ ID NOS: 5 or 7 or 9 and the other transposon end comprises at least 15, at least 16, at least 17, at least 18, at least 19, at least 20, at least 22, at least 25, at least 30 contiguous nucleotides from SEQ ID NOS: 6 or 8. In one embodiment, each transposon inverted terminal repeat (ITR) comprises SEQ ID NO: 42. In one embodiment, one inverted terminal repeat (ITR) comprises SEQ ID NO: 38 and one ITR comprises SEQ ID NO: 41. In one embodiment, one transposon end is at least 90% identical to SEQ ID NO: 5 and the other transposon end is at least 90% identical to SEQ ID NO: 6.

In some embodiments, the heterologous polynucleotide comprises a promoter. In some embodiments the promoter is an EF1a promoter, a CMV promoter, a GAPDH promoter, a Herpes Simplex Virus thymidine kinase (HSV-TK) promoter, an actin promoter, a PGK promoter or an ubiquitin promoter. In some embodiments the heterologous polynucleotide is in a gene transfer vector; in some embodiments, the heterologous polynucleotide is part of the transposon. In some embodiments, the gene transfer vector further comprises a transposon. In some embodiments, the heterologous polynucleotide further comprises a second promoter. The direction of transcription from the first and second promoters may be the same or different. In some embodiments, the promoter is operably linked to at least one or more of: i) an open reading frame; ii) a selectable marker; iii) a counter-selectable marker, iii) a nucleic acid encoding a regulatory protein; iv) a nucleic acid encoding an inhibitory RNA. In some preferred embodiments, the promoter is active in a eukaryotic cell.

In other embodiments, the heterologous polynucleotide comprises one or more sequence elements that increase expression by enhancing RNA processing or export from the nucleus. The RNA processing or export elements are selected from but not limited to WPRE, HPRE (SEQ ID NO: 104-105), SAR (SEQ ID NOS: 108-111), AGS (SEQ ID NOS: 106-107). In other embodiments, the heterologous polynucleotide comprises a pair of insulators. The insulators are selected from but not limited to SEQ ID NOS: 112-113. In some embodiments, the nucleic acid comprising the gene transfer vector further comprises one or more viral replication sequences, In some embodiments, the nucleic acid comprising the transposon further comprises one or more viral replication sequences, such that the replication sequences are not capable of transposition by the transposase. The viral replication sequences may include the SV40ori, SV40 large T antigen, EBVoriP and EBNA.

In some embodiments, the heterologous polynucleotide operably linked to a promoter comprises two open reading frames (ORFs), wherein the two ORFs are linked by coupling elements selected from IRES or CHYSEL. In some embodiments, IRES elements are selected from but not limited to SEQ ID NOS: 58-100. In some embodiments, CHYSEL elements are selected from but not limited to SEQ ID NO: 101. In some embodiments, IRES are at least 80%, at least 85%, at least 90%, at least 95%, at least 98% identical to any of SEQ ID NOS: 58-100. In some embodiments, IRES is selected from picornavirus 5' UTR elements. In some embodiments, IRES have at least 80%, at least 85%, at least 90%, at least 95%, at least 98% identical to picornavirus 5' UI'R elements. In some embodiments, the two open reading frames encode: i) an antibody heavy chain (HC); ii) an antibody light chain (LC). In some embodiments, IRESs are used to control ratios of two, three four or more open reading frames (ORFs). In some embodiments, two or more IRESs control expression levels of three ORFs. The IRESs selected may be the same or different. A kit comprising an expression vector with one or more IRESs selected from SEQ ID NOS: 58-100. A kit comprising a nucleic acid panel of IRES sequences selected from SEQ ID) NOS: 58-100.

A method for modifying the genomic DNA of a cell comprising: a) Introducing into a cell of a target organism: i) a transposase at least 90% identical to SEQ ID NO: 44; and ii) a transposon comprising transposon ends flanking a nucleic acid heterologous to the transposon ends, wherein the transposase inserts the transposon at a sequence 5'-TTAT-3' in the genome of the cell; b) Isolating the cell with the inserted transposon comprising the heterologous nucleic acid. A method for modifying the genomic DNA of a cell comprising: a) Introducing into a cell of a target organism: i) a transposase at least 90% identical to SEQ ID NO: 45; and ii) a transposon comprising transposon ends flanking a nucleic acid heterologous to the transposon ends; b) Isolating the cell with the inserted transposon comprising the heterologous nucleic acid. In some embodiments, the transposase is at least 85%, at least 95%, at least 98% identical to SEQ ID NO: 44. In some embodiments, the transposase is at least 85%, at least 95%, at least 98% identical to SEQ ID NO: 45. The method further comprises removing the heterologous polynucleotide inserted in the genome by treating the cell with a transposase. The transposase is least 85%, at least 95%, at least 98% identical to SEQ ID NO: 44. In some embodiments, the transposase is at least 85%, at least 95%, at least 98% identical to SEQ ID NO: 45. In some embodiments, the transposase is integration deficient. In some embodiments, the transposase is provided as a nucleic acid encoding the transposase, in other embodiments, the transposase is provided as a protein. In some embodiments, the host cell is obtained from a eukaryote; the cell is from a mammal; the cell is a Chinese Hamster ovary (CHO) cell or a Human embryonic kidney (HEK293) cell. A method for producing protein from a cell, the method comprising i) integrating a transposon encoding the heterologous protein and, ii) obtaining protein from the cell. The transposon comprises a heterologous polynucleotide operably linked to a promoter and comprises two open reading frames (ORFs), wherein the two ORFs are linked by coupling elements selected from IRES or CHYSEL. In some embodiments, a method of producing protein from a cell comprises i) introducing a gene transfer vector comprising a heterologous polynucleotide operably linked to a promoter and comprises two open reading frames (ORFs), wherein the two ORFs are linked by coupling elements selected from IRES or CHYSEL and, ii) obtaining protein from a cell. A method for producing an antibody from a cell, the method comprising: i) Integrating a transposon encoding the heterologous protein comprising heavy and light chains of the antibody linked by coupling elements selected from IRES or CHYSEL and, ii) obtaining antibody from the cell. A method for producing an antibody from a cell, the method comprising: i) Introducing a gene transfer vector encoding the heterologous protein comprising heavy and light chains of the antibody linked by coupling elements selected from IRES or CHYSEL and, ii) obtaining antibody from the cell.

Other embodiments are a cell line comprising the transposon as described above; a cell line produced by the method of modifying the genomic DNA of a cell as described above; a cell line created by removing the heterologous DNA inserted in the genome comprising treating the cell with a transposase. Other embodiments include a protein made by any of the methods described above. In some embodiments, the protein is an antibody, an antibody fragment or a derivative thereof. A transgenic animal comprising the transposon and; a pharmaceutical composition comprising the transposon and transposase together with a pharmaceutically acceptable carrier, adjuvant or vehicle.

In one embodiment, the transposon nucleic acid sequence comprises a sequence selected from SEQ ID NOS: 1-29. In one embodiment, the transposase nucleic acid sequence encodes an amino acid sequence selected from SEQ ID NOS: 43-56.

In one embodiment, the transposon is capable of inserting into the DNA of a cell.

In other embodiments, the transposon of the above embodiments further comprises a nucleic acid encoding a selectable marker, for example a gene encoding one of glutamine synthase, dihydrofolate reductase, a protein conferring resistance to puromycin, neomycin, hygromycin, zeocin or blasticidin.

In some embodiments, the transposon is inserted in a plasmid. In one embodiment, the transposon further comprises an open reading frame. It is expressly contemplated that the transposon may comprise combinations of any of the sequence elements described above, including promoters, enhancers, introns, terminators, translational initiation signals, polyadenylation signals, RNA processing and export elements and elements that affect chromatin structure. It is further contemplated that plasmids into which transposons are inserted may also comprise combinations of any transposases or virally derived replication elements.

In one embodiment, the invention features a gene transfer system comprising a transposon according to any of the above embodiments; and a *Bombyx mori* transposase. In a further embodiment, the transposase comprises an amino acid sequence corresponding to SEQ ID NOS: 43-44. In one embodiment, the invention features a gene transfer system comprising a transposon according to any of the above embodiments; and a *Xenopus tropicalis* transposase. In a further embodiment, the transposase comprises an amino acid sequence corresponding to SEQ ID NOS: 45-46. In some embodiments, the transposon and transposase are on separate plasmids; in some embodiments the transposon and transposase are on the same plasmid.

In some preferred embodiments, the gene transfer system comprising a transposon and a transposase further comprises IRES sequences (for example those described in SEQ ID NOS: 58-100 such that the relative expression of two open reading frames (ORFs) expressed from a single promoter can be specified based on IRES strength. In a further embodiment, the ORFs encode heavy and light chains of an antibody. In some embodiments, IRES sequences are used as enhancer elements. In some embodiments the IRES works well in combination with a secretion signal. This is an important aspect for secretion of the expressed polypeptides and is of particular importance for secreted expression of heavy and light chains of an antibody in stably transfected Chinese hamster ovary (CHO) and Human embryonic kidney (HEK293) cells.

In some embodiments, the transposon is inserted into the genome of a cell. In some embodiments, the cell is chosen from Chinese hamster ovary (CHO) or Human Embryonic kidney (HEK293) cell lines. In another embodiment, the cell is obtained from an animal. In another embodiment, the cell is from a vertebrate or invertebrate. In a further embodiment, the vertebrate is a mammal. In other embodiments, the present invention also features a cell comprising a transposon of any of the above-described embodiments.

In other embodiments, the present invention features a pharmaceutical composition comprising a *Bombyx mori* transposase and a transposon recognized and transposed by the transposase, together with a pharmaceutically acceptable carrier, adjuvant or vehicle. In other embodiments, the present invention features a pharmaceutical composition comprising a *Xenopus tropicalis* transposase and a transposon recognized and transposed by the transposase, together with a pharmaceutically acceptable carrier, adjuvant or vehicle.

The present invention also features a method for introducing exogenous DNA into a cell comprising contacting a cell with the gene transfer system of the above-described embodiments, thereby introducing exogenous DNA into a cell. In some embodiments, the cell is a eukaryotic cell. In some other embodiments, the cell is from a mammal. In some embodiments, the cell is a stem cell. In other embodiments, the cell is a Chinese hamster ovary (CHO) cell or Human embryonic kidney (HEK293) cell.

The present invention also includes a method for producing protein using the method for introducing exogenous DNA into a cell as described herein above. In some preferred embodiments, the protein is an antibody, an antibody fragment, or a derivative thereof. Other embodiments of the present invention include a cell line comprising a *Bombyx mori* transposon or a *Xenopus tropicalis* transposon; a transgenic animal comprising a *Bombyx mori* transposon or a *Xenopus tropicalis* transposon; or a cell line produced by the method described herein above.

In another embodiment, the present invention features a kit comprising a *Bombyx mori* transposon and a *Bombyx mori* transposase or a *Xenopus tropicalis* transposon and a *Xenopus tropicalis* transposase; and; instructions for introducing DNA into a cell. In another embodiment, the present invention also features a kit comprising: a *Bombyx mori* transposase or a *Xenopus tropicalis* transposase that is integration defective, and instructions for use.

The present invention also includes methods for producing two or more polypeptides within the same cell. In some embodiments this is achieved using translational coupling elements such as IRES elements. One embodiment includes a method for expressing a plurality of polypeptides from a single construct comprising a) a eukaryotic promoter and a plurality of polynucleotides encoding a plurality of polypeptides b) an IRES sequence linking each of the plurality of polynucleotides wherein the plurality of polynucleotide-IRES-polynucleotide are operably linked to a single eukaryotic promoter such that on insertion into a host cell, a plurality of polypeptides are expressed and expression level of each of the polypeptides is determined by the IRES sequence. The method wherein 2, 3, 4, 5, 6 or more IRES sequences link the plurality of polynucleotides is another embodiment. IRES sequences selected may be the same or different sequences.

Some embodiments comprise a polynucleotide comprising: a eukaryotic promoter operably linked to a first polynucleotide encoding a first polypeptide, an IRES sequence and a second polynucleotide encoding a second polypeptide wherein i) the first polynucleotide, IRES and second polynucleotide are operably linked to a single eukaryotic promoter such that on insertion into a host cell, both polypeptides are expressed, ii) the two polypeptide interact in the formation of a product such that the ratio of expression of the two polypeptides determines the amount of product formed, iii) the relative expression level of the polynucleotides is determined by the IRES sequence, iv) expression of the two polypeptides are operably linked to a regulatory sequence selected from SEQ ID NOS: 104-111. IRES elements selected include hybrid elements selected from SEQ ID NOS: 73-91, 95-97. In on embodiment, the polynucleotide comprises sequences encoding heavy chain and light chain of an antibody. The polynucleotide further comprises regulatory elements, wherein the expression of the two polypeptides is operably linked to a regulatory sequence selected from HPRE (SEQ ID NOS: 104-105), AGS (SEQ ID NOS: 106-107), SAR (108-111).

In some embodiments, a polynucleotide comprises an IRES element selected from SEQ ID NOS: 74-77, 81-91, 93-98, the IRES element is flanked by sequences encoding a heavy chain and light chain of an antibody operably linked to a single eukaryotic promoter. In other embodiments, the IRES element is flanked by sequences encoding a heavy chain or a light chain of an antibody and a reporter protein operably linked to a single eukaryotic promoter. The polynucleotide may comprise 2, 3, 4, 5, 6 or more IRES sequences. The IRES sequences are the same or different sequences. In some embodiments, a polynucleotide comprises an IRES element and regulatory sequences selected from HPRE (SEQ ID NOS: 104-105), AGS (SEQ ID NOS: 106-107), SAR (108-111). The IRES sequence is selected from SEQ ID NOS: 58-100. In some embodiments, the polynucleotide further comprising sequences encoding heavy chain and light chain of an antibody linked by an IRES sequence operably linked to a single eukaryotic promoter. In some embodiments, the polynucleotide may comprise 2, 3, 4, 5, 6 or more IRES sequences. Some embodiments comprise a polynucleotide comprising a first polynucleotide encoding a first polypeptide, an IRES sequence and a second polynucleotide encoding a second polypeptide operably linked to a single eukaryotic promoter, wherein the IRES sequence is selected from one of SEQ ID NOS: 58-100. In some embodiments, the IRES sequence is selected from SEQ ID NOS: 73-91, 95-97.

Some embodiments comprise a polynucleotide comprising sequences encoding heavy and light chains of an antibody linked by an IRES element operably linked to transcription control sequences. In some embodiments the transcription control sequences are flanked by insulators. The transcriptional control sequences are one or more sequences selected from promoters, enhancers, introns. 5'UTRs. In some embodiments introns are selected from SEQ ID NOS: 119, 123) and enhancers are selected from SEQ ID NOS: 116-119. In some embodiments, the polynucleotide further comprises secretion peptides at the amino termini of the polypeptides. In some embodiments, the IRES sequence is operably linked to a secretion peptide (SEQ ID NOS: 114-115). In some embodiments, the IRES sequence is one of SEQ ID NOS: 58-59. In some embodiments, the EF1a promoter is flanked by insulators (SEQ ID NOS: 112-113). In some embodiments, the polynucleotide further comprises sequences that promote integration into a host cell. In some embodiments, the polynucleotide further comprises RNA export elements. In some embodiments, RNA export elements are selected from WPRE. HPRE (SEQ ID NO: 104-105), SAR (SEQ ID NOS: 108-111). AGS (SEQ ID NOS: 106-107). In one embodiment, the polypeptide comprising transcriptional control elements comprise a CMV enhancer, an EF1a promoter, a hybrid intron (SEQ ID NO: 119), further comprising insulators (SEQ ID NOS: 112-113). In one embodiment, the polypeptide comprising transcriptional control elements comprise a CMV enhancer, an actin promoter, a hybrid actin intron (SEQ ID NO: 123) sequences and SV40 enhancer (SEQ ID NO: 117) sequence. In one embodiment, the polypeptide comprising transcriptional control elements comprise a CMV enhancer, a GAPDH promoter, a CMVc intron sequences and SV40 enhancer sequence. In one embodiment, the polypeptide comprising transcriptional control elements comprise a CMV enhancer, a CMV promoter, a SV40 enhancer sequences. In some embodiments, the polynucleotide further comprises comprising viral replication sequences selected from the SV40ori. SV40 large T antigen, EBVoriP and EBNA. Other embodiments comprise a host cell with the polynucleotide of the above embodiments, wherein the host cell is a eukaryotic cell, is from a mammal. A protein made by the methods described herein is another embodiment. In some embodiments, the protein is an antibody, an antibody fragment or a derivative thereof. Some embodiments comprise a pharmaceutical composition comprising the polynucleotides of the above embodiments.

Additional embodiments comprise a polynucleotide comprising sequences encoding heavy chain and light chain of an antibody, each sequence operably linked to transcriptional control sequences. In some embodiments, the two transcriptional control sequences comprise enhancers, promoters and introns. In some embodiments, the transcriptional control sequences are combinations of a CMV enhancer, an actin promoter, hybrid intron (SEQ ID NO: 123) and EF1a promoter and intron EF1a. In some embodiments, the transcriptional control sequences are combinations of a CMV enhancer, an actin promoter, hybrid intron (SEQ ID NO: 123) and CMV promoter with intron CMVc. In some embodiments, the polynucleotide further comprises polyadenylation signals at the 3'-end of the sequence encoding the polypeptide. In some embodiments, each promoter and polyadenylation signal is flanked by insulators. In some embodiments, the polynucleotide further comprises viral replication sequences selected from SV40 ori, SV40 large T antigen, EBV oriP, EBNA.

Other embodiments will be evident to those of ordinary skill in the art from the teachings contained herein in combination with what is known to the art.

4. BRIEF DESCRIPTION OF THE DRAWINGS

FIG. 1: shows a transposon comprising a heterologous polynucleotide between flanking transposon ends which each comprise inverted terminal repeats (ITRs) (shown by black and grey arrowheads). The transposon ITRs are adjacent to a direct repeat of its target sequence. For the *Trichoplusia ni* piggyBac and the *Xenopus* transposons of the invention, this target sequence is 5'-TTAA-3'. For the *Bombyx* transposons of the invention this target sequence is 5'-TTAT-3'. The target sequence here is therefore represented as 5'-TAW-3', where the W is A or T. When the transposon is transposed by the action of a transposase, it is excised from one DNA molecule where it leaves a single copy of the target sequence, and integrated into a second DNA molecule where it duplicates the target sequence such that the transposon remains flanked by the target sequence. The transposase may be provided either in cis (encoded in the same vector) or trans (encoded in a separate polynucleotide or as protein). When the transposase excises the transposon, the original sequence 5'-TAW-3' is perfectly restored.

Figure 2:
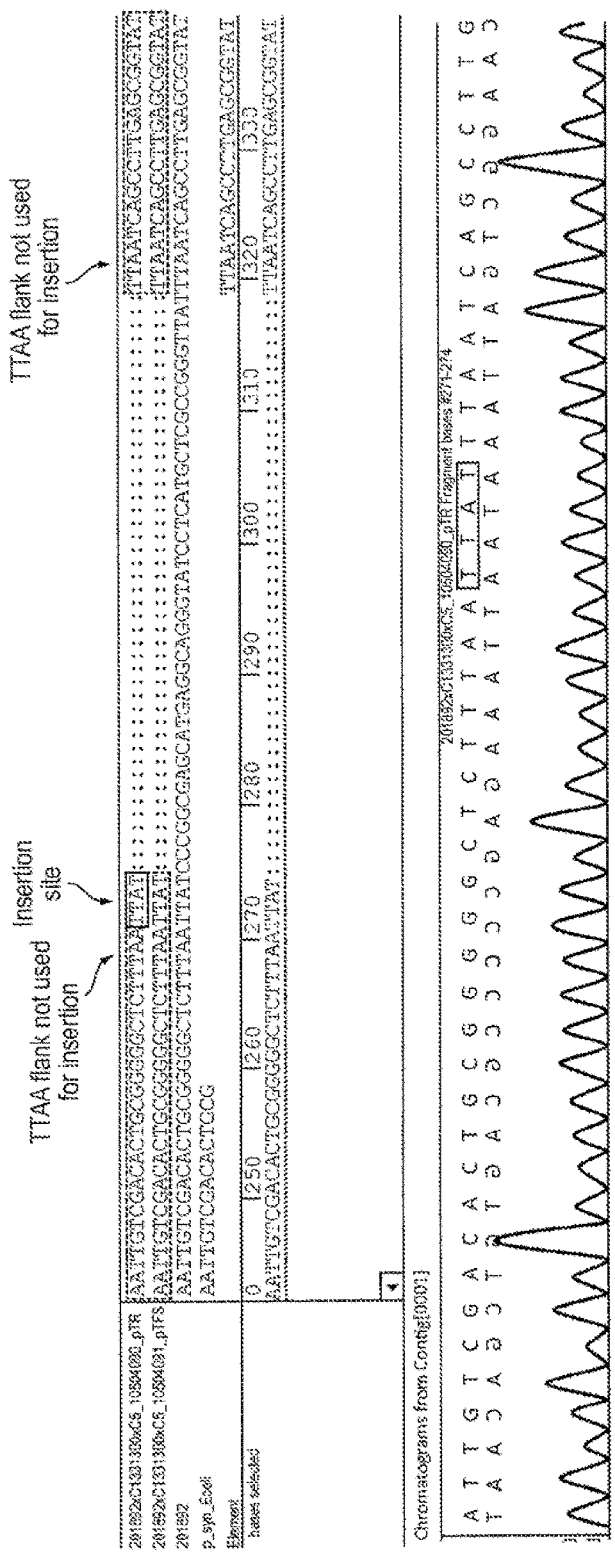

FIG. 2: shows sequencing results with the 5'-TTAT-3' target sequence left after integration and excision (shown by arrow) by a transposase from *Bombyx mori*. Chinese hamster ovary (CHO) cells were co-transfected with a transposon comprising transposon ends (SEQ ID NOS: 1 and 2) and a construct encoding a transposase (SEQ ID NO: 44) from *Bombyx mori*; cells were grown for 14 days post puromycin selection as described in Example 6.1.1. DNA was miniprepped from cell lysates and PCRed under standard cycling conditions with a 5 second extension time using nested amplification primers flanking the inverted terminal repeats (ITRs). PCR product was cloned into a cloning vector and transformed into *E. coli*. 16 clones from each of the amplified PCR products were picked and sequenced. All 16 clones showed a single 5'-TTAT-3' scar sequence showing the integration target sequence to be 5'-TTAT-3'.

Figure 3:
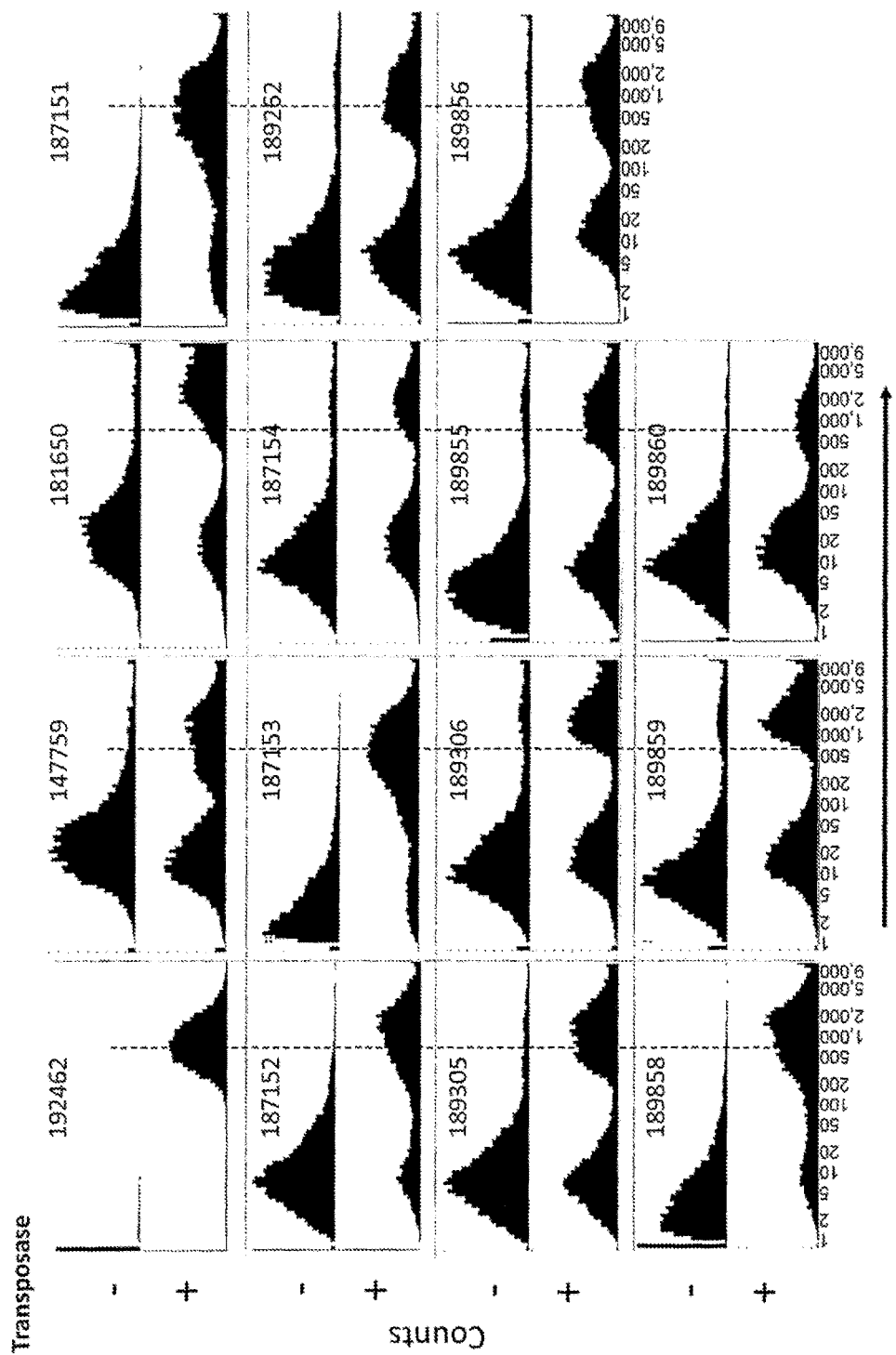

FIG. 3: shows FACS data for stably transfected Chinese hamster ovary (CHO) cell populations expressing DasherGFP (SEQ ID NO: 102). CHO cells were transfected with gene transfer vectors comprising *Xenopus tropicalis* transposon ends (SEQ ID NOS: 5, 6) flanking a heterologous nucleic acid encoding DasherGFP. The gene transfer vectors comprised different combinations of control elements including promoters and insulator sequences. Co-transfections with an expression vector encoding transposase (SEQ ID NO: 45) were done in parallel. Vectors with *Trichoplusia ni* piggyBac transposon ends (SEQ ID NOS: 30, 31) and hyperactive *Trichoplusia ni* piggyBac transposase (SEQ ID NO: 57) were tested under the same conditions. Cells were grown as described in Example 6.2. DasherGFP expressing cell populations are shown for CHO cells transfected in the absence of transposase (top panel) and after co-transfection with transposase (bottom panel).

Figure 4:
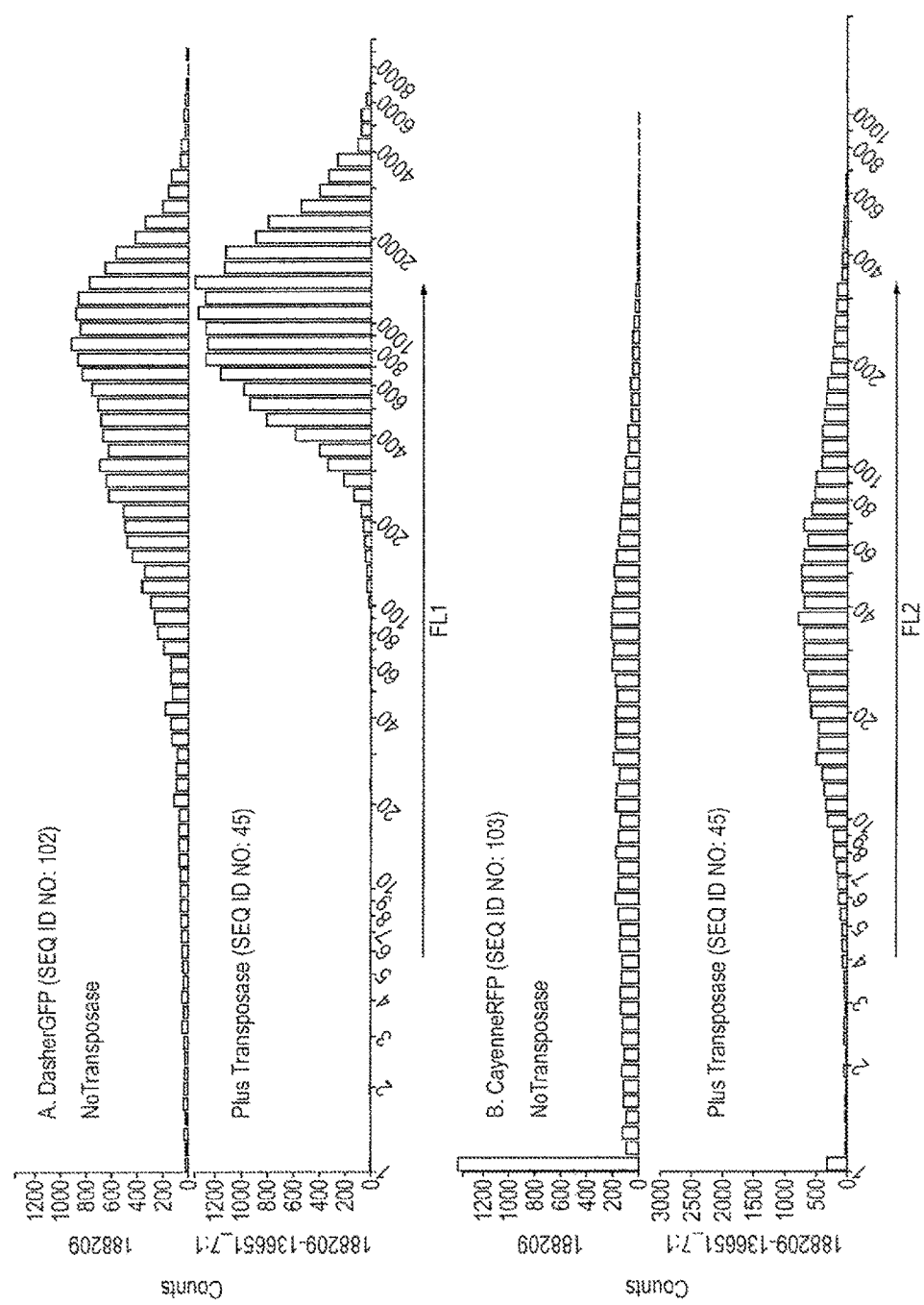

FIG. 4: shows FACS data for stably transfected Chinese hamster ovary (CHO) cell populations expressing DasherGFP (SEQ ID NO: 102) and CayenneRFP (SEQ ID NO: 103) linked by an IRES element (SEQ ID NO: 59) and operably linked to a single EF1a promoter. CHO cells were transfected with a gene transfer vector with configuration as shown in Table 13 lines 3 and 4. Co-transfections with an expression vector encoding a transposase (SEQ ID NO: 45) were done in parallel. Cells were grown as described in Example 6.2. DasherGFP expressing cell populations are shown (Panel A) for CHO cells transfected in the absence of transposase (top panel) and with co-transfection with transposase (bottom panel). CayenneRFP expressing cell populations are shown (Panel B) for CHO cells transfected in the absence of transposase (top panel) and after co-transfection with transposase (bottom panel).

Figure 5:
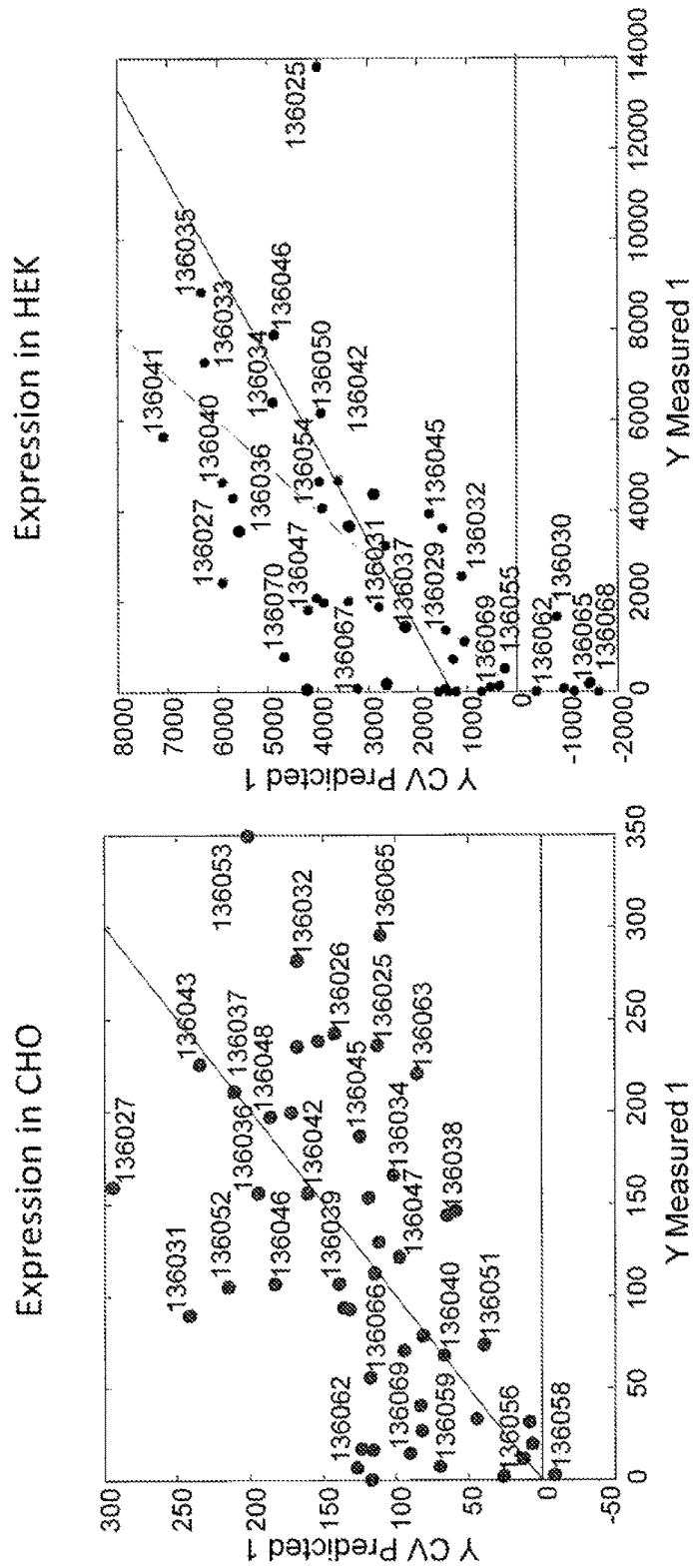

FIG. 5: shows two graphs in which the measured values of expression of DasherGFP are shown on the X-axis, where DasherGFP is expressed from vectors with configurations shown in Table 15, expression data is from Table 19. The Y-axis of each graph shows the value predicted for DasherGFP expression from these vectors, using a model constructed, using partial least squares regression, from the sequence data in Table 15 and the expression properties shown in Table 19.

5. DETAILED DESCRIPTION OF THE INVENTION

5.1 Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each sub combination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, N Y, 1991, provide one of skill with a general dictionary of many of the terms used in this invention. Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (for example, peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (for example, methyl phosphonates, phosphotriesters, phosphoramidates, carbamates, or the like) with negatively charged linkages (for example, phosphorothioates, phosphorodithioates, or the like), and with positively charged linkages (for example, aminoalkylphosphoramidates, aminoalkylphosphotriesters), those containing pendant moieties, such as, for example, proteins (including enzymes (for example, nucleases), toxins, antibodies, signal peptides, poly-L-lysine, or the like), those with intercalators (for example, acridine, psoralen, or the like), those containing chelates (of, for example, metals, radioactive metals, boron, oxidative metals, or the like), those containing alkylators, those with modified linkages (for example, alpha anomeric nucleic acids, or the like), as well as unmodified forms of the polynucleotide or oligonucleotide.

The terms "polynucleotide," "oligonucleotide," "nucleic acid" and "nucleic acid molecule" and "gene" refer to the entire sequence or gene or a fragment thereof. The fragment thereof can be a functional fragment. Where the polynucleotides are to be used to express encoded proteins, nucleotides that can perform that function or which can be modified (for example, reverse transcribed) to perform that function are used. Where the polynucleotides are to be used in a scheme that requires that a complementary strand be formed to a given polynucleotide, nucleotides are used which permit such formation.

As used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, for example, where one or more of the hydroxyl groups are replaced with halogen, aliphatic groups, or is functionalized as ethers, amines, or the like. The term "nucleotidic unit" is intended to encompass nucleosides and nucleotides.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH$_2$, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other non-natural base pairs may be synthesized by the method described in Piccirilli et al., 1990, Nature 343:33-37, hereby incorporated by reference in its entirety, for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 2 to 20 nucleotides in length to a full length genomic sequence of thousands or hundreds of thousands of base pairs.

The term "vector" or "DNA vector" or "gene transfer vector" refers to a polynucleotide sequence that is used to perform a "carrying" function for another polynucleotide. For example vectors are often used to allow a polynucleotide to be propagated within a living cell, or to allow a polynucleotide to be packaged for delivery into a cell, or to allow a polynucleotide to be integrated into the genomic DNA of a cell. A vector may further comprise additional functional elements, for example it may comprise a transposon.

A "gene transfer system" comprises a vector or gene transfer vector, or a polynucleotide cloned into a vector. A gene transfer system may also comprise other features to facilitate the process of gene transfer. For example a gene transfer system may comprise a vector and a lipid or viral packaging mix for enabling a first polynucleotide to enter a cell, or it may comprise a vector that includes a transposon and a second polynucleotide sequence encoding a transposase to enhance productive genomic integration of the transposon.

The term "host" means any prokaryotic or eukaryotic organism that can be a recipient of a nucleic acid. A "host," as the term is used herein, includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). As used herein, the terms "host," "host cell," "host system" and "expression host" be used interchangeably.

The term "expression construct" means any double-stranded DNA or double-stranded RNA designed to transcribe an RNA, for example, a construct that contains at least one promoter which is or may be operably linked to a downstream gene, coding region, or polynucleotide sequence (for example, a cDNA or genomic DNA fragment that encodes a polypeptide or protein, or an RNA effector molecule, for example, an antisense RNA, triplex-forming RNA, ribozyme, an artificially selected high affinity RNA ligand (aptamer), a double-stranded RNA, for example, an RNA molecule comprising a stem-loop or hairpin dsRNA, or a bi-finger or multi-finger dsRNA or a microRNA, or any RNA). An "expression construct" includes a double-stranded DNA or RNA comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression construct into a recipient cell allows the cell to express an RNA effector molecule, polypeptide, or protein encoded by the expression construct. An expression construct may be a genetically engineered plasmid, virus, recombinant virus, or an artificial chromosome derived from, for example, a bacteriophage, adenovirus, adeno-associated virus, retrovirus, lentivirus, poxvirus, or herpesvirus, or further embodiments described under "expression vector" below. An expression construct can be replicated in a living cell, or it can be made synthetically. For purposes of this application, the terms "expression construct", "expression vector", "vector", and "plasmid" are used interchangeably to demonstrate the application of the invention in a general, illustrative sense, and are not intended to limit the invention to a particular type of expression construct.

The term "expression vector" or "expression construct" means a DNA construct that contains at least one promoter which is or may be operably linked to a downstream gene, coding region, or polynucleotide sequence to be transcribed (for example, a cDNA or genomic DNA fragment that encodes a protein, optionally, operably linked to sequence lying outside a coding region, an antisense RNA coding region, or RNA sequences lying outside a coding region). An expression vector or expression construct may also be a DNA construct comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression vector into a recipient cell allows the cell to express RNA encoded by the expression vector. An expression vector may be a genetically engineered plasmid, virus, transposon or artificial chromosome derived from, for example, a bacteriophage, adenovirus, adeno-associated virus, retrovirus, poxvirus, or herpesvirus. Such expression vectors can include sequences from bacteria, viruses or phages. Such vectors include chromosomal, episomal and virus-derived vectors, for example, vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. Thus, one exemplary vector is a double-stranded DNA phage vector. Another exemplary vector is a double-stranded DNA viral vector. In one aspect, the invention relates to expression vectors, plasmids, and constructs as described herein, which are isolated and purified so as to be useful for any of a variety of applications, for example, as a reagent for scientific research, for human and/or veterinary use for therapeutic and/or prophylactic pharmaceutical purposes.

An 'isolated' polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, that is, it is essentially free from any other polypeptide or polynucleotide and associated cellular products or other impurities.

The term "Scar" refers to extra DNA sequences that are left as part of a polynucleotide construct that are an unavoidable consequence of the construction method rather than being incorporated because of their desirable functional properties. For example recombinases, integrases and restriction endonucleases often have recognition sequences that remain within the sequence of a polynucleotide that is constructed using the action of the recombinases, integrases and restriction endonucleases. The term "Scar Size" refers to the length of the extra DNA sequences. For example a scar size of 34 base pairs is left in a construct with a recognition sequence for Cre recombinase, a scar size of 25 base pairs is added on when attB integrase is used. Scars can interfere with the functions of other sequence elements within the construct.

The term "overhang" or "DNA overhang" refers to the single-stranded portion at the end of a double-stranded DNA molecule. Complementary overhangs are those which will base-pair with each other.

The term "Selectable marker" refers to a polynucleotide segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

The term "Counter Selectable Marker" refers to a polynucleotide sequence that confers a selective disadvantage upon a host cell. Examples of counter-selectable markers include sacB, rpsL, tetAR, pheS, thyA, gata-1, ccdB, kid and barnase (Bernard, 1995, Journal/Gene, 162: 159-160; Bernard et al., 1994. Journal/Gene, 148: 71-74; Gabant et al., 1997, Journal/Biotechniques, 23: 938-941; Gababt et al., 1998, Journal/Gene, 207: 87-92; Gababt et al., 2000, Journal/Biotechniques, 28: 784-788; Galvao and de Lorenzo, 2005, Journal/Appl Environ Microbiol, 71: 883-892; Hartzog et al., 2005, Journal/Yeat, 22:789-798; Knipfer et al., 1997, Journal/Plasmid, 37: 129-140; Reyrat et al., 1998, Journal/Infect Immun, 66: 4011-4017; Soderholm et al., 2001, Journal/Biotechniques, 31: 306-310, 312; Tamura et al., 2005, Journal Appl Environ Microbiol, 71: 587-590; Yazynin et al., 1999, Journal/FEBS Lett, 452: 351-354). Counter-selectable markers often confer their selective disadvantage in specific contexts. For example they may confer sensitivity to compounds that can be added to the environment of the host cell, or they may kill a host with one genotype but not kill a host with a different genotype. Conditions which do not confer a selective disadvantage upon a cell carrying a counter-selectable marker are described as "permissive". Conditions which do confer a selective disadvantage upon a cell carrying a counter-selectable marker are described as "restrictive".

The term "Recognition sequence" refers to particular DNA sequences which are recognized (and bound by) a protein, DNA, or RNA molecule, including a restriction endonuclease, a modification methylase, and a recombinase. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521-527 (1994). Other examples of recognition sequences are the attB, attP, attL, and attR sequences which are recognized by the integrase of bacteriophage lambda. AttB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, Current Opinion in Biotechnology 3:699-707 (1993). Such sites are also engineered according to the present invention to enhance methods and products.

The term "Recombinase" refers to an enzyme which catalyzes the exchange of DNA segments at specific recombination sites.

The term "Recombinational Cloning" refers to a method described herein, whereby segments of DNA molecules are exchanged, inserted, replaced, substituted or modified, in vitro or in vivo.

The term "Recombination proteins" includes excisive or integrative proteins, enzymes, co-factors or associated proteins that are involved in recombination reactions involving one or more recombination sites. See, Landy (1994), infra.

The term "expression system" refers to any in vivo or in vitro biological system that is used to produce one or more polypeptide encoded by a polynucleotide.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well known in the art for calculating these temperatures.

The term "translation" refers to the process by which a polypeptide is synthesized by a ribosome 'reading' the sequence of a polynucleotide.

The term "selectable protein" refers to a protein that provides a physical, chemical or biological method for selecting cells on the basis of how much of the selectable protein is expressed.

The term "coupling element" refers to a DNA sequence that allows the expression of a first polypeptide to be linked to the expression of a second polypeptide. Internal ribosome binding sites (IRES elements) and cis-acting hydrolase elements (CHYSEL elements) are examples of coupling elements.

The phrase "predetermined time period" refers to a specified amount of time. A "predetermined period of time" can be on the order of seconds, minutes, hours, days, weeks, or months. For example, a "predetermined time period" can be between 1 and 59 minutes, or any increment between 1 and 2 hours, or any increment between 2 and 4 hours, or any increment between 4 and 6 hours, or any increment between 6 and 12 hours, or any increment between 12 and 24 hours, or any increment between 1 day and 2 days, or any increment between 2 days and 4 days, and any increment between 4 days and 7 days, and any increment between 1 week and 4 weeks, and any increment between 1 month and 12 months, or any combination of incremental time periods therein.

The term "typeIIs restriction enzyme" is used herein to refer to any restriction enzyme that cleaves DNA at a defined distance outside its recognition sequence, and whose recognition sequence is non-palindromic.

The terms "ligatable ends" or "compatible ends" are used herein to describe two ends of polynucleotide molecules that are both blunt or that both possess overhangs of the same length and directionality (i.e. both are 5'-overhangs, or both are 3'-overhangs) and with perfectly complementary sequences, such that the DNA ends form standard Watson-Crick base pairs (i.e. C with G and T or U with A) and can be joined by a DNA ligase.

The term "operably linked" refers to functional linkage between two sequences such that one sequence modifies the behavior of the other. For example a first polynucleotide comprising a nucleic acid expression control sequence (such as a promoter, IRES sequence, enhancer or array of transcription factor binding sites) and a second polynucleotide are operably linked if the first polynucleotide affects transcription and/or translation of the second polynucleotide. Similarly a first amino acid sequence comprising a secretion signal or a subcellular localization signal and a second amino acid sequence are operably linked if the first amino acid sequence causes the second amino acid sequence to be secreted or localized to a subcellular location.

A "promoter" means a nucleic acid sequence sufficient to direct transcription of an operably linked nucleic acid molecule. Also included in this definition are those transcription control elements (for example, enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Desirably, a promoter is operably linked to a nucleic acid sequence, for example, a cDNA or a gene sequence, or an effector RNA coding sequence, in such a way as to enable expression of the nucleic acid sequence, or a promoter is provided in an expression cassette into which a selected nucleic acid sequence to be transcribed can be conveniently inserted.

'Integration defective' means a transposase that integrates a transposon at a lower frequency into the host genome than a corresponding wild type transposase.

As used herein, the term "transposon" or "transposable element" refers to a polynucleotide that can be excised from a first polynucleotide, for instance, a vector, and be integrated into a second position in the same polynucleotide, or into a second polynucleotide, for instance, the genomic or extrachromosomal DNA of a cell, by the action of a trans-acting transposase. A transposon comprises a first transposon end and a second transposon end which are polynucleotide sequences recognized by and transposed by a transposase. A transposon usually further comprises a first polynucleotide sequence between the two transposon ends, such that the first polynucleotide sequence is transposed along with the two transposon ends by the action of the transposase. Natural transposons frequently comprise DNA encoding a transposase that acts upon the transposon. The invention provides transposons in which a naturally present sequence encoding a functional transposase has been replaced with a sequence encoding a heterologous polynucleotide, which is transposable by virtue of its juxtaposition between the transposon ends.

As used herein, the term "transposon end" refers to cis-acting nucleotide sequences that are sufficient for recognition by and transposition by a transposase. A pair of transposon ends typically comprises paired perfect or imperfect repeats such that the respective repeats in the members of a pair are reverse complements of each other in the two different transposon ends. These are referred to as inverted terminal repeats (ITR) or terminal inverted repeats (TIR). In piggyBac-like transposons, each transposon end further comprises a target sequence immediately distal to the ITR (distal meaning on the side further from the transposase or heterologous polynucleotide transposed by the ITR). A transposon end may or may not include additional sequence proximal to the ITR that promotes or augments transposition.

As used herein, a "piggyBac-like transposase" means a transposase with at least 20% and preferably at least 30% sequence identity as identified using the TBLASTN algorithm to the piggyBac transposase from *Trichoplusia ni* (SEQ ID NO. 57), and as more fully described in Sakar, A. et. al., (2003). Mol. Gen. Genomics 270: 173-180. "Molecular evolutionary analysis of the widespread piggyBac transposon family and related 'domesticated' species", and further characterized by a DDE-like DDD motif, with aspartate residues at positions corresponding to D268, D346, and D447 of *Trichoplusia ni* piggyBac transposase on maximal alignment. A "piggyBac-like transposon" means a transposon having transposon ends which are the same or at least 80% and preferably at least 90, 95, 96, 97, 98 or 99% identical to the transposon ends of a naturally occurring transposon that encodes a piggyBac-like transposase. A piggyBac-like transposon includes an inverted repeat sequence of approximately 13 bases at each end, immediately adjacent to a sequence corresponding to the target sequence which is duplicated upon transposon integration (the Target Site Duplication or Target Sequence Duplication or TSD). piggyBac-like transposons and transposases have been identified in a wide range of organisms including *Argyrogramma agnate* (GU477713), *Anopheles gambiae* (XP_312615; XP_320414; XP_310729), *Aphis gossypii* (GU329918), *Acyrthosiphon pisum* (XP_001948139), *Agro-*

*tis ipsilon* (GU477714), *Bombyx mori* (BAD 11135), *Ciona intestinalis* (XP_002123602), *Chilo suppressalis* (JX294476), *Drosophila melanogaster* (AAL39784), *Daphnia pulicaria* (AAM76342), *Helicoverpa armigera* (ABS 18391), *Homo sapiens* (NP_689808), *Heliothis virescens* (ABD76335), *Macdunnoughia crassisigna* (EU287451), *Macaca fascicularis* (AB179012), *Mus musculus* (NP_741958), *Pectinophora gossypiella* (GU270322), *Rattus norvegicus* (XP_220453), *Tribolium castaneum* (XP_001814566), *Trichoplusia ni* (AAA87375) and *Xenopus tropicalis* (BAF82026).

A target nucleic acid is a nucleic acid into which a transposon is to be inserted. Such a target can be part of a chromosome, episome or vector. The target nucleic acid for a transposon of the present invention should contain at least one motif recognized by a transpose of the present invention (5'-TTAT-3' or 5'-TTAA-3').

As used herein, a "target site" or "target sequence" for a transposase is a site or sequence in a target DNA molecule into which a transposon can be inserted by a transposase. The piggyBac transposase from *Trichoplusia ni* inserts its transposon into the target sequence 5'-TTAA-3'.

As used herein, the term 'transposase' refers to a polypeptide that catalyzes the excision of a transposon from a donor polynucleotide, for example a vector, and (providing the transposase is not integration-deficient) the subsequent integration of the transposon into the genomic or extrachromosomal DNA of a target cell. The transposase binds a transposon end. The transposase may be present as a polypeptide. Alternatively, the transposase is present as a polynucleotide that includes a coding sequence encoding a transposase. The polynucleotide can be RNA, for instance an mRNA encoding the transposase, or DNA, for instance a coding sequence encoding the transposase. When the transposase is present as a coding sequence encoding the transposase, in some aspects of the invention the coding sequence may be present on the same vector that includes the transposon, that is, in cis. In other aspects of the invention, the transposase coding sequence may be present on a second vector, that is, in trans.

"IRES" or "internal ribosome entry site" means a specialized sequence that directly promotes ribosome binding, independent of a cap structure.

"Open Reading Frame" or ORF means a portion of a DNA molecule that, when translated into amino acids, contains no stop codons. The genetic code reads DNA sequences in groups of three base pairs, which means that a double-stranded DNA molecule can read in any of six possible reading frames-three in the forward direction and three in the reverse. A long open reading frame is likely a part of a gene.

Two elements are heterologous to one another if not naturally associated. For example, a nucleic acid sequence encoding a protein linked to a heterologous promoter means a promoter other than that which naturally expresses the protein. A heterologous nucleic acid flanked by transposon ends or ITRs means a heterologous nucleic acid not naturally flanked by those transposon ends or ITRs, such as a nucleic acid encoding a polypeptide other than a transposase, including an antibody heavy or light chain. Heterologous nucleic acids flanked by transposon ends or ITRs can vary in length, for example ranging from 20 base pairs to 20 kilo base pairs or more. A nucleic acid is heterologous to a cell if not normally found in the cell or in a different location (e.g., episomal or different genomic location) than the location naturally present within a cell.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): tip, tyr, phe. Conservative substitutions involve substitutions between amino acids in the same class. Non-conservative substitutions constitute exchanging a member of one of these classes for a member of another.

The "configuration" of a polynucleotide means the functional sequence elements within the polynucleotide, and the order and direction of those elements. For example Tables 6-18

5.2 Description

5.2.1 Vector Components

The properties of a biological system including natural as well as non-natural systems with respect to any measurable function depends on the interaction between different nucleic acid sequence elements, which may be located at positions throughout the total nucleic acid component of the system, herein referred to as the "nucleic acid construct" of the system. The ability to rationally design a nucleic acid construct with an optimal configuration of elements is advantageous for various applications such as protein synthesis via vector optimization, cell line development and strain engineering. Protein synthesis is a highly dynamic and multi-step process and which plays a central role in synthetic biology, pharmaceutical production and other applications in biotechnology. This importance has led to the development of various parts or genetic control elements able to modulate and precisely control various aspects of protein expression. This capability is not only essential for the successful construction of more complex synthetic biological systems, but also provides tools needed for the tuning of their function for improved performance and reliability.

A limitation with the current state of the art is that effects of many control elements are dependent on the genetic context in which they are used. For example, combining the same promoter with different RBSs and genes can result in very different levels of expression.

While effects of combinations of one or two transcriptional or translational elements have been studied including the genetic context in which they are used, there remains a need in the art to identify optimal configurations of multiple functional elements. Such elements can include those that influence DNA copy number, sites of DNA integration into chromosomes, RNA transcription rate, RNA degradation, RNA processing, RNA localization, translation initiation rate, and transcriptional termination. Examples of such elements are promoters, enhancers, introns, polyadenylation signals, ribosome binding sites, Kozak sequences, 5' untranslated sequences, origins of replication, nuclear export signals, internal ribosome entry sites and transcriptional terminators. Functional elements may also include those that encode functional polypeptides, such as secretion signals, resistance markers, anchoring peptides, localization signals, fusion tags, affinity tags, chaperonins and proteases. The ability to rationally engineer multiple elements within the DNA content of a host cell or expression system is an important aspect of this invention. In another embodiment, engineering of multiple elements within the DNA content of host cell or expression system along with variables of environmental stress or culture conditions is another aspect of this invention. Such environmental variables can include media components (whether complex or defined media), aeration, temperature, matrix for growth and others.

5.2.2 Genomic Integration

In some embodiments, the nucleic acid construct is a vector with enhanced expression and integration properties. For example, an optimal configuration of vector elements for enhanced transient expression as well as more efficient stable integration and expression was identified by the methods described herein. A mammalian vector construct variant set was generated using multiple combinations of various transposon ends or insulators, enhancers, promoters, introns, 5' untranslated regions (UTRs), 3' untranslated regions (UTRs), RNA export modulating sequence, polyadenylation sequences, terminators and matrix attachment element. The mammalian vector variant set was used to express DasherGFP in Human embryonic kidney (HEK 293) cells and Chinese hamster ovary (CHO) cells. Vector constructs with different promoter combinations were also shown to affect DasherGFP expression. Further optimization of this vector construct for different cell lines using the methods described herein is expressly contemplated. An advantage of the methods described herein is to quickly identify a subset of sequence elements most likely to influence desired activity as well as to facilitate predictable construction of optimal configuration of elements.

In some embodiments, elements that are useful in enhancing performance may include those localized to the genomic DNA of a cell. For example expression may be influenced by the levels of RNA polymerases, chaperonins, proteases, processing enzymes, or other factor encoded by DNA on the cell chromosome. It might also be advantageous to augment the host chromosome with functional elements that influence performance. In some embodiments, a variable for engineering is the site at which a functional gene is integrated into a host cell chromosome.

In some embodiments, the nucleic acid construct is a polynucleotide comprising of elements or combinations of elements arranged in an optimal configuration. In some embodiments, the polynucleotide is linear. In some embodiments, the elements in a nucleic acid construct comprise functional genetic features, for example, promoters, enhancers, introns, polyadenylation signals, origins of replication, and terminators. In some embodiments, the elements in a nucleic acid construct comprise protein encoding elements such as secretion signals, resistance markers, anchoring peptides, localization signals, and fusion tags. In some embodiments, the plurality of elements comprises three or more elements, six or more elements, between three and twenty elements or between three and hundred elements. In some embodiments, nucleic acid construct variants include substitutions in a single element comprising one or more positions, three or more positions, six or more positions. In some embodiments, nucleic acid variants include substitutions wherein the substitutions are variations in elements and/or presence or absence of elements. In some embodiments, the substitutions include changes in the position of one or more elements. In some embodiments, nucleic acid variants include a change in the order of one or more elements.

5.2.3 Novel Transposons

DNA transposons undergo a 'cut and paste' system of replication in which the elements are physically excised from the one DNA molecule and reinserted in a second. The DNA transposons are characterized by inverted terminal repeats (ITRs) and are mobilized by an element-encoded transposase.

While DNA transposons are widespread and active in a variety of eukaryotes, they have been thought to be transpositionally inactive in mammalian genomes.

The natural process of horizontal gene transfer can be mimicked under laboratory conditions. In plants, transposons of the Ac/Ds and Spm families have been routinely transfected into heterologous species. In animals, however, a considerable obstacle to the transfer of an active transposon system from one species to another has been that of species-specificity of transposition due to the requirement for factors produced by the natural host.

A number of transposable elements have been described in the art that show no host-restriction in vertebrates, for example, an engineered transposon from the genome of salmonid fish called Sleeping Beauty; piggyBac transposon from lepidopteran cells; piggyBat transposon from the bat *Myotis lucifugus*; mariner transposon first discovered in *Drosophila* and; an engineered transposon and transposon inverted repeats from the frog species, *Rana pipiens* called frog prince; but the efficiency of transposition in cell lines derived from different species is variable. Therefore, it is advantageous to have a palette of different transposons with different host preferences to widen the potential of transposons as genomic tools in vertebrates.

It is currently used for many purposes including genome editing, enhancer trapping, gene discovery and identifying gene function in insects and mammals. The piggyBac transposon/transposase system is particularly useful because of the precision with which the transposon is integrated and excised (see for example "Fraser, M. J. (0.2001) The TTAA-Specific Family of Transposable Elements: Identification, Functional Characterization, and Utility for Transformation of Insects. Insect Transgenesis: Methods and Applications. A. M. Handler and A. A. James. Boca Raton, Fla., CRC Press: 249-268"; and "US 20070204356 A1: PiggyBac constructs in vertebrates" and references therein). This integration and excision is shown schematically in FIG. 1.

Many sequences with sequence similarity to the piggyBac transposase from *Trichoplusia ni* have been found in the genomes of phylogenetically distinct species from fungi to mammals, but very few have been shown to possess transposase activity (see for example Wu M, et al (2011) Genetica 139:149-54. Cloning and characterization of piggyBac-like elements in lepidopteran insects, and references therein). To discover novel transposons and transposases capable of transposing a heterologous polynucleotide into the genome of a host cell, we identified the sequences of 14 putative transposases (SEQ ID NO: 43-56) by searching public sequence databases for polypeptides with sequence similarity to known active transposases. We then identified their corresponding transposon ends by taking the non-coding region associated with the gene sequence of the transposase. We designed and synthesized a polynucleotide to express each of the 14 transposases under control of the CMV promoter, and a second polynucleotide to express each of the 14 transposases fused to a heterologous nuclear localization signal under control of the CMV promoter. For each transposase we further designed two corresponding transposons. The first transposon comprised a heterologous polynucleotide comprising a puromycin resistance gene under control of a murine PGK promoter and a DasherGFP gene under control of a human EF1a promoter, with the two promoters oriented such that transcription from them is in opposite directions and divergent, surrounded by a pair of transposon ends. Sequences of transposon ends and corresponding transposases are described in Example 6.1.1 and shown in Tables 1 and 2. The second transposon comprised a heterologous polynucleotide comprising a puromycin resistance gene under control of a murine PGK promoter, with a DasherGFP gene translationally coupled to the puromycin-resistance gene through a CHYSEL sequence, surrounded by a pair of transposon ends. Sequences of transposon ends and corresponding transposases are described in Example 6.1.4 and shown in Table 5. We then transfected each transposon into CHO cells, in parallel sets with or without its corresponding transposase. Transposases that increased the reporter fluorescence from their transposons relative to the transposon-alone comprised novel transposon-transposase pairs that could integrate a heterologous polynucleotide into the genome of a cell.

As described in Examples 6.6.1 and 6.1.4 and shown in Tables 1, 2 and 5, of 14 that we identified and synthesized, only 4 showed detectable transposase activity. Thus sequence similarity to the *Trichoplusia ni* piggyBac sequence is insufficient to characterize a sequence as a transposase.

Using this method, we have identified two novel active piggyBac-like transposases together with their transposon ends and the ITR sequences on which they act.

One transposon was identified from the genome of *Xenopus tropicalis* with functional transposon ends being contained within SEQ ID NOS: 5, 6. Two transposases that can recognize and transpose these transposon ends are SEQ ID NOS: 45 and 46. Excision activity has been identified in Txb transposases from *Xenopus* (Hikosaka et. al., Mol. Biol. Evol., 24(12):2648-2656, 2007), but the authors conclude "In the present study, we demonstrated that the Xtr-Uribo2 Tpase has excision activity toward the target transposon, although there is no evidence for the integration of the excised target into the genome" Here we have identified transposon ends including ITRs that can be placed at either end of a heterologous polynucleotide sequence to effect the efficient integration of the polynucleotide into genomic DNA by the action of the *Xenopus* transposase. Gene transfer vectors comprising *Xenopus* transposon ends and with optimal configurations of vector elements described herein (Section 5.2.6) show stable genomic integration even in the absence of transposase. In the presence of transposase, the expression from stably integrated transposons is increased 3-70 fold (see for example Table 14).

One transposon was identified from the genome of *Bombyx mori* with the functional transposon ends being contained within SEQ ID NOS: 1, 2. A transposase that can recognize and transpose a transposon comprising these transposon ends is SEQ ID NOS: 44. We noted that the transposon end sequence associated with SEQ ID NO: 43 (SEQ ID NOS: 121 and 122) were terminated by the canonical 5'-TTAA-3' integration sequence always observed for transposons with significant sequence identity to *Trichoplusia ni* piggyBac. In contrast the transposon end sequence associated with SEQ ID NO: 44 (SEQ ID NOS: 1 and 2) were terminated by 5'-TTAT-3' sequences adjacent to the ITRs. We did not initially know whether this indicated that the transposase really used a novel integration sequence. Previous studies have indicated that the *Trichoplusia ni* piggyBac transposase is unable to transpose a transposon whose ends comprise a target sequence other than 5'-TTAA-3' (Mitra et al (2008) EMBO Journal 27: 1097-1109 "piggyBac can bypass DNA synthesis during cut and paste transposition"). Alternative possibilities for the 5'-TTAT-3' target sequence in the transposon ends within SEQ ID NOS: 1, 2 included sequencing errors or that the transposon had mutated and the transposase was no longer capable of transposing the sequence. Because active piggyBac-like transposons have only been described to use 5'-TTAA-3' integration sequences, we added the sequence 5'-TTAA-3' to both ends of the *Bombyx* transposon when we synthesized it to maximize the chance that we could reconstitute an active transposon (so the transposon sequence was arranged 5'-TTAATTAT-transposon end 1-heterologous polynucleotide-transposon end 2-TTATTTAA-3'). Contrary to the claims of Daimon et al (who describe *Bombyx* transposases as being essentially inactive, see Daimon T et al, 2010. Genome. 53:585-93. "Recent transposition of yabusame, a novel piggyBac-like transposable element in the genome of the silkworm, *Bombyx mori*.") we found that the *Bombyx* transposon was highly active (see Examples 6.6.1 and Tables 1 and 2), we wished to determine its integration sequence. As shown in FIG. 1, when a piggyBac-like transposon is transposed, it leaves a single copy of its target sequence in the DNA from which it is excised. We therefore sequenced plasmids from which transposons had been excised by transposases. FIG. 2 shows a sequence trace file from a plasmid from which the *Bombyx* transposon has been excised. Both copies of the 5'-TTAA-3' sequence that we placed around the transposon ends are still present; however only a single copy of the 5'-TTAT-3' site remains. We examined 16 independent transposition events from *Bombyx* transposons, and all 16 left only a single perfectly intact copy of the 5'-TTAT-3' integration sequence. In contrast, when we examined 16 independent transposition events from *Xenopus* transposons, all 16 left only a single perfectly intact copy of the 5'-TTAA-3' integration sequence. Both *Xenopus* and *Bombyx* transposons disclosed here are transposed by their respective transposases with the same precision as has been described for *Trichoplusia ni* piggyBac, a precision which is highly advantageous for any genomic modifications that may be desirable to make reversibly. In contrast to *Trichoplusia ni* piggyBac, however, the *Bombyx mori* transposon thus comprises a 5'-TTAT-3' integration sequence, and the *Bombyx mori* transposase can excise and integrate *Bombyx mori* transposons at 5'-TTAT-3' recognition sequences. This is in contrast to all other known transposases with homology to *Trichoplusia ni* piggyBac, all of which recognize and insert transposons at the sequence 5'-TTAA-3'. This difference may be highly advantageous: *Trichoplusia ni* piggyBac has a preference for inserting transposons into transcriptionally inactive DNA. Because 5'-TTAT-3' is a reverse complement of 5'-ATAA-3' which is part of the canonical mammalian polyA signal 5'-aATAAa-3'. Thus the 5'-TTAT-3' insertion site recognized by the

*Bombyx mori* transposase will occur at almost every polyA signal. PolyA signals are associated with transcriptionally active regions of the chromosome. Thus transposons that insert at 5'-TTAT-3' sites, including the *Bombyx mori* transposons, are likely to yield higher expression levels of the genes they carry than transposons that insert 5'-TTAA-3' sites.

The invention provides a heterologous polynucleotide flanked by inverted repeats, which are in turn flanked by a direct repeat of the target sequence, 5'-TTAT-3'. In other words, from 5' to 3' such polynucleotides comprise a 5'-TTAT-3' target sequence, an ITR, a heterologous polynucleotide not naturally flanked by the ITR and 5'-TTAT-3', a second ITR in reverse orientation to the first ITR, and a second 5'-TTAT-3' target sequence. Transposition of such a transposon by a transposase leaves a single 5'-TTAT-3' motif in the locus previously occupied in a transposon. The transposon is transposed to a second polynucleotide including a 5'-TTAT-3' motif to generate a modified second polynucleotide including the transposon with the same components as when the transposon occupied the first polynucleotide.

The present application discloses a piggyBac-like *Bombyx* transposon (AB162707.1 GI:42600553) comprising transposon ends (each end including an ITR) corresponding to SEQ ID NO. 1 and 2, which has a target sequence corresponding to 5'-TTAT-3'. It also comprises a sequence encoding a transposase (SEQ ID NO. 44). A previously described *Bombyx* transposon (AB159601.1 GI:41016737) comprises one transposon end also identical to SEQ ID NO. 1 and a second transposon end corresponding to SEQ ID NO. 122. SEQ ID NO, 122 is very similar to SEQ ID NO. 2, but has a large insertion shortly before the ITR. Although the ITR sequences for the two transposons are identical (they are both identical to SEQ ID NO. 32), they have different target sequences: the second transposon has a target sequence corresponding to 5'-TTAA-3', providing evidence that no change in ITR sequence is necessary to modify the target sequence specificity. The *Bombyx* transposase (SEQ ID NO: 43), which is associated with the 5'-TTAA-3' target site differs from the 5'-TTAT-3'-associated transposase (SEQ ID NO: 44) by only 4 amino acid changes (D322Y, S473C, A507T, H582R). The transposase (SEQ ID NO: 43), which is associated with the 5'-TTAA-3' target site is less active than the 5'-TTAT-3'-associated transposase (SEQ ID NO: 44) on the transposon with 5'-TTAT-3' ends (see for example Table 5). These results provide evidence that other transposons with 5'-TTAA-3' target duplication sites can be converted to transposases with 5'-TTAT-3' target duplication sites by replacing 5'-TTAA-3' target duplication sites with 5'-TTAT-3'. Such novel transposons can be used either with *Bombyx* transposase (SEQ ID NO:43), which recognizes the 5'-TTAT-3' target sequence, or with a variant of the transposase originally associate with the 5'-TTAA-3' transposon. The high similarity between *Bombyx* 5'-TTAA-3' and 5'-TTAT-3' transposases provides evidence that very few changes to the amino acid sequence of a piggyBac-like transposase may confer altered target sequence specificity. The invention therefore provides transposon transposase transfer systems which can be formed by modification of any piggyBac-like transposon-transposase gene transfer system of which there are many known examples, in which 5'-TTAA-3' target sequences are replaced with 5'-TTAT-3'-target sequences, the ITRs remain the same, and the transposase is the original transposase or a variant thereof resulting from using a low-level mutagenesis to introduce mutations into the transposase. Similarly the invention also provides transposon transposase transfer systems which can be formed by modification of a 5'-TTAT-3'-active piggyBac-like transposon-transposase gene transfer system such as the *Bombyx* system disclosed herein, in which 5'-TTAT-3' target sequences are replaced with 5'-TTAA-3'-target sequences, the ITRs remain the same, and the transposase is the original transposase or a variant thereof resulting from using a low-level mutagenesis to introduce mutations into the transposase.

Transposases that are active on a new target sequence such as a 5'-TTAT-3' target sequence can be selected, for example by coupling transposon excision to the production of a full coding sequence for a selectable marker. A transposon whose ITRs are flanked by the new target sequences (for example 5'-TTAT-3' target sequences) can be inserted into a selectable marker such that expression of the selectable marker is prevented. For example the transposon may be in the middle of an open reading frame encoding a selectable marker such that the presence of the transposon prevents the translation of a functional version of the selectable marker, or the transposon may be in an intron within an open reading frame encoding a selectable marker, such that the presence of the transposon prevents the splicing of the intron and thus prevents synthesis of the selectable marker. The transposon is placed such that when it is excised, the selectable marker regains functionality. For example the transposon may be placed at the sequence 5'-TTAT-3' within the coding sequence for a selectable marker such as an auxotrophic marker, the precise excision of the transposon from the open reading frame of the selectable marker restores the coding sequence of the selectable marker. A gene encoding the transposon-interrupted selectable marker and a gene encoding a transposase are introduced into a cell. The cell is then subjected to restrictive conditions that require expression of the selectable marker to enable the cell to survive. Expression of the selectable marker in turn depends upon excision of the transposon which in turn requires an active transposase. Cell survival can thus be used to identify active transposases. An example of such a selection scheme has been described by Yusa et al (Yusa et. al., PNAS, vol 108, no. 4, 1531-1536, 2011).

A transposase with modified activity, either for activity on a new target sequence including a 5'-TI'TAT-3' target sequence, or increased activity on an existing target sequence may be obtained by using variations of the selection scheme outlined above. To create the modified transposase, an existing transposase is used as a starting point, for example any of SEQ ID NOS: 43-57 or any other piggyBac-like transposase. One or more variant transposase sequences are created. These can be created in a variety of different ways, for example the gene may be subjected to random mutagenesis; the gene may be "DNA shuffled" with one or more homologous genes; systematic substitutions may be introduced into the gene including the creation of all possible single amino acid substitutions; substitutions may be introduced based on phylogenetic analysis and other rules for example as described in U.S. Pat. No. 8,635,029 B2. The sequence encoding the one or more variant transposases are operably linked to a promoter such that the transposases may be expressed in a cell. Each variant transposase is introduced into a cell that contains the transposon-interrupted transposable marker, and the cell is then subjected to restrictive conditions for which it requires the active selectable marker to survive. When a transposase is able to excise the transposon the cell will survive, and the gene encoding the active transposase may be recovered from the cell, for example by PCR. The process may be performed in pools of variants: a more active transposase will create active selectable markers more frequently, and will thus be more highly represented in the population.

A comparable process may be used to increase the transposability of the transposon ends by a transposase. In this case, the transposon may comprise a first active selectable marker. Transposon ends may be selected from any of SEQ ID NOS: 1-31 or 32-42 or from any other piggyBac-like transposon including those associated with the inverted terminal repeats shown in SEQ ID NOS: 125-130. The sequence of one or both transposon ends may be subjected to random or pre-determined sequence changes, including changes to the target sequence, the ITR or to other parts of the transposon ends. The transposon may then be introduced into a first cell that contains a target polynucleotide comprising a second active selectable marker and an active transposase. If the transposase is able to transpose the transposon, some fraction of the transposons will be transposed into the target polynucleotide. The target polynucleotide is purified from the first cell, and introduced into a second cell which is subjected to restrictive conditions for which it requires the first selectable marker and the second selectable marker to survive. The transposon may be recovered, for example by sequencing out from the transposon to identify the flanking sequence, and then amplifying the transposon using PCR. The process may be performed in pools of variants: a more active transposon will create target polynucleotides containing both selectable markers more frequently, and will thus be more highly represented in the population. In this process, the transposon may optionally be present as a reversible interruption in a selectable marker as described for the transposase activity screen. However this is not necessary for the transposon activity screen, since the transposed transposons are detected directly.

These new transposases allow effective insertion of a transposon into a eukaryotic cell, including a mammalian cell such as a Chinese hamster ovary (CHO) cell or a Human embryonic kidney (HEK293) cell.

As well as exemplified transposases having sequences SEQ ID NOS. 43, 44, 45 and 46, the invention provides variants having at least 90, 91, 92, 93, 94, 95, 96, 97, 98 or 99% sequence identity to an exemplified sequence retaining transposase activity. Variations can be conservative or non-conservative substitutions, insertions and deletions. Deletions can be from the N-terminal or C-terminal end or internal. Some variants resulting from alanine scanning mutagenesis contain an alanine substitution at single positions throughout the molecule. Variations retain transposase activity on a transposon in which the exemplified transposase is activity. We have identified active transposases from Bombyx mori (SEQ ID NOS: 44) and Xenopus tropicalis (SEQ ID NOS: 45 and 46) that show variations in at least 4 residues that serve as a starting point for further studies for identification of hyperactive variants and integration deficient variants that retain excision activity. As used herein a Bombyx mori transposase or a Bombyx transposase refers to a polypeptide with at least 90% sequence identity with SEQ ID NO: 44 that can recognize and transpose a transposon. In some embodiments the transposon comprises two transposon ends, each of which comprises SEQ ID NO: 32 in inverted orientations in the two transposon ends. As used herein a Xenopus tropicalis transposase or a Xenopus transposase refers to a polypeptide with at least 90% sequence identity with SEQ ID NO: 45 or SEQ ID NO: 46 that can recognize and transpose a transposon. In some embodiments the transposon comprises two transposon ends each of which comprise SEQ ID NO: 42 in inverted orientations in the two transposon ends.

These new transposases allow effective insertion of a transposon into a eukaryotic cell, including a mammalian cell such as a Chinese hamster ovary (CHO) cell or a Human embryonic kidney (HEK293) cell.

As well as exemplified transposases having sequences SEQ ID NOS. 43, 44, 45 and 46, the invention provides variants having at least 90, 91, 92, 93, 94, 95, 96, 97, 98 or 99% sequence identity to an exemplified sequence retaining transposase activity. Variations can be conservative or non-conservative substitutions, insertions and deletions. Deletions can be from the N-terminal or C-terminal end or internal. Some variants resulting from alanine scanning mutagenesis contain an alanine substitution at single positions throughout the molecule. Variations retain transposase activity on a transposon in which the exemplified transposase is activity. We have identified active variants of transposases from Bombyx mori (SEQ ID NOS: 43 and 44) and Xenopus tropicalis (SEQ ID NOS: 45 and 46) that show variations in at least 4 residues that serve as a starting point for further studies for identification of hyperactive variants and integration deficient variants that retain excision activity. As used herein a Bombyx mori transposase or a Bombyx transposase refers to a polypeptide with at least 90% sequence identity with SEQ ID NO: 43 or SEQ ID NO: 44 that can recognize and transpose a transposon. In some embodiments the transposon comprises two transposon ends, each of which comprises SEQ ID NO: 32 in inverted orientations in the two transposon ends. As used herein a Xenopus tropicalis transposase or a Xenopus transposase refers to a polypeptide with at least 90% sequence identity with SEQ ID NO: 45 or SEQ ID NO: 46 that can recognize and transpose a transposon. In some embodiments the transposon comprises two transposon ends each of which comprise SEQ ID NO: 42 in inverted orientations in the two transposon ends.

The invention also provides variants of exemplified sequences of transposon ends. The Bombyx transposase recognizes a transposon with a left sequence corresponding to SEQ ID NO: 1, and a right sequence corresponding to SEQ ID NO: 2. It will excise the transposon from one DNA molecule by cutting the DNA at the 5'-TTAT-3' sequence at the left end of one transposon end to the 5'-TTAT-3' at the right end of the second transposon end, including any heterologous DNA that is placed between them, and insert the excised sequence into a second DNA molecule. Truncated and modified versions of the left and right transposon ends will also function as part of a transposon that can be transposed by the Bombyx transposase. For example the left transposon end can be replaced by a shorter sequence corresponding to SEQ ID NO: 3, or the right transposon end can be replaced by a shorter sequence corresponding to SEQ ID NO: 4. It is thus expressly contemplated that modified versions of the transposon end sequences will be tolerated by the transposase, and may even result in increased transposition. In addition, we note that the left and right transposon ends share a 16 bp repeat sequence at their ends (SEQ ID NO: 32) immediately adjacent to the 5'-TTAT-3' insertion site, which is inverted in the orientation in the two ends. That is the left transposon end begins with the sequence 5'-TTATCCCGGCGAGCATGAGG-3' (SEQ ID NO: 33), and the right transposon ends with the reverse complement of this sequence: 5'-CCCTCATGCTCGCCGGGTTAT-3' (SEQ ID NO: 34). The perfect conservation of this 16 bp sequence at both ends of the transposon suggests that it is important for function. One embodiment of the invention is a transposon that comprises a heterologous polynucleotide inserted between SEQ ID NO: 33 and SEQ ID NO: 34. As used herein, a *Bombyx mori* transposon or a *Bombyx* transposon means a transposon comprising a heterologous polynucleotide and any of SEQ ID NOS: 32-34 or SEQ ID NOS: 1-4, or sub-sequences of SEQ ID NOS: 1-4, such that the heterologous polynucleotide can be transposed by a transposase at least 90% identical to SEQ ID NOS: 43 or 44.

The *Xenopus* transposase recognizes a transposon end with a left sequence corresponding to SEQ ID NO: 5, and a right sequence corresponding to SEQ ID NO: 6. It will excise the transposon from one DNA molecule by cutting the DNA at the 5'-TTAA-3' sequence at the left end of one transposon end to the 5'-TTAA-3' at the right end of the second transposon end, including any heterologous DNA that is placed between them, and insert the excised sequence into a second DNA molecule. Truncated and modified versions of the left and right transposon ends will also function as part of a transposon that can be transposed by the *Xenopus tropicalis* transposase. For example the left transposon end can be replaced by a sequence corresponding to SEQ ID NO: 7 or SEQ ID NO: 9, the right transposon end can be replaced by a shorter sequence corresponding to SEQ ID NO: 8. In addition, we note that the left and right transposon ends share an 18 bp almost perfectly repeated sequence at their ends (5'-TTAACCYTTTKMCTGCCA: SEQ ID NO: 42) that includes the 5'-TTAA-3' insertion site, which sequence is inverted in the orientation in the two ends. That is in SEQ ID NO: 5 and SEQ ID NO: 9 the left transposon end begins with the sequence 5'-TTAACCTTTTTACTGCCA-3' (SEQ ID NO: 37), or in SEQ ID NO: 7 the left transposon end begins with the sequence 5'-TTAACCCTTTGCCTGCCA-3' (SEQ ID NO: 38); the right transposon ends with approximately the reverse complement of this sequence: in SEQ ID NO: 6 it ends 5'-TGGCAGTAAAAGGGTTAA-3' (SEQ ID NO: 40), in SEQ ID NO: 8 it ends 5'-TGGCAGTGAAAGGGTTAA-3' (SEQ ID NO: 41) The near-perfect conservation of this 18 hp sequence at both ends of the transposon suggests that it is important for function. One embodiment of the invention is a transposon that comprises a heterologous polynucleotide inserted between two transposon ends each comprising SEQ ID NO: 42 in inverted orientations in the two transposon ends. In some embodiments one transposon end comprises a sequence selected from SEQ ID NOS: 37-39. In some embodiments one transposon end comprises a sequence selected from SEQ ID NOS: 40-41.

Further studies to identify additional variants of transposon ends and transposase sequences with enhanced activity are expressly contemplated. Generation of hyperactive variants is another aspect of this invention wherein mutational studies identify mutations in the transposase, which give rise to hyperactivity (Yusa et. al., PNAS, vol 108, no. 4, 1531-1536, 2011). Once the individual mutants are identified and verified for their transposition activity in cells, these mutations or combinations of mutations can be combined into one sequence to generate a hyperactive transposase that shows higher rates of transposition than the wild-type transposase. Hyperactive variants also include variants with enhanced integration activity, enhanced excision activity or both. Another aspect of this invention includes integration deficient variants, wherein the transposase shows lower integration activity but enhanced excision activity.

Accordingly, the present invention features *Bombyx* or *Xenopus* transposons and transposases. Another aspect of this invention refers to a transposon, that comprises a heterologous polynucleotide sequence, as described herein, positioned between at least two ITRs, at least one repeat on either side of the heterologous polynucleotide, wherein these repeats can bind to a transposase protein and wherein the transposon is capable of inserting into DNA of a cell. Accordingly, repeats are preferably sequences that are recognized and bound by the transposase as defined herein.

According to certain preferred embodiments of the present invention, a transposon that is bound by a transposase contains a pair of repeat sequences. In certain preferred embodiments, the first repeat is typically located upstream of the heterologous polynucleotide and the second repeat is typically located downstream of the heterologous polynucleotide. The second repeat represents the same sequence as the first repeat, but shows an inverted orientation compared with the first repeat. That is, considering only one strand of a double-stranded DNA molecule, the second repeat will occur as the reverse complement of the first repeat. In some embodiments these repeats are identical inverted sequences. In some embodiments these inverted repeats may be highly similar but not identical, differing by 1, 2, 3 or 4 nucleotides. These repeats are then termed "inverted repeats" (IRs) or "inverted terminal repeats" (ITRs), due to the fact that each repeat is an inversely repeated copy of the other. In certain embodiments, repeats may occur in a multiple number upstream and downstream of the above mentioned nucleic acid sequence. In certain embodiments, the repeats are short, between 10-20 base pairs, and preferably 14-16 base pairs. In some other embodiments, the transposon ends further comprise additional sequences that may or may not be repeats.

In some embodiments, the *Xenopus* transposon comprises one end comprising at least 14 or 16 or 18 or 20 or 30 or 40 contiguous nucleotides from SEQ ID NO: 5, 7 or 9; in some embodiments, the *Xenopus* transposon comprises one end comprising at least 14 or 16 or 18 or 20 or 30 or 40 contiguous nucleotides from SEQ ID NO: 6 or 8. In some embodiments, the *Xenopus* transposon comprises one end with at least 90% identity to SEQ ID NO: 5 or 7 or 9; in some embodiments, the *Xenopus* transposon comprises one end with at least 90% identity to SEQ ID NO: 6 or 8. In some embodiments of the *Xenopus* transposon, each inverted terminal repeat (ITR) comprises SEQ ID NO: 42. In some embodiments of the *Xenopus* transposon, one ITR comprises a sequence selected from SEQ ID NOS: 37-39. In some embodiments of the *Xenopus* transposon, one ITR comprises a sequence selected from SEQ ID NOS: 40-41.

In some embodiments, the *Bombyx* transposon comprises one end comprising at least 14 or 16 or 18 or 20 or 30 or 40 contiguous nucleotides from SEQ ID NO: 1 or 3; in some embodiments, the *Bombyx* transposon comprises one end comprising at least 14 or 16 or 18 or 20 or 30 or 40 contiguous nucleotides from SEQ ID NO: 2 or 4. In some embodiments, the *Bombyx* transposon comprises one end with at least 90% identity to SEQ ID NO: 1 or 3; in some embodiments, the *Bombyx* transposon comprises one end with at least 90% identity to SEQ ID NO: 2 or 4.

In some embodiments, the *Bombyx* transposon comprises one end comprising at least 16 contiguous nucleotides from SEQ ID NO: 33 and one end comprising at least 16 contiguous nucleotides from SEQ ID NO: 34. In some embodiments, each ITR of the *Bombyx* transposon comprises SEQ ID NO: 32. In these embodiments, SEQ ID NO: 32 is immediately adjacent to the sequence 5'-TAT-3' or 5'-TTAA-3'.

The ITRs as described herein preferably flank a nucleic acid sequence which is inserted into the DNA of a cell. The nucleic acid sequence can include all or part of an open reading frame of a gene (i.e., that part of a protein encoding gene), one or more expression control sequences (i.e., regulatory regions in nucleic acid) alone or together with all or part of an open reading frame. Preferred expression control sequences include, but are not limited to promoters, enhancers, introns, polyadenylation sequences, border control elements, locus-control regions; expression enhancers that enhance RNA export from the nucleus, including woodchuck hepatitis post-transcriptional regulatory element (WPRE), hepatitis B virus post-transcriptional regulatory element (HPRE) (for example but not limited to SEQ ID NO: 104-105) and arctic ground squirrel post-transcriptional regulatory element (AGS) (for example but not limited to SEQ ID NOS: 106-107); and elements whose mechanism of action may not be known, such as scaffold attachment region (SAR) sequences (for example but not limited to SEQ ID NOS: 108-111), and insulator sequences that are thought to prevent the spread of condensed chromatin that might otherwise silence expression and prevent interference from a distal enhancer on a promoter, for example HS4 (for example but not limited to SEQ ID NOS: 112-113) (Yusufzai et. al., PNAS, vol. 101, no. 23, 8620-8624, June 2004).

Cells whose genomes contain a *Bombyx mori* transposon or a *Xenopus tropicalis* transposon are an aspect of the invention.

In a preferred embodiment, the nucleic acid sequence comprises a promoter operably linked to an open reading frame. The open reading frame may comprise a selectable marker that enables selection by a demonstrable phenotype, for example a fluorescent reporter. According to certain preferred embodiment, transposons of the present invention can preferably occur as a linear transposon (extending from the 5' end to the 3' end, by convention) that can be used as a linear fragment or circularized, for example in a plasmid.

Activity of transposases may be increased by fusion of nuclear localization signal (NLS) at the N-terminus, C-terminus, both at the N- and C-termini or internal regions of the transposase protein so long as transposase activity is retained. A nuclear localization signal or sequence (NLS) is an amino acid sequence that 'tags' or facilitates interaction of a protein, either directly or indirectly with nuclear transport proteins for import into the cell nucleus. Nuclear localization signals (NLS) used can include, but are not limited to, consensus NLS sequences, viral NLS sequences, cellular NLS sequences, and combinations thereof. In preferred embodiments, the NLS sequences are operably linked to the transposase.

The transposase protein can be introduced into a cell as a protein or as a nucleic acid encoding the transposase, for example as a ribonucleic acid, including mRNA, as DNA, e.g. as extrachromosomal DNA including, but not limited to, episomal DNA, as plasmid DNA, or as viral nucleic acid. Furthermore, the nucleic acid encoding the transposase protein can be transfected into a cell as a nucleic acid vector such as a plasmid, or as a gene expression vector, including a viral vector. The nucleic acid can be circular or linear. A vector, as used herein, refers to a plasmid, a viral vector or a cosmid that can incorporate nucleic acid encoding the transposase protein or the transposon of this invention. DNA encoding the transposase protein can be stably inserted into the genome of the cell or into a vector for constitutive or inducible expression. Where the transposase protein is transfected into the cell or inserted into the vector as nucleic acid, the transposase encoding sequence is preferably operably linked to a heterologous promoter. There are a variety of promoters that could be used including, but not limited to, constitutive promoters, tissue-specific promoters, inducible promoters, and the like. All DNA or RNA sequences encoding the *Bombyx mori* or *Xenopus tropicalis* transposase proteins are expressly contemplated.

5.2.4 Gene Transfer System

The present invention also features a gene transfer system comprising a *Bombyx mori* transposase and a transposon comprising a heterologous polynucleotide between a left ITR and a right ITR that are recognized and transposed by the transposase. The present invention also features a gene transfer system comprising a *Xenopus tropicalis* transposase and a transposon comprising a heterologous polynucleotide between a left ITR and a right ITR that are recognized and transposed by the transposase. The transposase can be encoded on the same polynucleotide as the transposon in the gene transfer system, or it may be encoded on a second polynucleotide. If the transposase is encoded on the same nucleic acid molecule as the transposon, the transposase is preferably in a part of the molecule that is not transposed. The gene transfer system of this invention, therefore, preferably comprises two components: the transposase as described herein and a transposon as described herein. In combination these two components provide active transposon activity and allow the transposon to be relocated. In use, the transposase binds to the transposon ends and promotes insertion of the intervening nucleic acid sequence into DNA of a cell as defined below.

In some embodiments, a gene transfer vector further comprises sequences encoding the transposase fused to certain protein functional domains. Such protein functional domains can include, but are not limited to, one or more DNA binding domains, one or more nuclear localization signals, one or more flexible hinge regions that can facilitate one or more domain fusions, and combinations thereof. Fusions can be made either to the N-terminus, C-terminus, or internal regions of the transposase protein so long as transposase activity is retained. DNA binding domains used can include, but are not limited to, a helix-turn-helix domain, Zn-finger domain, a leucine zipper domain, or a helix-loop-helix domain. Specific DNA binding domains used can include, but are not limited to, a Gal4 DNA binding domain, a LexA DNA binding domain, or a Zif268 DNA binding domain. Nuclear localization signals (NLS) used can include, but are not limited to, consensus NLS sequences, viral NLS sequences, cellular NLS sequences, and combinations thereof. Flexible hinge regions used can include, but are not limited to, glycine/serine linkers and variants thereof.

In further exemplary embodiments, the gene transfer system comprises a *Bombyx mori* transposon as defined above in combination with a *Bombyx mori* transposase protein (or nucleic acid encoding the *Bombyx mori* transposase protein to provide its activity in a cell). In other embodiments, the gene transfer system comprises a *Xenopus tropicalis* transposon as defined above in combination with a *Xenopus tropicalis* transposase protein (or nucleic acid encoding the *Xenopus tropicalis* transposase protein to provide its activity in a cell). This combination preferably results in the insertion of the nucleic acid sequence into the DNA of the cell. Alternatively, it is possible to insert the *Bombyx mori* or *Xenopus tropicalis* transposon into DNA of a cell through non-homologous recombination through a variety of reproducible mechanisms, and even without the activity of a transposase. In either event the described transposon can be used for gene transfer by using this gene transfer system.

In certain embodiments, a gene transfer vector further comprises a recombination protein, for example a recombinase, an integrase or a transposase including a *Bombyx mori* transposase or *Xenopus tropicalis* transposase and two or more site specific integration recognition sites to facilitate integration of an expression cassette into the genome of an expression host. In certain embodiments, these integration-facilitating sequences include a 5'-TTAA-3'-target sequence specific insertion element. In some other embodiments, the integration-facilitating sequences include a 5'-TTAT-3'-target sequence specific insertion element. In certain embodiments the integration-facilitating sequences are recognized by an integrase or a transposase, in certain embodiments the integrase is a *Bombyx mori* integrase, in other embodiments the integrase is a *Xenopus tropicalis* integrase. In certain embodiments the gene transfer vector further comprises a gene encoding the integrase. In certain embodiments, an expression vector further comprises Lentiviral LTR (long terminal repeats) or inverted repeats (IR) to facilitate integration of an expression cassette into the genome of an expression host.

In some embodiments, a gene transfer vector has restriction endonuclease sites in the expression cassette between the promoter and terminator sequence that facilitate cloning of heterologous polynucleotides for insertion. In preferred embodiments, these restriction endonuclease sites are type IIs restriction sites. TypeIIs restriction endonucleases recognize asymmetric DNA sequences and cleave both DNA strands at fixed positions, typically several base pairs away from the recognition sites. This property makes typeIIs restriction endonucleases particularly useful for assembling DNA fragments, where fragments with matching type IIs-generated ends are annealed and ligated, leaving an assembled DNA product without restriction recognition sequence scars at the ligation junctions. Type IIs restriction endonucleases that recognize non-palindromic sequences of 5, 6 or 7 base pairs, are found at an average frequency of one in 512, 2048 or 8192 base pairs respectively. It is therefore, relatively easy to identify typeIIs restriction endonucleases that do not cut inside a typical gene-sized DNA fragment or a gRNA fragment.

A gene transfer vector can be constructed to permit cloning using typeIIs restriction endonucleases and ligase by incorporating a stuffer, comprising a counter-selectable marker and flanked by typeIIs restriction sites, into a vector comprising a selectable marker. It is advantageous if the typeIIs restriction sites are chosen such that cleavage of the gene transfer vector with one or more typeIIs restriction enzymes yields a linear nucleic acid fragment comprising a selectable marker and with ends that are not compatible with each other. This design allows directional insertion of an insert DNA fragment that has cohesive ends compatible with the linear nucleic acid fragment of the gene transfer vector. The insert DNA fragment may be prepared by annealing a pair of oligonucleotides, or more preferably by PCR amplification and restriction digestion. In preferred embodiments the gene transfer vector ends are also not pseudo-compatible with each other; that is they do not anneal with each other by forming at least one non-standard Watson-Crick base pair (i.e., T or U with G) in a way that can be joined by a DNA ligase with reasonable efficiency.

In certain preferred embodiments, the gene transfer system mediates insertion of the *Bombyx mori* or *Xenopus tropicalis* transposon into the DNA of a variety of cell types and a variety of species by using the *Bombyx mori* or *Xenopus tropicalis* transposase protein. Preferably, such cells include any cell suitable in the present context, including but not limited to animal cells or cells from bacteria, fungi (example, yeast and more) or plants. Preferred animal cells can be vertebrate or invertebrate. For example, preferred vertebrate cells include cells from mammals including, but not limited to, rodents, such as rats or mice, ungulates, such as cows or goats, sheep, swine or cells from a human. Target cells also include without being limited thereto, lymphocytes, hepatocytes, neural cells, muscle cells, a variety of blood cells, and a variety of cells of an organism, embryonic stem cells, somatic stem cells e.g. hematopoietic cells, embryos, zygotes, sperm cells (some of which are open to be manipulated by an in vitro setting).

In other further exemplary embodiments, such cells, particularly cells derived from a mammal as defined above, can be pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). These cells are advantageously used to affirm stable expression of the transposase or to obtain a multiple number of cells already transfected with the components of the gene transfer system. Additionally, cells such as oocytes, eggs, and one or more cells of an embryo may also be considered as targets for stable transfection with the present gene transfer system. In certain preferred embodiments of the invention, the cells are Chinese hamster ovary (CHO) cells or Human embryonic kidney (HEK293) cells.

In other certain exemplary embodiments, the cell DNA that acts as a recipient of the transposon described herein includes any DNA present in a cell (as mentioned above) to be transfected, if the *Bombyx mori* or *Xenopus tropicalis* transposon is in contact with a *Bombyx mori* or *Xenopus tropicalis* transposase protein within the cell. For example, the DNA can be part of the cell genome or it can be extrachromosomal, such as an episome, a plasmid, a circular or linear DNA fragment. Typical targets for insertion are for example, double-stranded DNA.

The components of the gene transfer system described herein, that is the *Bombyx mori* or *Xenopus tropicalis* transposase protein (either as a protein or encoded by a nucleic acid as described herein) and the *Bombyx mori* or *Xenopus tropicalis* transposon can be transfected into a cell, preferably into a cell as defined above, and more preferably into the same cell. Transfection of these components may furthermore occur in subsequent order or in parallel. For example, the *Bombyx mori* or *Xenopus tropicalis* transposase protein or its encoding nucleic acid may be transfected into a cell as defined above prior to, simultaneously with or subsequent to transfection of the *Bombyx mori* or *Xenopus tropicalis* transposon. Alternatively, the transposon may be transfected into a cell as defined above prior to, simultaneously with or subsequent to transfection of the *Bombyx mori* or *Xenopus tropicalis* transposase protein or its encoding nucleic acid. If transfected in parallel, preferably both components are provided in a separated formulation and/or mixed with each other directly prior to administration to avoid transposition prior to transfection. Additionally, administration of at least one component of the gene transfer system may occur repeatedly, for example, by administering at least one, two or multiple doses of this component.

For any of the above transfection reactions, the gene transfer system may be formulated in a suitable manner as known in the art, or as a pharmaceutical composition or kit as described herein. In further preferred embodiments, the components of the gene transfer system may preferably be transfected into one or more cells by techniques such as particle bombardment, electroporation, microinjection, combining the components with lipid-containing vesicles, such as cationic lipid vesicles, DNA condensing reagents (example, calcium phosphate, polylysine or polyethyleneimine), and inserting the components (that is the nucleic acids thereof into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

In another embodiment, the nucleic acid encoding the *Bombyx mori* or *Xenopus tropicalis* transposase protein may be RNA or DNA. Similarly, either the nucleic acid encoding the *Bombyx mori* or *Xenopus tropicalis* transposase protein or the transposon of this invention can be transfected into the cell as a linear fragment or as a circularized fragment, preferably as a plasmid or as recombinant viral DNA.

In another embodiment, the nucleic acid encoding the *Bombyx mori* or *Xenopus tropicalis* transposase protein is thereby preferably stably or transiently inserted into the genome of the cell to facilitate temporary or prolonged expression of the *Bombyx mori* or *Xenopus tropicalis* transposase protein in the cell.

5.2.5 Increasing Expression by Selection

Sequences that are integrated at regions of the genome that are highly transcriptionally active may result in high levels of expression of encoded genes. In addition, or alternatively, sequences that are integrated into the genome in multiple copies may result in high levels of expression of encoded genes.

Methods are known in the art to increase the expression of a first polypeptide encoded by a construct (the expression polypeptide) by attempting to link the expression of the first polypeptide to the expression of a second quantitatively selectable polypeptide. For example, Glutamine synthase (GS) is used as a selectable marker that allows selection via glutamine metabolism. Glutamine synthase is the enzyme responsible for the biosynthesis of glutamine from glutamate and ammonia, and is a crucial component of the only pathway for glutamine formation in a mammalian cell. In the absence of glutamine in the growth medium, the GS enzyme is essential for the survival of mammalian cells in culture. Some cell lines, for example mouse myeloma cells do not express sufficient GS to survive without added glutamine. In these cells a transfected GS can function as a selectable marker by permitting growth in a glutamine-free medium. In other cell lines, for example Chinese hamster ovary (CHO) cells express sufficient GS to survive without exogenously added glutamine. These cell lines can be manipulated by genome editing techniques including CRISPR/Cas9 to reduce or eliminate the activity of the GS enzyme. In all of these cases, GS inhibitors such as methionine sulphoximine (MSX) can be used to inhibit a cell's endogenous GS activity. Selection protocols known in the art include introducing a construct comprising sequences encoding a first polypeptide and a glutamine synthase selectable marker, and then treating the cell with inhibitors of glutamine synthase such as methionine sulphoximine. The higher the levels of methionine sulphoximine that are used, the higher the level of glutamine synthase expression is required to allow the cell to synthesize sufficient glutamine to survive. Some of these cells will also show an increased expression of the first polypeptide.

A second system for increasing expression by selection uses the enzyme dihydrofolate reductase (DHFR) which is required for catalyzing the reduction of 5,6-dihydrofolate (DHF) to 5,6,7,8-tetrahydrofolate (THF) and is used as a selectable marker. DHFR confers resistance to methotrexate (MTX). DHFR can be inhibited by higher levels of methotrexate. Selection protocols known in the art include introducing a construct comprising sequences encoding a first polypeptide and a DHFR selectable marker into a cell, and then treating the cell with inhibitors of DHFR such as methotrexate. The higher the levels of methotrexate that are used, the higher the level of DHFR expression is required to allow the cell to synthesize sufficient DHFR to survive. Some of these cells will also show an increased expression of the first polypeptide.

The use of transposons and transposases in conjunction with such quantitatively selectable markers has several advantages over non-transposon constructs. One is that linkage between expression of the first polypeptide and the quantitatively selectable marker is better for transposons, because a transposase will integrate the entire sequence that lies between the two transposon ends into the genome. In contrast when heterologous DNA is introduced into the nucleus of a eukaryotic cell, for example a mammalian cell, it is gradually broken into random fragments which may either be integrated into the cell's genome, or degraded. Thus if a construct comprising sequences that encode a first polypeptide and a quantitatively selectable marker is introduced into a population of cells, some cells will integrate the sequences encoding the quantitatively selectable marker but not those encoding the first polypeptide, and vice versa. Selection of cells expressing high levels of selectable marker is thus only somewhat correlated with cells that also express high levels of the first polypeptide. In contrast, because the transposase integrates all of the sequences between the transposon ends, cells expressing high levels of selectable marker are highly likely to also express high levels of the first polypeptide.

A second advantage of transposons and transposases is that they are much more efficient at integrating DNA sequences into the genome. Thus a much higher fraction of the cell population is likely to receive one or more copies of the construct in their genomes, so there will be a correspondingly higher likelihood of good stable expression of both the selectable marker and the first polypeptide.

One embodiment of the present invention is thus a transposon such as described above, that further comprises a sequence encoding a first polypeptide and a selectable marker that can be inhibited by a small molecule inhibitor. In one embodiment the first polypeptide is part of an antibody. Other aspects of the invention include methods for introducing the transposon into the genome of a cell using a transposase, and selecting for high levels of expression of the quantitatively selectable marker. In some embodiments the selectable marker is glutamine synthase, in some embodiments the selectable marker is DHFR.

DNA transposases use a cut-and-paste mechanism for inserting their transposon into a DNA molecule. The number of copies of a transposon that can be integrated into the genome by a transposase is thus limited by the number of copies of the transposon that are present in the cell. The number of nuclear non-integrated copies of a plasmid in a eukaryotic cell can be increased if it contains viral replication sequences. For example in mammalian cells including CHO cells and HEK cells the SV40 origin of replication causes increases in the number of copies of a plasmid especially in the presence of the SV40 large T antigen. Similarly the Epstein-Barr virus origin of replication (OriP) causes increases in the number of copies of a plasmid especially in the presence of the Epstein-Barr virus nuclear antigen 1 (EBNA) and its truncated derivatives. Plasmids comprising a transposon in addition to viral replication sequences such as the SV40 origin of replication or the Epstein-Barr virus OriP which are not contained within the transposable portion of the transposon will therefore accumulate within the nucleus, providing more substrate copies of the transposon to be integrated into the cell genome. Such plasmids are an aspect of the current invention. The use of such plasmids to increase the number of copies of a transposon that is integrated into a target cell genome is also an aspect of the current invention. These plasmids may further comprise sequences encoding the SV40 large T antigen or the Epstein-Barr virus nuclear antigen 1 (EBNA).

Plasmids comprising viral replication sequences and transposons may be introduced into cells together with the transposase, or they may be introduced sequentially. Higher numbers of integrated transposons may be selected using quantitatively selectable markers such as DHFR or glutamine synthase.

5.2.6 Gene Transfer Vector Components

The function of sequence elements is dependent upon the context relative to the other sequences within the DNA sequence. An embodiment of the present invention provides a method for constructing a gene transfer vector variant set to improve an expression property of a polynucleotide encoding a polypeptide. In some embodiments the expression property is an amount of the polypeptide expressed, in some embodiments the expression property is an amount of soluble polypeptide expressed, in some embodiments the expression property is an amount of active polypeptide expressed. In the method, a plurality of sequence elements are identified in a gene transfer vector. The plurality of elements are classified by functional grouping, for example the elements are classified as enhancers, promoters, introns, 5' untranslated regions, 3' untranslated regions, RNA export promoting elements, elements that modulate chromatin structure, polyadenylation signals or transcriptional terminators. In addition, if the gene transfer vector will express more than one gene, the elements are further grouped according to the gene to which they are operably linked. A first gene transfer vector variant set comprising a plurality of configurations of the gene transfer vector is selected, such that members of the gene transfer vector set are related to one another by the substitution of one or more sequence elements, with a different element from the same functional group, or by the complete removal of an element of that functional group. For example a second member of the polynucleotide vector set may have the same configuration as a first member, but with a first enhancer element replaced by a second enhancer element, or a second member of the polynucleotide vector set may have the same configuration as a first member, but lack an enhancer element. A functional group in which there is more than one possible element in the gene transfer vector variant set is referred to as a variant group.

The number of variant groups and the number of elements that can be tested at each of those group positions is then calculated, such that each element will be present in a statistically representative fraction of the first gene transfer vector variant set. Additionally, when using search methods like Tabu, Ant optimization or similar techniques, the space can be searched on a sequence by sequence basis by using a memory of the space that has been visited previously and the properties encountered.

In some embodiments, selection of the variant set comprises applying complete factorial design, a $2^k$ factorial design, a $2^k$ fractional factorial design, a latin squares approach, a greco-latin squares approach, a Plackett-Burmann design, a Taguchi design, a monte carlo algorithm, a genetic algorithm, combinations thereof or some other statistical method for Design of Experiment, to the distribution of elements in the gene transfer vector variant set.

A first expression set, comprising a first expression polynucleotide in all or a portion of the first gene transfer vector variant set, is constructed. An expression property of the first expression set is measured. In some embodiments the expression polynucleotide encodes a first polypeptide, and the expression property is an amount of the polypeptide expressed, or an amount of soluble polypeptide expressed, or an amount of active polypeptide expressed. In some embodiments the first expression polynucleotide is the same sequence in all of the sequences of the first expression set.

In some embodiments of the invention the expression property is measured in one of the following expression systems: bacterial expression systems including *Escherichia coli, Salmonella* species, *Bacillus* species, *Streptomyces* species, *Pseudomonas* species, *Ralstonia eutropha, Chlamydomonas* species; yeast expression systems including *Saccharomyces, Pichia, Klebsiella* and *Candida* species, *Saccharomyces cerevisiae, Pichia pastoris, Pichia methanolica, Klebsiella lactis*; fungal expression systems including *Cryptosporidium* and *Trichoderma* species, filamentous fungal protein production systems, protozoan expression systems including *Plasmodium falciparum* (the causative agent of malaria), *Leishmania* model organisms including *Caenorhabditis elegans, Drosophila melanogaster, Xenopus laevis*; plants including soybean, bushbean, maize, cotton, tobacco, *Arabidopsis*, tissue culture expression systems including COS cells, Chinese Hamster Ovary cells and fibroblasts including 3T3 cells, cell lines infected with adenovirus, insect cell lines such as those derived from *Spodptera* species for growing baculovirus; model organisms for the study of disease and tests of the efficacies of DNA vaccines such as macaques, mice, rats, guinea pigs, sheep, goats and rabbits; in vitro expression systems prepared from extracts of living cells including *E coli* extracts, wheat germ extracts, rabbit reticulocyte lysates; in vitro expression systems prepared by assembly of purified individual components.

Standard techniques may be utilized to measure the expression property value for each respective polynucleotide in the plurality of polynucleotides of the first expression set. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine an expression property value of a respective polynucleotide (e.g., an amount of a protein encoded by the respective polynucleotide) in the plurality of polynucleotides present in an expression system. Other methods for detection of specific polypeptides include mass spectroscopy and mass spectroscopy of protein samples that have been treated with one or more site specific proteases to produce polypeptide fragments which can be uniquely identified by mass spectroscopy. One exemplary agent for detecting a protein of interest is an antibody capable of specifically binding to a protein of interest, preferably an antibody detectably labeled, either directly or indirectly.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio (ed.), 1980,

*Enzyme Immunoassay*, CRC Press, Boca Raton, Fla.; Ishikawa et al., (eds.), 1981, *Enzyme Immunoassay*, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

The method of systematic variation of vector elements and analysis of expression is conceptually quite different from previous methods described in the art, and is an aspect of the present invention. These previous methods have used very small numbers of different vector configurations and anecdotal correlations between vectors and expression properties to derive rules for optimal vector design. Such data are very unlikely to provide a basis from which to accurately model the effects of element choices within the vector upon expression. This is because there has been no systematic variation of vector elements, and because elements frequently interact, so that without systematic design in which co-variation of elements is minimized, it is impossible to attribute an effect to a particular element. In contrast the method of the present invention can be performed without assumptions regarding the element preferences of the expression host, or the underlying mechanism of such preference. Instead, the expression system is interrogated with systematically varied sets of sequences and measurements of the expression properties to determine the element configurations that result in desired expression properties. This method may be applied to any expression system as well as to identify an optimal configuration for high expression in multiple systems if a gene transfer vector is to be used in different systems.

An expression property of each of the polynucleotides in the plurality of polynucleotides of the first expression set can be compared to the element configuration in each of the polynucleotides to ascertain a relationship between element configuration and the expression property. Such correlation can also be achieved using pattern classification methods or statistical methods. Examples of pattern classification methods or statistical methods include, but are not limited to linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, *The Elements of Statistical Learning*, Springer, New York; and Agresti 1996, *An Introduction to Categorical Data Analysis*, John Wiley & Sons, New York, each of which is hereby incorporated by reference herein for such purpose. Such modeling or correlation can then be used to assign values for the different elements in the expression system. The design and synthesis of a gene transfer vector variant set and measurement of an expression property of the polynucleotides within a gene transfer vector variant set for the purpose of evaluating different vector element choices within an expression system is an aspect of the present invention.

In some embodiments, the method further comprises the steps of (i) modeling a sequence-activity relationship between (a) one or more substitutions at one or more elements in the gene transfer vector variant set and (b) the expression property measured for all or the portion of the variants in the variant set, and (ii) defining a second gene transfer variant set to comprise variants that include substitutions in the plurality of elements that are selected based on a function of the sequence-activity relationship. In some embodiments the modeling a sequence-activity relationship comprises modeling a plurality of sequence-activity relationships each of which uses only a subset of the available sequence and activity data.

Several methods exist for regression of multivariate data, where predictive relationships between some or all of the independent variables and expression level are determined. Examples of such methods are Partial Least Squares (PLS) and Principal Components Regression (PCR) (Wold et al., 1993, "DNA and peptide sequences and chemical processes multivariately modeled by principal component analysis and partial least-squares projections to latent structures," Analytica Chimica Acta 277, 239-253). PLS algorithms, for example, seek to maximize the correlation of the X-data (e.g., codon frequencies) and expression while simultaneously maximizing the X-data variance captured in the model. In doing so, the algorithm determines new orthogonal variables, called latent variables, which are linear combinations of the original variables that best capture the X-data and explain Y variation.

In some embodiments, the sequence-expression relationship has the form:

$$Y=f(w_1x_1, w_2x_2, \ldots w_ix_i)$$

where,

Y is a quantitative measure of the expression property;

$x_i$ is a descriptor of a substitution, a combination of substitutions, or a component of one or more substitutions, at one or more positions in the plurality of positions;

$w_i$ is a weight applied to descriptor $x_i$; and f( ) is a mathematical function.

In some embodiments, the modeling comprises regressing:

$$Y=f(w_1x_1, w_2x_2, \ldots w_ix_i).$$

In some instances this regressing comprises linear regression, non-linear regression, logistic regressing, or partial least squares projection to latent variables.

A sequence-expression relationship derived from the expression properties of a first expression variant set may be used to design gene transfer vectors to express a second polypeptide with a different amino acid sequence. The use of a sequence-expression relationship to design vectors for the expression of a polypeptide of interest, where the sequence-expression relationship was derived from polynucleotides encoding polypeptides that are not the polypeptide of interest is an aspect of the invention.

In some embodiments, modeling techniques are used to derive sequence-expression relationships. Such modeling techniques include linear and non-linear approaches. Linear and non-linear approaches are differentiated from each other based on the algebraic relationships used between variables and responses in such approaches. In the system being modeled, the input data (e.g., variables that serve as descriptors of the biopolymer sequence), in turn, can be linearly related to the variables provided or non-linear combinations of the variables. It is therefore possible to perform different combinations of models and data-types: linear input variables can be incorporated into a linear model, non-linear input variables can be incorporated into a linear model and non-linear variables can be incorporated into non-linear models.

In some embodiments, supervised learning techniques are used to identify relationships between vector element configurations in the expression set and measured expression properties. Such supervised learning techniques include, but are not limited to, Bayesian modeling, nonparametric techniques (e.g., Parzen windows, $k_n$-Nearest-Neighbor algorithms, and fuzzy classification), neural networks (e.g., hopfield network, multilayer neural networks and support vector machines), and machine learning algorithms (e.g., algorithm-independent machine learning). See, for example, Duda et al., *Pattern Classification*, $2^{nd}$ edition, 2001, John Wiley & Sons, Inc. New York; and Pearl, *Probabilistic Reasoning in Intelligent Systems: Networks of Plausible Inference*, Revised Second Printing, 1988, Morgan Kaufmann, San Francisco. For example, the sequence-expression data can be used to predict the expression property of any sequence given the codon descriptors for a sequence using a neural network. The input for the network is the descriptors and the output is the predicted value of Y. The weights and the activation function can be trained using supervised decision based learning rules. The learning is performed on a subset of variants called the training set and performance of the network is evaluated on a test set.

In some embodiments, unsupervised learning techniques are used to identify relationships between vector element configurations in the expression set and measured expression properties. Such unsupervised learning techniques include, but are not limited to stochastic searches (e.g., simulated annealing, Boltzmann learning, evolutionary methods, principal component analysis, and clustering methods). See, for example, Duda et al., *Pattern Classification*, $2^{nd}$ edition, 2001, John Wiley & Sons, Inc. New York. For example, the weights in equation B can be adjusted by using monte carlo and genetic algorithms. The optimization of weights for non-linear functions can be complicated and no simple analytical method can provide a good solution in closed form. Genetic algorithms have been successfully used in search spaces of such magnitude. Genetic algorithms and genetic programming techniques can also be used to optimize the function form to best fit the data. For instance, many recombinations of functional forms applied on descriptors of the sequence variants can be applied.

In some embodiments, boosting techniques are used to construct and/or improve models developed using any of the other techniques described herein. A model of the sequence-expression relationship can be described as a functional form whose parameters have been trained for the input data (Y and $x_i$). Many algorithms/techniques to build models have been described. Algorithms applied on a specific dataset can be weak in that the predictions can be less accurate or "weak" (yielding poor models). Models can be improved using boosting techniques. See, for example, Hastie et al., *The Elements of Statistical Learning*, 2001, Springer, New York. The purpose of boosting is to combine the outputs of many "weak" predictors into a powerful "committee." In one embodiment of the invention, boosting is applied using the AdaBoost algorithm. Here, the prediction algorithm is sequentially applied to repeatedly modified versions of the data thereby producing a sequence of models. The predictions from all of these models are combined through a weighted majority vote to produce the final prediction. The data modification at each step consists of applying weights ($W^b_i$) to each of the i training observations. Initially weights are set to 1/N, where N is the number of training observation (sequence-activity data). The weights are modified individually in each successive iteration. Training observations that were predicted poorly by a particular model have their weights increased and training observations that were predicted more accurately have their weights decreased. This forces each successive model to concentrate on those training observations that are issued by the previous model. The step of combining the models to produce a "committee" assigns a weight to each model based on the overall prediction error of that model.

The various modeling techniques and algorithms described herein can be adapted to derive relationships between one or more expression properties and the element configuration of a polynucleotide and therefore to make multiple predictions from the same model. Modeling techniques that have been adapted to derive sequence-expression relationships for polynucleotides are within the scope of the present invention. Some of these methods derive linear relationships (for example partial least squares projection to latent structures) and others derive non-linear relationships (for example neural networks). Algorithms that are specialized for mining associations in the data are also useful for designing sequences to be used in the next iteration of sequence space exploration. These modeling techniques can robustly deal with experimental noise in the activity measured for each variant. Often experiments are performed in replicates and for each variant there will be multiple measurement of the same activity. These multiple measurements (replicate values) can be averaged and treated as a single number for every variant while modeling the sequence-expression relationship. The average can be a simple mean or another form of an average such as a geometric or a harmonic mean. In the case of multiple measurements, outliers can be eliminated. In addition, the error estimation for a model derived using any algorithm disclosed herein can incorporate the multiple measurements through calculating the standard deviation of the measurement and comparing the predicted activity from the model with the average and estimate the confidence interval within which the prediction lies. Weights for observations to be used in models can also be derived from the accuracy of measurement, for example, through estimating standard deviation and confidence intervals. This procedure can put less emphasis on variants whose measurements are not accurate. Alternatively, these replicate values can be treated independently. This will result in duplicating the sequences in the dataset. For example, if sequence variant, represented by descriptor values $\{x_j\}^{i1}$, has been measured in triplicates($Y_{i1}$, $Y_{i2}$, $Y_{i3}$), the training set for modeling will include descriptor value $\{x_j\}^{i2}$ with activity $Y_{i2}$ and $\{x_j\}^{i3}$ with activity $Y^{i3}$ in addition to $\{x_j\}^{i1}$ with activity $Y_{i1}$, where $\{x_j\}^{i1}=\{x_j\}^{i2}=\{x_j\}^{i3}$.

The models developed using various algorithms and methods in the previous step can be evaluated by cross validation methods. For example, by randomly leaving data out to build a model and making predictions of data not incorporated into the model is a standard technique for cross validation. In some instances, data may be generated over a period of months. The data can be added incrementally to the modeling procedure as and when such data becomes available. This can allow for validation of the model with partial or additional datasets, as well as predictions for the properties of gene transfer vector configurations for which activities are still not available. This information may then be used to validate the model.

In one embodiment of the present invention, average values and standard deviations for weight functions can be obtained by omitting a part of the available data. Either individual sequences and their associated expression activities or individual codons can be left out. A sequence-expression relationship can then be constructed from this partial data. This process can be repeated many times, each time the data to leave out is selected randomly. Finally an average and range of values for each weight function is calculated. The weight functions can then also be ranked in order of their importance to activity. The range of values for each weight can provide a measure of the confidence with which the weight is assigned. It can also provide a measure of the importance of the variable in determining the expression property. For example in some instances, the larger the standard deviation for a variable weight, the larger the range of values for that variable that are associated with desirable expression properties.

In some instances the mean value for the variable weight is used to indicate the likely contribution of the element or combination of elements to vector performance. In some instances the mean value for the variable weight minus the standard deviation of the weight is used to indicate the likely contribution of the element or combination of elements to vector performance. In some instances an element or combination of elements is selected if the mean value of the variable weight is above a predetermined value. In some instances an element or combination of elements is selected if the mean value of the weight minus the standard deviation of the weight is above a predetermined value. In some instances the predetermined value is the mean value of all of the variable weights in the model. In some instances the predetermined value is greater than the value of 95% of the variable weights; in some instances the predetermined value is greater than the value of 90% of the variable weights; in some instances the predetermined value is greater than the value of 80% of the variable weights; in some instances the predetermined value is greater than the value of 50% of the variable weights.

In some instances the modeling comprises partial least squares regression and the weight is a regression vector. The regression vector for each variable is used to identify elements that are most favorable for expression in a system. In some instances an element is selected if its regression vector is the highest in the element set, or if it has one of the top 2 or top 3 or top 4 or top 5 or top 6 or top 7 or top 8 or top 9 or top 10 values for regression vectors.

The initial set of data can be small, so models built from it can be inaccurate. Improving the modeled relationship further depends upon obtaining better values for weights whose confidence scores are low. To obtain this data, additional variants designed will provide additional data useful in establishing more precise sequence-expression relationships.

In some embodiments, defining the second variant set comprises adding one or more variants each having an element not present in any variant in the first variant set. In some embodiments, defining the second variant set comprises adding one or more variants each having an element changed in a group not varied in any variant in the first variant set.

Sequence-activity modeling requires an adequate amount of data from variants with statistically distributed element compositions. In some embodiments the first expression set comprises between 5 and 200 gene transfer vectors which each differ from the other members of the set by at least 1 functional element, in preferred embodiments the first expression set comprises at least 10 gene transfer vectors which each differ from the other members of the set by at least 2 functional elements, in some embodiments the first expression set comprises between 10 and 100 gene transfer vectors which each differ from the other members of the set by at least 2 functional elements, in some embodiments the first expression set comprises between 15 and 60 gene transfer vectors which each differ from the other members of the set by at least 2 functional elements.

Examples of such polynucleotide vector sets are shown in Tables 15-18. For two or more functional groups, the polynucleotide vector set is constructed with a first coding polynucleotide that encodes a first expression polypeptide. In some embodiments the first expression polypeptide is a fluorescent protein, or an antibody chain. An expression property is measured for all or a portion of the variants in the variant set. A sequence-activity relationship is modeled between (i) one or more substitutions at one or more elements of the polynucleotide vector set and (ii) the property measured for all or the portion of the variants in the variant set. The variant set is then redefined to comprise variants that include substitutions in the plurality of elements that are selected based on a function of the sequence-activity relationship. In preferred embodiments the variant set comprises between 5 and 200 vector configurations, in preferred embodiments the variant set comprises between 10 and 100 vector configurations, in preferred embodiments the variant set comprises between 15 and 60 vector configurations.

The properties of a biological system including natural as well as non-natural systems with respect to any measured property depends on the interaction between multiple nucleic acid sequence elements, which may be located at positions throughout the polynucleotide. The ability to rationally design a nucleic acid construct with an optimal configuration of elements is advantageous for various applications such as protein synthesis via vector optimization, cell line development and strain engineering. Protein synthesis is a highly dynamic and multi-step process and which plays a central role in synthetic biology, pharmaceutical production and other applications in biotechnology. This importance has led to the development of various parts or genetic control elements able to modulate and precisely control various aspects of protein expression. This capability is not only essential for the successful construction of more complex synthetic biological devices, but also provides tools needed for the tuning of their function for improved performance and reliability.

Many different types of parts capable of controlling transcriptional and translational aspects of the protein synthesis process have been developed. At the transcriptional level, libraries of promoters have been created spanning a wide range of expression levels (Mey et. al., 2007 BMC Biotechnology; Hartner et. al., 2008 Nucleic Acids Research) and efforts have been made to understand potential rules governing promoter structure (Blount et. al., 2012 PLoS One 7; Blazeck et. al., 2013 Biotecnology Journal; Lubliner et. al., 2013 Nucleic Acids Research). At the translational level, libraries of ribosome binding sites (RBSs) have been generated (Mutalik et. al., 2013 Nature Methods) and some rational approaches developed (Salis et.

al., 2009 Nature Biotechnology). Biophysical models of interactions between the ribosome and mRNA have successfully been used to predict relative ribosome initiation strengths and applied in a forward-engineering mode to suggest potential RBS sequences with a desired strength (Salis et. al., 2009 Nature Biotechnology). In addition to RBSs, the speed of translation has been found to be strongly influenced by synonymous codon usage within the gene being expressed. Changes in codon usage have been shown to strongly affect overall expression levels (Welch et. al., 2009 PLoS; Kudla et. al., 2009 Science), influence correct folding of active proteins (Zhang et. al., 2009 Nature Structural and Molecular Biology), and to enable dynamic responses to environmental stresses (Wohlgemuth et. al., 2013 Nucleic Acids Research).

Configurations of polynucleotide vectors with improved expression properties are an aspect of the present invention, including the configurations shown in Tables 6-18.

In preferred embodiments, a gene transfer vector comprises expression elements capable of driving high protein expression, for example a mammalian enhancer selected from amongst the CMV immediate early enhancer (see for example, DQ000968.1 GI:66276969; KF853603.1 GI:576890587), the EF1a enhancer (see for example, J04617.1 GI:181962), the adenoviral major late protein enhancer (see for example, JX173086.1 GI:406679291), the SV40 enhancer (see for example, KM486843.1 GI:731516977; JQ394984.1 GI:41058488); a promoter selected from amongst the EF1a promoter (see for example, J04617.1 GI:181962; AC097023.6 GI:49615137; NM_010106.2 GI:126032328; AY188393.1 GI:30313796) from any mammalian or avian species including but not limited to human, rat, mice, chicken and Chinese hamster, the CMV promoter (see for example, DQ000968.1 GI:66276969; M64943.1 GI:330637), the GAPDH promoter (see for example, J04038.1 GI: 182980) from any mammalian species, the Herpes Simplex Virus thymidine kinase (HSV-TK) promoter (see for example, J04327.1 GI:330219), the actin promoter (see for example, X00182.1 GI:63017) from any mammalian or avian species including but not limited to human, rat, mice, chicken and Chinese hamster, and the ubiquitin promoter (see for example, BC000379.2 GI:33875368); an intron selected from among CMV intron A (see for example, M21295.1 GI:330620), CMV intron B (see for example, M21295.1 GI:330620), CMV intron C (see for example, M21295.1 GI:330620), the EF1a intron (see for example, J04617.1 GI:181962) from any mammalian or avian species including but not limited to human, rat, mice, chicken and Chinese hamster, the actin intron (see for example, X00182.1 GI:63017) from any mammalian or avian species including but not limited to human, rat, mice, chicken and Chinese hamster, the GAPDH intron (see for example, J04038.1 GI: 182980) from any mammalian or avian species including but not limited to human, rat, mice, chicken and Chinese hamster, the adenoviral major late protein intron (see for example, U89672.1 GI:1899166), the PGK promoter (see for example, KC710227.1 GI:501416041) from any mammalian or avian species including but not limited to human, rat, mice, chicken and Chinese hamster; 5' untranslated regions (5' UTRs) from any mammalian or avian species including but not limited to human, rat, mice, chicken and Chinese hamster.

In preferred embodiments the gene transfer vector may comprise selectable markers to enable selection of cells with stably integrated transposons. Examples include genes that confer resistance to puromycin, neomycin, hygromycin, blasticidin and zeocin. The gene transfer vector may comprise a bacterial resistance marker and a bacterial origin of replication to facilitate manipulation in prokaryotic cells. These prokaryotic elements are preferably contained within the non-transposable portion of the vector.

In preferred embodiments gene transfer vector may comprise other sequence elements that enhance expression of the genes that they encode. Examples include elements that are believed to enhance RNA processing and nuclear export such as woodchuck hepatitis post-transcriptional regulatory element (WPRE), hepatitis B virus post-transcriptional regulatory element (HPRE) (for example but not limited to SEQ ID NO: 104-105) and arctic ground squirrel post-transcriptional regulatory element (AGS) (for example but not limited to SEQ ID NOS: 106-107). Examples also include polyadenylation sequences such as the polyadenylation sequences from BGH (bovine growth hormone) (see for example, M57764.1 GI:163091; KF992215.1 GI:593024220), HGH (human growth hormone) (see for example, M13438.1 GI:183156), the polyadenylation signals from human (see for example, X03145.1 GI:34173) or rabbit (see for example, NM_001082260.2 GI: 129270172; EF186084.1 GI: 122893039) beta globin, viral polyadenylation signals including those from SV40 (see for example, AY122060.1 GI:22001016) or herpes simplex virus (see for example, M38699.1 GI:330309) and terminator sequences from gastrin. Examples also include sequences that are thought to act as insulators by preventing the spread of heterochromatin or promoter interference such as but not limited to the HS4 (SEQ ID NOS: 112) and HS4 core (SEQ ID NOS: 113). In some preferred embodiments, a pair of insulators surround the expressible sequences. Examples also include sequences believed to mediate attachment to the chromatin scaffold such as but not limited to SEQ ID NOS: 108-111. Regardless of their actual mechanism, incorporation of expression enhancing elements into gene transfer vectors and transposons is expressly contemplated. In preferred embodiments, gene transfer vectors comprise transposons.

In some embodiments, the nucleic acid construct is a vector with enhanced expression and integration properties. For example, an optimal configuration of vector elements for enhanced transient expression as well as more efficient stable integration and expression was identified by the methods described herein. A mammalian vector construct variant set was generated using multiple combinations of various transposon ends, insulators, enhancers, promoters, 5' untranslated regions (UTRs), 3' untranslated regions (UTRs), RNA export modulating sequence, polyadenylation sequences, terminators, matrix attachment element and transposases. The mammalian vector variant set was tested for optimal DasherGFP expression in Human embryonic kidney (HEK 293) cells to identify an optimized vector construct. Other optimized vector constructs were identified with optimal configurations of elements listed above that show high expression of DasherGFP in HEK 293 and CHO cell lines as shown in Tables 6-20. Vector configurations with different promoter combinations were also shown to affect DasherGFP expression. Further optimization of this vector construct for different cell lines using the methods described herein is expressly contemplated. An advantage of the methods described herein is to quickly identify a subset of sequence elements most likely to influence desired activity as well as to facilitate predictable construction of optimal configuration of elements.

In some embodiments, two promoters are placed in opposite orientation, each driving an expression cassette such that transcription from the two promoters diverges. Such a configuration greatly improves expression of transcripts from the expression cassettes.

In some embodiments, elements that are useful in enhancing performance may include those localized to the genomic DNA of a cell. For example expression may be influenced by the levels of RNA polymerases, chaperonins, proteases, processing enzymes, or other factor encoded by DNA on the cell chromosome. It might also be advantageous to augment the host chromosome with functional elements that influence performance. In some embodiments, a variable for engineering is the site at which a functional gene is integrated into a host cell chromosome.

In some embodiments, the nucleic acid construct is a polynucleotide comprising elements or combinations of elements arranged in an optimal configuration. In some embodiments, the polynucleotide is linear. In some embodiments, the elements in a nucleic acid construct comprise functional genetic features, for example, promoters, enhancers, introns, polyadenylation signals, origins of replication, and terminators. In some embodiments, the elements in a nucleic acid construct comprise protein-encoding elements such as secretion signals, resistance markers, anchoring peptides, localization signals, and fusion tags. In some embodiments, the plurality of elements comprises three or more elements, six or more elements, between three and twenty elements or between three and hundred elements. In some embodiments, nucleic acid construct variants include substitutions in a single element comprising one or more positions, three or more positions, six or more positions. In some embodiments, nucleic acid variants include substitutions wherein the substitutions are variations in elements and/or presence or absence of elements. In some embodiments, the substitutions include changes in the position of one or more elements. In some embodiments, nucleic acid variants include a change in the order of one or more elements.

An important aspect of the present invention is that it enables the assessment of the performance of different types of elements: those that affect transcription, those that affect RNA processing, those that affect RNA export from the nucleus of the cell, those that affect integration into the host genome, those that affect replication within the host cell, those that affect translational initiation and those that affect translational elongation. The present invention allows sets of polynucleotide constructs to be designed to test the interactions of these types of elements.

In some embodiments, the configuration of sequence elements in the transposon will result in highly efficient integration into the genome of the target cell. In these instances addition of the transposase may provide only a small improvement in the expression of genes on the transposon, or no improvement at all. The present invention expressly contemplates that under some circumstances, the configuration of sequence elements within the transposon will be sufficient so that the gene transfer system will not need to include the transposase.

5.2.7 Use of Coupling Elements in a Gene Transfer System

Messenger RNA molecules in eukaryotic cells are generally monocistronic, that is, they usually encode a single polypeptide. This is because translation in eukaryotes generally occurs by a process in which the ribosome binds to a structure at the 5' end of the mRNA and then "scans" down the mRNA until it finds an initiation codon (generally AUG) where it begins translation. It then translates the mRNA, producing the encoded polypeptide, until it reaches a termination codon (generally UAA, UAG or UGA) which causes the ribosome to end translation and dissociate from the mRNA. Certain eukaryotic viruses have evolved mechanisms by which they can express more than one polypeptide from a single mRNA. These include internal ribosome entry sites (IRES), and cis-acting hydrolase element (CHYSEL) sequences.

An IRES provides a structure to which the ribosome can bind that does not need to be at the 5' end of the mRNA. It can therefore direct a ribosome to initiate translation at a second initiation codon within an mRNA, allowing more than 1 polypeptide to be produced from a single mRNA. A CHYSEL sequence causes a translating eukaryotic ribosome to release the growing polypeptide chain that it is synthesizing without dissociating from the mRNA. The ribosome continues translating, and therefore produces a second polypeptide. A single genetic construct can contain more than one IRES or CHYSEL sequence, and it can contain both IRES and CHYSEL sequences, so can therefore encode 2 or 3 or 4 or 5 or 6 or more than 6 polypeptides on a single mRNA.

IRES or CHYSEL sequences can therefore be used as coupling elements, to link the expression of two or more polypeptides. For example the expression of a first polypeptide may be linked to the expression of a selectable protein that provides a physical, chemical or biological method for selecting cells on the basis of how much of the selectable protein is expressed. The use of certain selectable proteins to indicate the status or functionality of a genetic construct within an organism is an aspect of the invention. The combining of selectable proteins with IRES or CHYSEL sites to indicate the status or functionality of a polynucleotide, or to indicate the level of expression of a polynucleotide or polypeptide is another aspect of the invention. IRES sequences are used to simultaneously express two or more proteins from a single promoter.

Another important application of translational coupling sequences, particularly IRES sequences, is in allowing the co-expression of two polypeptide chains that function together, either to catalyze different steps in a metabolic pathway, or as parts of the same molecule. A particularly important example is in the formation of a human antibody; a full human antibody consists of two heavy and two light chains. For antibody production, it is desirable for the heavy and light chains to be expressed in an optimal ratio. Monoclonal antibodies (Mab) are heterotetramers consisting of an equimolar ratio of heavy chain (HC) to light chain (LC) genes encoded on either one or two plasmids. Although the chains are present at equimolar amounts ratio in the final antibody molecule, higher amounts of antibody are generally expressed if the light chain is more highly expressed than the heavy chain. Further, although the optimal ratio May be as high as 5× as much light chain as heavy chain, the exact ratio that gives most assembled antibody tetramer depends on the exact antibody being expressed.

Optimization of the ratio of heavy and light chain is typically accomplished in one of two ways. In the first, polynucleotides encoding the heavy chain and the light chain are carried on two different plasmids and co-transfected into a host cell. In the second, a single plasmid carries both polynucleotides (encoding the heavy chain and the light chain), each with its own promoter and polyadenylation sequence. In the case of co-transfection, individual cells take up different numbers of each plasmid. Because it is only possible to control the average number of each plasmid taken up by each cell, many cells do not end up expressing the optimal ratio of heavy and light chain. This problem is amplified in the case of stable cell lines, because there is the further variable of integration location which also affects expression levels. Dual promoter constructs overcome these difficulties, and can often be effective. However they can become large and genetically unstable because of repeated sequences: promoters, enhancers, polyadenylation sequences, RNA export sequences such as WPRE and HPRE and matrix attachment regions may all need to be duplicated. This can compromise transfection efficiency and performance; there can also be interference between two eukaryotic promoters in the same construct.

These drawbacks may be overcome by using IRES sequences, providing a set of IRES sequences are available which can produce different levels of expression of the second polypeptide relative to the first. This allows the equivalent of the titration that is currently accomplished by co-transfecting different amounts of the two plasmids. However it has the significant advantage that each cell gets an equal number of copies of the polynucleotides encoding the first polypeptide and the second polypeptide (because they are on the same plasmid), even though different cells may get different numbers of plasmids. Thus even though the amount of each polypeptide may vary from cell to cell, the ratio of the amount of the first polypeptide to the second polypeptide should be much less variable.

The most commonly used IRES in mammalian systems is that from Encephalomyocarditis virus, which includes four amino acids of the N-terminus of the second open reading frame (MATT). There are thus two significant limitations in the currently available tools for co-expression of multiple genes in eukaryotic cells. Firstly, there is no readily available set of IRES sequences that give a known range of ratios of expression between the first and second open reading frame, so it is difficult to control the relative expression of two proteins. Secondly, the most commonly used IRES sequence requires an N-terminal extension of the second protein, which may compromise or modify the function of that protein. There is thus a need in the art for a set of characterized sequences that can be easily incorporated between a first and a second open reading frame to create an optimal expression balance for a downstream function or product of the cell.

We synthesized sequences inspired by the 5' untranslated regions of positive strand RNA viruses, cloned them under control of a single promoter into a vector between a polynucleotide encoding a green fluorescent protein and a polynucleotide encoding a red fluorescent protein, transfected the construct into mammalian cells and measured the expression of red and green fluorescence. Using this test we identified IRES sequences that function in human embryonic kidney (HEK) and Chinese hamster ovary (CHO) cells (SEQ ID NOS: 58-100) and that show different expression levels of the second (IRES-controlled) protein relative to the first. This is of particular importance since Chinese hamster ovary (CHO) cells are the dominant host for industrial monoclonal antibody production because of their capacity for proper protein folding, assembly and appropriate post-translational modifications. Each of these active sequences can be used to search sequence databases for similar sequences, and similar sequences can in turn be tested using the same system. In preferred embodiments, the IRES sequence is selected from bat picornavirus sequences or rodent picornavirus sequences. Very similar sequences have quite large differences in function. One method to improve the function of individual IRESes is to create consensus sequences. Another method is to identify sequences from viral strains that are reported to be most virulent. Another method is to create libraries of variant sequences and to test members of these libraries using a pair of fluorescent reporter proteins.

In some embodiments, the IRES sequence has at least 80% similarity to SEQ ID NOS: 58-100, or is a chimera of two or more of these sequences. In some other embodiments, the IRES sequence has at least 90% similarity to SEQ ID NOS: 58-100. In some embodiments, the nucleic acid encodes IRES sequences, wherein the nucleic acid has at least at least 80%, at least 90% at least 95%, at least 98% or at least 99% sequence identity to a consensus sequence derived from a set of naturally occurring sequences of the 5' untranslated region of RNA viral genomes; in some embodiments the consensus sequence is not itself identical to any naturally occurring sequence. In some embodiments, an IRES sequence has at least 50%, at least 60%, at least 70%, at least 80%, at least 90% similarity to 5' untranslated regions (UTRs) of the picornavirus family of viruses. In some embodiments, the IRES elements of the invention are incorporated into an expression vector with a single promoter and one or more IRES elements that allow control of the expression ratios of one or more genes. In other embodiments, IRES elements that function as enhancers are incorporated into an expression vector wherein the IRES elements function to enhance expression of one or multiple genes.

Use of IRES sequences to control expression levels of two or more proteins in a gene transfer vector comprising transposons for stable integration with or without transposases identified herein, with particular emphasis on expressing antibodies in Chinese hamster ovary cells (CHO) or Human embryonic kidney (HEK) cells is another important aspect of this invention. For example, expression of heavy and light chains of an antibody can be controlled by selecting an IRES with the appropriate strength.

Another aspect of the invention is the use of IRES sequences in transient expression vectors. Use of IRES elements to control expression levels of two or more proteins in expression vectors comprising elements or combinations of elements arranged in an optimal configuration as described herein (Section 5.2.6) above is another embodiment of the invention. Additional embodiments include use of IRES sequences to control expression levels of two or more polypeptides in expression vectors (with transposons for stable integration and without for transient expression) with viral replication sequences to increase copy number of the plasmid. Use of IRES sequences in any of the vector configurations shown in any of the Tables here shown is an aspect of the invention.

Ratios of expressed gene(s) can be controlled using the various IRES elements identified. This is particularly useful when the gene products are to be expressed in a fixed ratio to get optimal results.

In some preferred embodiments, IRES sequences are selected from SEQ ID NOS: 58-100.

In some embodiments, it is advantageous to include secretory peptides at the amino-terminus of a protein that enables translocation of the protein to the endoplasmic reticulum (ER). This helps not only in the ease of purification but also allows proper folding of complex disulfide bonds and glycosylation. Proper selection of a signal peptide can have dramatic consequences on protein over-expression. A number of efficient secretion peptides have been described, for example interleukin-2, CD5, the immunoglobulin kappa light chain, trypsinogen, serum albumin and prolactin. We have identified secretion peptides (SEQ ID NOS: 114-115) that function well in combination with IRES sequences. This is especially important for expression of antibodies in a single construct using IRES elements as described herein.

A kit comprising a single expression vector with one or more IRES elements and reagents to facilitate cloning of ORFs into the vector is another aspect of the invention. The kit can additionally include a set of IRES elements as templates, such that the IRES elements can be incorporated into an expression vector of choice.

5.2.8 Additional Applications of the Gene Transfer System

Using the gene transfer system for methods such as gene discovery and/or gene tagging, permits, for example, identification, isolation, and characterization of genes involved with growth and development through the use of transposons as insertional mutagens or identification, isolation and characterization of transcriptional regulatory sequences controlling growth and development.

The gene transfer system of the invention represents a considerable refinement of non-viral DNA-mediated gene transfer. For example, adapting viruses as agents for gene therapy restricts genetic design to the constraints of that virus genome in terms of size, structure and regulation of expression. Non-viral vectors, as described herein, are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors. Additionally, the gene transfer system of the present invention is a non-viral gene transfer system that facilitates insertion into DNA and markedly improves the frequency of stable gene transfer.

An efficient method for using transposon-transposase combinations of the present invention to stably introduce a chimeric antigen receptor (CAR) to redirect the specificity of human T-cells is expressly contemplated and is an important aspect of the invention. For example, redirecting the specificity of T cells for B-lineage antigens and advanced B-cell malignancies by infusion of such tumor-specific T cells (adoptive cell transfer) modified by the transposon-transposase of the present invention is another embodiment. Combining cell-based therapies with gene-based therapies, in which genetically engineered chimeric antigen receptors (CARs) or tumor-specific T-cell receptor genes are expressed in immune effector cells has enormous therapeutic potential. CARs combine intracellular signaling domains with a single-chain variable fragment of an antibody (Ab) into a single chimeric protein. Engineering immune cells (T-cells) to recognize and attack their tumors is a powerful approach especially in treating B-cell malignancies or lymphomas. A chimeric antigen receptor (CAR) recognizes cell-surface tumor-associated antigen independent of human leukocyte antigen (HLA) and employs one or more signaling molecules to activate genetically modified T cells for killing, proliferation, and cytokine production. For example, targeting CD19 has been achieved through the enforced expression of a CAR that recognizes CD19 independent of HLA. In contrast to methods that genetically modify T cells using recombinant retrovirus, a non-viral gene transfer approach using the transposon-transposase system to enforce expression of the introduced CAR is a viable alternative and avoids some of the issues such as preferential integration sites associated with most viruses. To improve therapeutic potential, CAR signaling through CD28 and CD3- to sustain T-cell proliferation and recycle effector functions in vivo is also contemplated.

The present invention further provides an efficient method for producing transgenic animals, including the step of applying the gene transfer system of the present invention to an animal. Transgenic DNA has not been efficiently inserted into chromosomes. Only about one in a million of the foreign DNA molecules are inserted into the cellular genome, generally several cleavage cycles into development. Consequently, most transgenic animals are mosaic (Hackett et al. 'The molecular biology of transgenic fish'; Biochemistry and Molecular Biology of Fishes ((Hochachka & Mommsen, eds.) Vol. 2, pp. 207-240, 1993). As a result, animals raised from embryos into which transgenic DNA has been delivered must be cultured until gametes can be assayed for the presence of inserted foreign DNA. Many transgenic animals fail to express the transgene due to position effects. A simple, reliable procedure that directs early insertion of exogenous DNA into the chromosomes of animals at the one-cell stage is needed. The present system helps to fill this need.

In certain preferred embodiments, the gene transfer system of this invention can readily be used to produce transgenic animals that carry a particular marker or express a particular protein in one or more cells of the animal. Generally, methods for producing transgenic animals are known in the art and incorporation of the gene transfer system of the present invention into these techniques does not require undue experimentation, e.g. there are a variety of methods for producing transgenic animals for research or for protein production including, but not limited to Hackett et al. (1993, supra). Other methods for producing transgenic animals are described in the art (e.g. M. Markkula et al. Rev. Reprod., 1, 97-106 (1996); R. T. Wall et al., J. Dairy ScL, 80, 2213-2224 (1997)), J. C. Dalton, et al. (Adv. Exp. Med. Biol, 411, 419-428 (1997)) and H. Lubon et al. (Transfus. Med. Rev., 10, 131-143 (1996)). A transposon including one or more protein encoding nucleic acids to be expressed in the transgenic animal flanked by ITRs can be introduced into a suitable cells, for example, a zygote, embryonic stem cell or adult cell for nuclear transfer together with a transposase, either in protein form or encoded by the same or different nucleic acid than the transposon. The transposon integrates into the genome of the cell. The cell is then propagated to an embryo, and then into a transgenic animal as is conventional transgenesis.

In another embodiment, the present invention features a transgenic animal produced by the methods described herein, preferably by using the gene transfer system presently described. For example, transgenic animals may preferably contain a nucleic acid sequence inserted into the genome of the animal by the gene transfer system, thereby enabling the transgenic animal to produce its gene product, for example, a protein. In transgenic animals this protein is preferably a product for isolation from a cell, for example the inventive protein can be produced in quantity in milk, urine, blood or eggs. Promoters can be used that promote expression in milk, urine, blood or eggs and these promoters include, but are not limited to, casein promoter, the mouse urinary protein promoter, beta-globin promoter and the ovalbumin promoter respectively. Recombinant growth hormone, recombinant insulin, and a variety of other recombinant proteins have been produced using other methods for producing protein in a cell. Nucleic acids encoding these or other proteins can be inserted into the transposon of this invention and transfected into a cell. Expression from a transposon of the present invention can be improved when a transposase protein is present to catalyze integration of the transposon into the DNA of a cell. Where the cell is part of a tissue or part of transgenic animal, large amounts of recombinant protein can be obtained. Transgenic animals may be selected from vertebrates and invertebrates, for example, fish, birds, mammals including, but not limited to, rodents, such as rats or mice, ungulates, such as cows or goats, sheep, swine or humans.

The present invention furthermore provides a method for gene therapy comprising the step of introducing the gene transfer system into cells as described herein. Therefore, the transposon as described herein preferably comprises a gene to provide a gene therapy to a cell or an organism. Preferably, the gene is placed under the control of a tissue specific promoter or of a ubiquitous promoter or one or more other expression control regions for the expression of a gene in a cell in need of that gene. Presently, a variety of genes are being tested for a variety of gene therapies including, but not limited to, the CFTR gene for cystic fibrosis, adenosine deaminase (ADA) for immune system disorders, factor IX and interleukin-2 (IL-2) for blood cell diseases, alpha-1-antitrypsin for lung disease, and tumor necrosis factors (INFs) and multiple drug resistance (MDR) proteins for cancer therapies. These and a variety of human or animal specific gene sequences including gene sequences to encode marker proteins and a variety of recombinant proteins are available in the known gene databases such as GenBank.

An advantage of the gene transfer system of the present invention for gene therapy purposes is that it is limited to a much lesser extent by the size of the polynucleotide between the transposon ends than is the case for many other gene transfer systems. There is no known limit on the size of the nucleic acid sequence that can be inserted into DNA of a cell using the transposase proteins of the present invention. In particular preferred embodiments, for gene therapy purposes, but also for other inventive purposes, the gene transfer system may be transfected into cells by a variety of methods including by microinjection, lipid-mediated strategies or by viral-mediated strategies. For example, where microinjection is used, there is very little restraint on the size of the intervening sequence of the transposon of this invention. Similarly, lipid-mediated strategies do not have substantial size limitations. However, other strategies for introducing the gene transfer system into a cell, such as viral-mediated strategies could limit the length of the nucleic acid sequence positioned between the repeats.

Accordingly, in certain exemplary embodiments, the gene transfer system as described herein can be delivered to cells via viruses, including retroviruses (such as lentiviruses), adenoviruses, adeno-associated viruses, herpes viruses, and others. There are several potential combinations of delivery mechanisms that are possible for the transposon portion containing the heterologous polynucleotide flanked by the terminal repeats and the gene encoding the transposase. For example, both the transposon and the transposase gene can be contained together on the same recombinant viral genome; a single infection delivers both parts of the gene transfer system such that expression of the transposase then directs cleavage of the transposon from the recombinant viral genome for subsequent insertion into a cellular chromosome. In another example, the transposase and the transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for insertion into chromosomal DNA. In certain preferred embodiments of the present invention, transposons may be utilized for insertional mutagenesis, preferably followed by identification of the mutated gene. DNA transposons, particularly the transposons, have several advantages compared to approaches in the prior art, for example, with respect to viral and retroviral methods. For example, unlike proviral insertions, transposon insertions can be remobilized by supplying the transposase activity in trans. Thus, instead of performing time-consuming microinjections, it is possible according to the present invention to generate transposon insertions at new loci by crossing stocks transgenic for the above mentioned two components of the transposon system, the transposon and the transposase. In a preferred embodiment the gene transfer system is directed to the germline of the experimental animals to mutagenize germ cells. Alternatively, transposase expression can be directed to particular tissues or organs by using a variety of specific promoters. In addition, remobilization of a mutagenic transposon out of its insertion site can be used to isolate revertants and, if transposon excision is associated with a deletion of flanking DNA, the gene transfer system of the present invention may be used to generate deletion mutations. Furthermore, since transposons are composed of DNA, and can be maintained in simple plasmids, gene transfer systems and transposons of the present invention are much safer and easier to work with than highly infectious retroviruses. The transposase activity can be supplied in the form of DNA, mRNA or protein as defined above in the desired experimental phase.

In another embodiment, the present invention also provides an efficient system for gene discovery, for example genome mapping, by introducing a transposon as defined above into a gene using a gene transfer system as described in the present invention. In one example, the transposon in combination with the transposase protein or a nucleic acid encoding the transposase protein is transfected into a cell. In certain preferred embodiments, the transposon preferably comprises a nucleic acid sequence positioned between at least two repeats, wherein the repeats bind to transposase protein and wherein the transposon is inserted into the DNA of the cell in the presence of the transposase protein. In certain preferred embodiments, the nucleic acid sequence includes a marker protein, such as GFP and a restriction endonuclease recognition site. Following insertion, the cell DNA is isolated and digested with the restriction endonuclease. For example, if the endonuclease recognition site is a 6-base recognition site and a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the repeats in the transposon. The amplified fragments are then sequenced and the DNA flanking the direct repeats is used to search computer databases such as GenBank.

In another exemplary embodiment of the present invention, the invention provides a method for mobilizing a nucleic acid sequence in a cell. According to this method the *Bombyx mori* or *Xenopus tropicalis* transposon is inserted into DNA of a cell, as described herein. A protein or nucleic acid encoding the *Bombyx mori* or *Xenopus tropicalis* transposase protein is transfected into the cell and the protein is able to mobilize (i.e. move) the transposon from a first position within the DNA of the cell to a second position within the DNA of the cell. The DNA of the cell is preferably genomic DNA or extrachromosomal DNA. The inventive method allows movement of the transposon from one location in the genome to another location in the genome, or for example, from a plasmid in a cell to the genome of that cell.

In other embodiments, the gene transfer system can also be used as part of a method involving RNA-interference techniques. RNA interference (RNAi), is a technique in which exogenous, double-stranded RNAs (dsRNAs), being complementary to mRNA's or genes/gene fragments of the cell, are introduced into this cell to specifically bind to a particular mRNA and/or a gene and thereby diminishing or abolishing gene expression. The technique has proven effective in *Drosophila, Caenorhabditis elegans*, plants, and recently, in mammalian cell cultures. To apply this technique in context with the present invention, the transposon preferably contains short hairpin expression cassettes encoding small interfering RNAs (siRNAs), which are complementary to mRNA's and/or genes/gene fragments of the cell. These siRNAs have preferably a length of 20 to 30 nucleic acids, more preferably a length of 20 to 25 nucleic acids and most preferably a length of 21 to 23 nucleic acids. The siRNA may be directed to any mRNA and/or a gene, that encodes any protein as defined above, e.g. an oncogene. This use, particularly the use of transposons for integration of siRNA vectors into the host genome provides a long-term expression of siRNA in vitro or in vivo and thus enables a long-term silencing of specific gene products.

5.2.9 Pharmaceutical Compositions

The present invention further includes pharmaceutical compositions containing either i) a *Bombyx mori* transposase as a protein or encoded by a nucleic acid, and/or a *Bombyx mori* transposon, or a gene transfer system comprising a *Bombyx mori* transposase as a protein or encoded by a nucleic acid, in combination with an active *Bombyx mori* transposon or; ii) a *Xenopus tropicalis* transposase as a protein or encoded by a nucleic acid, and/or a *Xenopus tropicalis* transposon, or a gene transfer system comprising a *Xenopus tropicalis* transposase as a protein or encoded by a nucleic acid, in combination with an active *Xenopus tropicalis* transposon.

The pharmaceutical composition may optionally be provided together with a pharmaceutically acceptable carrier, adjuvant or vehicle. In this context, a pharmaceutically acceptable carrier, adjuvant or vehicle according to the invention refers to a non-toxic carrier, adjuvant or vehicle that does not destroy the pharmacological activity of the component(s) with which it is formulated.

Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally or via an implanted reservoir.

The term parenteral as used herein includes subcutaneous, intravenous, intramuscular, intra-articular, intra-synovial, intrasternal, intrathecal, intrahepatic, intralesional and intracranial injection or infusion techniques. Preferably, the pharmaceutical compositions are administered orally, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the gene transfer system or components thereof with a suitable non-irritating excipient that is solid at room temperature but liquid at rectal temperature and therefore will melt in the rectum to release the drug. Such materials include cocoa butter, beeswax and polyethylene glycols. The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

For topical applications, the pharmaceutically acceptable compositions may be formulated in a suitable ointment containing the gene transfer system or components thereof suspended or dissolved in one or more carriers. Carriers for topical administration of the components of this invention include, but are not limited to, mineral oil, liquid petrolatum, white petrolatum, propylene glycol, polyoxyethylene, polyoxypropylene component, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the components of the present invention that may be combined with the carrier materials to produce a composition in a single dosage form will vary depending upon the host treated, the particular mode of administration. It has to be noted that a specific dosage and treatment regimen for any particular patient will depend upon a variety of factors, including the activity of the specific component employed, the age, body weight, general health, sex, diet, time of administration, rate of excretion, drug combination, and the judgment of the treating physician and the severity of the particular disease being treated. The amount of a component of the present invention in the composition will also depend upon the particular component(s) in the composition. The pharmaceutical composition is preferably suitable for the treatment of diseases, particular diseases caused by gene defects such as cystic fibrosis, hypercholesterolemia, hemophilia, immune deficiencies including HIV, Huntington disease, .alpha.-anti-Trypsin deficiency, as well as cancer selected from colon cancer, melanomas, kidney cancer, lymphoma, acute myeloid leukemia (AML), acute lymphoid leukemia (ALL), chronic myeloid leukemia (CML), chronic lymphocytic leukemia (CLL), gastrointestinal tumors, lung cancer, gliomas, thyroid cancer, mamma carcinomas, prostate tumors, hepatomas, diverse virus-induced tumors such as e.g. papilloma virus induced carcinomas (e.g. cervix carcinoma), adeno carcinomas, herpes virus induced tumors (e.g. Burkitt's lymphoma, EBV induced B cell lymphoma), Hepatitis B induced tumors (Hepato cell carcinomas), HTLV-I and HTLV-2 induced lymphoma, lung cancer, pharyngeal cancer, anal carcinoma, glioblastoma, lymphoma, rectum carcinoma, astrocytoma, brain tumors, stomach cancer, retinoblastoma, basalioma, brain metastases, medullo blastoma, vaginal cancer, pancreatic cancer, testis cancer, melanoma, bladder cancer, Hodgkin syndrome, meningeoma, Schneeberger's disease, bronchial carcinoma, pituitary cancer, mycosis fungoides, gullet cancer, breast cancer, neurinoma, spinalioma, Burkitt's lymphoma, lyryngeal cancer, thymoma, corpus carcinoma, bone cancer, non-Hodgkin lymphoma, urethra cancer, CUP-syndrome, oligodendroglioma, vulva cancer, intestinal cancer, oesphagus carcinoma, small intestine tumors, craniopharyngeoma, ovarial carcinoma, ovarian cancer, liver cancer, leukemia, or cancers of the skin or the eye; and more.

5.3 Kits

The present invention also features kits comprising a *Bombyx mori* transposase as a protein or encoded by a nucleic acid, and/or a *Bombyx mori* transposon; or a gene transfer system as described herein comprising a *Bombyx mori* transposase as a protein or encoded by a nucleic acid as described herein, in combination with a *Bombyx mori* transposon; optionally together with a pharmaceutically acceptable carrier, adjuvant or vehicle, and optionally with instructions for use. Any of the components of the inventive kit may be administered and/or transfected into cells in a subsequent order or in parallel, e.g. the *Bombyx mori* transposase protein or its encoding nucleic acid may be administered and/or transfected into a cell as defined above prior to, simultaneously with or subsequent to administration and/or transfection of the *Bombyx mori* transposon. Alternatively, the *Bombyx mori* transposon may be transfected into a cell as defined above prior to, simultaneously with or subsequent to transfection of the *Bombyx mori* transposase protein or its encoding nucleic acid. If transfected in parallel, preferably both components are provided in a separated formulation and/or mixed with each other directly prior to administration to avoid transposition prior to transfection. Additionally, administration and/or transfection of at least one component of the kit may occur in a time staggered mode, e.g. by administering multiple doses of this component.

In addition, the present invention also features kits comprising a *Xenopus tropicalis* transposase as a protein or encoded by a nucleic acid, and/or a *Xenopus laevis* transposon; or a gene transfer system as described herein comprising a *Xenopus tropicalis* transposase as a protein or encoded by a nucleic acid as described herein, in combination with a *Xenopus tropicalis* transposon; optionally together with a pharmaceutically acceptable carrier, adjuvant or vehicle, and optionally with instructions for use. Any of the components of the inventive kit may be administered and/or transfected into cells in a subsequent order or in parallel, e.g. the *Xenopus tropicalis* transposase protein or its encoding nucleic acid may be administered and/or transfected into a cell as defined above prior to, simultaneously with or subsequent to administration and/or transfection of the *Xenopus tropicalis* transposon. Alternatively, the *Xenopus tropicalis* transposon may be transfected into a cell as defined above prior to, simultaneously with or subsequent to transfection of the *Xenopus tropicalis* transposase protein or its encoding nucleic acid. If transfected in parallel, preferably both components are provided in a separated formulation and/or mixed with each other directly prior to administration to avoid transposition prior to transfection. Additionally, administration and/or transfection of at least one component of the kit may occur in a time staggered mode, e.g. by administering multiple doses of this component.

6. EXAMPLES

The following examples are intended to illustrate the methods, compositions and kits disclosed herein and should not be construed as limiting in any way. Various equivalents will be apparent to one skilled in the art from the following examples; such equivalents are also contemplated to be part of the invention disclosed herein.

6.1.1 Stable Integration in Chinese Hamster Ovary (Cho) Cells

In some embodiments, a gene transfer system comprises a transposon and a transposase. The transposon comprises a heterologous expression polynucleotide that includes expression control elements and a sequence encoding a first expressible polypeptide. Cells into which the transposon and transposase have both been introduced express higher levels of the expressible polypeptide than cells into which only the transposon have been introduced.

Tables 1 and 2 show data obtained from parallel triplicate experiments testing expression from an expression polynucleotide comprising a puromycin resistance gene under control of a murine PGK promoter and a DasherGFP gene under control of a human EF1a promoter, with the two promoters oriented such that transcription from them is in opposite directions and divergent. The expression polynucleotide was inserted between putative pairs of transposon ends to create a series of putative transposons. SEQ IDs of the transposon ends are indicated in the tables. The transposons were then either transfected alone into CHO cells, or co-transfected with a transposase. The ratio of transposon DNA to transposase-encoding DNA is indicated in the tables.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Lipofectamine 2000 as per manufacturer's protocol. Media with puromycin was added 72 hours post transfection. Cells were grown for 14 days post puromycin selection with two passages and two changes of media. Fluorescence of the ORF encoding fluorescent reporter DasherGFP (SEQ ID: 102) was measured at Ex/Em of 488/518 nm.

A fluorescence signal that was higher in cells that received the transposon plus the transposase than the transposon alone indicated that the transposase was able to recognize the transposon ends and enhance integration into the genomic DNA, either by integrating more copies of the DNA or by integrating the DNA at places in the genome that were more favorable for expression.

Table 1 shows that expression from a transposon comprising *Bombyx mori* transposon ends SEQ ID NOS: 1 and 2 is increased approximately 5-fold when the transposon is co-transfected with a vector encoding a *Bombyx mori* transposase SEQ ID NO: 44. Tables 1 and 2 show that expression from a transposon comprising *Xenopus tropicalis* transposon ends SEQ ID NOS: 5 and 6 is increased between 50% and 2.5-fold when the transposon is co-transfected with a vector encoding a *Xenopus tropicalis* transposase SEQ ID NO: 45 or 46, when the transposase was fused to a nuclear localization signal.

Identifying and testing hyperactive variants of the identified transposases is also expressly contemplated and is another aspect of this invention.

6.1.2 Insulator Elements Enhance Stable Expression in Cho Cells

In some embodiments, a gene transfer system comprises a polynucleotide that includes expression control elements and a sequence encoding a first expressible polypeptide. Expression of the expressible polypeptide can be increased in some configurations of the gene transfer system by incorporating insulator sequences. In some embodiments the polynucleotide and the insulator sequences are part of a transposon, and expression can be further increased by the action of a transposase.

Table 3 shows data obtained from parallel triplicate experiments testing expression from an expression polynucleotide comprising a puromycin resistance gene under control of a murine PGK promoter and a DasherGFP gene under control of a second promoter as indicated in the table. The expression polynucleotide was optionally inserted between pairs of insulator sequences as indicated in the table. The resulting polynucleotides were then inserted between pairs of transposon ends as indicated in the table. These transposons were then transfected into CHO cells, either alone or together with a transposase, as indicated in the table. The transposases in this example were fused to a heterologous nuclear localization signal.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Roche Extreme Gene 9 reagent (2:1 ratio) as per manufacturer's protocol. Media with 5 µg/l puromycin was added 72 hours post transfection. Puromycin selection was carried out for 72 hours. Cells were grown for 14 days post puromycin selection with two passages and changes of media. Fluorescence represents expression of the ORF encoding fluorescent reporter DasherGFP from stably integrated transposons and was measured at Ex/Em of 488/518 nm.

Table 3 shows that the presence of HS4 insulators, either the full sequence or just the core sequence, can significantly increase expression from the transposon even in the absence of a transposase (for example compare Table 3 rows 1 and 3 or rows 5 and 9). This effect appears to be influenced by the promoter that is being used to drive expression of the expressible polypeptide: in this vector context the HS4 insulator increases expression from an EF1a promoter on the transposon by 50% to 4-fold, but there is no effect observed when the expressible polypeptide is under the control of the CMV promoter (Table 3 rows 11, 13 and 15). In the presence of the transposase, expression from almost all of the transposons increased, from 50% to more than 10-fold. Increases in expression from the transposon as a result of the insulators and the transposases appeared to be synergistic. Preferred embodiments of gene transfer systems comprise a gene encoding a *Xenopus* or *Bombyx* transposase fused to a nuclear localization signal and a *Xenopus* or *Bombyx* transposon comprising two HS4 or HS4 core insulators.

6.1.3 Transposases can be Provided in Cis or in Trans

In some embodiments, a gene transfer system comprises a transposon and a transposase. The transposon comprises a heterologous polynucleotide that includes expression control elements and a sequence encoding a first expressible polypeptide. In some embodiments the transposase is encoded on a polynucleotide vector that also comprises the transposon.

Table 4 shows data obtained from parallel triplicate experiments testing expression from an expression polynucleotide comprising a puromycin resistance gene under control of a murine PGK promoter and a DasherGFP gene under control of a second promoter as indicated in the table. The DasherGFP gene is followed by an RNA export element, as indicated in the table. The expression polynucleotide was optionally inserted between pairs of insulator sequences as indicated in the table. The resulting polynucleotides were then inserted between pairs of transposon ends as indicated in the table. These transposons were then optionally cloned into vectors that also contained a gene for expression of a transposase, under control of a promoter as indicated (P_Transposase). Some transposases were fused to a nuclear localization signal, as indicated in the table.

Transposons were then transfected into CHO cells, either alone or together with a transposase, as indicated in the table.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Roche Extreme Gene 9 reagent (2:1 ratio) as per manufacturer's protocol. Media with 5 µg/l puromycin was added 72 hours post transfection. Puromycin selection was carried out for 72 hours. Cells were grown for 14 days post puromycin selection with two passages and changes of media. Fluorescence represents expression of the ORF encoding fluorescent reporter DasherGFP from stably integrated transposons and was measured at Ex/Em of 488/518 nm.

Table 4 shows that expression of transposase from the same vector that contained the transposon produced comparable levels of expression improvement to the expression increases obtained by co-transfecting a second plasmid carrying the gene for the transposase. This improvement is observed in many different vector configurations, as shown in the table. Thus expression from a *Bombyx mori* transposon or a *Xenopus tropicalis* transposon can be increased by the action of a transposase that is provided either in cis or in trans.

The transposons described in Table 4 also comprised an RNA export element selected from WPRE and HPRE; they also comprised the expression enhancing element SAR1. Preferred embodiments of gene transfer vectors comprise one or more of these elements.

6.1.4 Transposases with Nuclear Localization Signals

In some embodiments, a gene transfer system comprises a transposon and a transposase, where the transposase is fused with a nuclear localization signal. The transposon comprises a heterologous polynucleotide that includes expression control elements and a sequence encoding a first expressible polypeptide. Cells into which the transposon and transposase fused to the nuclear localization signal have both been introduced express higher levels of the expressible polypeptide than cells into which only the transposon have been introduced.

Table 5 shows data obtained from parallel triplicate experiments testing expression from an expression polynucleotide comprising a puromycin resistance gene under control of a murine PGK promoter, with a DasherGFP gene translationally coupled to the puromycin-resistance gene through a CHYSEL sequence. The expression polynucleotide was inserted between putative pairs of transposon ends to create a series of putative transposons. SEQ IDs of the transposon ends are indicated in the tables. The transposons were then either transfected alone into CHO cells, or co-transfected with a transposase fused to a nuclear localization sequence. The ratio of transposon DNA to transposase-encoding DNA is indicated in the tables.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Lipofectamine 2000 as per manufacturer's protocol. Media with puromycin was added 72 hours post transfection. Cells were grown for 14 days post puromycin selection with two passages and two changes of media. Fluorescence of the ORF encoding fluorescent reporter DasherGFP was measured at Ex/Em of 488/518 nm.

A fluorescence signal that was higher in cells that received the transposon plus the transposase fused to the nuclear localization signal than the transposon alone indicated that the transposase fused to the nuclear localization signal was able to recognize the transposon ends and enhance integration into the genomic DNA, either by integrating more copies of the DNA or by integrating the DNA at places in the genome that were more favorable for expression.

*Trichoplusia ni* piggyBac and *Bombyx mori* and *Xenopus tropicalis* transposases were all active when fused to N-terminus nuclear localization signals (NLS). A preferred embodiment of a gene transfer system comprises a gene encoding a transposase that is fused to a nuclear localization signal.

6.1.5 Stable Integration in Human Embryonic Kidney (Hek 293) Cells

In some embodiments the gene transfer system comprises a transposon and transposase that are used to integrate an expression polynucleotide into the genome of a mammalian cell; in some embodiments the cell is a CHO cell, in some embodiments the cell is an HEK cell.

Table 6 shows data obtained from parallel triplicate experiments testing expression from an expression polynucleotide in a *Xenopus* transposon with ends SEQ ID NO: 9 and 6, comprising a puromycin resistance gene under control of a murine PGK promoter. The expression polynucleotide further comprised a DasherGFP gene operably linked to various promoters, introns, RNA export sequences and polyadenylation sequences as indicated in the table. Transcription from the two promoters was in opposite directions and divergent. The transposons were then either transfected alone into HEK cells, or co-transfected with a gene encoding *Xenopus* transposase SEQ ID NO: 45 fused to a nuclear localization sequence.

HEK 293 cells were grown in EMEM (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 pg DNA with Roche Extreme Gene 9 reagent (2:1 ratio) as per manufacturer's protocol. Media with 5 µg/µl puromycin was added 72 hours post transfection. Puromycin selection was carried out for 72 hours and passaged into complete media minus puromycin. Cells were grown for 14 days post puromycin selection with two passages and changes of media. Fluorescence represents expression of the ORF encoding fluorescent reporter DasherGFP from stably integrated transposons and was measured at Ex/Em of 488/518 nm.

All gene transfer vector configurations tested showed improved expression in HEK cells when the transposase gene was co-transfected. Preferred embodiments of a gene transfer vector include all vector configurations shown in Table 6

6.1.6 Expression Levels of Two Polypeptides Using Ires Elements in Transient Expression in Hek293 and Cho Cells In some embodiments a gene transfer system comprises genes encoding two polypeptides. In some embodiments the two polypeptides are encoded on a single polynucleotide. In some embodiments the two polypeptides interact after they are synthesized. In some embodiments the relative amounts of the two polypeptides expressed by a cell is important for the functioning of the two polypeptides. In some embodiments the two polypeptides are enzymes in a pathway. In some embodiments the two polypeptides bind together or are subunits of a larger molecule; in some embodiments the two polypeptides are the heavy and light chains of an antibody.

Tables 7-11 show the expression levels observed in HEK and CHO cells for two different polypeptides (in this case two different fluorescent proteins, Dasher GFP and CayenneRFP) encoded on a single gene transfer vector. The genes for the two different proteins were operably linked to a single enhancer, promoter, polyadenylation signal and optionally an intron, as indicated in the tables. Expression of the two genes was operably linked by an IRES element, as indicated in the tables, with the order of elements being DasherGFP-IRES-CayenneRFP.

HEK 293a cells (from ATCC) were grown in EMEM (from ATCC)+10% FBS (from ATCC)+1% Penicillin-streptomycin (from ATCC) at 37° C., 5% $CO_2$ to 80% confluence, 1E+05 cells were plated in 24-well tissue culture plates and incubated at 37° C., 5% $CO_2$ for 24 hours prior to transfection, transfections were set up in triplicates. Each transfection used 0.5 µg DNA with Lipofectamine 2000 as per manufacturer's protocol. Cells were harvested 72 hours post transfection. Fluorescence of the two ORFs encoding fluorescent reporters DasherGFP (SEQ ID NO: 102) and CayenneRFP (SEQ ID NO: 103) was measured at Ex/Em of 488/518 nm for DasherGFP and Ex/Em of 525/580 nm for CayenneRFP.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used 0.5 µg DNA with Lipofectamine 2000 as per manufacturer's protocol. Cells were harvested 72 hours post transfection. Fluorescence of the two ORFs encoding fluorescent reporters DasherGFP and CayenneRFP was measured at Ex/Em of 488/518 nm for DasherGFP and Ex/Em of 525/580 nm for CayenneRFP.

Gene transfer vectors comprising the two proteins translationally coupled by a CHYSEL sequence (e.g. construct 135171 in Table 7) express the two proteins at an equimolar ratio and can be used to normalize for different fluorescent intensities of the proteins. Tables 7-11 show that different IRES elements can be used to obtain different ratios of expression between two different polynucleotides in a variety of vector configurations. The use of IRES elements is particularly advantageous for expression of polypeptides when the ratio of expression is important at the level of individual cells, for example in the expression of antibodies where the light chain is often thought to perform a chaperonin function for the heavy chain.

We have identified IRES elements that show different levels of activity as seen from the varying expression levels for the two open reading frames (ORFs) linked by an IRES element (Tables 7-11). A choice of IRES elements with varying activities allows the appropriate IRES element to be used for controlling the relative expression levels of two ORFs. This is especially useful for expression of antibodies wherein the ratios of expression of the heavy chain to light chain influences proper assembly of the functional antibody. Use of the identified IRES elements for antibody expression is an important aspect of this invention. We have shown use of one IRES element linking two transcripts operably linked to one promoter, similarly use of two or more IRES elements linking three or more ORFs is expressly contemplated and is another aspect of the invention. Expression constructs with two or more IRES elements selected such that transcript levels of two or more ORFs is selectively modulated is expressly contemplated and is an important aspect of the invention. The identified IRES elements of the invention work well in both transient and stable integration vectors in the two cell lines tested, Human embryonic kidney (HEK293) cells and Chinese hamster ovary (CHO) cells. Preferred embodiments of a gene transfer vector include all vector configurations shown in Tables 7-11, and all IRES elements shown in these tables.

6.1.7 Expression of Antibodies Using Ires Elements in Transiently Transfected Hek293 Cells In some embodiments the gene transfer system is used to express an antibody. In some embodiments genes encoding the two antibody chains are operably linked to separate promoters. In some embodiments genes encoding the two chains are operably linked to the same promoter and to each other by a translational coupling element, in some embodiments the translational coupling element is an IRES or a CHYSEL sequence.

Table 12 shows a variety of vector configurations expressing two antibody chains from a single gene transfer vector. In some configurations genes encoding the two chains are each operably linked to separate promoters and polyadenylation signals, in some configurations the genes were operably linked to a single promoter preceding the first gene and a single polyA signal following the second gene, where the two genes are operably linked by an IRES sequence. The number 1 indicates promoters preceding or polyA signals following the first gene, the number 2 indicates promoters preceding or polyA signals following the second gene.

All of these vectors further comprised a viral amplification sequence encoding the SV40T antigen, and the SV40 origin of replication. Antibody expression from these gene transfer vectors was measured by ELISA, and compared with the expression obtained by co-transfection of two gene transfer vectors, one encoding the heavy chain and the other encoding the light chain, transfected at different ratios as indicated in the table.

HEK 293a cells (from ATCC) were grown in EMEM (from ATCC)+10% FBS (from ATCC)+1% Penicillin-streptomycin (from ATCC) at 37° C., 5% $CO_2$ to 80% confluence, 1E+05 cells were plated in 24-well tissue culture plates and incubated at 37° C., 5% $CO_2$ for 24 hours prior to transfection, transfections were set up in triplicates. Each transfection used 0.5 µg DNA with Lipofectamine 2000 as per manufacturer's protocol. Cells were harvested 72 hours post transfection. Culture supernatants were harvested and used in an ELISA assay for quantitation of heavy chain (HC) (Table 12) and run on a gel for a western blot for detection of the heavy and light chains (data not shown).

96-well ELISA plates (Cat. No. M9410, Sigma) were coated with 50 µl per well of goat anti-Human IgG (Fc specific) antibody (Cat No. 12136, Sigma) at 1 µg/ml in 1×PBS (Cat. No. P-7059, Sigma) and incubated overnight at 4° C. Plates were washed 4 times with 300 µl per well PBST (Cat. No. P3563, Sigma) and blocked with 300 µl per well ELISA Block solution (PBST+1% BSA (Cat. No. 85040C), Sigma) for 1 hour at room temperature. ELISA Block solution was removed and culture supernatants from the transient transfections above diluted in ELISA Block solution at dilutions ranging from 1:50 to 1:200,000 at 100 µl per well were added to plates and incubated for 1 hour at room temperature. Plates were washed 4 times with 300 µl per well PBST (Sigma) and antibody was detected by incubation with 100 µl/well (0.16 µg/ml) HRP conjugated-goat anti- Human IgG (Fab specific) (Cat. No. 31482, Thermo Scientific) in ELISA Block solution for 1 hour at room temperature. Plates were washed 4 times with 300 µl per well PBST (Sigma) and bound HRP-goat anti-Human IgG measured by adding 100 µl/well QuantaBlu Fluorogenic Peroxidase substrate (Cat. No. 15162, Thermo Scientific). Plates were incubated for 5 minutes at room temperature, reaction stopped by adding 100 µl/well stop solution (Cat. No. 15162, Thermo Scientific) and fluorescence measured using fluorimeter at excitation (Ex) 325 nm and emission (Em) 420 nm. Antibody concentration was calculated by comparing to a standard curve generated using dilutions of purified Human IgG (Thermo Scientific) using a 4-parameter logistic curve fit. Concentrations of IgG calculated shown in Table 12 were in good agreement with quantitation from western blot (data not shown).

Table 12 shows that many gene transfer vector configurations using dual promoters or IRES elements produce comparable or better antibody expression than co-transfection of two separate gene transfer vectors. Preferred embodiments of a gene transfer vector include all vector configurations shown in Table 12, and all IRES elements shown in Tables 7-11.

Using IRES sequences which can produce different levels of expression of the second polypeptide relative to the first has advantages over methods wherein dual-transfections are used. In the case of co-transfection, individual cells take up different numbers of each plasmid. Because it is only possible to control the average number of each plasmid taken up by each cell, many cells do not end up expressing the optimal ratio of heavy and light chain. This problem is amplified in the case of stable cell lines, because there is the further variable of integration location which also affects expression levels. Use of IRES sequences to control expression levels of two or more ORFs, in particular expression of ORFs encoding heavy and light chains in stable integration expression vectors is expressly contemplated and is an important aspect of the invention.

6.1.8 Expression of Two ORFS Linked by Ires Elements in Stably Transfected Cho Cells In some embodiments a gene transfer system comprises genes encoding two polypeptides encoded on a single polynucleotide to be stably integrated into the genome of a cell. In some embodiments the polynucleotide comprises a transposon. In some embodiments the two polypeptides are the heavy and light chains of an antibody.

Table 13 shows the configurations of a set of transposons comprising transposon ends SEQ ID NO: 9 and 6. Transposons comprised genes encoding DasherGFP and/or CayenneRFP as indicated in the table. In some configurations the two genes were each operably linked to separate promoters and polyadenylation signals, in some configurations the genes were operably linked to a single promoter preceding the first gene and a single polyA signal following the second gene, where the two genes are operably linked by an IRES sequence. The number 1 indicates promoters preceding or polyA signals following the first gene, the number 2 indicates promoters preceding or polyA signals following the second gene. All of these sequences further comprised an SAR sequence and an HPRE sequence following the second gene and preceding polyA2. Transposons were transfected into CHO cells, either alone or together with a gene encoding a transposase (SEQ ID NO: 45) fused to a nuclear localization signal.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Roche Extreme Gene 9 reagent (2:1 ratio) as per manufacturer's protocol. Media with 5 µg/l puromycin was added 72 hours post transfection. Puromycin selection was carried out for 72 hours. Cells were grown for 14 days post puromycin selection with two passages and changes of media. Fluorescence represents expression of the ORFs encoding fluorescent reporter DasherGFP from stably integrated transposons measured at Ex/Em of 488/518 nm and CayenneRFP was measured at Ex/Em of 525/580 nm.

Co-transfection of transposons with the vector encoding the transposase increased expression of both proteins encoded by the transposon between 4-fold and nearly 20-fold relative to transfections with the transposon alone. A transposon comprising genes encoding two polypeptides and a gene encoding a transposase fused to a nuclear localization signal is a preferred embodiment of a gene transfer system. Configurations shown in Table 13 are preferred embodiments.

FIG. 4 shows FACS analysis of populations of cells transfected with the gene transfer systems described in Table 13 rows 3 and 4.

6.1.9 Stable Integration of Transposons in Chinese Hamster OVARY (CHO) CELLS

In some embodiments, a gene transfer system comprises a transposon and a transposase. The transposon comprises a heterologous expression polynucleotide that includes expression control elements and a sequence encoding a first expressible polypeptide. Cells into which the transposon and transposase have both been introduced express higher levels of the expressible polypeptide than cells into which only the transposon have been introduced. In some embodiments the cell is a mammalian cell, in some embodiments the cell is a CHO cell or an HEK cell.

Table 14 shows a set of gene transfer vector configurations for expression of a DasherGFP. Each vector comprised transposon ends SEQ ID NO: 9 and 6. All of these sequences except for 192462 further comprised an SAR sequence and an HPRE sequence following the sequence encoding DasherGFP. All of these sequences further comprised a rabbit globin polyA sequence. Some transposons further comprised a pair of HS4 insulator sequences between the transposon ends, as indicated in the table. Transposons were transfected into CHO cells, either alone or together with a gene encoding a transposase (SEQ ID NO: 45) fused to a nuclear localization signal.

Chinese hamster ovary (CHO) cells were grown and transfected as described in Example 6.2 above.

Table 14 shows that expression from the transposon was increased for each configuration tested by co-transfection with a gene encoding the transposase. The expression increases were between 2-fold and 80-fold. Gene transfer systems comprising a transposase and a transposon with a configuration shown in Table 14 are preferred embodiments of the invention.

FIG. 3 shows a FACS analysis of the same stably transfected cell populations as shown in Table 14. FACS shows the expression level of DasherGFP in individual cells in the stably transfected population. FIG. 3 shows that for every gene transfer vector in the set, the transposase causes a shift of a part of the population from the poorly expressing group to the highly expressing group. This may be caused by an increase in the number of copies of the transposon that have been stably integrated, or it may be caused by the transposon integrating into genomic loci that result in improved expressibility.

We have shown preferred configurations of vector elements including enhancers, promoters, introns, 5' UTRs, RNA export sequences, poly A and insulators that contribute to expression activity seen from integrated transposons. Other vector configurations of control elements shown in Tables 15-18, placed into a transposon context for stable integration, are also preferred embodiments.

In a preferred embodiment for stable integration into a mammalian genome, a gene transfer vector comprises a transposon for expression of a first polynucleotide, wherein the expression of the first polynucleotide is operably linked to a mammalian promoter selected from amongst the EF1a (translation elongation factor 1a) promoter from any mammalian or avian species including but not limited to human, rat, mice, chicken and Chinese hamster; the CMV (cytomegalovirus) promoter, the GAPDH (glyceraldehyde-3-phosphate dehydrogenase) promoter from any mammalian species; the MCI and HSV-TK (Herpes Simplex Virus thymidine kinase) viral promoters; the actin promoter from any mammalian or avian species including but not limited to human, rat, mice, chicken and Chinese hamster; the PGK (phosphoglycerate kinase) promoter from any mammalian or avian species including but not limited to human, rat, mice, chicken and Chinese hamster; the SV40 (Simian virus 40) promoter and the ubiquitin promoter. In preferred embodiments the promoter may be operably linked to an enhancer selected from amongst the CMV immediate early enhancer, the EF1a enhancer (for example but not limited to SEQ ID NO: 116), the adenoviral major late protein enhancer (for example but not limited to SEQ ID NO: 118), the SV40 enhancer (for example but not limited to SEQ ID NO: 117), and a retroviral LTR. In further preferred embodiments expression of the first polynucleotide is operably linked to an intron selected from among a CMV(cytomegalovirus) intron, including CMV introns A, B and C; an EF1a (translation elongation factor 1a) intron from any mammalian or avian species including but not limited to human, rat, mice, chicken and Chinese hamster, the actin intron from any mammalian or avian species including but not limited to human, rat, mice, chicken and Chinese hamster; a GAPDH (glyceraldehyde-3-phosphate dehydrogenase) intron from any mammalian or avian species including but not limited to human, rat, mice, chicken and Chinese hamster; synthetic introns (for example but not limited to SEQ ID NO: 119) and chimeric natural introns (for example SEQ ID NO: 123). In further preferred embodiments expression of the first polynucleotide is operably linked to an RNA export element (for example but not limited to SEQ ID NOS: 104-107), an insulator sequence (for example but not limited to SEQ ID NOS: 112-113), or an expression enhancing element (for example but not limited to SEQ ID NOS: 108-111).

Regardless of their actual mechanism, we have shown incorporation of expression enhancing elements into gene transfer vectors with transposon ends greatly enhances protein expression from these vectors, both in the absence and presence of transposase.

In addition to vector elements within the transposon, use of vector elements located in the vector such that these elements are not transposed by the transposase, for example viral replication elements such as SV40 origin of replication (SV40 ori) with the SV40 large T antigen and EBV (Epstein Barr virus) oriP with EBNA (Epstein-Barr nuclear antigen) is another aspect of the invention.

6.1.10 Creating and Testing Combinations of Vector Elements in Transiently Transfected Hek and Cho Cells In some embodiments preferred configurations of expression control elements in a gene transfer vector are determined by creating a set of vectors comprising different combinations of elements, and then measuring expression from the set. In preferred embodiments the set comprises between 5 and 200 members, in preferred embodiments the set comprises between 10 and 100 members, in preferred embodiments the set comprises between 15 and 60 members.

48 vectors were designed such that the set of vectors comprised 3 different enhancer elements (CMV, SV40, none); 9 different promoter elements (CMV, Ub-B, SV40, PGK, MCI, HSV-TK, GAPDH, EF1a, chick actin); 10 different intron elements (CMV intron a, CMV intron c, chick actin (partial), GAPDH, chick actin/rabbit, EF1a-v1, EF1a-v2, EF1a-hybrid, synthetic and none); 2 different 5' UTRs (CMV and none); 7 different polyadenylation sequences (SV40 late, SV40 early, bovine growth hormone, synthetic, human beta globin, rabbit beta globin, HSV-TK); 3 different viral replication origins (Epstein Barr virus oriP, SV40 ori and none) and 3 different viral replication proteins (Epstein Barr virus EBNA, SV40 T antigen and none). The specific combinations in the set are shown in Table 15. The total number of possible combinations of these elements is 34,020.

Dasher GFP was cloned into each of the vectors, and each construct was transfected in triplicate into HEK cells and CHO cells. Cells were plated in 24-well plates in DMEM (ATCC)+10% FBS+Penicillin/Streptomycin for HEK293a cells and F12K (ATCC)+10% FBS+Penicillin/Streptomycin for CHO-K1 cells and grown for 24 hours to approximately 70-80% confluence. Cells were transfected in duplicate in 24-well plates using 1 µl Lipofectamine 2000 per 0.5 µg DNA. After 72 hours the cells were lysed using 200 l/well M-PER Mammalian Protein Extraction Reagent (Thermo Scientific Pierce®) and total fluorescence measured on a fluorescence plate reader at excitation/emission wavelengths of 505/525 nm. The average fluorescence readings are shown in Table 19.

Partial Least Squares regression models were constructed from the fluorescence data, and regression weights were calculated for each of the sequence elements. The regression weights indicate the importance of the element for performance of the vector. It is clear that some elements or combinations of elements are more favorable for expression in both HEK and CHO (CMV enhancer, promoter and CMV intron a for example); some elements are more favorable for expression in HEK but less favorable for expression in CHO (SV40 ori plus SV40 T antigen, HSVTK polyadenylation signal, EBV oriP); some elements are more favorable for expression in CHO but less favorable for expression in HEK (GAPDH promoter, human beta globin polyadenylation signal); some elements are less favorable for expression in either HEK or CHO (SV40 late polyadenylation signal, HSV-TK promoter).

Particularly favorable for expression in HEK cells were vectors that contained the SV40 origin of replication and the SV40 T antigen. These were even more effective when combined with the CMV enhancer plus the chick actin promoter plus the chick actin/rabbit intron, or the CMV enhancer with the CMV promoter with CMV intron a. Particularly favorable for expression in CHO cells were vectors that lacked any viral replication sequences. Vector configurations shown in Table 15 are preferred embodiments of the invention.

6.1.11 Creating and Testing a Second Set of Combinations of Vector Elements in Transiently Transfected Hek and Cho Cells In some embodiments preferred configurations of expression control elements in a gene transfer vector are determined by creating a set of vectors comprising different combinations of elements, measuring expression from the set, and then designing a second set of vectors in which the most favorable elements for expression from the first set are retained and recombined, and, optionally, new elements are added into the new set of vectors. In preferred embodiments the second set comprises between 5 and 200 members, in preferred embodiments the second set comprises between 10 and 100 members, in preferred embodiments the second set comprises between 15 and 60 members.

48 vectors were designed such that the set of vectors comprised 4 different enhancer elements (CMV, synthetic, EF1a, none); 4 different promoter elements (CMV, GAPDH, EF1a, EF1a_LTR-HTLV); 6 different intron elements (CMV intron a, CMV intron c, GAPDH, chick actin/rabbit, EF1a and none); 8 different 5' UTRs (CMV, satellite tobacco necrosis virus (sTNV), human beta globin, polyhedrin, tobacco necrosis virus (TNV), barley yellow dwarf virus (BYDV), *Xenopus* globin, and none); 6 different 3' UTRs (satellite tobacco necrosis virus (sTNV), polyhedrin, tobacco necrosis virus (TNV), barley yellow dwarf virus (BYDV), *Xenopus* globin, and none); 6 different polyadenylation sequences (bovine growth hormone, bovine growth hormone plus gastrin terminator, rabbit beta globin, rabbit beta globin plus gastrin terminator, HSV-TK, HSV-TK plus gastrin terminator); 3 different viral replication origins (Epstein Barr virus oriP, SV40 ori and none) and 3 different viral replication proteins (Epstein Barr virus EBNA, SV40 T antigen and none). The specific combinations in the set are shown in Table 16. The total number of possible combinations of these elements is 248,832.

Dasher GFP was cloned into each of the vectors, and each construct was transfected in triplicate into HEK cells and CHO cells. Cells were plated in 24-well plates in DMEM (ATCC)+10% FBS+Penicillin/Streptomycin for HEK293a cells and F12K (ATCC)+10% FBS+Penicillin/Streptomycin for CHO-K1 cells and grown for 24 hours to approximately 70-80% confluence. Cells were transfected in duplicate in 24-well plates using 1 µl Lipofectamine 2000 per 0.5 µg DNA. After 72 hours the cells were lysed using 200 µl/well M-PER Mammalian Protein Extraction Reagent (Thermo Scientific Pierce®) and total fluorescence measured on a fluorescence plate reader at excitation/emission wavelengths of 505/525 nm. The average fluorescence readings relative to control constructs are shown in Table 20.

Partial Least Squares regression models were constructed from the fluorescence data, and regression weights were again calculated for each of the sequence elements. Again some elements are more favorable for expression in both HEK and CHO, some elements are more favorable for expression in HEK but less favorable in CHO, some elements are more favorable for expression in CHO but less favorable in HEK and some elements are less favorable for expression in both HEK and CHO.

Particularly favorable for expression in HEK cells were vectors that combined the CMV enhancer with the CMV promoter, CMV intron a or intron c, and the polyadenylation signal from rabbit beta globin or the polyadenylation signal from HSV-TK plus the gastrin terminator. Even more favorable combinations also included the SV40 origin of replication and the SV40 T antigen. Vector configurations shown in Table 16 are preferred embodiments of the invention.

6.1.12 Creating and Testing a Set of Combinations of Vector ELEMENTS IN TRANSIENTLY TRANSFECTED CHO CELLS In some embodiments preferred configurations of expression control elements in a gene transfer vector are determined by creating a set of vectors comprising different combinations of elements, measuring expression from the set, and then designing a second set of vectors in which the most favorable elements for expression from the first set are retained and recombined, and, optionally, new elements are added into the new set of vectors. In some embodiments this process is repeated.

The most favorable elements for CHO were selected to create a third set of vectors as shown in Table 17. Dasher GFP was cloned into each of the vectors, and each construct was transfected in triplicate into CHO cells. Cells were plated in 24-well plates in DMEM (ATCC)+10% FBS+Penicillin/Streptomycin for HEK293a cells and F12K (ATCC)+10% FBS+Penicillin/Streptomycin for CHO-K1 cells and grown for 24 hours to approximately 70-80% confluence. Cells were transfected in duplicate in 24-well plates using 1 µl Lipofectamine 2000 per 0.5 µg DNA. After 72 hours the cells were lysed using 200 al/well M-PER Mammalian Protein Extraction Reagent (Thermo Scientific Pierce®) and total fluorescence measured on a fluorescence plate reader at excitation/emission wavelengths of 505/525 nm. The average fluorescence readings relative to control constructs are shown in Table 17.

Vector configurations shown in Table 17 are preferred embodiments of the invention. Particularly favorable vector elements for expression in CHO include the CMV enhancer together with the CMV promoter, the GAPDH promoter and the actin promoter. Expression is enhanced with the GAPDH intron, the CMV intron A or CMV intron C or the adenoviral major late protein enhancer.

6.1.13 Creating and Testing a Set of Combinations of Vector Elements in Stably Transfected Cho Cells In some embodiments a gene transfer vector comprises an RNA export element. Table 18 shows a set of different vector configurations. The vectors further comprised an SAR sequence. A gene encoding DasherGFP was cloned into the vectors, stably transfected into CHO cells, and expression of the Dasher GFP was measured. The transposons were not co-transfected with transposases.

CHO-K1 cells (from ATCC) were grown in F12-K (from ATCC)+10% FBS (from ATCC)+1% Penicillin-streptomycin (from ATCC) at 37° C., 5% $CO_2$ to 80% confluence. 5E+05 cells were plated in 24-well tissue culture plates and incubated at 37° C., 5% $CO_2$ for 24 hours prior to transfection, transfections were set up in triplicates. Each transfection used a total of 0.5 µg DNA with Roche Extreme Gene 9 reagent (2:1 ratio) as per manufacturer's protocol. Media with 5 µg/l puromycin was added 72 hours post transfection. Puromycin selection was carried out for 72 hours. Cells were grown for 14 days post puromycin selection with two passages and changes of media. Fluorescence represents expression of the ORFs encoding fluorescent reporter DasherGFP from stably integrated transposons measured at Ex/Em of 488/518 nm.

Particularly favorable for expression in stably transfected CHO cells were vectors that combined the SAR plus HPRE RNA export elements. Even more favorable combinations also included the EF1a promoter or HS4 insulators. Particularly favorable for expression in stably transfected HEK cells were vectors that combined the SAR plus HPRE or SAR plus AGS_1 or SAR plus AGS_3 RNA export elements.

6.1.14 Selecting Vector Elements Preferred by Different Expression Systems

In some embodiments a set of gene transfer vectors are tested for an expression property of a first polynucleotide in an expression system. In some embodiments a sequence-activity model is constructed between an expression property and the element configuration in the gene transfer vectors. In some embodiments the expression system is a mammalian cell, in some embodiments the mammalian cell is an human cell or a rodent cell, in some embodiments the mammalian cell is an HEK293 cell or a Chinese hamster ovary cell.

A model relating the elements of gene transfer vectors shown in Table 15, and the expression data shown in Table 19 was constructed using partial least square regression. A comparison between the measured expression property and the predicted expression property is shown in FIG. 5. Table 21 shows the regression weights for each element or combination of elements calculated from the model for HEK and CHO expression systems.

Table 21 shows that different combinations of elements are more favorable in different expression systems. Elements may be selected or rejected for incorporation into new vector configurations, depending on the regression weights from the model. For example the SV40 viral amplification system is highly favorable for expression in an HEK expression system (regression weight 2,679) but unfavorable for a CHO system (regression weight −113). Thus SV40 replication sequences were included in a new set of vectors designed for HEK (Table 16) but not in a new set of vectors designed for CHO (Table 17). The model also indicates that there are some polyA signals that are favorable for both systems (for example the sequence from rabbit beta globin and some that are less favorable (the SV40 late polyadenylation signal).

BRIEF DESCRIPTION OF TABLES

Table 1. Expression from gene transfer systems comprising transposons and transposases. Transposons comprising an expression cassette for DasherGFP, and with transposon end sequences as identified in columns D and E, were transfected into CHO cells, optionally together with a gene encoding a transposase (column G) at a predetermined ratio (column C). Cells were selected and expression of the DasherGFP measured (columns I-K) as described in Example 6.1.1.

Table 2. Expression from gene transfer systems comprising transposons and transposases. Transposons comprising an expression cassette for DasherGFP, and with transposon end sequences as identified in columns D and E, were transfected into CHO cells, optionally at a predetermined ratio (column C) together with a gene encoding a transposase (column G) which was optionally fused to a heterologous nuclear localization sequence (column H). Cells were selected and expression of the DasherGFP measured (columns I and J) as described in Example 6.1.1.

Table 3. Expression from gene transfer systems comprising transposons and transposases. Transposons comprised transposon end sequences (columns B and C), an expression cassette with a promoter (column E) operably linked to a gene encoding DasherGFP, and optionally insulator sequences on either side of the Dasher expression cassette (column F). Transposons were transfected into CHO cells, optionally together with a gene encoding a transposase (column G) fused to a heterologous nuclear localization signal. Cells were selected and expression of the DasherGFP measured columns H-J) as described in Example 6.1.2.

Table 4. Expression from gene transfer systems comprising transposons and transposases. Transposons comprised transposon end sequences (columns B and C), an expression cassette with a promoter (column E) and an element to enhance RNA export (column F) operably linked to a gene encoding DasherGFP, and optionally insulator sequences on either side of the Dasher expression cassette (column G). Transposons were transfected into CHO cells, optionally together with a gene encoding a transposase (column H) optionally fused to a heterologous nuclear localization signal (column L) and operably linked to a promoter (column K). In some configurations a single polynucleotide comprised the transposon and the gene encoding the transposase (column J). Cells were selected and expression of the DasherGFP measured (columns M-O) as described in Example 6.1.3.

Table 5. Expression from gene transfer systems comprising transposons and transposases. Transposons comprising an expression cassette for DasherGFP, and with transposon end sequences as identified in columns C and D, were transfected into CHO cells, optionally at a predetermined ratio (column B) together with a gene encoding a transposase (column F) which was optionally fused to a heterologous nuclear localization sequence (column G). Cells were selected and expression of the DasherGFP measured (columns H-J) as described in Example 6.1.4.

Table 6. Expression from gene transfer systems comprising transposons and transposases. Transposons comprised transposon end sequences SEQ ID NO. 9 and SEQ ID NO. 6, and an expression cassette with an enhancer (column C), promoter (column D), intron (column E), element to enhance RNA export (column F) and polyadenylation sequence (column G) operably linked to a gene encoding DasherGFP. Transposons were transfected into CHO cells, optionally together with a gene encoding a transposase (SEQ ID NO. 45) fused to a heterologous nuclear localization signal. Cells were selected and expression of the DasherGFP measured (columns H and I, no transposase, columns J and K plus transposase) as described in Example 6.1.5.

Table 7. Expression from gene transfer systems comprising genes encoding two polypeptides linked by translational coupling elements. Gene transfer vectors comprised an enhancer (column E), promoter (column F), intron (column G) and polyadenylation signal (column I) operably linked to a gene encoding DasherGFP (rows 1 and 3-22) or CayenneRFP (row 2). For rows 3-22, vectors further comprised a gene encoding CayenneRFP operably linked to the expression control elements by a translational-coupling sequence (sequences identified in column H). Vectors were transfected into HEK293 cells (columns J-M) or CHO cells (columns N-Q), and expression of the fluorescent proteins measured as described in Example 6.1.6.

Table 8. Expression from gene transfer systems comprising genes encoding two polypeptides linked by translational coupling elements. Gene transfer vectors comprised an enhancer (column E), promoter (column F), intron (column G) and polyadenylation signal (column I) operably linked to a gene encoding DasherGFP (rows 1-27 and 29) or CayenneRFP (row 28). For rows 1-27, vectors further comprised a gene encoding CayenneRFP operably linked to the expression control elements by a translational-coupling sequence (sequences identified in column H). Vectors were transfected into HEK293 cells (columns J-M) or CHO cells (columns N-Q), and expression of the fluorescent proteins measured as described in Example 6.1.6.

Table 9. Expression from gene transfer systems comprising genes encoding two polypeptides linked by translational coupling elements. Gene transfer vectors comprised an enhancer (column E), promoter (column F), intron (column G) and polyadenylation signal (column I) operably linked to a gene encoding DasherGFP (rows 1-20) or CayenneRFP (row 21). For rows 1-19, vectors further comprised a gene encoding CayenneRFP operably linked to the expression control elements by a translational-coupling sequence (sequences identified in column H). Vectors were transfected into CHO cells and expression of the fluorescent proteins measured (columns J-M) as described in Example 6.1.6.

Table 10. Expression from gene transfer systems comprising genes encoding two polypeptides linked by translational coupling elements. Gene transfer vectors comprised an enhancer (column E), promoter (column F), intron (column G) and polyadenylation signal (column I) operably linked to a gene encoding DasherGFP (rows 1-22) or CayenneRFP (row 23). For rows 1-21, vectors further comprised a gene encoding CayenneRFP operably linked to the expression control elements by a translational-coupling sequence (sequences identified in column H). Vectors were transfected into HEK293 cells (columns J-M) or CHO cells (columns N-Q), and expression of the fluorescent proteins measured as described in Example 6.1.6.

Table 11. Expression from gene transfer systems comprising genes encoding two polypeptides linked by translational coupling elements. Gene transfer vectors comprised an enhancer (column E), promoter (column F), intron (column G) and polyadenylation signal (column I) operably linked to a gene encoding DasherGFP (rows 1-12) or CayenneRFP (row 13). For rows 1-11, vectors further comprised a gene encoding CayenneRFP operably linked to the expression control elements by a translational-coupling sequence (sequences identified in column H). Vectors were transfected into CHO cells and expression of the fluorescent proteins measured (columns J-M) as described in Example 6.1.6.

Table 12. Expression of antibodies from gene transfer systems comprising genes encoding both antibody chains. Gene transfer vectors comprised an enhancer (column C), promoter (column D), intron (column E) and polyadenylation signal (column F) operably linked to a gene encoding Herceptin light chain. For rows 7-12 and 17, vectors further comprised a gene encoding Herceptin heavy chain operably linked to the expression control elements by a translational-coupling sequence (sequences identified in column G). For rows 1-6, vectors further comprised a gene encoding Herceptin heavy chain operably linked to a second enhancer (column I), a second promoter (column J), a second intron (column K) and a second polyadenylation signal (column L). Optionally an insulator sequence was interposed between the first polyadenylation signal and the second enhancer (column H). Vectors were transfected into HEK293 cells, and expression of the assembled secreted antibody proteins measured as described in Example 6.1.7. Vectors encoding the two chains separately were also co-transfected at 3 different ratios (rows 13-15).

Table 13. Expression of fluorescent proteins from a gene transfer system comprising a transposon and a transposase. Transposons comprised transposon end sequences SEQ ID NO. 9 and SEQ ID NO. 6, and an enhancer (column F), promoter (column G), intron (column H) and polyadenylation signal (column I) operably linked to a gene encoding DasherGFP. For rows 3-6, vectors further comprised a gene encoding CayenneRFP operably linked to the expression control elements by a translational-coupling sequence (sequences identified in column J). For rows 7-18, vectors further comprised a gene encoding Cayenne RFP operably linked to a second enhancer (column L), a second promoter (column M), a second intron (column N) and a second polyadenylation signal (column O). Optionally an insulator sequence was interposed between the first polyadenylation signal and the second enhancer (column K). Transposons were transfected into CHO cells, optionally together with a gene encoding a transposase (SEQ ID NO. 45) fused to a heterologous nuclear localization signal, cells were selected and expression of the fluorescent proteins measured (columns Q-V) as described in Example 6.1.8. Rows 1-2 and 19-20 show the transfection of constructs encoding only GFP (rows 1-2) or RFP (rows 19-20). Rows 21 and 22 shows the co-transfection of the constructs shown in rows 1 and 19.

Table 14. Expression of a fluorescent protein from a gene transfer system comprising a transposon and a transposase. Transposons comprised transposon end sequences SEQ ID NO. 9 and SEQ ID NO. 6, an enhancer (column B), promoter (column C), intron (column D) and rabbit beta globin polyadenylation signal operably linked to a gene encoding DasherGFP, and optionally insulator sequences on either side of the Dasher expression cassette (column E). Transposons were transfected into CHO cells, optionally together with a gene encoding a transposase (column G) fused to a heterologous nuclear localization signal, cells were selected and expression of the fluorescent protein measured (columns H-J) as described in Example 6.1.9.

Table 15. Vector element combinations used in gene transfer vectors. Gene transfer vectors comprised a gene encoding DasherGFP operably linked to an enhancer (column B), a promoter (column C), an intron (column D), a 5'UTR (column E), a sequence to enhance RNA export (column F) and a polyadenylation signal (column G). Some vectors further comprised a viral replication origin (column H) and/or a gene encoding a viral replication protein (column I), as described in Example 6.1.10.

Table 16. Vector element combinations used in gene transfer vectors. Gene transfer vectors comprised a gene encoding DasherGFP operably linked to an enhancer (column B), a promoter (column C), an intron (column D), a 5'UTR (column E), a 3'UTR (column F), a sequence to enhance RNA export (column G) and a polyadenylation signal (column H). Some vectors further comprised a viral replication origin (column I) and/or a gene encoding a viral replication protein (column J), as described in Example 6.1.11.

Table 17. Vector element combinations used in gene transfer vectors. Gene transfer vectors comprised a gene encoding DasherGFP operably linked to an enhancer (column B), a promoter (column C), an intron (column D), a 5'UTR (column E), a sequence to enhance RNA export (column F) and a polyadenylation signal (column G). Vectors were transfected into CHO cells and DasherGFP measured (columns H-J), as described in Example 6.1.12.

Table 18. Vector element combinations used in gene transfer vectors.

Transposons comprised transposon end sequences SEQ ID NO. 9 and SEQ ID NO. 6, an enhancer (column B), promoter (column C), intron (column D) and polyadenylation signal (column F) operably linked to a gene encoding DasherGFP, and optionally insulator sequences on either side of the Dasher expression cassette (column G). Transposons were transfected into CHO cells, cells were selected and expression of the fluorescent protein measured (columns H-J), as described in Example 6.1.13.

Table 19. Expression of a fluorescent protein from a gene transfer systems designed to test control element configurations. Gene transfer vectors configured as shown in Table 15 were tested for expression in HEK (D-E) and CHO (B-C) cells as described in Example 6.1.10. Average fluorescent counts from independent triplicate transfections are shown.

Table 20. Expression of a fluorescent protein from a gene transfer systems designed to test control element configurations. Gene transfer vectors configured as shown in Table 16 were tested for expression in HEK (D-E) and CHO (B-C) cells as described in Example 6.1.11. Average fluorescent counts from independent triplicate transfections are shown.

Table 21. Regression weights for vector elements used in transient expression in HEK and CHO cells. A model relating the elements of gene transfer vectors shown in Table 15, and the expression data shown in Table 19 was constructed using partial least square regression. The regression weights for each element or combination of elements calculated from the model for HEK and CHO expression systems is indicated.

TABLES

TABLE 1

Expression from gene transfer vectors comprising transposons and transposase.

| A Row | B Ratio (Tn:TP) | C Transposon (Tn) Left end | D Right end | E Gene id. | F Transposase (TP) | G TP NLS fusion | H GFP Expression 1 | I 2 | J 3 |
|---|---|---|---|---|---|---|---|---|---|
| 1 | N/A | SEQ ID NO: 30 | SEQ ID NO: 31 | 133371 | none | N/A | 549 | 703 | 592 |
| 2 | 3:1 | SEQ ID NO: 30 | SEQ ID NO: 31 | 133371 | SEQ ID NO: 57 | no | 5,279 | 4,421 | 4,528 |
| 3 | 5:1 | SEQ ID NO: 30 | SEQ ID NO: 31 | 133371 | SEQ ID NO: 57 | no | 4,992 | 5,328 | 5,512 |
| 4 | 1:1 | SEQ ID NO: 30 | SEQ ID NO: 31 | 133371 | SEQ ID NO: 57 | no | 3,717 | 3,910 | 3,056 |
| 5 | N/A | SEQ ID NO: 1 | SEQ ID NO: 2 | 133365 | none | N/A | 709 | 554 | 655 |
| 6 | 3:1 | SEQ ID NO: 1 | SEQ ID NO: 2 | 133365 | SEQ ID NO: 44 | no | 3,193 | 3,052 | 3,981 |
| 7 | 5:1 | SEQ ID NO: 1 | SEQ ID NO: 2 | 133365 | SEQ ID NO: 44 | no | 3,043 | 3,165 | 2,929 |
| 8 | 1:1 | SEQ ID NO: 1 | SEQ ID NO: 2 | 133365 | SEQ ID NO: 44 | no | 3,848 | 3,641 | 3,664 |
| 9 | N/A | SEQ ID NO: 5 | SEQ ID NO: 6 | 134925 | none | N/A | 316 | 330 | 314 |
| 10 | 3:1 | SEQ ID NO: 5 | SEQ ID NO: 6 | 134925 | SEQ ID NO: 46 | yes | 535 | 422 | 542 |
| 11 | 5:1 | SEQ ID NO: 5 | SEQ ID NO: 6 | 134925 | SEQ ID NO: 46 | yes | 498 | 420 | 524 |
| 12 | 1:1 | SEQ ID NO: 5 | SEQ ID NO: 6 | 134925 | SEQ ID NO: 46 | yes | 509 | 478 | 518 |
| 13 | N/A | SEQ ID NO: 27 | SEQ ID NO: 28 | 134924 | none | N/A | 582 | 640 | 554 |
| 14 | 3:1 | SEQ ID NO: 27 | SEQ ID NO: 28 | 134924 | SEQ ID NO: 55 | no | 294 | 462 | 545 |
| 15 | 5:1 | SEQ ID NO: 27 | SEQ ID NO: 28 | 134924 | SEQ ID NO: 55 | no | 606 | 489 | 466 |
| 16 | 1:1 | SEQ ID NO: 27 | SEQ ID NO: 28 | 134924 | SEQ ID NO: 55 | no | 698 | 613 | 699 |

TABLE 2

Expression from gene transfer vectors comprising transposons and transposase.

| A Row | C Ratio (Tn:TP) | D Transposon (Tn) Left end | E Right end | F Gene id | G Transposase (TP) | H TP NLS fusion | I GFP Expression Average (N = 3) | J sd |
|---|---|---|---|---|---|---|---|---|
| 1 | N/A | SEQ ID NO: 5 | SEQ ID NO: 6 | 134925 | none | N/A | 172 | N/A |
| 2 | 2:1 | SEQ ID NO: 5 | SEQ ID NO: 6 | 134925 | SEQ ID NO: 45 | no | 204 | 1.19 |
| 3 | 6:1 | SEQ ID NO: 5 | SEQ ID NO: 6 | 134925 | SEQ ID NO: 45 | no | 281 | 1.63 |
| 4 | 2:1 | SEQ ID NO: 5 | SEQ ID NO: 6 | 134925 | SEQ ID NO: 46 | no | 184 | 1.07 |
| 5 | 6:1 | SEQ ID NO: 5 | SEQ ID NO: 6 | 134925 | SEQ ID NO: 46 | no | 161 | 0.94 |
| 6 | 2:1 | SEQ ID NO: 5 | SEQ ID NO: 6 | 134925 | SEQ ID NO: 45 | yes | 577 | 3.36 |
| 7 | 6:1 | SEQ ID NO: 5 | SEQ ID NO: 6 | 134925 | SEQ ID NO: 45 | yes | 483 | 2.81 |
| 8 | N/A | SEQ ID NO: 30 | SEQ ID NO: 31 | 133371 | none | N/A | 288 | N/A |
| 9 | 6:1 | SEQ ID NO: 30 | SEQ ID NO: 31 | 133371 | SEQ ID NO: 57 | no | 3674 | 12.8 |
| 10 | N/A | SEQ ID NO: 24 | SEQ ID NO: 25 | 134922 | none | N/A | 327 | N/A |
| 11 | 2:1 | SEQ ID NO: 24 | SEQ ID NO: 25 | 134922 | SEQ ID NO: 47 | no | 103 | 0.59 |
| 12 | 6:1 | SEQ ID NO: 24 | SEQ ID NO: 25 | 134922 | SEQ ID NO: 47 | no | 277 | 0.85 |
| 13 | N/A | SEQ ID NO: 10 | SEQ ID NO: 11 | 133366 | none | N/A | 332 | N/A |
| 14 | 2:1 | SEQ ID NO: 10 | SEQ ID NO: 11 | 133366 | SEQ ID NO: 48 | no | 5 | 0.02 |
| 15 | 6:1 | SEQ ID NO: 10 | SEQ ID NO: 11 | 133366 | SEQ ID NO: 48 | no | 393 | 1.18 |
| 16 | N/A | SEQ ID NO: 12 | SEQ ID NO: 13 | 133367 | none | N/A | 505 | N/A |
| 17 | 2:1 | SEQ ID NO: 12 | SEQ ID NO: 13 | 133367 | SEQ ID NO: 48 | no | 185 | 0.37 |
| 18 | 6:1 | SEQ ID NO: 12 | SEQ ID NO: 13 | 133367 | SEQ ID NO: 48 | no | 179 | 0.36 |
| 19 | N/A | SEQ ID NO: 22 | SEQ ID NO: 23 | 134717 | none | N/A | 303 | N/A |
| 20 | 2:1 | SEQ ID NO: 22 | SEQ ID NO: 23 | 134717 | SEQ ID NO: 52 | no | 208 | 0.68 |
| 21 | 6:1 | SEQ ID NO: 22 | SEQ ID NO: 23 | 134717 | SEQ ID NO: 52 | no | 177 | 0.58 |
| 22 | N/A | SEQ ID NO: 14 | SEQ ID NO: 15 | 133368 | none | N/A | 277 | N/A |
| 23 | 2:1 | SEQ ID NO: 14 | SEQ ID NO: 15 | 133368 | SEQ ID NO: 49 | no | 243 | 0.88 |
| 24 | 6:1 | SEQ ID NO: 14 | SEQ ID NO: 15 | 133368 | SEQ ID NO: 49 | no | 169 | 0.61 |
| 25 | N/A | SEQ ID NO: 16 | SEQ ID NO: 17 | 133369 | none | N/A | 266 | N/A |
| 26 | 2:1 | SEQ ID NO: 16 | SEQ ID NO: 17 | 133369 | SEQ ID NO: 50 | no | 161 | 0.63 |
| 27 | 6:1 | SEQ ID NO: 16 | SEQ ID NO: 17 | 133369 | SEQ ID NO: 50 | no | 184 | 0.72 |
| 28 | N/A | SEQ ID NO: 18 | SEQ ID NO: 19 | 133370 | none | N/A | 248 | N/A |
| 29 | 2:1 | SEQ ID NO: 18 | SEQ ID NO: 19 | 133370 | SEQ ID NO: 56 | no | 148 | 0.6 |

TABLE 2-continued

Expression from gene transfer vectors comprising transposons and transposase.

| | C | D | E | F | | | I | J |
|---|---|---|---|---|---|---|---|---|
| A | Ratio | Transposon (Tn) | | | G | H | GFP Expression | |
| Row | (Tn:TP) | Left end | Right end | Gene id | Transposase (TP) | TP NLS fusion | Average (N = 3) | sd |
| 30 | 6:1 | SEQ ID NO: 18 | SEQ ID NO: 19 | 133370 | SEQ ID NO: 56 | no | 135 | 0.54 |
| 31 | N/A | SEQ ID NO: 20 | SEQ ID NO: 21 | 134716 | none | N/A | 97 | N/A |
| 32 | 2:1 | SEQ ID NO: 20 | SEQ ID NO: 21 | 134716 | SEQ ID NO: 51 | no | 67 | 0.69 |
| 33 | 6:1 | SEQ ID NO: 20 | SEQ ID NO: 21 | 134716 | SEQ ID NO: 51 | no | 92 | 0.96 |
| 34 | N/A | SEQ ID NO: 26 | SEQ ID NO: 27 | 134923 | none | N/A | 319 | N/A |
| 35 | 2:1 | SEQ ID NO: 26 | SEQ ID NO: 27 | 134923 | SEQ ID NO: 54 | no | 189 | 0.59 |
| 36 | 6:1 | SEQ ID NO: 26 | SEQ ID NO: 27 | 134923 | SEQ ID NO: 54 | no | 270 | 0.85 |

TABLE 3

Expression from gene transfer vectors comprising transposons and transposase.

| | B | C | D | E | F | | H | I | J |
|---|---|---|---|---|---|---|---|---|---|
| A | | Transposon | | | | G | GFP Expression | | |
| Row | Left end | Right end | Gene id | P_GFP | Insulator | Transposase | 1 | 2 | 3 |
| 1 | SEQ ID NO: 5 | SEQ ID NO: 6 | 147759 | EF1a | no | none | 203 | 188 | 218 |
| 2 | SEQ ID NO: 5 | SEQ ID NO: 6 | 147759 | EF1a | no | SEQ ID NO: 45 | 640 | 638 | 661 |
| 3 | SEQ ID NO: 5 | SEQ ID NO: 6 | 181650 | EF1a | HS4 | none | 784 | 865 | 838 |
| 4 | SEQ ID NO: 5 | SEQ ID NO: 6 | 181650 | EF1a | HS4 | SEQ ID NO: 45 | 3,924 | 3,643 | 4,645 |
| 5 | SEQ ID NO: 1 | SEQ ID NO: 2 | 194091 | EF1a | no | none | 660 | 638 | 746 |
| 6 | SEQ ID NO: 1 | SEQ ID NO: 2 | 194091 | EF1a | no | SEQ ID NO: 44 | 70 | 81 | 111 |
| 7 | SEQ ID NO: 1 | SEQ ID NO: 2 | 194092 | EF1a | HS4 core | none | 552 | 520 | 534 |
| 8 | SEQ ID NO: 1 | SEQ ID NO: 2 | 194092 | EF1a | HS4 core | SEQ ID NO: 44 | 3,001 | 2,830 | 3,236 |
| 9 | SEQ ID NO: 1 | SEQ ID NO: 2 | 194093 | EF1a | HS4 | none | 968 | 1,034 | 1,238 |
| 10 | SEQ ID NO: 1 | SEQ ID NO: 2 | 194093 | EF1a | HS4 | SEQ ID NO: 44 | 4,601 | 4,445 | 5,530 |
| 11 | SEQ ID NO: 1 | SEQ ID NO: 2 | 194094 | CMV | no | none | 92 | 117 | 95 |
| 12 | SEQ ID NO: 1 | SEQ ID NO: 2 | 194094 | CMV | no | SEQ ID NO: 44 | 815 | 931 | 915 |
| 13 | SEQ ID NO: 1 | SEQ ID NO: 2 | 194095 | CMV | HS4 core | none | 57 | 56 | 62 |
| 14 | SEQ ID NO: 1 | SEQ ID NO: 2 | 194095 | CMV | HS4 core | SEQ ID NO: 44 | 684 | 852 | 663 |
| 15 | SEQ ID NO: 1 | SEQ ID NO: 2 | 194096 | CMV | HS4 | none | 97 | 84 | 82 |
| 16 | SEQ ID NO: 1 | SEQ ID NO: 2 | 194096 | CMV | HS4 | SEQ ID NO: 44 | 1,327 | 1,196 | 1,257 |

TABLE 4

Expression from gene transfer vectors comprising transposons and transposase.

| | B | C | D | E | F | G |
|---|---|---|---|---|---|---|
| A | | Transposon | | | | |
| Row | Left end | Right end | Gene id | P_GFP | RNA element | Insulator |
| 1 | SEQ ID NO: 9 | SEQ ID NO: 6 | 187151 | CMV | HPRE | no |
| 2 | SEQ ID NO: 9 | SEQ ID NO: 6 | 187151 | CMV | HPRE | no |
| 3 | SEQ ID NO: 9 | SEQ ID NO: 6 | 198993 | CMV | HPRE | no |
| 4 | SEQ ID NO: 9 | SEQ ID NO: 6 | 181650 | EF1a | HPRE | HS4 |
| 5 | SEQ ID NO: 9 | SEQ ID NO: 6 | 181650 | EF1a | HPRE | HS4 |
| 6 | SEQ ID NO: 9 | SEQ ID NO: 6 | 197821 | EF1a | HPRE | HS4 |
| 7 | SEQ ID NO: 9 | SEQ ID NO: 6 | 198994 | EF1a | HPRE | HS4 |
| 8 | SEQ ID NO: 30 | SEQ ID NO: 31 | 133371 | EF1a | WPRE | no |
| 9 | SEQ ID NO: 30 | SEQ ID NO: 31 | 133371 | EF1a | WPRE | no |
| 10 | SEQ ID NO: 30 | SEQ ID NO: 31 | 94097 | EF1a | WPRE | no |
| 11 | SEQ ID NO: 1 | SEQ ID NO: 2 | 194094 | CMV | HPRE | no |
| 12 | SEQ ID NO: 1 | SEQ ID NO: 2 | 194094 | CMV | HPRE | no |
| 13 | SEQ ID NO: 1 | SEQ ID NO: 2 | 198176 | CMV | HPRE | no |
| 14 | SEQ ID NO: 1 | SEQ ID NO: 2 | 198997 | CMV | HPRE | HS4core |
| 15 | SEQ ID NO: 1 | SEQ ID NO: 2 | 194092 | EF1a | HPRE | HS4core |
| 16 | SEQ ID NO: 1 | SEQ ID NO: 2 | 194092 | EF1a | HPRE | HS4core |
| 17 | SEQ ID NO: 1 | SEQ ID NO: 2 | 198154 | EF1a | HPRE | HS4core |
| 18 | SEQ ID NO: 1 | SEQ ID NO: 2 | 198996 | EF1a | HPRE | HS4core |
| 19 | SEQ ID NO: 1 | SEQ ID NO: 2 | 194093 | EF1a | HPRE | HS4 |
| 20 | SEQ ID NO: 1 | SEQ ID NO: 2 | 194093 | EF1a | HPRE | HS4 |
| 21 | SEQ ID NO: 1 | SEQ ID NO: 2 | 197822 | EF1a | HPRE | HS4 |
| 22 | SEQ ID NO: 1 | SEQ ID NO: 2 | 198995 | EF1a | HPRE | HS4 |

TABLE 4-continued

Expression from gene transfer vectors comprising transposons and transposase.

| A Row | H Transposase | I Gene id | J All-in-one | K P_TP | L NLS | M 1 | N GFP Expression 2 | O 3 |
|---|---|---|---|---|---|---|---|---|
| 1 | none | N/A | N/A | N/A | N/A | 42 | 50 | 58 |
| 2 | SEQ ID NO: 45 | 136651 | no | CMV | yes | 1,004 | 903 | 894 |
| 3 | SEQ ID NO: 45 | 136651 | yes | SV40 | yes | 511 | 506 | 523 |
| 4 | none | N/A | N/A | N/A | N/A | 1,649 | 1,675 | 1,634 |
| 5 | SEQ ID NO: 45 | 136651 | no | CMV | yes | 3,849 | 3,935 | 4,226 |
| 6 | SEQ ID NO: 45 | 136651 | yes | CMV | yes | 2,287 | 2,482 | 2,263 |
| 7 | SEQ ID NO: 45 | 136651 | yes | SV40 | yes | 2,475 | 2,340 | 2,604 |
| 8 | none | N/A | N/A | N/A | N/A | 490 | 579 | 603 |
| 9 | SEQ ID NO: 57 | 133255 | no | CMV | none | 3,947 | 3,069 | 3,518 |
| 10 | SEQ ID NO: 57 | 133255 | yes | CMV | none | 5,314 | 4,133 | 4,830 |
| 11 | none | N/A | N/A | N/A | N/A | 57 | 56 | 49 |
| 12 | SEQ ID NO: 44 | 136653 | no | CMV | yes | 1,461 | 1,412 | 1,443 |
| 13 | SEQ ID NO: 44 | 136653 | yes | CMV | yes | 1,530 | 1,574 | 1,727 |
| 14 | SEQ ID NO: 44 | 136653 | yes | SV40 | yes | 932 | 1,058 | 1,035 |
| 15 | none | N/A | N/A | N/A | N/A | 1,584 | 1,518 | 1,215 |
| 16 | SEQ ID NO: 44 | 136653 | no | CMV | yes | 3,343 | 3,482 | 3,427 |
| 17 | SEQ ID NO: 44 | 136653 | yes | CMV | yes | 4,732 | 3,481 | 3,543 |
| 18 | SEQ ID NO: 44 | 136653 | yes | SV40 | yes | 2,056 | 2,147 | 2,258 |
| 19 | none | N/A | N/A | N/A | N/A | 1,185 | 1,252 | 1,560 |
| 20 | SEQ ID NO: 44 | 136653 | no | CMV | yes | 4,348 | 4,605 | 6,072 |
| 21 | SEQ ID NO: 44 | 136653 | yes | CMV | yes | 4,331 | 3,786 | 4,459 |
| 22 | SEQ ID NO: 44 | 136653 | yes | SV40 | yes | 864 | 1,089 | 844 |

TABLE 5

Expression from gene transfer vectors comprising transposons and transposases.

| A Row | B Ratio (Tn:TP) | C Transposon (Tn) left end | D right end | E Gene | F Transposase (Tpase) | G NLS | H 1 | I GFP Expression 2 | J 3 |
|---|---|---|---|---|---|---|---|---|---|
| 1 | N/A | SEQ ID NO: 30 | SEQ ID NO: 31 | 136214 | none | N/A | 15 | 13 | 16 |
| 2 | 5:1 | SEQ ID NO: 30 | SEQ ID NO: 31 | 136214 | SEQ ID NO: 57 | yes | 78 | 76 | 83 |
| 3 | N/A | SEQ ID NO: 5 | SEQ ID NO: 6 | 192462 | none | N/A | 15 | 16 | 19 |
| 4 | 3:1 | SEQ ID NO: 5 | SEQ ID NO: 6 | 192462 | SEQ ID NO: 45 | yes | 50 | 49 | 40 |
| 5 | N/A | SEQ ID NO: 7 | SEQ ID NO: 8 | 195739 | none | N/A | 15 | 18 | 18 |
| 6 | 3:1 | SEQ ID NO: 7 | SEQ ID NO: 8 | 195739 | SEQ ID NO: 45 | yes | 46 | 56 | 54 |
| 7 | N/A | SEQ ID NO: 1 | SEQ ID NO: 2 | 192465 | none | N/A | 13 | 16 | 11 |
| 8 | 3:1 | SEQ ID NO: 1 | SEQ ID NO: 2 | 192465 | SEQ ID NO: 44 | yes | 31 | 25 | 24 |
| 9 | N/A | SEQ ID NO: 1 | SEQ ID NO: 2 | 192465 | SEQ ID NO: 43 | yes | 11 | 11 | 9 |
| 10 | 3:1 | SEQ ID NO: 1 | SEQ ID NO: 2 | 192465 | SEQ ID NO: 44 | no | 36 | 41 | 41 |
| 11 | N/A | SEQ ID NO: 24 | SEQ ID NO: 25 | 192459 | none | N/A | 9 | 11 | 11 |
| 12 | 3:1 | SEQ ID NO: 24 | SEQ ID NO: 25 | 192459 | SEQ ID NO: 53 | yes | 8 | 10 | 11 |
| 13 | N/A | SEQ ID NO: 26 | SEQ ID NO: 27 | 192460 | none | N/A | 8 | 12 | 12 |
| 14 | 3:1 | SEQ ID NO: 26 | SEQ ID NO: 27 | 192460 | SEQ ID NO: 54 | yes | 12 | 10 | 12 |
| 15 | N/A | SEQ ID NO: 20 | SEQ ID NO: 21 | 192463 | none | N/A | 7 | 9 | 11 |
| 16 | 3:1 | SEQ ID NO: 20 | SEQ ID NO: 21 | 192463 | SEQ ID NO: 51 | yes | 4 | 7 | 4 |
| 17 | N/A | SEQ ID NO: 22 | SEQ ID NO: 23 | 192464 | none | N/A | 15 | 16 | 11 |
| 18 | 3:1 | SEQ ID NO: 22 | SEQ ID NO: 23 | 192464 | SEQ ID NO: 52 | yes | 8 | 11 | 7 |
| 19 | N/A | SEQ ID NO: 10 | SEQ ID NO: 11 | 192466 | none | N/A | 10 | 6 | 7 |
| 20 | 3:1 | SEQ ID NO: 10 | SEQ ID NO: 11 | 192466 | SEQ ID NO: 47 | yes | 9 | 10 | 9 |
| 21 | N/A | SEQ ID NO: 12 | SEQ ID NO: 13 | 192467 | none | N/A | 8 | 12 | 12 |
| 22 | 3:1 | SEQ ID NO: 12 | SEQ ID NO: 13 | 192467 | SEQ ID NO: 48 | yes | 9 | 13 | 9 |
| 23 | N/A | SEQ ID NO: 14 | SEQ ID NO: 15 | 192468 | none | N/A | 11 | 7 | 12 |
| 24 | 3:1 | SEQ ID NO: 14 | SEQ ID NO: 15 | 192468 | SEQ ID NO: 49 | yes | 9 | 9 | 7 |
| 25 | N/A | SEQ ID NO: 16 | SEQ ID NO: 17 | 192469 | none | N/A | 13 | 13 | 15 |
| 26 | 3:1 | SEQ ID NO: 16 | SEQ ID NO: 17 | 192469 | SEQ ID NO: 50 | yes | 9 | 8 | 10 |
| 27 | N/A | SEQ ID NO: 18 | SEQ ID NO: 19 | 192470 | none | N/A | 15 | 13 | 14 |
| 28 | 3:1 | SEQ ID NO: 18 | SEQ ID NO: 19 | 192470 | SEQ ID NO: 56 | yes | 6 | 6 | 6 |
| 29 | N/A | SEQ ID NO: 28 | SEQ ID NO: 29 | 192461 | none | N/A | 16 | 16 | 11 |
| 30 | 3:1 | SEQ ID NO: 28 | SEQ ID NO: 29 | 192461 | SEQ ID NO: 55 | yes | 5 | 10 | 9 |

TABLE 6

Expression from gene transfer vectors comprising transposons and transposases.

| A Row | B Construct | C Enhancer | D Promoter | E Intron | F RNA export | G polyA | H No transposase GFP Exp. (Mean) | sd | J Plus transposase GFP Exp. (Mean) | K sd |
|---|---|---|---|---|---|---|---|---|---|---|
| 1 | 145736 | CMV | CMV | none | WPRE | BGH | 1,046 | 63 | 6,986 | 737 |
| 2 | 145737 | CMV | CMV | CMVa | WPRE | BGH | 1,172 | 133 | 6,380 | 206 |
| 3 | 187151 | CMV | CMV | none | HPRE | rabbit globin | 1,378 | 80 | 7,243 | 382 |
| 4 | 187152 | CMV | CMV | CMVa | HPRE | rabbit globin | 1,073 | 27 | 4,902 | 254 |
| 5 | 189858 | CMV | CMV | synthetic (eMLP) | HPRE | rabbit globin | 1,527 | 63 | 6,437 | 398 |

TABLE 7

Expression from gene transfer vectors comprising genes encoding two polypeptides linked by translational coupling elements.

| A Row | B Gene | C GFP | D RFP | E Enhancer | F Promoter | G Intron | H IRES/Other | I PolyA | J HEK293 cells Avg. GFP (N = 3) | K sd | L Avg. RFP (N = 3) | M sd | N CHO cells Avg. GFP (N = 3) | O sd | P Avg. RFP (N = 3) | Q sd |
|---|---|---|---|---|---|---|---|---|---|---|---|---|---|---|---|---|
| 1 | 143090 | yes | no | CMV | CMV | CMVc | none | rabbit globin | 13,565 | 426 | 3 | 1 | 21,909 | 1,128 | 4 | 1 |
| 2 | 188552 | no | yes | CMV | CMV | eMLP | none | rabbit globin | 7 | 1 | 1,620 | 42 | 5 | 1 | 1,316 | 241 |
| 3 | 135171 | yes | yes | CMV | CMV | none | SEQ ID NO: 101 | BGH | 1,064 | 54 | 293 | 11 | 548 | 108 | 168 | 13 |
| 4 | 186390 | yes | yes | CMV | CMV | CMVc | SEQ ID NO: 75 | rabbit globin | 5,252 | 180 | 286 | 11 | 1,786 | 140 | 136 | 5 |
| 5 | 183439 | yes | yes | CMV | CMV | CMVc | SEQ ID NO: 68 | rabbit globin | 3,687 | 329 | 249 | 26 | 12,618 | 712 | 170 | 3 |
| 6 | 186386 | yes | yes | CMV | CMV | CMVc | SEQ ID NO: 64 | rabbit globin | 3,678 | 221 | 11 | 1 | 4,428 | 310 | 59 | 5 |
| 7 | 183432 | yes | yes | CMV | CMV | CMVc | SEQ ID NO: 98 | rabbit globin | 3,515 | 290 | 69 | 9 | 7,656 | 1,229 | 250 | 28 |
| 8 | 180533 | yes | yes | CMV | CMV | CMVc | SEQ ID NO: 61 | rabbit globin | 3,275 | 590 | 268 | 49 | 2,775 | 193 | 273 | 31 |
| 9 | 183431 | yes | yes | CMV | CMV | CMVc | SEQ ID NO: 63 | rabbit globin | 2,788 | 250 | 186 | 17 | 1,760 | 428 | 163 | 42 |
| 10 | 180536 | yes | yes | CMV | CMV | CMVc | SEQ ID NO: 62 | rabbit globin | 2,324 | 315 | 159 | 25 | 13,203 | 1,030 | 251 | 25 |
| 11 | 183437 | yes | yes | CMV | CMV | CMVc | SEQ ID NO: 67 | rabbit globin | 1,940 | 200 | 195 | 25 | 9,170 | 781 | 272 | 20 |
| 12 | 186382 | yes | yes | CMV | CMV | CMVc | SEQ ID NO: 74 | rabbit globin | 743 | 30 | 51 | 3 | 5,384 | 108 | 85 | 0 |
| 13 | 180530 | yes | yes | CMV | CMV | CMVc | SEQ ID NO: 58 | rabbit globin | 1,714 | 173 | 72 | 11 | 1,660 | 232 | 93 | 12 |
| 14 | 183429 | yes | yes | CMV | CMV | CMVc | SEQ ID NO: 59 | rabbit globin | 1,581 | 53 | 195 | 6 | 2,060 | 353 | 231 | 31 |
| 15 | 188326 | yes | yes | CMV | CMV | none | SEQ ID NO: 99 | SV40 | 1,425 | 86 | 88 | 14 | 6,901 | 484 | 158 | 7 |
| 16 | 188220 | yes | yes | CMV | CMV | none | SEQ ID NO: 63 | SV40 | 1,380 | 125 | 80 | 9 | 1,887 | 142 | 160 | 15 |
| 17 | 188697 | yes | yes | CMV | CMV | none | SEQ ID NO: 100 | SV40 | 1,363 | 36 | 6 | 1 | 6,081 | 1,338 | 97 | 29 |
| 18 | 188222 | yes | yes | CMV | CMV | none | SEQ ID NO: 67 | SV40 | 1,537 | 81 | 143 | 9 | 6,558 | 600 | 205 | 14 |
| 19 | 188221 | yes | yes | CMV | CMV | none | SEQ ID NO: 59 | SV40 | 2,788 | 165 | 326 | 19 | 4,217 | 180 | 491 | 25 |
| 20 | 188210 | yes | yes | EF1a | EF1a | EF1a | SEQ ID NO: 67 | rabbit globin | 362 | 41 | 43 | 6 | 5,915 | 542 | 196 | 25 |
| 21 | 188208 | yes | yes | EF1a | EF1a | EF1a | SEQ ID NO: 63 | rabbit globin | 269 | 44 | 19 | 3 | 2,044 | 372 | 154 | 39 |
| 22 | 188209 | yes | yes | EF1a | EF1a | EF1a | SEQ ID NO: 59 | rabbit globin | 499 | 65 | 61 | 7 | 3,356 | 723 | 306 | 51 |

TABLE 8

Expression from gene transfer vectors comprising genes encoding two polypeptides linked by translational coupling elements.

| | | | | | | | | | J | K | L | M | N | O | P | Q |
|---|---|---|---|---|---|---|---|---|---|---|---|---|---|---|---|---|
| | | | | | | | | | HEK293 cells | | | | CHO cells | | | |
| A Row | B Gene | C GFP | D RFP | E Enhancer | F Promoter | G Intron | H IRES/Other | I PolyA | Avg GFP (N=3) | sd | Avg RFP (N=3) | sd | Avg GFP (N=3) | sd | Avg RFP (N=3) | sd |
| 1 | 188220 | yes | no | CMV | CMV | None | SEQ ID NO: 63 | SV40 | 6,259 | 227 | 400 | 14 | 152 | 44 | 13 | 3 |
| 2 | 188222 | yes | yes | CMV | CMV | None | SEQ ID NO: 67 | SV40 | 5,752 | 864 | 657 | 88 | 1,147 | 25 | 66 | 2 |
| 3 | 188223 | yes | yes | CMV | CMV | None | SEQ ID NO: 68 | SV40 | 8,322 | 1,051 | 611 | 48 | 1,826 | 385 | 39 | 3 |
| 4 | 188224 | yes | yes | CMV | CMV | None | SEQ ID NO: 62 | SV40 | 7,542 | 652 | 661 | 50 | 3,391 | 563 | 93 | 15 |
| 5 | 188225 | yes | yes | CMV | CMV | None | SEQ ID NO: 61 | SV40 | 4,551 | 111 | 377 | 10 | 774 | 75 | 63 | 6 |
| 6 | 188226 | yes | yes | CMV | CMV | None | SEQ ID NO: 70 | SV40 | 3,389 | 314 | 66 | 4 | 1,889 | 103 | 13 | 1 |
| 7 | 188227 | yes | yes | CMV | CMV | None | SEQ ID NO: 71 | SV40 | 2,415 | 180 | 29 | 2 | 1,246 | 22 | 4 | 0 |
| 8 | 188228 | yes | yes | CMV | CMV | None | SEQ ID NO: 64 | SV40 | 5,767 | 1,300 | 17 | 3 | 1,057 | 88 | 17 | 0 |
| 9 | 188326 | yes | yes | CMV | CMV | None | SEQ ID NO: 99 | SV40 | 5,227 | 436 | 395 | 25 | 2,446 | 311 | 89 | 11 |
| 10 | 188697 | yes | yes | CMV | CMV | None | SEQ ID NO: 100 | SV40 | 3,687 | 93 | 14 | 1 | 3,684 | 64 | 37 | 1 |
| 11 | 191353 | yes | yes | CMV | CMV | None | SEQ ID NO: 94 | SV40 | 5,681 | 273 | 630 | 48 | 1,850 | 131 | 93 | 18 |
| 12 | 191354 | yes | yes | CMV | CMV | None | SEQ ID NO: 95 | SV40 | 6,248 | 132 | 114 | 2 | 4,169 | 737 | 66 | 16 |
| 13 | 191355 | yes | yes | CMV | CMV | None | SEQ ID NO: 96 | SV40 | 5,315 | 834 | 108 | 18 | 2,024 | 27 | 18 | 2 |
| 14 | 191356 | yes | yes | CMV | CMV | None | SEQ ID NO: 88 | SV40 | 3,659 | 773 | 415 | 124 | 4,075 | 674 | 218 | 39 |
| 15 | 191357 | yes | yes | CMV | CMV | None | SEQ ID NO: 97 | SV40 | 3,428 | 420 | 7 | 1 | 3,062 | 223 | 5 | 1 |
| 16 | 191435 | yes | yes | CMV | CMV | None | SEQ ID NO: 73 | SV40 | 4,648 | 451 | 835 | 54 | 2,223 | 21 | 207 | 2 |
| 17 | 191436 | yes | yes | CMV | CMV | None | SEQ ID NO: 75 | SV40 | 10,885 | 549 | 599 | 42 | 1,915 | 103 | 143 | 4 |
| 18 | 191437 | yes | yes | CMV | CMV | None | SEQ ID NO: 76 | SV40 | 8,745 | 662 | 262 | 19 | 1,742 | 86 | 75 | 4 |
| 19 | 191438 | yes | yes | CMV | CMV | None | SEQ ID NO: 77 | SV40 | 4,764 | 409 | 593 | 61 | 3,587 | 149 | 203 | 1 |
| 20 | 191439 | yes | yes | CMV | CMV | None | SEQ ID NO: 78 | SV40 | 5,242 | 640 | 555 | 77 | 3,229 | 338 | 163 | 19 |
| 21 | 191440 | yes | yes | CMV | CMV | None | SEQ ID NO: 79 | SV40 | 5,381 | 413 | 175 | 16 | 3,358 | 246 | 53 | 8 |
| 22 | 191441 | yes | yes | CMV | CMV | None | SEQ ID NO: 80 | SV40 | 5,277 | 723 | 155 | 21 | 4,136 | 1,024 | 78 | 18 |
| 23 | 191442 | yes | yes | CMV | CMV | None | SEQ ID NO: 74 | SV40 | 4,447 | 261 | 321 | 17 | 4,219 | 572 | 138 | 21 |
| 24 | 191433 | yes | yes | CMV | CMV | None | SEQ ID NO: 58 | SV40 | 8,177 | 606 | 406 | 11 | 2,082 | 138 | 101 | 6 |
| 25 | 188221 | yes | yes | CMV | CMV | None | SEQ ID NO: 59 | SV40 | 8,144 | 979 | 1,110 | 98 | 228 | 95 | 29 | 12 |
| 26 | 189939 | yes | yes | CMV | CMV | None | SEQ ID NO: 101 | SV40 | 3,710 | 638 | 1,407 | 223 | 1,326 | 114 | 466 | 39 |
| 27 | 189940 | yes | yes | CMV | CMV | None | SEQ ID NO: 101 | SV40 | 3,049 | 111 | 911 | 41 | 962 | 34 | 260 | 14 |
| 28 | 135149 | no | yes | CMV | CMV | None | none | BGH | 8 | 2 | 1,398 | 50 | 10 | 6 | 133 | 9 |
| 29 | 136032 | yes | no | CMV | CMV | None | none | SV40 | 16,336 | 416 | 3 | 1 | 4,879 | 270 | 1 | 1 |

TABLE 9

Expression from gene transfer vectors comprising genes encoding two polypeptides linked by translational coupling elements.

| | | | | | | | | | J | K | L | M |
|---|---|---|---|---|---|---|---|---|---|---|---|---|
| | | | | | | | | | \multicolumn{4}{c}{CHO cells} |
| A Row | B Gene | C GFP | D RFP | E Enhancer | F Promoter | G Intron | H IRES/Other | I PolyA | Avg GFP (N = 3) | sd | Avg RFP (N = 3) | sd |
| 1 | 188220 | yes | yes | CMV | CMV | None | SEQ ID NO: 63 | SV40 | 1,971 | 149 | 145 | 8 |
| 2 | 188222 | yes | yes | CMV | CMV | None | SEQ ID NO: 67 | SV40 | 5,448 | 151 | 252 | 36 |
| 3 | 188223 | yes | yes | CMV | CMV | None | SEQ ID NO: 68 | SV40 | 6,338 | 332 | 93 | 7 |
| 4 | 188224 | yes | yes | CMV | CMV | None | SEQ ID NO: 62 | SV40 | 4,817 | 139 | 99 | 3 |
| 5 | 188225 | yes | yes | CMV | CMV | None | SEQ ID NO: 92 | SV40 | 1,360 | 100 | 112 | 18 |
| 6 | 188326 | yes | yes | CMV | CMV | None | SEQ ID NO: 99 | SV40 | 6,534 | 940 | 228 | 29 |
| 7 | 188697 | yes | yes | CMV | CMV | None | SEQ ID NO: 100 | SV40 | 6,221 | 321 | 67 | 4 |
| 8 | 191353 | yes | yes | CMV | CMV | None | SEQ ID NO: 94 | SV40 | 5,785 | 1,222 | 303 | 31 |
| 9 | 191356 | yes | yes | CMV | CMV | None | SEQ ID NO: 88 | SV40 | 6,700 | 1,054 | 309 | 51 |
| 10 | 191433 | yes | yes | CMV | CMV | None | SEQ ID NO: 58 | SV40 | 1,863 | 162 | 79 | 8 |
| 11 | 191435 | yes | yes | CMV | CMV | None | SEQ ID NO: 73 | SV40 | 5,740 | 459 | 467 | 39 |
| 12 | 191436 | yes | yes | CMV | CMV | None | SEQ ID NO: 75 | SV40 | 2,809 | 363 | 176 | 15 |
| 13 | 191437 | yes | yes | CMV | CMV | None | SEQ ID NO: 76 | SV40 | 3,328 | 643 | 130 | 21 |
| 14 | 191438 | yes | yes | CMV | CMV | None | SEQ ID NO: 77 | SV40 | 7,817 | 847 | 336 | 25 |
| 15 | 191439 | yes | yes | CMV | CMV | None | SEQ ID NO: 78 | SV40 | 7,492 | 87 | 280 | 9 |
| 16 | 191440 | yes | yes | CMV | CMV | None | SEQ ID NO: 79 | SV40 | 5,242 | 135 | 63 | 5 |
| 17 | 191442 | yes | yes | CMV | CMV | None | SEQ ID NO: 74 | SV40 | 5,065 | 432 | 122 | 10 |
| 18 | 188221 | yes | yes | CMV | CMV | None | SEQ ID NO: 59 | SV40 | 4,838 | 275 | 492 | 35 |
| 19 | 189939 | yes | yes | CMV | CMV | None | SEQ ID NO: 101 | SV40 | 1,755 | 70 | 583 | 65 |
| 20 | 136032 | yes | no | CMV | CMV | None | none | SV40 | 8,170 | 694 | 2 | 0 |
| 21 | 191432 | no | yes | CMV | CMV | None | none | SV40 | 9 | 1 | 915 | 85 |

TABLE 10

Expression from gene transfer vectors comprising genes encoding two polypeptides linked by translational coupling elements.

| | | | | | | | | | J | K | L | M | N | O | P | Q |
|---|---|---|---|---|---|---|---|---|---|---|---|---|---|---|---|---|
| | | | | | | | | | \multicolumn{4}{c}{HEK293 cells} | \multicolumn{4}{c}{CHO cells} |
| A Row | B Gene | C GFP | D RFP | E Enhancer | F Promoter | G Intron | H IRES/Other | I PolyA | Avg GFP (N = 3) | sd | Avg RFP (N = 3) | sd | Avg GFP (N = 3) | stdv | Avg RFP (N = 3) | sd |
| 1 | 188220 | yes | yes | CMV | CMV | None | SEQ ID NO: 63 | SV40 | 7,076 | 337 | 475 | 12 | 1,927 | 143 | 160 | 13 |
| 2 | 188222 | yes | yes | CMV | CMV | None | SEQ ID NO: 67 | SV40 | 4,915 | 872 | 528 | 99 | 5,552 | 558 | 182 | 20 |
| 3 | 188223 | yes | yes | CMV | CMV | None | SEQ ID NO: 68 | SV40 | 8,119 | 1,600 | 703 | 120 | 4,245 | 232 | 109 | 5 |
| 4 | 188224 | yes | yes | CMV | CMV | None | SEQ ID NO: 62 | SV40 | 5,101 | 851 | 539 | 94 | 4,406 | 1,929 | 119 | 13 |
| 5 | 188225 | yes | yes | CMV | CMV | None | SEQ ID NO: 92 | SV40 | 5,122 | 547 | 422 | 40 | 1,084 | 44 | 95 | 5 |
| 6 | 188326 | yes | yes | CMV | CMV | None | SEQ ID NO: 99 | SV40 | 3,916 | 692 | 278 | 56 | 5,147 | 699 | 132 | 20 |
| 7 | 191353 | yes | yes | CMV | CMV | None | SEQ ID NO: 94 | SV40 | 5,769 | 76 | 598 | 16 | 6,647 | 818 | 209 | 34 |
| 8 | 191356 | yes | yes | CMV | CMV | None | SEQ ID NO: 88 | SV40 | 4,501 | 231 | 447 | 25 | 6,001 | 105 | 218 | 12 |
| 9 | 191435 | yes | yes | CMV | CMV | None | SEQ ID NO: 73 | SV40 | 5,105 | 754 | 800 | 126 | 3,423 | 214 | 278 | 12 |
| 10 | 191436 | yes | yes | CMV | CMV | None | SEQ ID NO: 75 | SV40 | 8,299 | 2,248 | 533 | 153 | 1,270 | 122 | 88 | 8 |
| 11 | 101438 | yes | yes | CMV | CMV | None | SEQ ID NO: 77 | SV40 | 5,539 | 462 | 618 | 61 | 3,346 | 416 | 119 | 20 |
| 12 | 195055 | yes | yes | CMV | CMV | None | SEQ ID NO: 81 | SV40 | 4,596 | 57 | 493 | 12 | 4,730 | 714 | 164 | 33 |
| 13 | 195056 | yes | yes | CMV | CMV | None | SEQ ID NO: 82 | SV40 | 4,752 | 474 | 492 | 40 | 6,161 | 395 | 228 | 15 |
| 14 | 195057 | yes | yes | CMV | CMV | None | SEQ ID NO: 83 | SV40 | 3,883 | 821 | 408 | 92 | 4,952 | 243 | 185 | 9 |
| 15 | 195063 | yes | yes | CMV | CMV | None | SEQ ID NO: 84 | SV40 | 9,428 | 1,292 | 626 | 95 | 2,619 | 92 | 198 | 8 |
| 16 | 195064 | yes | yes | CMV | CMV | None | SEQ ID NO: 85 | SV40 | 6,625 | 696 | 569 | 56 | 1,809 | 16 | 181 | 3 |

TABLE 10-continued

Expression from gene transfer vectors comprising genes encoding two polypeptides linked by translational coupling elements.

| | | | | | | | | | J | K | L | M | N | O | P | Q |
|---|---|---|---|---|---|---|---|---|---|---|---|---|---|---|---|---|
| | | | | | | | | | HEK293 cells | | | | CHO cells | | | |
| A Row | B Gene | C GFP | D RFP | E Enhancer | F Promoter | G Intron | H IRES/Other | I PolyA | Avg GFP (N = 3) | sd | Avg RFP (N = 3) | sd | Avg GFP (N = 3) | stdv | Avg RFP (N = 3) | sd |
| 17 | 195065 | yes | yes | CMV | CMV | None | SEQ ID NO: 86 | SV40 | 7,983 | 1,660 | 394 | 66 | 3,470 | 314 | 217 | 19 |
| 18 | 195066 | yes | yes | CMV | CMV | None | SEQ ID NO: 87 | SV40 | 6,951 | 863 | 270 | 35 | 2,211 | 77 | 92 | 2 |
| 19 | 191433 | yes | yes | CMV | CMV | None | SEQ ID NO: 58 | SV40 | 6,599 | 827 | 377 | 42 | 2,068 | 9 | 109 | 1 |
| 20 | 188221 | yes | yes | CMV | CMV | None | SEQ ID NO: 59 | SV40 | 8,283 | 1,439 | 1,082 | 243 | 3,045 | 192 | 342 | 27 |
| 21 | 189939 | yes | yes | CMV | CMV | None | SEQ ID NO: 101 | SV40 | 3,916 | 554 | 1,588 | 231 | 1,202 | 63 | 410 | 18 |
| 22 | 136032 | yes | no | CMV | CMV | None | none | SV40 | 12,110 | 1,502 | 2 | 1 | 7,378 | 244 | 2 | 0 |
| 23 | 191432 | no | yes | CMV | CMV | None | none | SV40 | 5 | 0 | 898 | 72 | 34 | 17 | 890 | 35 |

TABLE 11

Expression from gene transfer vectors comprising genes encoding two polypeptides linked by translational coupling elements.

| A Row | B Gene | C GFP | D RFP | E Enhancer | F Promoter | G Intron | H IRES/Other | I PolyA | J Avg GFP (N = 3) | K stdv | L Avg RFP (N = 3) | M stdv |
|---|---|---|---|---|---|---|---|---|---|---|---|---|
| 1 | 188224 | yes | yes | CMV | CMV | None | SEQ ID NO: 62 | SV40 | 4,755 | 220 | 88 | 7 |
| 2 | 191435 | yes | yes | CMV | CMV | None | SEQ ID NO: 73 | SV40 | 3,195 | 176 | 219 | 12 |
| 3 | 191436 | yes | yes | CMV | CMV | None | SEQ ID NO: 93 | SV40 | 1,370 | 198 | 76 | 5 |
| 4 | 195055 | yes | yes | CMV | CMV | None | SEQ ID NO: 81 | SV40 | 3,995 | 128 | 105 | 4 |
| 5 | 195056 | yes | yes | CMV | CMV | None | SEQ ID NO: 82 | SV40 | 3,038 | 608 | 83 | 15 |
| 6 | 195063 | yes | yes | CMV | CMV | None | SEQ ID NO: 84 | SV40 | 1,679 | 23 | 105 | 2 |
| 7 | 195064 | yes | yes | CMV | CMV | None | SEQ ID NO: 85 | SV40 | 1,234 | 19 | 96 | 1 |
| 8 | 201084 | yes | yes | CMV | CMV | None | SEQ ID NO: 89 | SV40 | 3,494 | 250 | 234 | 18 |
| 9 | 201085 | yes | yes | CMV | CMV | None | SEQ ID NO: 90 | SV40 | 3,221 | 92 | 204 | 10 |
| 10 | 201086 | yes | yes | CMV | CMV | None | SEQ ID NO: 91 | SV40 | 3,489 | 745 | 260 | 59 |
| 11 | 188221 | yes | yes | CMV | CMV | None | SEQ ID NO: 59 | SV40 | 2,257 | 109 | 236 | 13 |
| 12 | 189939 | yes | yes | CMV | CMV | None | SEQ ID NO: 101 | SV40 | 1,190 | 103 | 355 | 6 |
| 13 | 136032 | yes | no | CMV | CMV | None | none | SV40 | 4,789 | 1,049 | 2 | 0 |

TABLE 12

Expression of antibodies from gene transfer vectors comprising genes encoding both antibody chains.

| A Row | B Gene(s) | C Enhancer 1 | D Promoter 1 | E Intron 1 | F polyA1 | G IRES | H Intergenic insulators | I Enhancer 2 | J Promoter 2 | K Intron 2 | L pA 2 | M Ab (µg/ml) 1 | N 2 | O 3 |
|---|---|---|---|---|---|---|---|---|---|---|---|---|---|---|
| 1 | 201223 | CMV | Actin | Actin | HSV-TK | N/A | no | CMV | CMV | CMVc | BGH | 173 | 138 | 133 |
| 2 | 201224 | CMV | Actin | Actin | HSV-TK | N/A | no | CMV | CMV | none | BGH | 158 | 91 | 137 |
| 3 | 201225 | CMV | Actin | Actin | HSV-TK | N/A | no | CMV | GAPDH | eMLP | BGH | 44 | 33 | 36 |
| 4 | 201226 | CMV | Actin | Actin | HSV-TK | N/A | 2x HS4 core | N/A | EF1a | EF1a | BGH | 48 | 31 | 28 |
| 5 | 201227 | CMV | Actin | Actin | HSV-TK | N/A | 2x HS4 core | CMV | GAPDH | GAPDH | BGH | 136 | 118 | 130 |
| 6 | 201228 | CMV | Actin | Actin | HSV-TK | N/A | 2x HS4 core | CMV | CMV | none | BGH | 138 | 139 | 100 |
| 7 | 201238 | CMV | Actin | Actin | BGH | SEQ ID NO: 68 | no | N/A | N/A | N/A | none | 31 | 30 | 23 |
| 8 | 201239 | CMV | Actin | Actin | BGH | SEQ ID NO: 62 | no | N/A | N/A | N/A | none | 9 | 7 | 11 |
| 9 | 201240 | CMV | Actin | Actin | BGH | SEQ ID NO: 73 | no | N/A | N/A | N/A | none | 129 | 91 | 108 |

TABLE 12-continued

Expression of antibodies from gene transfer vectors comprising genes encoding both antibody chains.

| A | B | C | D | E | F | G | H | I | J | K | L | M | N | O |
|---|---|---|---|---|---|---|---|---|---|---|---|---|---|---|
| | | Enhancer | Promoter | Intron | | | Intergenic | Enhancer | Promoter | Intron | pA | | Ab (µg/ml) | |
| Row | Gene(s) | 1 | 1 | 1 | polyA1 | IRES | insulators | 2 | 2 | 2 | 2 | 1 | 2 | 3 |
| 10 | 201241 | CMV | Actin | Actin | BGH | SEQ ID NO: 93 | no | N/A | N/A | N/A | none | 61 | 39 | 54 |
| 11 | 201242 | CMV | Actin | Actin | BGH | SEQ ID NO: 78 | no | N/A | N/A | N/A | none | 57 | 47 | 73 |
| 12 | 201243 | CMV | Actin | Actin | BGH | SEQ ID NO: 86 | no | N/A | N/A | N/A | none | 21 | 19 | 25 |
| 13 | 145409 & 145443 1HC:1LC | CMV | Actin | Actin | BGH | N/A | no | N/A | N/A | N/A | N/A | 94 | 131 | 122 |
| 14 | 145409 & 145443 5HC:1LC | CMV | Actin | Actin | BGH | N/A | no | N/A | N/A | N/A | N/A | 17 | 19 | 17 |
| 15 | 145409 & 145443 1HC:5LC | CMV | Actin | Actin | BGH | N/A | no | N/A | N/A | N/A | N/A | 110 | 98 | 147 |
| 16 | 150153 | CMV | Actin | Actin | glob (rabbit) | N/A | no | CMV | CMV | CMVc | BGH | 137 | 157 | 189 |
| 17 | 150154 | CMV | Actin | Actin | BGH | SEQ ID NO: 59 | no | N/A | N/A | N/A | none | 191 | 196 | 295 |

TABLE 13

Expression of fluorescent proteins from a gene transfer system comprising a transposon and a transposase.

| A | B | C | D | E | F | G | H | I | J | K | L |
|---|---|---|---|---|---|---|---|---|---|---|---|
| | | | | | | Transposon | | | | | |
| Row | Gene id 1 | Gene id 2 | GFP | RFP | Enhancer 1 | Promoter 1 | Intron 1 | polyA1 | IRES | intergenic insulator | Enhancer 2 |
| 1 | 187151 | N/A | yes | no | CMV | CMV | none | (rabbit) | N/A | N/A | N/A |
| 2 | 187151 | N/A | yes | no | CMV | CMV | none | (rabbit) | N/A | N/A | N/A |
| 3 | 188209 | N/A | yes | yes | none | EF1a | EF1a | (rabbit) | SEQ ID NO: 59 | N/A | none |
| 4 | 188209 | N/A | yes | yes | none | EF1a | EF1a | (rabbit) | SEQ ID NO: 59 | N/A | none |
| 5 | 188219 | N/A | yes | yes | none | EF1a | EF1a | (rabbit) | SEQ ID NO: 73 | N/A | none |
| 6 | 188219 | N/A | yes | yes | none | EF1a | EF1a | (rabbit) | SEQ ID NO: 73 | N/A | none |
| 7 | 198833 | N/A | yes | yes | CMV | CMV | none | HSV-TK | none | none | CMV |
| 8 | 198833 | N/A | yes | yes | CMV | CMV | none | HSV-TK | none | none | CMV |
| 9 | 198834 | N/A | yes | yes | CMV | CMV | none | HSV-TK | none | none | CMV |
| 10 | 198834 | N/A | yes | yes | CMV | CMV | none | HSV-TK | none | none | CMV |
| 11 | 198835 | N/A | yes | yes | CMV | CMV | none | HSV-TK | none | none | CMV |
| 12 | 198835 | N/A | yes | yes | CMV | CMV | none | HSV-TK | none | none | CMV |
| 13 | 198836 | N/A | yes | yes | CMV | CMV | none | HSV-TK | none | core | none |
| 14 | 198836 | N/A | yes | yes | CMV | CMV | none | HSV-TK | none | core | none |
| 15 | 198837 | N/A | yes | yes | CMV | CMV | none | HSV-TK | none | core | CMV |
| 16 | 198837 | N/A | yes | yes | CMV | CMV | none | HSV-TK | none | core | CMV |
| 17 | 198838 | N/A | yes | yes | CMV | CMV | none | HSV-TK | none | core | CMV |
| 18 | 198838 | N/A | yes | yes | CMV | CMV | none | HSV-TK | none | core | CMV |
| 19 | 200967 | N/A | no | yes | CMV | CMV | none | (rabbit) | none | N/A | N/A |
| 20 | 200967 | N/A | no | yes | CMV | CMV | none | (rabbit) | none | N/A | N/A |
| 21 | 187151 | 200967 | yes | yes | CMV | CMV | none | (rabbit) | N/A | N/A | N/A |
| 22 | 187151 | 200967 | yes | yes | CMV | CMV | none | (rabbit) | N/A | N/A | N/A |

| A | M | N | O | P | Q | R | S | T | U | V |
|---|---|---|---|---|---|---|---|---|---|---|
| | | Transposon | | | | | | | | |
| | Promoter | Intron | | | | GFP Expression | | | RFP Expression | |
| Row | 2 | 2 | pA2 | Transposase | 1 | 2 | 3 | 1 | 2 | 3 |
| 1 | N/A | N/A | N/A | none | 70 | 66 | 65 | 2 | 2 | 2 |
| 2 | N/A | N/A | N/A | 45 | 1,250 | 1,083 | 1,330 | 1 | 2 | 1 |
| 3 | none | none | none | none | 706 | 660 | 698 | 62 | 60 | 66 |
| 4 | none | none | none | 45 | 6,764 | 4,922 | 5,238 | 643 | 467 | 480 |
| 5 | none | none | none | none | 307 | 370 | 375 | 32 | 38 | 36 |
| 6 | none | none | none | 45 | 3,656 | 4,019 | 4,243 | 407 | 452 | 474 |
| 7 | CMV | CMVc | (rabbit) | none | 20 | 17 | 17 | 15 | 12 | 17 |
| 8 | CMV | CMVc | (rabbit) | 45 | 87 | 94 | 99 | 113 | 120 | 126 |
| 9 | CMV | none | (rabbit) | none | 19 | 22 | 21 | 9 | 10 | 10 |
| 10 | CMV | none | (rabbit) | 45 | 152 | 128 | 141 | 64 | 56 | 62 |

TABLE 13-continued

Expression of fluorescent proteins from a gene transfer system comprising a transposon and a transposase.

| | | | | | | | | | | |
|---|---|---|---|---|---|---|---|---|---|---|
| 11 | GAPDH | eMLP | (rabbit) | none | 26 | 32 | 27 | 17 | 17 | 18 |
| 12 | GAPDH | eMLP | (rabbit) | 45 | 272 | 231 | 222 | 306 | 257 | 237 |
| 13 | EF1a | EF1a | (rabbit) | none | 38 | 39 | 36 | 104 | 94 | 98 |
| 14 | EF1a | EF1a | (rabbit) | 45 | 320 | 374 | 449 | 1,102 | 1,245 | 1,471 |
| 15 | GAPDH | H | (rabbit) | none | 67 | 55 | 55 | 58 | 45 | 42 |
| 16 | GAPDH | H | (rabbit) | 45 | 396 | 470 | 411 | 418 | 483 | 425 |
| 17 | CMV | none | (rabbit) | none | 25 | 27 | 22 | 11 | 13 | 10 |
| 18 | CMV | none | (rabbit) | 45 | 280 | 260 | 245 | 122 | 118 | 104 |
| 19 | N/A | N/A | N/A | none | 5 | 5 | 4 | 4 | 10 | 11 |
| 20 | N/A | N/A | N/A | 45 | 5 | 6 | 6 | 375 | 389 | 392 |
| 21 | N/A | N/A | N/A | none | 34 | 33 | 35 | 7 | 8 | 8 |
| 22 | N/A | N/A | N/A | 45 | 546 | 583 | 628 | 186 | 196 | 197 |

TABLE 14

Expression of a fluorescent protein from a gene transfer system comprising a transposon and a transposase.

| A | B | C | D | E | F | G | H | I | J |
|---|---|---|---|---|---|---|---|---|---|
| | | | | | | | \multicolumn{3}{c}{DasherGFP} |
| Row | Enhancer 1 | Promoter 1 | Intron 1 | HS4 insulators | Gene | Transposase | 1 | 2 | 3 |
| 1 | none | EF1a | EF1a | no | 147759 | none | 283 | 415 | 373 |
| 2 | none | EF1a | EF1a | no | 147759 | SEQ ID NO: 45 | 865 | 846 | 500 |
| 3 | none | EF1a | EF1a | yes | 181650 | none | 858 | 980 | 944 |
| 4 | EF1a | EF1a | EF1a | yes | 181650 | SEQ ID NO: 45 | 3,147 | 2,878 | 2,565 |
| 5 | CMV | CMV | none | no | 187151 | none | 59 | 42 | 42 |
| 6 | CMV | CMV | none | no | 187151 | SEQ ID NO: 45 | 891 | 868 | 902 |
| 7 | CMV | CMV | CMVa | no | 187152 | none | 70 | 94 | 86 |
| 8 | CMV | CMV | CMVa | no | 187152 | SEQ ID NO: 45 | 1,157 | 1,239 | 946 |
| 9 | CMV | Actin | Actin | no | 187153 | none | 43 | 48 | 46 |
| 10 | CMV | Actin | Actin | no | 187153 | SEQ ID NO: 45 | 845 | 974 | 833 |
| 11 | CMV | EF1a | EF1a | no | 187154 | none | 430 | 497 | 385 |
| 12 | CMV | EF1a | EF1a | no | 187154 | SEQ ID NO: 45 | 905 | 1,046 | 1,143 |
| 13 | CMV | GAPDH | GAPDH | yes | 189262 | none | 230 | 212 | 215 |
| 14 | CMV | GAPDH | GAPDH | yes | 189262 | SEQ ID NO: 45 | 525 | 776 | 699 |
| 15 | CMV | Actin | Actin | yes | 189305 | none | 232 | 217 | 254 |
| 16 | CMV | Actin | Actin | yes | 189305 | SEQ ID NO: 45 | 900 | 828 | 822 |
| 17 | CMV | EF1a | EF1a | yes | 189306 | none | 582 | 547 | 594 |
| 18 | CMV | EF1a | EF1a | yes | 189306 | SEQ ID NO: 45 | 1,166 | 1,239 | 1,501 |
| 19 | CMV | GAPDH | eMLP | yes | 189855 | none | 350 | 273 | 347 |
| 20 | CMV | GAPDH | EF1a | yes | 189855 | SEQ ID NO: 45 | 890 | 1,121 | 513 |
| 21 | eMLP | EF1a | EF1a + eMLP | no | 189856 | none | 388 | 221 | 349 |
| 22 | eMLP | EF1a | EF1a + eMLP | no | 189856 | SEQ ID NO: 45 | 796 | 661 | 807 |
| 23 | CMV | CMV | EF1a | no | 189858 | none | 57 | 57 | 55 |
| 24 | CMV | CMV | EF1a | no | 189858 | SEQ ID NO: 45 | 794 | 1,228 | 1,493 |
| 25 | CMV | EF1a | EF1a + eMLP | yes | 189859 | none | 602 | 329 | 695 |
| 26 | CMV | EF1a | EF1a + eMLP | yes | 189859 | SEQ ID NO: 45 | 1,578 | 1,275 | 1,144 |
| 27 | CMV | Actin | Actin + eMLP | no | 189860 | none | 183 | 169 | 185 |
| 28 | CMV | Actin | Actin + eMLP | no | 189860 | SEQ ID NO: 45 | 460 | 491 | 436 |
| 29 | none | PGK | none | no | 192462 | none | 7 | 7 | 6 |
| 30 | none | PGK | none | no | 192462 | SEQ ID NO: 45 | 443 | 687 | 484 |

TABLE 15

Vector element combinations used in gene transfer vectors.

| A | B | C | D | E | F | G | H | I |
|---|---|---|---|---|---|---|---|---|
| Construct | Enhancer | Promoter | Intron | 5' UTR | RNA export | polyA | viral ori | viral rep prot |
| 128975 | CMV | Actin | Chick actin (partial) | none | none | sv40 late | none | none |
| 128986 | CMV | CMV | none | none | WPRE | GH-bovine | oriP | EBNA |
| 129966 | CMV | CMV | none | none | none | GH-bovine | none | none |
| 128978 | CMV | CMV | none | none | none | sv40 late | none | none |
| 128985 | CMV | CMV | CMV intron c | none | none | sv40 late | none | none |
| 129091 | CMV | CMV | none | none | WPRE | GH-bovine | oriP | none |
| 133139 | CMV | GAPDH | GAPDH | none | none | sv40 late | none | none |
| 136024 | CMV | CMV | none | none | none | synthetic polyA | SV40 | SV40 T |
| 136025 | CMV | Chick actin | Chick actin/rabbit | none | none | GH-bovine | SV40 | SV40 T |
| 136026 | CMV | Chick actin | Chick actin/rabbit | none | none | sv40 early | oriP | none |

TABLE 15-continued

Vector element combinations used in gene transfer vectors.

| A Construct | B Enhancer | C Promoter | D Intron | E 5' UTR | F RNA export | G polyA | H viral ori | I viral rep prot |
|---|---|---|---|---|---|---|---|---|
| 136027 | CMV | Chick actin | Chick actin/rabbit | none | none | sv40 late | none | none |
| 136028 | CMV | Chick actin | Chick actin (partial) | none | none | beta globin-human | SV40 | SV40 T |
| 136029 | CMV | Chick actin | Chick actin (partial) | none | none | beta globin-rabbit | none | none |
| 136030 | CMV | Chick actin | Chick actin (partial) | none | none | sv40 early | oriP | none |
| 136031 | CMV | CMV | none | none | none | beta globin-rabbit | oriP | EBNA |
| 136032 | CMV | CMV | none | none | none | sv40 early | none | none |
| 136033 | CMV | CMV | CMV intron a | CMV | none | beta globin-rabbit | oriP | none |
| 136034 | CMV | CMV | CMV intron a | CMV | none | GH-bovine | oriP | EBNA |
| 136035 | CMV | CMV | CMV intron a | CMV | none | sv40 late | SV40 | SV40 T |
| 136036 | CMV | CMV | CMV intron a | CMV | none | synthetic polyA | none | none |
| 136037 | CMV | CMV | CMV intron c | none | none | beta globin-human | none | none |
| 136038 | CMV | CMV | CMV intron c | none | none | HSV-TK | oriP | EBNA |
| 136039 | CMV | CMV | CMV intron c | none | none | sv40 late | oriP | none |
| 136040 | CMV | CMV | CMV intron c | none | none | synthetic polyA | SV40 | SV40 T |
| 136041 | CMV | EF1a | EF1a_v1 | none | none | beta globin-rabbit | SV40 | SV40 T |
| 136042 | CMV | EF1a | EF1a_v1 | none | none | HSV-TK | oriP | none |
| 136043 | CMV | EF1a | EF1a_v1 | none | none | sv40 early | none | none |
| 136044 | CMV | EF1a | EF1a_v1 | none | none | sv40 late | oriP | EBNA |
| 136045 | CMV | EF1a | EF1a_v2 | none | none | beta globin-human | none | none |
| 136046 | CMV | EF1a | EF1a_v2 | none | none | beta globin-rabbit | SV40 | SV40 T |
| 136047 | CMV | EF1a | EF1a_v2 | none | none | GH-bovine | oriP | EBNA |
| 136048 | CMV | EF1a | EF1a_v2 | none | none | HSV-TK | none | none |
| 136049 | CMV | EF1a | EF1a_hybrid | none | none | GH-bovine | oriP | none |
| 136050 | CMV | EF1a | EF1a_hybrid | none | none | HSV-TK | SV40 | SV40 T |
| 136051 | CMV | EF1a | EF1a_hybrid | none | none | synthetic polyA | oriP | EBNA |
| 136052 | CMV | GAPDH | GAPDH | none | none | beta globin-human | oriP | none |
| 136053 | CMV | GAPDH | GAPDH | none | none | beta globin-rabbit | none | none |
| 136054 | CMV | GAPDH | GAPDH | none | none | HSV-TK | SV40 | SV40 T |
| 136055 | CMV | GAPDH | GAPDH | none | none | sv40 late | oriP | EBNA |
| 136056 | none | HSV-TK | none | none | none | beta globin-human | oriP | EBNA |
| 136057 | none | HSV-TK | none | none | none | GH-bovine | none | none |
| 136058 | none | HSV-TK | none | none | none | sv40 late | oriP | none |
| 136059 | none | MC1 | none | none | none | GH-bovine | oriP | none |
| 136060 | none | MC1 | none | none | none | HSV-TK | oriP | EBNA |
| 136061 | none | MC1 | none | none | none | sv40 early | SV40 | SV40 T |
| 136062 | none | PGK | none | none | none | sv40 early | oriP | EBNA |
| 136063 | none | PGK | none | none | none | sv40 late | none | none |
| 136064 | none | PGK | none | none | none | synthetic polyA | oriP | none |
| 136065 | E_SV40 | SV40 | none | none | none | beta globin-human | none | none |
| 136066 | E_SV40 | SV40 | none | none | none | HSV-TK | none | none |
| 136067 | E_SV40 | SV40 | none | none | none | sv40 early | SV40 | SV40 T |
| 136068 | E_SV40 | SV40 | none | none | none | synthetic polyA | oriP | EBNA |
| 136069 | none | Ub-B | none | none | none | beta globin-rabbit | oriP | EBNA |
| 136070 | none | Ub-B | none | none | none | GH-bovine | SV40 | SV40 T |
| 136071 | none | Ub-B | none | none | none | synthetic polyA | none | none |
| 128979 | CMV | CMV | none | none | WPRE | sv40 early | none | none |
| 128980 | CMV | CMV | none | none | WPRE | beta globin-human | none | none |
| 128986 | CMV | CMV | none | none | WPRE | GH-bovine | oriP | EBNA |
| 129091 | CMV | CMV | none | none | WPRE | GH-bovine | oriP | none |
| 128977 | CMV | CMV | Synthetic | none | none | sv40 early | none | none |
| 133528 | CMV | CMV | none | none | none | GH-bovine | SV40 | none |
| 134746 | CMV | CMV | none | none | WPRE | HSV-TK | SV40 | none |

TABLE 16

Vector element combinations used in gene transfer vectors.

| A Construct | B Enhancer | C Promoter | D Intron | E 5' UTR | F 3' UTR | G RNA export | H polyA | I viral ori | J viral rep prot |
|---|---|---|---|---|---|---|---|---|---|
| 143088 | CMV | CMV | none | CMV | none | AGS | HSV-TK | oriP | EBNA |
| 143089 | | EF1a | EF1a | none | none | WPRE | HSV-TK | oriP | none |
| 143090 | CMV | CMV | CMVc | CMV | none | none | Globin-rabbit | none | none |
| 143091 | CMV | CMV | CMVc | CMV_sTNV | sTNV | none | GH-bovine | oriP | none |
| 143092 | CMV | GAPDH | GAPDH | none | none | AGS | Globin-rabbit | none | none |
| 143093 | CMV | CMV | CMVa | bglob-Hs | bglob-Xl | AGS | GH-bovine | oriP | EBNA |
| 143094 | synthetic | EF1a_LTR-HTLV | none | polyhedrin | polyhedrin | none | HSV-TK | none | none |
| 143095 | CMV | CMV | none | none | none | none | GH-bovine_gastrin | none | none |
| 143096 | CMV | GAPDH | Chick actin/rabbit | none | none | none | Globin-rabbit_gastrin | none | none |

TABLE 16-continued

Vector element combinations used in gene transfer vectors.

| A Construct | B Enhancer | C Promoter | D Intron | E 5' UTR | F 3' UTR | G RNA export | H polyA | I viral ori | J viral rep prot |
|---|---|---|---|---|---|---|---|---|---|
| 143097 | CMV | CMV | CMVa | CMV_sTNV | sTNV | none | GH-bovine | none | none |
| 143098 | CMV | CMV | none | TNV | TNV | WPRE | HSV-TK | none | none |
| 143099 | CMV | CMV | none | CMV_TNV | TNV | none | GH-bovine_gastrin | SV40 | SV40 T |
| 143100 | CMV | GAPDH | Chick actin/rabbit | none | none | none | GH-bovine | oriP | none |
| 143101 | CMV | CMV | Chick actin/rabbit | none | none | AGS | HSV-TK | none | none |
| 143102 | EF1a | EF1a_LTR-HTLV | none | none | none | none | HSV-TK | oriP | EBNA |
| 143103 | none | EF1a_LTR-HTLV | none | none | none | AGS | Globin-rabbit | oriP | EBNA |
| 143104 | EF1a | EF1a_LTR-HTLV | none | TNV | TNV | AGS | HSV-TK | oriP | none |
| 143105 | CMV | GAPDH | GAPDH | none | none | none | Globin-rabbit | SV40 | SV40 T |
| 143106 | none | EF1a | EF1a | bglob-Hs | bglob-XI | none | HSV-TK | SV40 | SV40 T |
| 143107 | CMV | GAPDH | Chick actin/rabbit | none | none | none | HSV-TK | none | none |
| 143108 | CMV | GAPDH | GAPDH | BYDV | BYDV | none | HSV-TK | SV40 | SV40 T |
| 143109 | CMV | GAPDH | Chick actin/rabbit | none | none | WPRE | Globin-rabbit | SV40 | SV40 T |
| 143110 | CMV | CMV | none | none | none | none | HSV-TK | SV40 | SV40 T |
| 143111 | none | EF1a | EF1a | none | none | none | Globin-rabbit_gastrin | SV40 | SV40 T |
| 143112 | none | EF1a_LTR-HTLV | none | BYDV | BYDV | AGS | Globin-rabbit | oriP | EBNA |
| 143113 | CMV | CMV | Chick actin/rabbit | bglob-XI | bglob-XI | none | HSV-TK | oriP | none |
| 143114 | CMV | GAPDH | GAPDH | none | none | none | HSV-TK | oriP | none |
| 143115 | none | EF1a_LTR-HTLV | none | TNV | TNV | WPRE | GH-bovine | oriP | EBNA |
| 143116 | none | EF1a_LTR-HTLV | none | bglob-Hs | bglob-XI | none | GH-bovine | none | none |
| 143117 | CMV | GAPDH | GAPDH | sTNV | sTNV | none | Globin-rabbit | oriP | EBNA |
| 143118 | none | EF1a_LTR-HTLV | none | bglob-XI | bglob-XI | none | GH-bovine | none | none |
| 143119 | synthetic | EF1a_LTR-HTLV | none | sTNV | sTNV | AGS | GH-bovine | SV40 | SV40 T |
| 143120 | none | EF1a_LTR-HTLV | none | none | none | none | Globin-rabbit | oriP | none |
| 143121 | none | EF1a | EF1a | TNV | TNV | AGS | GH-bovine | none | none |
| 143122 | CMV | CMV | CMVa | CMV | none | none | GH-bovine | oriP | none |
| 143123 | none | EF1a_LTR-HTLV | none | polyhedrin | polyhedrin | WPRE | GH-bovine | SV40 | SV40 T |
| 143124 | CMV | CMV | CMVc | CMV | none | none | GH-bovine | oriP | EBNA |
| 143125 | CMV | CMV | CMVc | CMV_bglob-XI | bglob-XI | AGS | HSV-TK | oriP | EBNA |
| 143126 | synthetic | EF1a_LTR-HTLV | none | bglob-Hs | bglob-XI | AGS | GH-bovine | SV40 | SV40 T |
| 143127 | CMV | CMV | none | polyhedrin | polyhedrin | none | HSV-TK | oriP | none |
| 143128 | CMV | CMV | CMVa | CMV | none | none | HSV-TK | SV40 | SV40 T |
| 143129 | none | EF1a_LTR-HTLV | none | none | none | WPRE | Globin-rabbit | none | none |
| 143130 | CMV | CMV | Chick actin/rabbit | polyhedrin | polyhedrin | none | Globin-rabbit | SV40 | SV40 T |
| 143131 | CMV | CMV | CMVa | CMV_bglob-Hs | bglob-XI | none | Globin-rabbit | SV40 | SV40 T |
| 143132 | CMV | CMV | none | CMV_BYDV | BYDV | none | Globin-rabbit | oriP | none |
| 143133 | CMV | CMV | none | CMV | none | AGS | Globin-rabbit | oriP | none |
| 143134 | CMV | CMV | CMVa | CMV_bglob-Hs | bglob-XI | none | HSV-TK_gastrin | SV40 | SV40 T |
| 143135 | CMV | GAPDH | Chick actin/rabbit | none | none | none | GH-bovine | oriP | EBNA |

TABLE 17

Vector element combinations used in gene transfer vectors.

| A Construct | B Enhancer | C Promoter | D Intron | E 5' UTR | F RNA export | G polyA | H GFP Expression 1 | I GFP Expression 2 | J GFP Expression 3 |
|---|---|---|---|---|---|---|---|---|---|
| 136053 | CMV | GAPDH | GAPDH | None | None | beta globin-rabbit | 14,964 | 13,968 | N/A |
| 143090 | CMV | CMV | CMVc | CMV | None | Globin-rabbit | 16,825 | 15,882 | 12,666 |
| 180102 | CMV | CMV | MLP | TPL | None | Globin-rabbit (trunc) | 14,213 | 14,600 | 12,166 |
| 184141 | CMV | Actin | Chick actin/rabbit | None | HPRE | Globin-rabbit | 13,339 | 14,374 | 11,753 |
| 184142 | CMV | CMV | GAPDH | CMV | AGSPRE | Globin-rabbit | 5,893 | 6,734 | 4,947 |
| 184143 | CMV | CMV | CMVa | CMV | None | Globin-rabbit | 17,123 | 18,100 | 13,429 |
| 184144 | CMV | GAPDH | Chick actin/rabbit | bglob-XI | None | HSV-TK_gastrin | 15,608 | 14,932 | 12,082 |
| 184145 | CMV | CMV | MLP | CMV_TPL | HPRE | HSV-TK_gastrin | 10,837 | 8,024 | 9,687 |
| 184146 | CMV | EF1a | GAPDH | TPL | None | Globin-rabbit | 787 | 963 | 957 |
| 184147 | CMV | GAPDH | GAPDH | TPL | HPRE | Globin-rabbit | 993 | 1,167 | 713 |
| 184148 | CMV | EF1a | CMVa | None | HPRE | HSV-TK_gastrin | 6,479 | 6,230 | 2,848 |
| 184149 | CMV | GAPDH | GAPDH | bglob-XI | None | HSV-TK_gastrin | 18,036 | 17,007 | 9,516 |
| 184150 | CMV | EF1a | None | bglob-XI | None | Globin-rabbit | 13,987 | 14,431 | 11,176 |
| 184151 | CMV | EF1a | None | None | None | BGH | 13,502 | 14,312 | 12,185 |

TABLE 17-continued

Vector element combinations used in gene transfer vectors.

| A Construct | B Enhancer | C Promoter | D Intron | E 5' UTR | F RNA export | G polyA | H GFP Expression 1 | I GFP Expression 2 | J GFP Expression 3 |
|---|---|---|---|---|---|---|---|---|---|
| 184152 | CMV | EF1a | GAPDH_MLP | TPL | AGSPRE | HSV-TK_gastrin | 8,403 | 9,626 | 7,187 |
| 184153 | CMV | Actin | GAPDH | None | None | Globin-rabbit | 3,164 | 3,903 | 2,821 |
| 184154 | CMV | Actin | CMVa | TPL | AGSPRE | HSV-TK_gastrin | 645 | 717 | 639 |
| 184155 | CMV | CMV | GAPDH | CMV_bglob-XI | HPRE | BGH | 9,977 | 9,493 | 8,187 |
| 184156 | CMV | GAPDH | None | None | AGSPRE | BGH | 5,069 | 4,789 | 2,429 |
| 184157 | CMV | EF1a | CMVa | bglob-XI | AGSPRE | Globin-rabbit | 6,879 | 6,645 | 6,182 |
| 184158 | CMV | Actin | GAPDH_MLP | TPL | None | BGH | 9,739 | 10,908 | 8,815 |
| 184159 | CMV | CMV | CMVa | CMV_bglob-XI | None | BGH | 11,174 | 12,611 | 10,503 |
| 184160 | CMV | CMV | Chick actin/rabbit_MLP | CMV_TPL | AGSPRE | Globin-rabbit | 5,202 | 4,660 | 3,895 |
| 184162 | CMV | EF1a | Chick actin/rabbit | TPL | None | BGH | 758 | 923 | 779 |
| 184163 | CMV | GAPDH | CMVa_MLP | TPL | None | Globin-rabbit | 13,667 | 15,531 | 14,426 |
| 184164 | CMV | CMV | None | CMV_TPL | None | HSV-TK_gastrin | 409 | 400 | 424 |
| 188000 | CMV | Actin | None | bglob-XI | AGSPRE_3 | Globin-rabbit | 10,467 | 10,274 | 10,189 |
| 189478 | CMV | GAPDH | MLP | None | None | Globin-rabbit | 13,341 | 13,005 | 11,990 |
| 189479 | CMV | CMV | MLP | None | None | Globin-rabbit | 12,099 | 12,077 | 12,621 |

TABLE 18

Vector element combinations used in gene transfer vectors.

| A Construct | B Enhancer | C Promoter | D Intron | E RNA export | F polyA | G insulator | H GFP Expression 1 | I GFP Expression 2 | J GFP Expression 3 |
|---|---|---|---|---|---|---|---|---|---|
| 178620 | CMV | CMV | none | SEQ ID NO: 104 | BGH | none | 1,513 | 1,572 | 1,490 |
| 178621 | CMV | CMV | none | SEQ ID NO: 106 | BGH | none | 1,272 | 1,185 | 1,109 |
| 178622 | CMV | CMV | none | SEQ ID NO: 107 | BGH | none | 865 | 891 | 979 |
| 178623 | none | EF1a | EF1a | SEQ ID NO: 104 | BGH | HS4 | 2,698 | 2,302 | 2,388 |
| 178624 | none | EF1a | EF1a | SEQ ID NO: 106 | BGH | HS4 | 138 | 122 | 114 |
| 178625 | none | EF1a | EF1a | SEQ ID NO: 107 | BGH | HS4 | 2,547 | 2,303 | 2,551 |
| 178626 | CMV | CMV | none | SEQ ID NO: 104 | BGH | HS4 | 245 | 258 | 137 |
| 178627 | CMV | CMV | none | SEQ ID NO: 106 | BGH | HS4 | 950 | 884 | 844 |
| negative | none | none | none | none | none | none | 29 | 12 | 30 |
| 145736 | CMV | CMV | none | WPRE | BGH | none | 908 | 1,106 | 952 |
| 142628 | none | EF1a | EF1a | WPRE | synthetic | HS4 | 3,377 | 4,151 | 3,699 |
| 150708 | CMV | CMV | none | WPRE | synthetic | HS4 | 1,074 | 1,080 | 1,056 |
| 150711 | CMV | EF1a | EF1a | WPRE | synthetic | HS4 | 1,634 | 1,246 | 1,798 |
| 147759 | none | EF1a | EF1a | SEQ ID NO: 104 | BGH | none | 850 | 812 | 1,003 |

TABLE 19

Expression of a fluorescent protein from a gene transfer systems designed to test control element configurations.

| A Construct | B CHO Avg-neg | C sd | D HEK Avg-neg | E sd |
|---|---|---|---|---|
| 136024 | 146.1 | 25.3 | 4,650.6 | 245.1 |
| 136025 | 235.9 | 23.3 | 13,829.7 | 673.1 |
| 136026 | 242.2 | 50.6 | 4,299.9 | 199.1 |
| 136027 | 159.1 | 27.7 | 2,444.3 | 109.4 |
| 136028 | 0.4 | 0.5 | 51.6 | 14.8 |
| 136029 | 238.6 | 22.4 | 1,356.0 | 126.4 |
| 136030 | 70.2 | 12.7 | 1,651.3 | 112.8 |
| 136031 | 90.1 | 4.7 | 2,021.1 | 91.0 |
| 136032 | 281.8 | 16.8 | 2,560.9 | 127.2 |
| 136033 | 235.2 | 46.3 | 7,308.9 | 582.5 |
| 136034 | 166.1 | 22.2 | 6,412.6 | 491.3 |
| 136035 | 94.0 | 12.5 | 8,838.9 | 566.1 |
| 136036 | 156.1 | 10.4 | 3,557.0 | 260.5 |
| 136037 | 211.2 | 14.5 | 3,237.3 | 72.4 |
| 136038 | 143.7 | 4.3 | 3,662.4 | 220.0 |
| 136039 | 106.8 | 7.8 | 4,368.4 | 31.9 |
| 136040 | 68.1 | 13.6 | 4,669.5 | 646.8 |
| 136041 | 199.4 | 24.0 | 5,646.5 | 517.9 |
| 136042 | 155.8 | 13.1 | 4,685.6 | 274.3 |
| 136043 | 225.5 | 24.0 | 3,638.9 | 377.8 |
| 136044 | 153.6 | 28.2 | 1,887.9 | 141.2 |
| 136045 | 187.1 | 8.0 | 3,942.0 | 5.1 |
| 136046 | 106.6 | 13.6 | 7,872.8 | 105.1 |
| 136047 | 121.2 | 8.3 | 1,824.1 | 116.9 |
| 136048 | 196.9 | 7.5 | 2,091.8 | 14.4 |
| 136049 | 112.5 | 7.5 | 1,994.0 | 100.3 |
| 136050 | 78.2 | 10.0 | 6,189.9 | 136.0 |
| 136051 | 74.0 | 24.9 | 738.6 | 19.7 |
| 136052 | 105.4 | 19.2 | 1,123.3 | 68.9 |
| 136053 | 349.3 | 30.9 | 1,433.4 | 59.5 |
| 136054 | 92.9 | 8.3 | 4,068.8 | 396.1 |
| 136055 | 129.8 | 9.9 | 522.5 | 6.4 |
| 136056 | 1.7 | 0.6 | 2.2 | 1.6 |
| 136057 | 6.9 | 1.0 | 0.6 | 1.2 |
| 136058 | 2.6 | 0.5 | 1.2 | 1.3 |
| 136059 | 7.5 | 1.0 | 8.5 | 2.2 |

TABLE 19-continued

Expression of a fluorescent protein from a gene transfer systems designed to test control element configurations.

| A Construct | B CHO Avg-neg | C sd | D HEK Avg-neg | E sd |
|---|---|---|---|---|
| 136060 | 11.4 | 1.5 | 6.2 | 2.0 |
| 136061 | 32.2 | 0.9 | 172.0 | 3.4 |
| 136062 | 17.1 | 2.9 | 10.4 | 1.2 |
| 136063 | 220.9 | 8.8 | 129.8 | 2.8 |
| 136064 | 27.0 | 1.8 | 18.5 | 2.4 |
| 136065 | 295.5 | 60.6 | 84.0 | 3.5 |
| 136066 | 55.9 | 8.3 | 76.9 | 5.1 |
| 136067 | 16.9 | 1.8 | 69.7 | 3.3 |
| 136068 | 33.9 | 8.9 | 18.5 | 5.4 |
| 136069 | 15.1 | 2.1 | 108.7 | 13.8 |
| 136070 | 19.6 | 3.5 | 789.6 | 86.2 |
| 136071 | 41.1 | 4.6 | 191.5 | 16.4 |
| 128979 | 175.4 | 30.5 | 2,884.7 | 160.0 |
| 128980 | 189.2 | 12.6 | 2,377.4 | 63.7 |
| 128986 | 97.5 | 21.7 | 5,160.8 | 32.4 |
| 129091 | 74.7 | 11.4 | 4,410.3 | 156.4 |
| 128977 | 67.9 | 6.8 | 2,453.4 | 205.9 |
| 133528 | 28.0 | 0.9 | 2,089.0 | 56.0 |
| 134746 | 47.1 | 2.2 | 4,004.1 | 345.9 |

TABLE 20

Expression of a fluorescent protein from a gene transfer systems designed to test control element configurations.

| A Construct | B CHO: Rel to 129091 | C CHO: Rel to 136025 | D HEK: Rel to 129091 | E sd |
|---|---|---|---|---|
| 143088 | 0.90 | 0.64 | 1.16 | 0.07 |
| 143089 | 0.85 | 0.61 | 0.22 | 0.01 |
| 143090 | 1.49 | 1.06 | 2.52 | 0.22 |
| 143091 | 0.06 | 0.04 | 0.09 | 0.01 |
| 143092 | 1.01 | 0.72 | 0.17 | 0.01 |
| 143093 | 1.13 | 0.81 | 1.51 | 0.12 |
| 143094 | 0.70 | 0.50 | 0.06 | 0.00 |
| 143095 | 0.62 | 0.44 | 0.41 | 0.03 |
| 143096 | 2.21 | 1.58 | 0.57 | 0.06 |
| 143097 | 0.13 | 0.10 | 0.11 | 0.01 |
| 143098 | 0.44 | 0.31 | 0.39 | 0.04 |
| 143099 | 0.37 | 0.27 | 1.72 | 0.10 |
| 143100 | 0.71 | 0.51 | 0.35 | 0.02 |
| 143101 | 0.99 | 0.70 | 1.02 | 0.06 |
| 143102 | 0.42 | 0.30 | 0.06 | 0.01 |
| 143103 | 0.55 | 0.39 | 0.09 | 0.01 |
| 143104 | 0.03 | 0.03 | 0.01 | 0.00 |
| 143105 | 0.11 | 0.13 | 0.74 | 0.02 |
| 143106 | 0.39 | 0.48 | 0.89 | 0.04 |
| 143107 | 0.15 | 0.19 | 0.07 | 0.01 |
| 143108 | 0.05 | 0.06 | 0.49 | 0.01 |
| 143109 | 0.48 | 0.58 | 0.93 | 0.03 |
| 143110 | 0.32 | 0.38 | 1.81 | 0.09 |
| 143111 | 0.51 | 0.61 | 1.23 | 0.03 |
| 143112 | 0.07 | 0.08 | 0.02 | 0.00 |
| 143113 | 0.73 | 0.89 | 1.89 | 0.29 |
| 143114 | 0.64 | 0.78 | 0.24 | 0.01 |
| 143115 | 0.17 | 0.21 | 0.08 | 0.00 |
| 143116 | 0.96 | 1.16 | 0.11 | 0.01 |
| 143117 | 0.26 | 0.32 | 0.06 | 0.00 |
| 143118 | 0.85 | 1.03 | 0.07 | 0.00 |
| 143119 | 0.06 | 0.08 | 0.07 | 0.00 |
| 143120 | 0.45 | 0.32 | 0.00 | 0.00 |
| 143121 | 0.79 | 0.57 | 0.00 | 0.00 |
| 143122 | 1.25 | 0.89 | 0.29 | 0.03 |
| 143123 | 0.69 | 0.49 | 0.04 | 0.01 |
| 143124 | 1.40 | 1.00 | 1.24 | 0.12 |
| 143125 | 1.81 | 1.29 | 1.15 | 0.11 |
| 143126 | 0.46 | 0.33 | 0.01 | 0.00 |
| 143127 | 0.48 | 0.34 | 0.31 | 0.04 |
| 143128 | 1.56 | 1.11 | 3.31 | 0.31 |
| 143129 | 2.28 | 1.63 | 0.14 | 0.02 |
| 143130 | 1.05 | 0.75 | 2.59 | 0.26 |
| 143131 | 1.48 | 1.05 | 4.02 | 0.38 |
| 143132 | 0.38 | 0.27 | 0.95 | 0.09 |
| 143133 | 0.92 | 0.65 | 0.17 | 0.02 |
| 143134 | 1.45 | 1.03 | 3.78 | 0.35 |
| 143135 | 1.56 | 1.12 | 0.38 | 0.03 |

TABLE 21

Regression weights for vector elements used in transient expression in HEK and CHO cells.

| Enhancer | Promoter | Intron | polyA | viral ori | viral rep prot | CHO weight | HEK weight |
|---|---|---|---|---|---|---|---|
| CMV | CMV | | | | | 51.37 | 682.70 |
| CMV | Chick actin | Chick actin/rabbit | | | | 93.79 | 3,925.31 |
| CMV | Actin | Chick actin (partial) | | | | −44.92 | −1,676.55 |
| CMV | CMV | CMV intron a | | | | 52.61 | 4,103.61 |
| CMV | CMV | CMV intron c | | | | 30.18 | 1,923.01 |
| CMV | EF1a | EF1a_v1 | | | | 63.03 | 1,452.29 |
| CMV | EF1a | EF1a_v2 | | | | 29.90 | 1,179.46 |
| CMV | EF1a | EF1a_hybrid | | | | 6.34 | 110.31 |
| CMV | GAPDH | GAPDH | | | | 44.57 | −972.75 |
| none | HSV-TK | | | | | −121.04 | −1,898.14 |
| none | MC1 | | | | | −80.29 | −2,735.93 |
| none | PGK | | | | | −24.59 | −1,364.48 |
| E_SV40 | SV40 | | | | | −7.61 | −2,138.04 |
| none | Ub-B | | | | | −93.35 | −2,590.80 |
| | | | synthetic polyA | | | −39.44 | −554.30 |
| | | | GH-bovine | | | 7.05 | 599.58 |
| | | | sv40 early | | | 0.53 | −485.28 |
| | | | sv40 late | | | −17.59 | −599.00 |
| | | | beta globin-human | | | 16.44 | −402.53 |
| | | | beta globin-rabbit | | | 43.28 | 869.96 |
| | | | HSV-TK | | | −10.28 | 571.57 |
| | | | | SV40 | SV40 T | −113.24 | 2,679.35 |

TABLE 21-continued

Regression weights for vector elements used in transient expression in HEK and CHO cells.

| Enhancer | Promoter | Intron | polyA | viral ori | viral rep prot | CHO weight | HEK weight |
|---|---|---|---|---|---|---|---|
| | | | | oriP | none | −84.67 | 593.83 |
| | | | | oriP | EBNA | −106.31 | −139.82 |

7. REFERENCES

All references cited herein are incorporated herein by reference in their entirety and for all purposes to the same extent as if each individual publication or patent or patent application was specifically and individually indicated to be incorporated by reference in its entirety for all purposes. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Any feature, step, element, embodiment, or aspect of the invention can be used in combination with any other unless specifically indicated otherwise.

What is claimed is:

1. A polynucleotide comprising a piggyBac-like transposon comprising a heterologous polynucleotide flanked by a pair of transposon ends, wherein one transposon end comprises at least 16 contiguous nucleotides from SEQ ID NO: 1 and the other transposon end comprises at least 16 contiguous nucleotides from SEQ ID NO: 2.

2. The polynucleotide of claim 1, wherein each transposon end comprises inverted terminal repeat (ITR) that is at least 90% identical to SEQ ID NO: 32.

3. The polynucleotide of claim 2, wherein the transposon comprises two inverted terminal repeat (ITR) sequences, each of which is SEQ ID NO: 32.

4. The polynucleotide of claim 1, wherein one transposon end comprises a sequence that is at least 90% identical to SEQ ID NO: 1 and the other transposon end is at least 90% identical to SEQ ID NO: 2.

5. The polynucleotide of claim 1, wherein the heterologous polynucleotide comprises a promoter.

6. The polynucleotide of claim 5 wherein the promoter is an EF1a promoter, a CMV promoter, a GAPDH promoter, a Herpes Simplex Virus thymidine kinase (HSV-TK) promoter, an actin promoter, a PGK promoter, and an ubiquitin promoter.

7. The polynucleotide of claim 5, wherein the heterologous polynucleotide further comprises a second promoter, and wherein the transcription directions from the first and second promoters are different.

8. The polynucleotide of claim 5, wherein the promoter is operably linked to one or more of: i) an open reading frame; ii) a selectable marker; iii) a counter-selectable marker; iii) a nucleic acid encoding a regulatory protein; iv) a nucleic acid encoding an inhibitory RNA.

9. The polynucleotide of claim 8, wherein the selectable marker is a gene encoding one of glutamine synthetase (GS), dihydrofolate reductase (DHFR), or a protein conferring resistance to puromycin, neomycin, hygromycin, zeocin or blasticidin.

10. The polynucleotide of claim 1, wherein the heterologous polynucleotide comprises one or more sequence elements that increase expression by enhancing RNA processing or export from the nucleus.

11. The polynucleotide of claim 10, wherein the sequence elements are selected from WPRE, HPRE (SEQ ID NO: 104-105), SAR (SEQ ID NOS: 108-111), AGS (SEQ ID NOS: 106-107).

12. The polynucleotide of claim 1, wherein the heterologous polynucleotide comprises a pair of insulators.

13. The polynucleotide of claim 12, wherein the insulators are selected from SEQ ID NOS: 112-113.

14. The polynucleotide of claim 5, wherein the promoter is active in a eukaryotic cell.

15. The polynucleotide of claim 1, wherein the heterologous polynucleotide comprises an internal ribosome entry site (IRES) sequences.

16. The polynucleotide of claim 15, wherein the IRES is one of SEQ ID NOs: 58-100.

17. The polynucleotide of claim 1, wherein the heterologous polynucleotide comprises a gene encoding an antibody chain.

18. The polynucleotide claim 1, wherein the heterologous polynucleotide comprises a gene encoding a chimeric antibody receptor.

19. An isolated eukaryotic cell or non-human transgenic animal, whose genome comprises an integrated copy of the polynucleotide of claim 1.

20. The isolated eukaryotic cell or non-human transgenic animal of claim 19, which is an isolated eukaryotic cell, wherein the cell is an animal cell.

* * * * *

(12) EX PARTE REEXAMINATION CERTIFICATE (11696th)
United States Patent
Minshull et al.

(10) Number: US 9,574,209 C1
(45) Certificate Issued: *Jul. 13, 2020

(54) ENHANCED NUCLEIC ACID CONSTRUCTS FOR EUKARYOTIC GENE EXPRESSION

(71) Applicant: DNA2.0, INC., Newark, CA (US)

(72) Inventors: Jeremy Minshull, Los Altos, CA (US); Mark Welch, Fremont, CA (US); Sridhar Govindrajan, Los Altos, CA (US); Kate Caves, San Jose, CA (US)

Reexamination Request:
No. 90/014,320, Jun. 19, 2019

Reexamination Certificate for:
Patent No.: 9,574,209
Issued: Feb. 21, 2017
Appl. No.: 15/195,905
Filed: Aug. 2, 2016

(*) Notice: This patent is subject to a terminal disclaimer.

Related U.S. Application Data

(63) Continuation of application No. 14/683,121, filed on Apr. 9, 2015, now Pat. No. 9,428,767.

(60) Provisional application No. 61/977,474, filed on Apr. 9, 2014, provisional application No. 62/003,397, filed on May 27, 2014, provisional application No. 62/046,705, filed on Sep. 5, 2014, provisional application No. 62/069,656, filed on Oct. 28, 2014, provisional application No. 62/120,522, filed on Feb. 25, 2015, provisional application No. 62/046,875, filed on Sep. 5, 2014.

(51) Int. Cl.
| | | |
|---|---|---|
| *C12N 15/85* | (2006.01) | |
| *C07K 16/00* | (2006.01) | |
| *C12N 9/12* | (2006.01) | |
| *C07K 16/32* | (2006.01) | |
| *C12N 15/90* | (2006.01) | |
| *A61K 31/00* | (2006.01) | |
| *A61K 31/7105* | (2006.01) | |
| *C07K 2/00* | (2006.01) | |
| *C07K 14/435* | (2006.01) | |
| *C07K 14/46* | (2006.01) | |
| *A61K 38/00* | (2006.01) | |

(52) U.S. Cl.
CPC ........... *C12N 9/1241* (2013.01); *A61K 31/00* (2013.01); *A61K 31/7105* (2013.01); *C07K 2/00* (2013.01); *C07K 14/43586* (2013.01); *C07K 14/463* (2013.01); *C07K 16/00* (2013.01); *C07K 16/32* (2013.01); *C12N 15/85* (2013.01); *C12N 15/907* (2013.01); *C12Y 207/07* (2013.01); *A61K 38/00* (2013.01); *C07K 2317/10* (2013.01); *C07K 2317/24* (2013.01); *C07K 2317/56* (2013.01); *C07K 2319/09* (2013.01); *C07K 2319/80* (2013.01); *C12N 2800/90* (2013.01); *C12N 2830/40* (2013.01); *C12N 2830/60* (2013.01)

(58) Field of Classification Search
None
See application file for complete search history.

(56) References Cited

To view the complete listing of prior art documents cited during the proceeding for Reexamination Control Number 90/014,320, please refer to the USPTO's public Patent Application Information Retrieval (PAIR) system under the Display References tab.

*Primary Examiner* — Padmashri Ponnaluri

(57) ABSTRACT

The present invention provides polynucleotide vectors for high expression of heterologous genes, and methods for constructing such vectors. Some vectors further comprise novel transposons and transposases that further improve expression. Further disclosed are vectors that can be used in a gene transfer system for stably introducing nucleic acids into the DNA of a cell. The gene transfer systems can be used in methods, for example, but not limited to, gene expression, gene therapy, insertional mutagenesis, or gene discovery.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-5 are cancelled.

Claims 6-20 were not reexamined.

\* \* \* \* \*